US008206970B2

(12) United States Patent
Eliot et al.

(10) Patent No.: US 8,206,970 B2
(45) Date of Patent: Jun. 26, 2012

(54) PRODUCTION OF 2-BUTANOL AND 2-BUTANONE EMPLOYING AMINOBUTANOL PHOSPHATE PHOSPHOLYASE

(75) Inventors: Andrew C. Eliot, Wilmington, DE (US); Vasantha Nagarajan, Wilmington, DE (US); Lixuan Lisa Huang, Hockessin, DE (US)

(73) Assignee: Butamax(TM) Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 11/741,892

(22) Filed: Apr. 30, 2007

(65) Prior Publication Data

US 2007/0259410 A1 Nov. 8, 2007

Related U.S. Application Data

(60) Provisional application No. 60/871,156, filed on Dec. 21, 2006, provisional application No. 60/796,816, filed on May 2, 2006.

(51) Int. Cl.

| | |
|---|---|
| ***C12N 1/20*** | (2006.01) |
| ***C12N 9/00*** | (2006.01) |
| ***C12N 9/02*** | (2006.01) |
| ***C12N 9/88*** | (2006.01) |
| ***C12N 15/00*** | (2006.01) |
| ***C12P 21/04*** | (2006.01) |
| ***C07H 21/04*** | (2006.01) |

(52) U.S. Cl. ..................... 435/252.3; 435/183; 435/189; 435/232; 435/320.1; 435/69.1; 435/71.1; 536/23.2

(58) Field of Classification Search ........................ None
See application file for complete search history.

(56) References Cited

U.S. PATENT DOCUMENTS

| | | | |
|---|---|---|---|
| 4,424,275 | A | 1/1984 | Levy |
| 4,568,643 | A | 2/1986 | Levy |
| 5,192,673 | A | 3/1993 | Jain et al. |
| 5,210,032 | A | 5/1993 | Kashket |
| 5,523,223 | A | 6/1996 | Kula et al. |
| 6,358,717 | B1 | 3/2002 | Blaschek et al. |
| 6,432,688 | B1 | 8/2002 | Ito et al. |
| 2002/0028492 | A1 | 3/2002 | Lenke et al. |
| 2007/0265477 | A1 | 11/2007 | Gupta et al. |
| 2007/0292927 | A1 | 12/2007 | Donaldson et al. |
| 2009/0155870 | A1 | 6/2009 | Donaldson et al. |
| 2009/0239275 | A1 | 9/2009 | Donaldson et al. |

FOREIGN PATENT DOCUMENTS

| | | | |
|---|---|---|---|
| CA | 2039245 | | 3/1991 |
| EP | 0 112 459 | A1 | 7/1984 |
| EP | 0 315 949 | A1 | 5/1989 |
| EP | 0 305 434 | B1 | 6/1995 |
| EP | 1 149 918 | A1 | 10/2001 |
| EP | 0 645 453 | B1 | 11/2004 |
| JP | 61-209594 | | 9/1986 |
| JP | 63-017695 | | 4/1988 |
| JP | 63-102687 | | 5/1988 |
| JP | 63-254986 | | 10/1988 |
| WO | 8807090 | A1 | 9/1988 |
| WO | WO 90/02193 | A1 | 3/1990 |
| WO | WO 98/51813 | A1 | 11/1998 |
| WO | WO 03/078615 | A1 | 9/2003 |
| WO | WO 2005/108593 | A1 | 11/2005 |

OTHER PUBLICATIONS

Bell et al. Accession Q6D510. NCBI Database, 2004.*

Sambrook et al. Molecular Cloning, 1989, Cold Spring Harbor Laboratory Press, pp. 8.46-8.52 and pp. 11.2-11.*

Ullmann's Encyclopedia of Industrial Chemistry, $6^{TH}$ Edition, 2003, vol. 5:727-732.

Breen et. al., Bimetallic Effects in the Liquid-Phase Hydrogenation of 2-Butanone, J. or Catalysis, 2005, vol. 236:270-281.

Butanols, Ullman's Encyclopedia of Industrial Chemiistry, $6^{TH}$ Edition, 2003, vol. 5:716-719.

Speranza et al., Conversion of Meso-2,3 Butanediol Into 2-Butanol by *Lactobacilli* Stereochemical and Enzymatic Aspects, J. Agric. Food Chem., 1997, vol. 45:3476-3480.

Girbal et. al., Regulation of Solvent Production in *Clostridium acetobutylicum*, Trends in Biotechnology, 1998, vol. 16:11-16.

Fontaine et. al., Molecular Characterization and Transcriptional Analysis of ADHE2, The Gene Encoding the NADH-Dependent Aldehyde/Alcohol Dehydrogenase Responsible for Butanol Production in Alcoholgenic Cultures of *Clostridium acetobutllicum* at, Journal of Bacteriology, 2002, vol. 184:821-830.

Cornillot et. al., The Genes for Butanol and Acetone Formation in *Clostridium acetobutylicum* ATCC 824 Reside on al Large Plasmid whose Loss Leads to Degeneration on the Strain, Journal of Bacteriology, 1997, vol. 179:5442-5447.

Bermejo et. al., Expression of *Clostridium acetobutylicum* ATCC 824 Genes in *Escherichia coli* for Acetone Production and Acetate Detoxification, Applied and Environmental, 1998, vol. 64:1079-1085.

D.R. Woods, The Genetic Engineering of Microbial Solvent Production, Trends in Biotechnology, 1995, vol. 13:259-264.

P. Durre, New Insights and Novel Developments in Clostridial Acetone/Butanol/Isopropanol Fermentation Applied Microbiology and Biotechnology, 1998, vol. 49:639-648.

(Continued)

*Primary Examiner* — Yong Pak

(74) *Attorney, Agent, or Firm* — Christine M. Lhulier, Esquire

(57) ABSTRACT

Methods for the fermentive production of four carbon alcohols are provided. Specifically, butanol, preferably 2-butanol is produced by the fermentive growth of a recombinant bacteria expressing a 2-butanol biosynthetic pathway. The recombinant microorganisms and methods of the invention can also be adapted to produce 2-butanone, an intermediate in the 2-butanol biosynthetic pathways disclosed herein.

13 Claims, 1 Drawing Sheet

OTHER PUBLICATIONS

Figure 1:
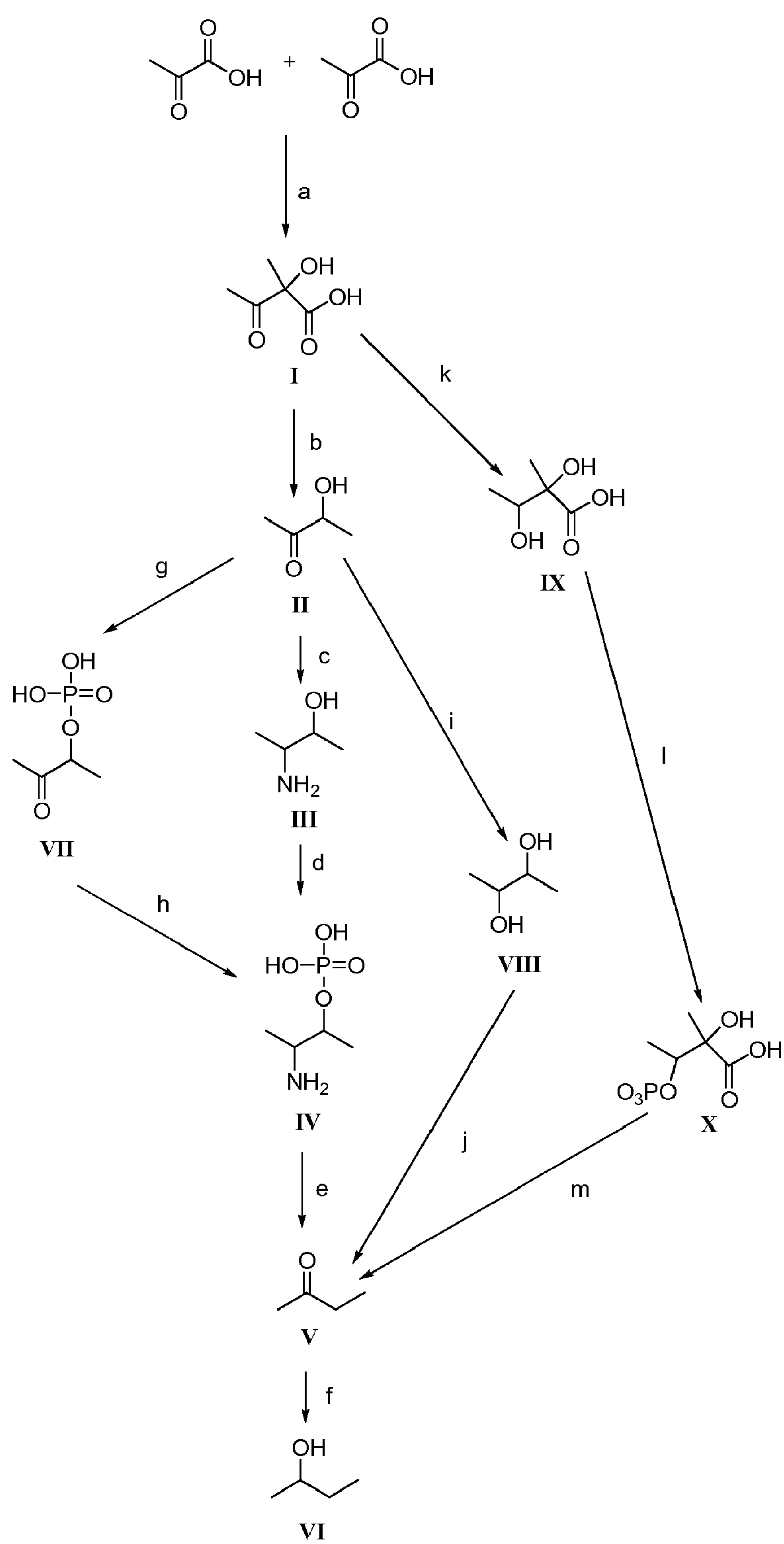

Harris et. al., Characterization of Recombinant Strains of the *Clostridium acetobutyrate* Kinase Inactivation Mutant:Need for New Phenomenological Models for Solventogenesis and Butanol Inhibition, Biotechnology and Bioengineering, 2000, vol. 67:1-11.

Blomqvist, Kristina et al., Characterization of Genes of the 2,3-Butanediol Operons from *Klebsiella terrigena* and *Enterobacter aerogenes*, Journal of Bacteriology, Mar. 1993, p. 1392-1404, vol. 175, No. 5, American Society for Microbiology.

Peng, Hwei-Ling et al., Cloning, sequencing and heterologous expression of a *Klebsiella pneumoniae* gene encoding an FAD-independent acetolactate synthase, Gene, 1992, p. 125-130, vol. 117, Elsevier Science Publisher B.V.

International Search Report, International Application No. PCT/US2007/010741, International Filing Date May 2, 2007.

Bell, K. S. et al., Genome sequence of the enterobacterial phytopathogen *Erwinia carotovora* subsp. *atroseptica* and characterization of virulence factors, PNAS, Jul. 27, 2004, pp. 11105-11110, vol. 101, No. 30.

Stewart et al., "A Chemist's Perspective on the Use of Genetically Engineered Microbes as Reagents for Organic Synthesis", Biotechnology and Genetic Engineering Reviews, 14:67-143 (1997).

Shin et al., "Exploring the Active Site of Amine:Pyruvate Amnotransferase on the Basis of the Substrate Structure-Reactivity Relationship: How the Enzyme Controls Substrate Specificity and Steroselectivity", J. Org. Chem., 67:2848-2853 (2002).

NCBI database access No. P27696.1 (Acetolactate synthase, catabolic; created: Aug 1, 1992); Printed Oct. 26, 2011. http://www.ncbi.nlm.nih.gov/protein/P27696.1.

NCBI database access No. NP_391481.1 (alpha-acetolactate decarboxylase [*Bacillus subtilis* subsp. *subtilis* str. 168]; Earliest direct submission date listed: Nov. 18, 1997); Printed Oct. 26, 2011; http://www.ncbi.nlm.nih.gov/protein/NP_391481.1.

NCBI database access No. YP_050154.1 (putative phosphotransferase [*Pectobacterium atrosepticum* SCRI1043]; Earliest direct submission date listed: Feb. 18, 2004); Printed Oct. 26, 2011; http://www.ncbi.nlm.nih.gov/protein/YP_050154.1.

NCBI database access No. YP_050155.1 (putative class-III aminotransferase [*Pectobacterium atrosepticum* SCRI1043]; Earliest direct submission date listed: Feb. 18, 2004); Printed Oct. 26, 2011: http://www.ncbi.nlm.nih.gov/protein/YP_050155.1.

NCBI database access No. CAD36475.1 (secondary alcohol dehydrogenase [*Rhodococcus ruber*]: Direct submission: Jun. 21, 2002); printed Mar. 9, 2010. http://www.ncbi.nlm.nih.gov/protein/21615553.

Jones et al., "1-aminopropan-2-ol and ethanolamine metabolism via propionaldehyde and acetaldehyde in a species of *Pseudomonas*" Biochem. J. (1973) 134, pp. 167-182.

Eichenberger et al. "The Program of Gene Transcription for a Single Differentiating Cell Type during Sporulation in *Bacillus subtilis*." PLoS Biol (2004) 2(10): e328.

Barbe et al. "From a consortium sequence to a unified sequence: the *Bacillus subtilis* 168 reference genome a decase later" Microbiology (2009) 155 (Pt 6), 1758-1775.

Mizuno, et al. "Systematic sequencing of the 283 kb 210 degrees-232 degrees region of the *Bacillus subtilis* genome containing the skin element and many sporulation genes" Microbiology (1996) 142 (Pt 11), 3103-3111.

Kunst, et al. "The complete genome sequence of the Gram-positive bacterium *Bacillus subtilis*" Nature (1997) 390, 249-256.

* cited by examiner

PRODUCTION OF 2-BUTANOL AND 2-BUTANONE EMPLOYING AMINOBUTANOL PHOSPHATE PHOSPHOLYASE

CROSS-REFERENCE TO RELATED APPLICATION

This application claims priority under 35 U.S.C. §119 from U.S. Provisional Application Ser. No. 60/796816, filed May 2, 2006 and U.S. Provisional Application Ser. No. 60/871156, filed Dec. 21, 2006.

FIELD OF THE INVENTION

The invention relates to the field of industrial microbiology and the production of alcohols. More specifically, 2-butanol is produced via industrial fermentation of a recombinant microorganism. The recombinant microorganisms and methods of the invention can also be adapted to produce 2-butanone, an intermediate in the 2-butanol biosynthetic pathways disclosed herein.

BACKGROUND OF THE INVENTION

Butanol is an important industrial chemical, useful as a fuel additive, as a feedstock chemical in the plastics industry, and as a food-grade extractant in the food and flavor industry. Each year 10 to 12 billion pounds of butanol are produced by petrochemical means and the need for this commodity chemical will likely increase. 2-Butanone, also referred to as methyl ethyl ketone (MEK), is a widely used solvent and is the most important commercially produced ketone, after acetone. It is used as a solvent for paints, resins, and adhesives, as well as a selective extractant and activator of oxidative reactions.

Methods for the chemical synthesis of 2-butanone are known, such as by dehydrogenation of 2-butanol or in a process where liquid butane is catalytically oxidized giving 2-butanone and acetic acid (*Ullmann's Encyclopedia of Industrial Chemistry*, $6^{th}$ edition, 2003, Wiley-VCHVerlag GmbH and Co., Weinheim, Germany, Vol. 5, pp.727-732). 2-Butanone may also be converted chemically to 2-butanol by hydrogenation (Breen et al., J. or Catalysis 236: 270-281 (2005)). Methods for the chemical synthesis of 2-butanol are known, such as n-butene hydration (*Ullmann's Encyclopedia of Industrial Chemistry*, $6^{th}$ edition, 2003, Wiley-VCHVerlag GmbH and Co., Weinheim, Germany, Vol. 5, pp. 716-719). These processes use starting materials derived from petrochemicals and are generally expensive, and are not environmentally friendly. The production of 2-butanone and 2-butanol from plant-derived raw materials would minimize greenhouse gas emissions and would represent an advance in the art.

Methods for producing 2-butanol by biotransformation of other organic chemicals are also known. For example, Stampfer et al. (WO 03/078615) describe the production of secondary alcohols, such as 2-butanol, by the reduction of ketones which is catalyzed by an alcohol dehydrogenase enzyme obtained from *Rhodococcus ruber*. Similarly, Kojima et al. (EP 0645453) describe a method for preparing secondary alcohols, such as 2-butanol, by reduction of ketones which is catalyzed by a secondary alcohol dehydrogenase enzyme obtained from *Candida parapsilosis*. Additionally, Kuehnle et al. (EP 1149918) describe a process that produces both 1-butanol and 2-butanol by the oxidation of hydrocarbons by various strains of *Rhodococcus ruber*. The process favored 1-butanol production with a selectivity of 93.8%.

The production of 2-butanol by certain strains of *Lactobacilli* is also known (Speranza et. al. *J. Agric. Food Chem.* (1997) 45:3476-3480). The 2-butanol is produced by the transformation of meso-2,3-butanediol. The production of 2-butanol from acetolactate and acetoin by these *Lactobacilli* strains was also demonstrated. However, there have been no reports of a recombinant microorganism designed to produce 2-butanol.

There is a need, therefore, for environmentally responsible, cost-effective processes for the production of 2-butanol and 2-butanone. The present invention addresses this need through the discovery of recombinant microbial production hosts expressing 2-butanol and 2-butanone biosynthetic pathways.

SUMMARY OF THE INVENTION

The invention provides a recombinant microorganism having an engineered 2-butanol biosynthetic pathway. Also provided is a recombinant microorganism having an engineered 2-butanone biosynthetic pathway, which is the same as the 2-butanol biosynthetic pathway with omission of the last step. The engineered microorganisms may be used for the commercial production of 2-butanol or 2-butanone.

Accordingly, the invention provides a recombinant microbial host cell comprising at least one DNA molecule encoding a polypeptide that catalyzes a substrate to product conversion selected from the group consisting of:

i) pyruvate to alpha-acetolactate;
ii) alpha-acetolactate to acetoin;
iii) acetoin to 3-amino-2-butanol
iv) 3-amino-2-butanol to 3-amino-2-butanol phosphate;
v) 3-amino-2-butanol phosphate to 2-butanone; and
vi) 2-butanone to 2-butanol;

wherein the at least one DNA molecule is heterologous to said microbial host cell and wherein said microbial host cell produces 2-butanol.

Similarly the invention provides a recombinant microbial host cell comprising at least one DNA molecule encoding a polypeptide that catalyzes a substrate to product conversion selected from the group consisting of:

i) pyruvate to alpha-acetolactate;
ii) alpha-acetolactate to acetoin;
iii) acetoin to 3-amino-2-butanol;
iv) 3-amino-2-butanol to 3-amino-2-butanol phosphate; and
v) 3-amino-2-butanol phosphate to 2-butanone;

wherein the at least one DNA molecule is heterologous to said microbial host cell and wherein said microbial host cell produces 2-butanone.

In another embodiment the invention provides a method for the production of 2-butanol comprising:

1) providing a recombinant microbial host cell comprising at least one DNA molecule encoding a polypeptide that catalyzes a substrate to product conversion selected from the group consisting of:
   i) pyruvate to alpha-acetolactate;
   ii) alpha-acetolactate to acetoin;
   iii) acetoin to 3-amino-2-butanol;
   iv) 3-amino-2-butanol to 3-amino-2-butanol phosphate;
   v) 3-amino-2-butanol phosphate to 2-butanone; and
   vi) 2-butanone to 2-butanol;
   wherein the at least one DNA molecule is heterologous to said microbial host cell; and
2) contacting the host cell of (1) with a fermentable carbon substrate in a fermentation medium under conditions whereby 2-butanol is produced.

Similarly the invention provides a method for the production of 2-butanone comprising:

1) providing a recombinant microbial host cell comprising at least one DNA molecule encoding a polypeptide that catalyzes a substrate to product conversion selected from the group consisting of:
   i) pyruvate to alpha-acetolactate;
   ii) alpha-acetolactate to acetoin;
   iii) acetoin to 3-amino-2-butanol;
   iv) 3-amino-2-butanol to 3-amino-2-butanol phosphate; and
   v) 3-amino-2-butanol phosphate to 2-butanone;
   wherein the at least one DNA molecule is heterologous to said microbial host cell; and
2) contacting the host cell of (1) with a fermentable carbon substrate in a fermentation medium under conditions whereby 2-butanone is produced.

In another embodiment the invention provides a 2-butanol or 2-butanone containing fermentation product medium produced by the methods of the invention.

BRIEF DESCRIPTION OF THE FIGURES AND SEQUENCE DESCRIPTIONS

The invention can be more fully understood from the following detailed description, figure, and the accompanying sequence descriptions, which form a part of this application.

FIG. 1 shows four different pathways for biosynthesis of 2-butanone and 2-butanol.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Summary of Nucleic Acid and Protein SEQ ID Numbers

| Description | SEQ ID Nucleic acid | SEQ ID Protein |
|---|---|---|
| budA, acetolactate decarboxylase from *Klebsiella pneumoniae* ATCC 25955 | 1 | 2 |
| alsD, acetolactate decarboxylase from *Bacillus subtilis* | 80 | 81 |
| budA, acetolactate decarboxylase from *Klebsiella terrigena* | 82 | 83 |
| budB, acetolactate synthase from *Klebsiella pneumoniae* ATCC 25955 | 3 | 4 |
| alsS, acetolactate synthase from *Bacillus subtilis* | 76 | 77 |
| budB, acetolactate synthase from *Klebsiella terrigena* | 78 | 79 |
| budC butanediol dehydrogenase from *Klebsiella pneumoniae* IAM1063 | 5 | 6 |
| butanediol dehydrogenase from *Bacillus cereus* | 84 | 85 |
| butanediol dehydrogenase from *Bacillus cereus* | 86 | 87 |
| butB, butanediol dehydrogenase from *Lactococcus lactis* | 88 | 89 |
| pddA, butanediol dehydratase alpha subunit from *Klebsiella oxytoca* ATCC 8724 | 7 | 8 |
| pddB, butanediol dehydratase beta subunit from *Klebsiella oxytoca* ATCC 8724 | 9 | 10 |
| pddC, butanediol dehydratase gamma subunit from *Klebsiella oxytoca* ATCC 8724 | 11 | 12 |

TABLE 1-continued

Summary of Nucleic Acid and Protein SEQ ID Numbers

| Description | SEQ ID Nucleic acid | SEQ ID Protein |
|---|---|---|
| pduC, B12 dependent diol dehydratase large subunit from *Salmonella typhimurium* | 92 | 93 |
| pduD, B12 dependent diol dehydratase medium subunit from *Salmonella typhimurium* | 94 | 95 |
| pduE, B12 dependent diol dehydratase small subunit from *Salmonella typhimurium* | 96 | 97 |
| pduC, B12 dependent diol dehydratase large subunit from *Lactobacillus collinoides* | 98 | 99 |
| pduD, B12 dependent diol dehydratase medium subunit from *Lactobacillus collinoides* | 100 | 101 |
| pduE, B12 dependent diol dehydratase small subunit from *Lactobacillus collinoides* | 102 | 103 |
| pddC, adenosylcobalamin-dependent diol dehydratase alpha subunit from *Klebsiella pneumoniae* | 104 | 105 |
| pddD, adenosylcobalamin-dependent diol dehydratase beta subunit from *Klebsiella pneumoniae* | 106 | 107 |
| pddD, adenosylcobalamin-dependent diol dehydratase gamma subunit from *Klebsiella pneumoniae* | 108 | 109 |
| ddrA, diol dehydratase reactivating factor large subunit from *Klebsiella oxytoca* | 110 | 111 |
| ddrB, diol dehydratase reactivating factor small subunit from *Klebsiella oxytoca* | 112 | 113 |
| pduG, diol dehydratase reactivating factor large subunit from *Salmonella typhimurium* | 114 | 115 |
| pduH, diol dehydratase reactivating factor small subunit from *Salmonella typhimurium* | 116 | 117 |
| pduG, diol dehydratase reactivating factor large subunit from *Lactobacillus collinoides* | 118 | 119 |
| pduH, diol dehydratase reactivating factor small subunit from *Lactobacillus collinoides* | 120 | 121 |
| sadH, butanol dehydrogenase from *Rhodococcus* ruber 219 | 13 | 14 |
| adhA, butanol dehydrogenase from *Pyrococcus furiosus* | 90 | 91 |
| chnA, cyclohexanol dehydrogenase from *Acinteobacter* sp. | 71 | 72 |
| yqhD, butanol dehydrogenase from *Escherichia coli* | 74 | 75 |
| amine: pyruvate transaminase from *Vibrio fluvialis* (an acetoin aminase) | 144 codon opt. | 122 |
| Aminobutanol kinase from *Erwinia carotovora* subsp. atroseptica | 123 | 124 |
| amino alcohol O-phosphate lyase from *Erwinia carotovora* subsp. atroseptica | 125 | 126 |
| budC, acetoin reductase (butanediol dehydrogenase) from *Klebsiella terrigena* (now Raoultella terrigena) | 133 | 134 |
| glycerol dehydratase alpha subunit from *Klebsiella pneumoniae* | 145 | 146 |
| glycerol dehydratase beta subunit from *Klebsiella pneumoniae* | 147 | 148 |
| glycerol dehydratase gamma subunit from *Klebsiella pneumoniae* | 149 | 150 |
| glycerol dehydratase reactivase large subunit from *Klebsiella pneumoniae* | 151 | 152 |
| glycerol dehydratase reactivase small subunit from *Klebsiella pneumoniae* | 153 | 154 |

SEQ ID NOs:15-65 are the nucleotide sequences of oligonucleotide PCR, cloning, screening, and sequencing primers used in the Examples.

SEQ ID NO:66 is nucleotide sequence of the deleted region of the yqhD gene in *E. coli* strain MG1655 ΔyqhCD, described in Example 11.

SEQ ID NO:67 is the nucleotide sequence of a variant of the glucose isomerase promoter 1.6GI.

SEQ ID NO:68 is the nucleotide sequence of the 1.5GI promoter.

SEQ ID NO:69 is the nucleotide sequence of the diol dehydratase operon from *Klebsiella oxytoca*.

SEQ ID NO:70 is the nucleotide sequence of the diol dehydratase reactivating factor operon from *Klebsiella oxytoca*.

SEQ ID NO:73 is the nucleotide sequence of pDCQ2, which is described in Example 9.

SEQ ID NOs:127-132 are the nucleotide sequences of additional oligonucleotide PCR and cloning primers used in the Examples.

SEQ ID NO:155 is a codon optimized coding region for the amino alcohol kinase of *Erwinia carotovora* subsp. *atroseptica*.

SEQ ID NO:156 is a codon optimized coding region for the amino alcohol O-phosphate lyase of *Erwinia carotovora* subsp. *atroseptica*.

SEQ ID NOs:157-163 are the nucleotide sequences of additional oligonucleotide PCR and cloning primers used in the Examples.

SEQ ID NO:164 is the nucleotide sequence of an operon from *Erwinia carotovora* subsp. *atroseptica*.

TABLE 2

Additional glycerol and diol dehydratase large, medium and small subunits

| [a]Description | [b]subunit | protein SEQ ID |
|---|---|---|
| Corresponding subunits from same organism[c] | | |
| Glycerol dehydratase alpha subunit from *Clostridium pasteurianum* | L | 135 |
| Glycerol dehydratase beta subunit from *Clostridium pasteurianum* | M | 136 |
| Glycerol dehydratase gamma subunit from *Clostridium pasteurianum* | S | 137 |
| Glycerol dehydratase alpha subunit from *Escherichia blattae* | L | 138 |
| Glycerol dehydratase beta subunit from *Escherichia blattae* | M | 139 |
| Glycerol dehydratase gamma subunit from *Escherichia blattae* | S | 140 |
| Glycerol dehydratase alpha subunit from *Citrobacter freundii* | L | 141 |
| Glycerol dehydratase beta subunit from *Citrobacter freundii* | M | 142 |
| Glycerol dehydratase gamma subunit from *Citrobacter freundii* | S | 143 |

[a]Description: from the Genbank annotation of the sequence and may not be correct including the glycerol or diol designation, or may not include subunit information.
[b]Subunit: identified by sequence homology to the large, medium, or small subunit.of the *Klebsiella oxytoca* enzyme.
[c]Subunts are listed together that are from the same organism and have annotations as the same enzyme, or have Genbank numbers close together indicating proximity in the genome.

DETAILED DESCRIPTION OF THE INVENTION

The present invention relates to methods for the production of 2-butanol using recombinant microorganisms. The present invention meets a number of commercial and industrial needs. Butanol is an important industrial commodity chemical with a variety of applications, where its potential as a fuel or fuel additive is particularly significant. Although only a four-carbon alcohol, butanol has an energy content similar to that of gasoline and can be blended with any fossil fuel. Butanol is favored as a fuel or fuel additive as it yields only $CO_2$ and little or no $SO_x$ or $NO_x$ when burned in the standard internal combustion engine. Additionally butanol is less corrosive than ethanol, the most preferred fuel additive to date.

In addition to its utility as a biofuel or fuel additive, butanol has the potential of impacting hydrogen distribution problems in the emerging fuel cell industry. Fuel cells today are plagued by safety concerns associated with hydrogen transport and distribution. Butanol can be easily reformed for its hydrogen content and can be distributed through existing gas stations in the purity required for either fuel cells or combustion engines in vehicles.

Finally the present invention produces 2-butanol from plant derived carbon sources, avoiding the negative environmental impact associated with standard petrochemical processes for butanol production.

The present invention also provides recombinant microorganisms and methods for producing 2-butanone, an intermediate in the 2-butanol biosynthetic pathways disclosed herein. 2-Butanone, also known as methyl ethyl ketone (MEK), is useful as a solvent in paints and other coatings. It is also used in the synthetic rubber industry and in the production of paraffin wax.

The following definitions and abbreviations are to be used for the interpretation of the claims and the specification.

The term "invention" or "present invention" as used herein is a non-limiting term and is not intended to refer to any single embodiment of the particular invention but encompasses all possible embodiments as described in the specification and the claims.

The term "2-butanol biosynthetic pathway" refers to the enzyme pathways to produce 2-butanol from pyruvate.

The term "2-butanone biosynthetic pathway" refers to the enzyme pathways to produce 2-butanone from pyruvate.

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (*Enzyme Nomenclature* 1992, Academic Press, San Diego) may be dependent on the cofactor thiamin pyrophosphate for its activity. Suitable acetolactate synthase enzymes are available from a number of sources, for example, *Bacillus subtilis* [GenBank Nos: AAA22222 NCBI (National Center for Biotechnology Information) amino acid sequence (SEQ ID NO:77), L04470 NCBI nucleotide sequence (SEQ ID NO:76)], *Klebsiella terrigena* [GenBank Nos: AAA25055 (SEQ ID NO:79), L04507 (SEQ ID NO:78)], and *Klebsiella pneumoniae* [GenBank Nos: AAA25079 (SEQ ID NO:4), M73842 (SEQ ID NO:3)].

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* [GenBank Nos: AAA22223 (SEQ ID NO:81), L04470 (SEQ ID NO:80)], *Klebsiella terrigena* [GenBank Nos: AAA25054 (SEQ ID NO:83), L04507 (SEQ ID NO:82)] and *Klebsiella pneumoniae* [GenBank Nos: AAU43774 (SEQ ID NO:2), AY722056 (SEQ ID NO:1)].

The term "acetoin aminase" or "acetoin transaminase" refers to a polypeptide (or polypeptides) having an enzyme activity that catalyzes the conversion of acetoin to 3-amino-2-butanol. Acetoin aminase may utilize the cofactor pyridoxal 5'-phosphate or NADH (reduced nicotinamide adenine dinucleotide) or NADPH (reduced nicotinamide adenine dinucleotide phosphate). The resulting product may have (R) or (S) stereochemistry at the 3-position. The pyridoxal phosphate-dependent enzyme may use an amino acid such as alanine or glutamate as the amino donor. The NADH- and NADPH-dependent enzymes may use ammonia as a second substrate. A suitable example of an NADH-dependent acetoin aminase, also known as amino alcohol dehydrogenase, is described by Ito et al. (U.S. Pat. No. 6,432,688). An example of a pyridoxal-dependent acetoin aminase is the amine:pyruvate aminotransferase (also called amine:pyruvate transaminase) described by Shin and Kim (*J. Org. Chem.* 67:2848-2853 (2002)).

The term "butanol dehydrogenase" refers to a polypeptide (or polypeptides) having an enzyme activity that catalyzes the interconversion of 2-butanone and 2-butanol. Butanol dehydrogenases are a subset of a broad family of alcohol dehydrogenases. Butanol dehydrogenase may be NAD- or NADP-dependent. The NAD-dependent enzymes are known as EC 1.1.1.1 and are available, for example, from *Rhodococcus ruber* [GenBank Nos: CAD36475 (SEQ ID NO:14), AJ491307 (SEQ ID NO:13)]. The NADP-dependent enzymes are known as EC 1.1.1.2 and are available, for example, from Pyrococcus furiosus [GenBank Nos: AAC25556 (SEQ ID NO:91), AF013169 (SEQ ID NO:90)]. Additionally, a butanol dehydrogenase is available from *Escherichia coli* [GenBank Nos:NP_417484 (SEQ ID NO:75), NC_000913 (SEQ ID NO:74)] and a cyclohexanol dehydrogenase is available from *Acinetobacter* sp. [GenBank Nos: AAG10026 (SEQ ID NO:72), AF282240 (SEQ ID NO:71)].

The term "acetoin kinase" refers to a polypeptide (or polypeptides) having an enzyme activity that catalyzes the conversion of acetoin to phosphoacetoin. Acetoin kinase may utilize ATP (adenosine triphosphate) or phosphoenolpyruvate as the phosphate donor in the reaction. Although there are no reports of enzymes catalyzing this reaction on acetoin, there are enzymes that catalyze the analogous reaction on the similar substrate dihydroxyacetone, for example, enzymes known as EC 2.7.1.29 (Garcia-Alles et al. (2004) *Biochemistry* 43:13037-13046).

The term "acetoin phosphate aminase" refers to a polypeptide (or polypeptides) having an enzyme activity that catalyzes the conversion of phosphoacetoin to 3-amino-2-butanol O-phosphate. Acetoin phosphate aminase may use the cofactor pyridoxal 5'-phosphate, NADH or NADPH. The resulting product may have (R) or (S) stereochemistry at the 3-position. The pyridoxal phosphate-dependent enzyme may use an amino acid such as alanine or glutamate. The NADH- and NADPH-dependent enzymes may use ammonia as a second substrate. Although there are no reports of enzymes catalyzing this reaction on phosphoacetoin, there is a pyridoxal phosphate-dependent enzyme that is proposed to carry out the analogous reaction on the similar substrate serinol phosphate (Yasuta et al. (2001) *Appl. Environ. Microbiol.* 67:4999-5009).

The term "aminobutanol phosphate phospho-lyase", also called "amino alcohol O-phosphate lyase", refers to a polypeptide (or polypeptides) having an enzyme activity that catalyzes the conversion of 3-amino-2-butanol O-phosphate to 2-butanone. Aminobutanol phosphate phospho-lyase may utilize the cofactor pyridoxal 5'-phosphate. There are no previous reports of enzymes catalyzing this reaction on aminobutanol phosphate, though there are reports of enzymes that catalyze the analogous reaction on the similar substrate 1-amino-2-propanol phosphate (Jones et al. (1973) *Biochem J.* 134:167-182). The present invention describes a newly identified aminobutanol phosphate phospho-lyase (SEQ ID NO: 126) from the organism *Erwinia carotovora*, with the activity demonstrated in Example 15 herein.

The term "aminobutanol kinase" refers to a polypeptide (or polypeptides) having an enzyme activity that catalyzes the conversion of 3-amino-2-butanol to 3-amino-2-butanol O-phosphate. Aminobutanol kinase may utilize ATP as the phosphate donor. Although there are no reports of enzymes catalyzing this reaction on 3-amino-2-butanol, there are reports of enzymes that catalyze the analogous reaction on the similar substrates ethanolamine and 1-amino-2-propanol (Jones et al., supra). The present invention describes, in Example 14, an amino alcohol kinase of *Erwinia carotovora* subsp. *atroseptica* (SEQ ID NO:124). The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of (R)- or (S)-stereochemistry in the alcohol product. (S)-specific butanediol dehydrogenases are known as EC 1.1.1.76 and are available, for example, from *Klebsiella pneumoniae* (GenBank Nos: BBA13085 (SEQ ID NO:6), D86412 (SEQ ID NO:5)). (R)-specific butanediol dehydrogenases are known as EC 1.1.1.4 and are available, for example, from *Bacillus cereus* [GenBank Nos. NP_830481 (SEQ ID NO:85), NC_004722 (SEQ ID NO:84); AAP07682 (SEQ ID NO:87), AE017000 (SEQ ID NO:86)], and *Lactococcus lactis* [GenBank Nos. AAK04995 (SEQ ID NO:89), AE006323 (SEQ ID NO:88)].

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone. Butanediol dehydratase may utilize the cofactor adenosyl cobalamin (vitamin B12). Adenosyl cobalamin-dependent enzymes are known as EC 4.2.1.28 and are available, for example, from *Klebsiella oxytoca* [GenBank Nos: BAA08099 (alpha subunit) (SEQ ID NO:8), D45071 (SEQ ID NO:7); BAA08100 (beta subunit) (SEQ ID NO:10), D45071 (SEQ ID NO:9); and BBA08101 (gamma subunit) (SEQ ID NO:12), D45071 (SEQ ID NO:11) (Note all three subunits are required for activity)], and *Klebsiella pneumoniae* [GenBank Nos: AAC98384 (alpha subunit) (SEQ ID NO:105), AF102064 (SEQ ID NO:104); GenBank Nos: AAC98385 (beta subunit) (SEQ ID NO:107), AF102064 (SEQ ID NO:106), GenBank Nos: AAC98386 (gamma subunit) SEQ ID NO:109), AF102064 (SEQ ID NO:108)]. Other suitable diol dehydratases include, but are not limited to, B12-dependent diol dehydratases available from *Salmonella typhimurium* [GenBank Nos: AAB84102 (large subunit) (SEQ ID NO:93), AF026270 (SEQ ID NO:92); GenBank Nos: AAB84103 (medium subunit) (SEQ ID NO:95), AF026270 (SEQ ID NO:94); GenBank Nos: AAB84104 (small subunit) (SEQ ID NO:97), AF026270 (SEQ ID NO:96)]; and *Lactobacillus collinoides* [GenBank Nos: CAC82541 (large subunit) (SEQ ID NO:99), AJ297723 (SEQ ID NO:98); GenBank Nos: CAC82542 (medium subunit) (SEQ ID NO:101); AJ297723 (SEQ ID NO:100); GenBank Nos: CAD01091 (small subunit) (SEQ ID NO:103), AJ297723 (SEQ ID NO:102)]; and enzymes from *Lactobacillus brevis* (particularly strains CNRZ 734 and CNRZ 735, Speranza et al., supra), and nucleotide sequences that encode the corresponding enzymes. Methods of diol dehydratase gene isolation are well known in the art (e.g., U.S. Pat. No. 5,686,276).

The term "glycerol dehydratase" refers to a polypeptide (or polypeptides) having an enzyme activity that catalyzes the conversion of glycerol to 3-hydroxypropionaldehyde. Adenosyl cobalamin-dependent glycerol dehydratases are known as EC 4.2.1.30. The glycerol dehydratases of EC 4.2.1.30 are similar to the diol dehydratases in sequence and in having three subunits. The glycerol dehydratases can also be used to convert 2,3-butanediol to 2-butanone. Some examples of glycerol dehydratases of EC 4.2.1.30 include those from *Klebsiella pneumoniae* (alpha subunit, SEQ ID NO:145, coding region and SEQ ID NO:146, protein; beta subunit, SEQ ID NO:147, coding region and SEQ ID NO:148, protein; and gamma subunit SEQ ID NO:149, coding region and SEQ ID NO:150, protein); from *Clostridium pasteurianum* [GenBank Nos: 3360389 (alpha subunit, SEQ ID NO:135), 3360390 (beta subunit, SEQ ID NO:136), and 3360391 (gamma subunit, SEQ ID NO:137)]; from *Escherichia blattae* [GenBank Nos: 60099613 (alpha subunit, SEQ ID NO:138), 57340191 (beta subunit, SEQ ID NO:139), and 57340192 (gamma subunit, SEQ ID NO:140)]; and from *Citrobacter freundii* [GenBank Nos: 1169287 (alpha subunit, SEQ ID NO:141), 1229154 (beta subunit, SEQ ID NO:142), and 1229155 (gamma subunit, SEQ ID NO:143)]. Note that all three subunits are required for activity. Additional glycerol dehydratases are listed in Table 2.

Diol and glycerol dehydratases may undergo suicide inactivation during catalysis. A reactivating factor protein, also referred to herein as "reactivase", can be used to reactivate the inactive enzymes (Mori et al., *J. Biol. Chem.* 272:32034 (1997)). Preferably, the reactivating factor is obtained from the same source as the diol or glycerol dehydratase used. For example, suitable diol dehydratase reactivating factors are available from *Klebsiella oxytoca* [GenBank Nos: AAC15871 (large subunit) (SEQ ID NO:111), AF017781 (SEQ ID NO:110); GenBank Nos: AAC15872 (small subunit) (SEQ ID NO:113), AF017781 (SEQ ID NO:112)]; *Salmonella typhimurium* [GenBank Nos: AAB84105 (large subunit) (SEQ ID NO:1 15), AF026270 (SEQ ID NO:1 14), GenBank Nos: AAD39008 (small subunit) (SEQ ID NO:117), AF026270 (SEQ ID NO:116)]; and *Lactobacillus collinoides* [GenBank Nos: CAD01092 (large subunit) (SEQ ID NO:119), AJ297723 (SEQ ID NO:118); GenBank Nos: CAD01093 (small subunit) (SEQ ID NO:121), AJ297723 (SEQ ID NO:120)]. Both the large and small subunits are required for activity. For example, suitable glycerol dehydratase reactivating factors are available from *Klebsiella pneumoniae* (large subunit, SEQ ID NO:151, coding region and SEQ ID NO:152, protein;, and small subunit, SEQ ID NO:153, coding region and SEQ ID NO:154, protein).

The term "a facultative anaerobe" refers to a microorganism that can grow in both aerobic and anaerobic environments.

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, an "isolated nucleic acid fragment" or "isolated nucleic acid molecule" or "genetic construct" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.,* 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine.

The terms "homology" and "homologous" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions (e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: N.Y. (1988); 2.) *Biocomputing: Informatics and Genome Projects* (Smith, D. W., Ed.) Academic: N.Y. (1993); 3.) *Computer Analysis of Sequence Data, Part I* (Griffin, A. M., and Griffin, H. G., Eds.) Humania: N.J. (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: N.Y. (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D.G. et al., *Comput. Appl. Biosci.,* 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D.G. et al., *Comput. Appl. Biosci.* 8:189-191(1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB ). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 24%, 30%, 35%, 40%, 45%, 50%, 55%, 60%, 65%, 70%, 75%, 80%, 85%, 90%, or 95%, or any integer percentage from 24% to 100% may be useful in describing the present invention, such as 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.,* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res., [Proc. lnt. Symp.]* (1994), Meeting Date 1992,111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

As used herein the term "coding sequence" or "CDS" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

The term "fermentation product medium" refers to a medium in which fermentation has occurred such that product is present in the medium.

Standard recombinant DNA and molecular cloning techniques used here are well known in the art and are described by Sambrook, J., Fritsch, E. F. and Maniatis, T., *Molecular Cloning: A Laboratory Manual, Second* Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987).

The 2-Butanol and 2-Butanone Biosynthetic Pathways

Carbohydrate utilizing microorganisms employ the Embden-Meyerhof-Parnas (EMP) pathway, the Entner-Doudoroff pathway and the pentose phosphate cycle as the central, metabolic routes to provide energy and cellular precursors for growth and maintenance. These pathways have in common the intermediate glyceraldehyde 3-phosphate, and, ultimately, pyruvate is formed directly or in combination with the EMP pathway. The combined reactions of sugar conversion to pyruvate produce energy (e.g. adenosine 5'-triphosphate, ATP) and reducing equivalents (e.g. reduced nicotinamide adenine dinucleotide, NADH, and reduced nicotinamide adenine dinucleotide phosphate, NADPH). NADH and NADPH must be recycled to their oxidized forms ($NAD^+$ and $NADP^+$, respectively). In the presence of inorganic electron acceptors (e.g. $O_2$, $NO_3^-$ and $SO_4^{2-}$), the reducing equivalents may be used to augment the energy pool; alternatively, a reduced carbon by-product may be formed.

The invention enables the production of 2-butanone or 2-butanol from carbohydrate sources with recombinant microorganisms by providing a complete biosynthetic pathway from pyruvate to 2-butanone or 2-butanol. Three additional pathways are described. Although 2-butanol is not known to be the major product of any bacterial fermentation, there are a number of possible pathways for the production of 2-butanol via known biochemical reaction types. These pathways are shown in FIG. 1. The letters and roman numerals cited below correspond to the letters and roman numerals in FIG. 1, which are used to depict the conversion steps and products, respectively. As described below, 2-butanone is an intermediate in all of these 2-butanol biosynthetic pathways.

All of the pathways begin with the initial reaction of two pyruvate molecules to yield alpha-acetolactate (I), shown as the substrate to product conversion (a) in FIG. 1. From alpha-acetolactate, there are 4 possible pathways to 2-butanone (V), referred to herein as 2-butanone biosynthetic pathways:

Pathway 1) I--->II--->III--->IV--->V (substrate to product conversions b,c,d,e); This is the pathway of the present invention.

2) I--->II--->VII--->IV--->V (substrate to product conversions b,g,h,e)

3) I--->II--->VIII--->V (substrate to product conversions b,i,j):

4) I--->IX--->X--->V (substrate to product conversions k,l,m)

The 2-butanol biosynthetic pathways conclude with the conversion of 2-butanone (V) to 2-butanol (VI). A detailed discussion of the substrate to product conversions in each pathway is given below.

Pathway 1:

(a) Pyruvate to Alipha-acetolactate:

The initial step in pathway 1 is the conversion of two molecules of pyruvate to one molecule of alpha-acetolactate (compound I in FIG. 1) and one molecule of carbon dioxide catalyzed by a thiamin pyrophosphate-dependent enzyme. Enzymes catalyzing this substrate to product conversion (generally called either acetolactate synthase or acetohydroxy acid synthase; EC 2.2.1.6 [switched from 4.1.3.18 in 2002]) are well-known, and they participate in the biosynthetic pathway for the proteinogenic amino acids leucine and valine, as well as in the pathway for fermentative production of 2,3-butanediol and acetoin of a number of organisms.

The skilled person will appreciate that polypeptides having acetolactate synthase activity isolated from a variety of sources will be useful in the present invention independent of sequence homology. Some example of suitable acetolactate synthase enzymes are available from a number of sources, for example, *Bacillus subtilis* [GenBank Nos: AAA22222 NCBI (National Center for Biotechnology Information) amino acid sequence (SEQ ID NO:77), L04470 NCBI nucleotide sequence (SEQ ID NO:76)], *Klebsiella terrigena* [GenBank Nos: AAA25055 (SEQ ID NO:79), L04507 (SEQ ID NO:78)], and *Klebsiella pneumoniae* [GenBank Nos: AAA25079 (SEQ ID NO:4), M73842 (SEQ ID NO:3)]. Preferred acetolactate synthase enzymes are those that have at least 80%-85% identity to SEQ ID NO's 4, 77, and 79, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(b) Alpha-acetolactate to Acetoin:

Alpha-acetolactate (I) is converted to acetoin (II) by the action of an enzyme such as acetolactate decarboxylase (EC 4.1.1.5). Like acetolactate synthase, this enzyme is thiamin pyrophosphate-dependent and is also involved in the production of 2,3-butanediol and acetoin by a number of organisms. The enzymes from different sources vary quite widely in size (25-50 kilodaltons), oligomerization (dimer-hexamer), localization (intracellular of extracellular), and allosteric regulation (for example, activation by branched-chain amino acids). For the purpose of the present invention, an intracellular location is preferable to extracellular, but other variations are generally acceptable.

The skilled person will appreciate that polypeptides having acetolactate decarboxylase activity isolated from a variety of sources will be useful in the present invention independent of sequence homology. Some example of suitable acetolactate decarboxylase enzymes are available from a number of sources, for example, *Bacillus subtilis* [GenBank Nos: AAA22223 (SEQ ID NO:81), L04470 (SEQ ID NO:80)], *Klebsiella terrigena* [GenBank Nos: AAA25054 (SEQ ID NO:83), L04507 (SEQ ID NO:82)] and *Klebsiella pneumoniae* [GenBank Nos: AAU43774 (SEQ ID NO:2), AY722056 (SEQ ID NO:1)].

Preferred acetolactate decarboxylase enzymes are those that have at least 80%-85% identity to SEQ ID NO's 2, 81 and 83, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(c) Acetoin to 3-amino-2-butanol:

There are two known types of biochemical reactions that could effect the substrate to product conversion of acetoin (II) to 3-amino-2-butanol (III), specifically, pyridoxal phosphate-dependent transamination utilizing an accessory amino donor and direct reductive amination with ammonia. In the latter case, the reducing equivalents are supplied in the form of a reduced nicotinamide cofactor (either NADH or NADPH). An example of an NADH-dependent enzyme catalyzing this reaction with acetoin as a substrate is reported by Ito et al. (U.S. Pat. No. 6,432,688). Any stereospecificity of this enzyme has not been assessed. An example of a pyridoxal phosphate-dependent transaminase that catalyzes the conversion of acetoin to 3-amino-2-butanol has been reported by Shin and Kim (supra). This enzyme was shown in Example 13 herein to convert both the (R) isomer of acetoin to the (2R,3S) isomer of 3-amino-2-butanol and the (S) isomer of acetoin to the (2S,3S) isomer of 3-amino-2-butanol. Either type of enzyme (i.e., transaminase or reductive aminase) is considered to be an acetoin aminase and may be utilized in the production of 2-butanol. Other enzymes in this group may have different stereospecificities.

The skilled person will appreciate that polypeptides having acetoin aminase activity isolated from a variety of sources will be useful in the present invention independent of sequence homology. One example of this activity has is described herein and is identified as SEQ ID NO:122. Accordingly preferred acetoin aminase enzymes are those that have at least 80%-85% identity to SEQ ID NO:122, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(d) 3-amino-2-butanol to 3-amino-2-butanol O-phosphate:

There are no enzymes known in the art that catalyze the substrate to product conversion of 3-amino-2-butanol (III) to 3-amino-2-butanol phosphate (IV). However, a few *Pseudomonas* and *Erwinia* species have been shown to express an ATP-dependent ethanolamine kinase (EC 2.7.1.82) which allows them to utilize ethanolamine or 1-amino-2-propanol as a nitrogen source (Jones et al. (1973) *Biochem. J.* 134:167-182). It is likely that this enzyme also has activity towards 3-amino-2-butanol or could be engineered to do so, thereby providing an aminobutanol kinase. The present invention describes in Example 14, a gene of *Erwinia carotovora* subsp. *atroseptica* (SEQ ID NO:123) that encodes a protein (SEQ ID NO:124). This protein has been identified as an amino alcohol kinase. This enzyme may be used to convert 3-amino-2-butanol to 3-amino-2-butanol O-phosphate.

The skilled person will appreciate that polypeptides having aminobutanol kinase activity isolated from a variety of sources will be useful in the present invention independent of sequence homology. One example of this activity has is described herein and is identified as SEQ ID NO:124. Accordingly preferred aminobutanol kinase enzymes are those that have at least 80%-85% identity to SEQ ID NO:124, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(e) 3-amino-2-butanol phosphate to 2-butanone:

Although there are no enzymes reported to catalyze the substrate to product conversion of 3-amino-2-butanol phosphate (IV) to 2-butanone (V), the substrate is very similar to those utilized by the pyridoxal phosphate-dependent phosphoethanolamine phospho-lyase enzyme, which has been found in a small number of *Pseudomonas* and *Erwinia* species. These enzymes have activity towards phosphoethanolamine and both enantiomers of 2-phospho-1-aminopropane (Jones et al. (1973) *Biochem. J.* 134:167-182), and may also have activity towards 3-amino-2-butanol O-phosphate. Identified herein is a gene of *Erwinia carotovora* subsp. *atroseptica* (SEQ ID NO:125) that encodes a protein (SEQ ID NO:126) with homology to class III aminotransferases. Example 15 demonstrates that this enzyme is active on both aminopropanol phosphate and aminobutanol phosphate substrates. The newly identified and characterized enzyme was able to catalyze the conversion of a mixture of (R)-3-amino-(S)-2-butanol and (S)-3-amino-(R)-2-butanol O-phosphate, and a mixture of (R)-3-amino-(R)-2-butanol and (S)-3-amino-(S)-2-butanol O-phosphate to 2-butanone. The newly identified and characterized enzyme was also able to catalyze the conversion of both (R) and (S)-2-amino-1-propanol phosphate to propanone, with a preference for (S)-2-amino-1-propanol phosphate. The highest activity was observed with the proposed natural substrate DL-1-amino-2-propanol phosphate, which was converted to propionaldehyde.

The skilled person will appreciate that polypeptides having aminobutanol phosphate phospho-lyase activity isolated from a variety of sources will be useful in the present invention independent of sequence homology. One example of a suitable aminobutanol phosphate phospho-lyase enzyme is described herein as SEQ ID NO: 126. Accordingly preferred aminobutanol phosphate phospho-lyase enzymes are those that have at least 80%-85% identity to SEQ ID NO's 126, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(f) 2-butanone to 2-butanol:

The final step in all pathways to produce 2-butanol from pyruvic acid is the reduction of 2-butanone (V) to 2-butanol (VI). This substrate to product conversion is catalyzed by some members of the broad class of alcohol dehydrogenases (types utilizing either NADH or NADPH as a source of hydride, depending on the enzyme) that may be called butanol dehydrogenases. Enzymes of each type that catalyze the reduction of 2-butanone are well known, as described above in the definition for butanol dehydrogenase.

The skilled person will appreciate that polypeptides having butanol dehydrogenase activity isolated from a variety of sources will be useful in the present invention independent of sequence homology. Some example of suitable butanol dehydrogenase enzymes are available from a number of sources, for example, *Rhodococcus ruber* [GenBank Nos: CAD36475 (SEQ ID NO:14), AJ491307 (SEQ ID NO:13)]. The NADP-dependent enzymes are known as EC 1.1.1.2 and are available, for example, from *Pyrococcus furiosus* [GenBank Nos: AAC25556 (SEQ ID NO:91), AF013169 (SEQ ID NO:90)]. Additionally, a butanol dehydrogenase is available from *Escherichia coll* [GenBank Nos:NP_417484 (SEQ ID NO:75), NC_000913 (SEQ ID NO:74)] and a cyclohexanol dehydrogenase is available from *Acinetobacter* sp. [GenBank Nos: AAG1 0026 (SEQ ID NO:72), AF282240 (SEQ ID NO:71)]. Preferred butanol dehydrogenase enzymes are those that have at least 80%-85% identity to SEQ ID NO's 14, 91, 75, and 72, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

Pathway 2:

(a) pyruvate to alpha-acetolactate:

This substrate to product conversion is the same as described above for Pathway 1.

(b) alpha-acetolactate to acetoin:

This substrate to product conversion is the same as described above for Pathway 1.

(g) acetoin to phosphoacetoin:

Although enzymes that catalyze the substrate to product conversion of acetoin (II) to phosphoacetoin (VII) have not been described, the structure of the substrate acetoin is very similar to that of dihydroxyacetone, and therefore acetoin may be an acceptable substrate for dihydroxyacetone kinase (EC 2.7.1.29), an enzyme which catalyzes phosphorylation of dihydroxyacetone. Protein engineering techniques for the alteration of substrate specificity of enzymes are well known (Antikainen and Martin (2005) *Bioorg. Med. Chem.* 13:2701-2716) and may be used to generate an enzyme with the required specificity. In this conversion, the phosphate moiety may be supplied by any high energy biological phosphate donor, with the common substrates being phosphoenolpyruvate (as in the *E. coli* dihydroxyacetone kinase) and ATP (as in the *Citrobacter freundii* dihydroxyacetone kinase) (Garcia-Alles et al. (2004) *Biochemistry* 43:13037-13045).

(h) phosphoacetoin to 3-amino-2-butanol O-phosphate:

Although enzymes that catalyze the substrate to product conversion of phosphoacetoin (VII) to 3-amino-2-butanol O-phosphate (IV) have not been described, the structure of the substrate is very similar to that of dihydroxyacetone phosphate a substrate for the proposed serinol phosphate aminotransferase encoded by the 5' portion of the rtxA gene in some species of *Bradyrhizobium* (Yasuta et al., supra). Thus a serinol phosphate aminotransferase may be functional in this step.

(e) 3-amino-2-butanol O-phosphate to 2-butanone:

This substrate to product conversion is the same as described above for Pathway 1.

(f) 2-butanone to 2-butanol:

This substrate to product conversion is the same as described above for Pathway 1.

Pathway 3:

(a) pyruvate to alpha-acetolactate:

This substrate to product conversion is the same as described above for Pathway 1. (b) alpha-acetolactate to acetoin:

This substrate to product conversion is the same as described above for Pathway 1.

(i) acetoin to 2,3-butanediol:

The substrate to product conversion of acetoin (II) to 2,3-butanediol (VIII) may be catalyzed by a butanediol dehydrogenase that may either utilize NADH or NADPH as the source of reducing equivalents when carrying out reductions. Enzymes with activity towards acetoin participate in the pathway for production of 2,3-butanediol in organisms that produce that compound. The reported enzymes (e.g., BudC from *Klebsiella pneumoniae* (Ui et al. (2004) *Letters in Applied Microbiology* 39:533-537) generally utilize NADH. Either cofactor is acceptable for use in the production of 2-butanol by this pathway.

(j) 2,3-butanediol to 2-butanone:

The substrate to product conversion of 2,3-butanediol (VIII) to 2-butanone (V) may be catalyzed by diol dehydratase enzymes (EC 4.2.1.28) and glycerol dehydratase enzymes (EC 4.2.1.30). The best characterized diol dehydratase is the coenzyme B12-dependent *Klebsiella oxytoca* enzyme, but similar enzymes are found in a number of enteric bacteria. The *K. oxytoca* enzyme has been shown to accept meso-2,3-butanediol as a substrate (Bachovchin etal. (1977) *Biochemistry* 16:1082-1092), producing the desired product 2-butanone. Example 17 demonstrates that the *Klebsiella pneumoniae* glycerol dehydratase was able to convert meso-2,3-butanediol to 2-butanone. The three subunits of the *Klebsiella pneumoniae* glycerol dehydratase (alpha: SEQ ID NO:145 (coding region) and 146 (protein); beta: SEQ ID NO: 147 (coding region) and 148 (protein); and gamma: SEQ ID NO: 149 (coding region) and 150 (protein)) were expressed in conjunction with the two subunits of the *Klebsiella pneumoniae* glycerol dehydratase reactivase (large subunit, SEQ ID NO: 151 (coding region) and 152 (protein); and small subunit, SEQ ID NO: 153 (coding region) and 154 (protein)) to provide activity.

There are also reports in the literature of a B12-independent diol dehydratase from *Clostridium glycolicum* (Hartmanis et al. (1986) *Arch. Biochem. Biophys.* 245:144-152). This enzyme has activity towards 2,3-butanediol, although this activity is less than 1% of the activity towards ethanediol, but the enzyme may be engineered to improve that activity. A better-characterized B12-independent dehydratase is the glycerol dehydratase from *Clostridium butyricum* (O'Brien et al. (2004) *Biochemistry* 43:4635-4645), which has high activity towards 1,2-propanediol as well as glycerol. This enzyme uses S-adenosylmethionine as a source of adenosyl radical. There are no reports of activity towards 2,3-butanediol, but such activity, if not already present, may possibly be engineered.

(f) 2-butanone to 2-butanol:

This substrate to product conversion is the same as described above for Pathway 1.

Pathway 4:

(a) pyruvate to alpha-acetolactate:

This substrate to product conversion is the same as described above for Pathway 1.

(k) alipha-acetolactate to 2,3-dihydroxy-2-methylbutanoic acid:

The substrate to product conversion of acetolactate (I) to 2,3-dihydroxy-2-methylbutanoic acid (IX) is not known in the art. However, the product of this conversion has been reported as a component of fermentation broths (Ziadi et al. (1973) *Comptes Rendus des Seances de l'Academie des Sciences, Serie D: Sciences Naturelles* 276:965-8), but the mechanism of formation is unknown. The likely mechanism of formation is reduction of acetolactate with NADH or NADPH as the electron donor. To utilize this pathway for production of 2-butanol, an enzyme catalyzing this reaction needs to be identified or engineered. However, the precedent for enzymatic reduction of ketones to alcohols is well established.

(I) 2,3-dihydroxy-2-methylbutanoic acid to 2-hvdroxy-2-methyl-3-phosphobutanoic acid:

There are no enzymes known that catalyze the substrate to product conversion of 2,3-dihydroxy-2-methylbutanoic acid (IX) to 2-hydroxy-2-methyl-3-phosphobutanoic acid (X). However, there are a large number of kinases in Nature that possess varying specificity. It is therefore likely that an enzyme could be isolated or engineered with this activity.

(m) 2-hydroxy-2-methyl-3-phosphobutanoic acid to 2-butanone:

There are no known enzymes that catalyze the substrate to product conversion of 2-hydroxy-2-methyl-3-phosphobutanoic acid (X) to 2-butanone (V). The combination of this reaction with the previous one is very similar to the multi-step reaction catalyzed by mevalonate-5-pyrophosphate (M5PP) decarboxylase, which consists of initial phosphorylation of M5PP to 3-phosphomevalonate-5-PP, followed by decarboxylation-dependent elimination of phosphate (Alvear et al. (1982) *Biochemistry* 21:4646-4650).

(f) 2-butanone to 2-butanol:

This substrate to product conversion is the same as described above for Pathway 1.

Thus, in providing multiple recombinant pathways from pyruvate to 2-butanol, there exists a number of choices to fulfill the individual conversion steps, and the person of skill in the art will be able to utilize publicly available sequences and sequences disclosed herein to construct the relevant pathways. A listing of a representative number of genes known in the art and useful in the construction of 2-butanol biosynthetic pathways is given above in Tables 1 and 2.

Microbial Hosts for 2-Butanol and 2-Butanone Production

Microbial hosts for 2-butanol or 2-butanone production may be selected from bacteria, cyanobacteria, filamentous fungi and yeasts. The microbial host used for 2-butanol or 2-butanone production should be tolerant to the product produced, so that the yield is not limited by toxicity of the product to the host. The selection of a microbial host for 2-butanol production is described in detail below. The same criteria apply to the selection of a host for 2-butanone production.

Microbes that are metabolically active at high titer levels of 2-butanol are not well known in the art. Although butanol-tolerant mutants have been isolated from solventogenic

*Clostridia*, little information is available concerning the butanol tolerance of other potentially useful bacterial strains. Most of the studies on the comparison of alcohol tolerance in bacteria suggest that butanol is more toxic than ethanol (de Cavalho et al., *Microsc. Res. Tech.* 64:215-22 (2004) and Kabelitz et al., *FEMS Microbiol. Lett.* 220:223-227 (2003)). Tomas et al. (*J. Bacteriol.* 186:2006-2018 (2004)) report that the yield of 1-butanol during fermentation in *Clostridium acetobutylicum* may be limited by butanol toxicity. The primary effect of 1-butanol on *Clostridium acetobutylicum* is disruption of membrane functions (Hermann et al., *Appl. Environ. Microbiol.* 50:1238-1243 (1985)).

The microbial hosts selected for the production of 2-butanol should be tolerant to 2-butanol and should be able to convert carbohydrates to 2-butanol using the introduced biosynthetic pathway. The criteria for selection of suitable microbial hosts include the following: intrinsic tolerance to 2-butanol, high rate of carbohydrate utilization, availability of genetic tools for gene manipulation, and the ability to generate stable chromosomal alterations.

Suitable host strains with a tolerance for 2-butanol may be identified by screening based on the intrinsic tolerance of the strain. The intrinsic tolerance of microbes to 2-butanol may be measured by determining the concentration of 2-butanol that is responsible for 50% inhibition of the growth rate (IC50) when grown in a minimal medium. The IC50 values may be determined using methods known in the art. For example, the microbes of interest may be grown in the presence of various amounts of 2-butanol and the growth rate monitored by measuring the optical density at 600 nanometers. The doubling time may be calculated from the logarithmic part of the growth curve and used as a measure of the growth rate. The concentration of 2-butanol that produces 50% inhibition of growth may be determined from a graph of the percent inhibition of growth versus the 2-butanol concentration. Preferably, the host strain should have an IC50 for 2-butanol of greater than about 0.5%. More suitable is a host strain with an IC50 for 2-butanol that is greater than about 1.5%. Particularly suitable is a host strain with an IC50 for 2-butanol that is greater than about 2.5%.

The microbial host for 2-butanol production should also utilize glucose and/or other carbohydrates at a high rate. Most microbes are capable of utilizing carbohydrates. However, certain environmental microbes cannot efficiently use carbohydrates, and therefore would not be suitable hosts.

The ability to genetically modify the host is essential for the production of any recombinant microorganism. Modes of gene transfer technology that may be used include by electroporation, conjugation, transduction or natural transformation. A broad range of host conjugative plasmids and drug resistance markers are available. The cloning vectors used with an organism are tailored to the host organism based on the nature of antibiotic resistance markers that can function in that host.

The microbial host also may be manipulated in order to inactivate competing pathways for carbon flow by inactivating various genes. This requires the availability of either transposons or chromosomal integration vectors to direct inactivation. Additionally, production hosts that are amenable to chemical mutagenesis may undergo improvements in intrinsic 2-butanol tolerance through chemical mutagenesis and mutant screening.

Based on the criteria described above, suitable microbial hosts for the production of 2-butanol and 2-butanone include, but are not limited to, members of the genera *Clostridium, Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Brevibacterium, Pichia, Candida, Hansenula and Saccharomyces.* Preferred hosts include: *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Pediococcus pentosaceus, Pediococcus acidilactici, Bacillus subtilis* and *Saccharomyces cerevisiae.*

Construction of Production Host

Recombinant organisms containing the necessary genes that encode the enzymatic pathway for the conversion of a fermentable carbon substrate to 2-butanol or 2-butanone may be constructed using techniques well known in the art. In the present invention, genes encoding the enzymes of the 2-butanol biosynthetic Pathway 1: acetolactate synthase, acetolactate decarboxylase, acetoin aminase (or amine:pyruvate transaminase), aminobutanol kinase, aminobutanol O-phosphate lyase and butanol dehydrogenase; or 2-butanone biosynthetic Pathway 1 omitting the butanol dehydrogenase, may be isolated from various sources, as described above.

Methods of obtaining desired genes from a bacterial genome are common and well known in the art of molecular biology. For example, if the sequence of the gene is known, primers may be designed and the desired sequence amplified using standard primer-directed amplification methods such as polymerase chain reaction (U.S. Pat. No. 4,683,202) to obtain amounts of DNA suitable for cloning into expression vectors. If a gene that is heterologous to a known sequence is to be isolated, suitable genomic libraries may be created by restriction endonuclease digestion and may be screened with probes having complementary sequence to the desired gene sequence. Once the sequence is isolated, the DNA may be amplified using standard primer-directed amplification methods such as polymerase chain reaction (U.S. Pat. No. 4,683, 202) to obtain amounts of DNA suitable for cloning into expression vectors, which are then tramsformed into appropriate host cells.

In addition, given the amino acid sequence of a protein with desired enzymatic activity, the coding sequence may be ascertained by reverse translating the protein sequence. A DNA fragment containing the coding sequence may be prepared synthetically and cloned into an expression vector, then transformed into the desired host cell.

In preparing a synthetic DNA fragment containing a coding sequence, this sequence may be optimized for expression in the target host cell. Tools for codon optimization for expression in a heterologous host are readily available. Some tools for codon optimization are available based on the GC content of the host organism. The GC contents of some exemplary microbial hosts are given Table 3.

TABLE 3

GC Contents of Microbial Hosts

| Strain | % GC |
|---|---|
| *B. licheniformis* | 46 |
| *B. subtilis* | 42 |
| *C. acetobutylicum* | 37 |
| *E. coli* | 50 |
| *P. putida* | 61 |
| *A. eutrophus* | 61 |
| *Paenibacillus macerans* | 51 |
| *Rhodococcus erythropolis* | 62 |
| *Brevibacillus* | 50 |
| *Paenibacillus polymyxa* | 50 |

Once the relevant pathway genes are identified and isolated they may be transformed into suitable expression hosts by means well known in the art. Vectors useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically the vector contains a selectable marker and sequences allowing autonomous replication or chromosomal integration in the desired host. In addition, suitable vectors comprise a promoter region which harbors transcriptional initiation controls and a transcriptional termination control region, between which a coding region DNA fragment may be inserted, to provide expression of the inserted coding region. Both control regions may be derived from genes homologous to the transformed host cell, although it is to be understood that such control regions may also be derived from genes that are not native to the specific species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, promoters derived from the following genes: CYC1, HIS3, GAL1, GAL10, ADH1, PGK, PHO5, GAPDH, ADC1, TRP1, URA3, LEU2, ENO, TPI, CUP1, FBA, GPD, and GPM (useful for expression in *Saccharomyces*); AOX1 (useful for expression in *Pichia*); as well as the lac, ara, tet, trp, $IP_L$, $IP_R$, T7, tac, and trc promoters (useful for expression in *Escherichia coli, Alcaligenes*, and *Pseudomonas*); the amy, apr, and npr promoters, and various phage promoters useful for expression in *Bacillus subtilis, Bacillus licheniformis*, and *Paenibacillus macerans; nisA* (useful for expression Gram-positive bacteria, Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)).

Termination control regions may also be derived from various genes native to the preferred hosts. Optionally, a termination site may be unnecessary, however, it is most preferred if included.

Certain vectors are capable of replicating in a broad range of host bacteria and can be transferred by conjugation. The complete and annotated sequence of pRK404 and three related vectors: pRK437, pRK442, and pRK442(H), are available. These derivatives have proven to be valuable tools for genetic manipulation in Gram-negative bacteria (Scott et al., *Plasmid* 50(1):74-79 (2003)). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to effect gene replacement in a range of Gram-positive bacteria (Maguin et al., *J. Bacteriol.* 174(17):5633-5638 (1992)). Additionally, in vitro transposomes are available from commercial sources such as EPICENTRE® to create random mutations in a variety of genomes.

The expression of a 2-butanol biosynthetic pathway in various preferred microbial hosts is described in more detail below. For the expression of a 2-butanone biosynthetic pathway, the same description applies, but the final substrate to product conversion of 2-butanone to 2-butanol is omitted.

Expression of a 2-butanol or 2-butanone Biosynthetic Pathway in *E. coli*

Vectors useful for the transformation of *E. coli* are common and commercially available from the companies listed above. For example, the genes of a 2-butanol biosynthetic pathway may be isolated from various sources, as described above, cloned onto a modified pUC19 vector and transformed into *E. coli* NM522, as described in Examples 6 and 7. Alternatively, the genes encoding a 2-butanol biosynthetic pathway may be divided into multiple operons, cloned onto expression vectors, and transformed into various *E. coli* strains, as described in Examples 9, 10, and 11. The 2-butanone biosynthesis pathway may be similarly expressed, omitting the butanol dehydrogenase.

Expression of a 2-butanol or 2-butanone Biosynthetic Pathway in *Rhodococcus erythroipolis*

A series of *E. coli-Rhodococcus* shuttle vectors are available for expression in *R. erythropolis*, including, but not limited to pRhBR17 and pDA71 (Kostichka et al., *Appl. Microbiol. Biotechnol.* 62:61-68 (2003)). Additionally, a series of promoters are available for heterologous gene expression in *R. erythropolis* (see for example Nakashima et al., *Appl. Environ. Microbiol.* 70:5557-5568 (2004), and Tao et al., *Appl. Microbiol. Biotechnol.* 2005, DOI 10.1 007/s00253-005-0064). Targeted gene disruptions in chromosomal genes of *R. erythropolis* may be created using the methods described by Tao et al., supra, and Brans et al. (*Appl. Envion. Microbiol.* 66: 2029-2036 (2000)).

The heterologous genes required for the production of 2-butanol, as described above, may be cloned initially in pDA71 or pRhBR71 and transformed into *E. coli.* The vectors may then be transformed into *R. erythropolis* by electroporation, as described by Kostichka et al., supra. The recombinants may be grown in synthetic medium containing glucose and the production of 2-butanol can be followed using fermentation methods known in the art. The 2-butanone biosynthesis pathway may be similarly expressed, omitting the butanol dehydrogenase.

Expression of a 2-butanol or 2-butanone Biosynthetic Pathway in *B. Subtilis*

Methods for gene expression and creation of mutations in *B. subtilis* are also well known in the art. For example, the genes of a 2-butanol biosynthetic pathway may be isolated from various sources, as described above, cloned into a modified *E. coli-Bacillus* shuttle vector and transformed into *Bacillus subtilis* BE1010, as described in Example 8, The desired genes may be cloned into a *Bacillus* expression vector and transformed into a strain to make a production host. Alternatively, the genes may be integrated into the *Bacillus* chromosome using conditional replicons or suicide vectors that are known to one skilled in the art. For example, the Bacillus Genetic Stock Center carries numerous integration vectors. The 2-butanone biosynthesis pathway may be similarly expressed, omitting the butanol dehydrogenase.

Expression of a 2-butanol or 2-butanone Biosynthetic Pathway in *B. licheniformis*

Most of the plasmids and shuttle vectors that replicate in *B. subtilis* may be used to transform *B. licheniformis* by either protoplast transformation or electroporation. The genes required for the production of 2-butanol may be cloned in plasmids pBE20 or pBE60 derivatives (Nagarajan et al., *Gene* 114:121-126 (1992)). Methods to transform *B. licheniformis* are known in the art (for example see Fleming et al. *Appl. Environ. Microbiol.*, 61(11):3775-3780 (1995)). The plasmids constructed for expression in *B. subtilis* may be transformed into *B. licheniformis* to produce a recombinant microbial host that produces 2-butanol. The 2-butanone biosynthesis pathway may be similarly expressed, omitting the butanol dehydrogenase.

Expression of a 2-butanol or 2-butanone Biosynthetic Pathway in *Paenibacillus macerans*

Plasmids may be constructed as described above for expression in *B. subtilis* and used to transform *Paenibacillus macerans* by protoplast transformation to produce a recombinant microbial host that produces 2-butanol. The 2-butanone biosynthesis pathway may be similarly expressed, omitting the butanol dehydrogenase.

Expression of a 2-butanol or 2-butanone Biosynthetic Pathway in *Alcaligenes* (*Ralstonia*) *eutrophus*

Methods for gene expression and creation of mutations in *Alcaligenes eutrophus* are known in the art (see for example Taghavi et al., *Appl. Environ. Microbiol.,* 60(10):3585-3591 (1994)). The genes for a 2-butanol biosynthetic pathway may be cloned in any of the broad host range vectors described above, and electroporated into *Alcaligenes eutrophus* to generate recombinants that produce 2-butanol. The poly(hydroxybutyrate) pathway in *Alcaligenes* has been described in detail, a variety of genetic techniques to modify the *Alcaligenes eutrophus* genome are known, and those tools can be applied for engineering a 2-butanol biosynthetic pathway. The 2-butanone biosynthesis pathway may be similarly expressed, omitting the butanol dehydrogenase.

Expression of a 2-butanol or 2-butanone Biosynthetic Pathway in *Pseudomonas putida*

Methods for gene expression in *Pseudomonas putida* are known in the art (see for example Ben-Bassat et al., U.S. Pat. No. 6,586,229, which is incorporated herein by reference). The genes of a 2-butanol biosynthetic pathway may be inserted into pPCU18, and this ligated DNA may be electroporated into electrocompetent *Pseudomonas putida* DOT-T1 C5aAR1 cells to generate recombinants that produce 2-butanol. The 2-butanone biosynthesis pathway may be similarly expressed, omitting the butanol dehydrogenase.

Expression of a 2-butanol or 2-butanone Biosynthetic Pathway in *Lactobacillus plantarum*

The *Lactobacillus* genus belongs to the Lactobacillales family and many plasmids and vectors used in the transformation of *Bacillus subtilis* and *Streptococcus* may be used for *Lactobacillus*. Non-limiting examples of suitable vectors include pAMβ1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Several plasmids from *Lactobacillus plantarum* have also been reported (van Kranenburg et al., *Appl. Environ. Microbiol.* 71(3):1223-1230 (2005)).

The various genes for a 2-butanol biosynthetic pathway may be assembled into any suitable vector, such as those described above. The codons can be optimized for expression based on the codon index deduced from the genome sequences of *Lactobacillus plantarum* or *Lactobacillus arizonensis*. The plasmids may be introduced into the host cell using methods known in the art, such as electroporation (Cruz-Rodz et al. *Molecular Genetics and Genomics* 224: 1252-154 (1990), Bringel, et al. *Appl. Microbiol. Biotechnol.* 33: 664-670 (1990), Alegre et al., *FEMS Microbiology letters* 241:73-77 (2004)), and conjugation (Shrago et al., *Appl. Environ. Microbiol.* 52:574-576 (1986)). The 2-butanol biosynthetic pathway genes can also be integrated into the chromosome of *Lactobacillus* using integration vectors (Hols et al., *Appl. Environ. Microbiol.* 60:1401-1403 (1990), Jang et al., *Micro. Lett.* 24:191-195 (2003)). The 2-butanone biosynthesis pathway may be similarly expressed, omitting the butanol dehydrogenase.

Expression of a 2-butanol or 2-butanone Biosynthetic Pathway in *Enterococcus faecium, Enterococcus gallinarium*, and *Enterococcus faecalis*

The Enterococcus genus belongs to the Lactobacillales family and many plasmids and vectors used in the transformation of *Lactobacillus, Bacillus subtilis*, and *Streptococcus*, described above, may be used for *Enterococcus*. Expression vectors for *E. faecalis* using the nisA gene from *Lactococcus* may also be used (Eichenbaum et al., *Appl. Environ. Microbiol.* 64:2763-2769 (1998). Additionally, vectors for gene replacement in the *E. faecium* chromosome may be used (Nallaapareddy et al., *Appl. Environ. Microbiol.* 72:334-345 (2006)).

The various genes for a 2-butanol biosynthetic pathway may be assembled into any suitable vector, such as those described above. The codons can be optimized for expression based on the codon index deduced from the genome sequences of *Enterococcus faecalis* or *Enterococcus faecium.* The plasmids may be introduced into the host cell using methods known in the art, such as electroporation, as described by Cruz-Rodz et al. (*Molecular Genetics and Genomics* 224:1252-154 (1990)) or conjugation, as described by Tanimoto et al. (*J. Bacteriol.* 184:5800-5804 (2002)) and Grohamann et al. (*Microbiol. Mol. Biol. Rev.* 67:277-301 (2003)). The 2-butanone biosynthesis pathway may be similarly expressed, omitting the butanol dehydrogenase.

Expression of a 2-butanol or 2-butanone Biosynthetic Pathway in *Pediococcus pentosaceus* and *Pediococcus acidilactici*

The *Pediococcus* genus belongs to the Lactobacillales family and many plasmids and vectors used in the transformation of *Bacillus subtilis* and *Streptococcus*, described above, may be used for *Pediococcus*. A non-limiting example of a suitable vector is pHPS9 (Bukhtiyarova et al. *Appl. Environ. Microbiol.* 60:3405-3408 (1994)). Several plasmids from *Pediococcus* have also been reported (Alegre et al., *FEMS Microbiol. Lett.* 250:151-156 (2005); Shareck et al. *Crit. Rev Biotechnol.* 24:155-208 (2004)).

The genes for a 2-butanol biosynthetic pathway may be assembled into any suitable vector, such as those described above. The codons can be optimized for expression based on the codon index deduced from the genome sequence of *Pediococcus pentosaceus*. The plasmids may be introduced into the host cell using methods known in the art, such as electroporation (see for example, Osmanagaoglu et al., *J. Basic Microbiol.* 40:233-241 (2000); Alegre et al., *FEMS Microbiol. Lett.* 250:151-156 (2005)) and conjugation (Gonzalez and Kunka, *Appl. Environ. Microbiol.* 46:81-89 (1983)). The 2-butanol biosynthetic pathway genes can also be integrated into the chromosome of Pediococcus using integration vectors (Davidson et al. *Antonie van Leeuwenhoek* 70:161-183 (1996)). The 2-butanone biosynthesis pathway may be similarly expressed, omitting the butanol dehydrogenase.

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., *Microb. Growth C1 Compd.*, [Int. Symp.], 7th (1993), 415-32, Editor (s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose, as well as mixtures of any of these sugars. Sucrose may be obtained from feedstocks such as sugar cane, sugar beets, cassava, and sweet sorghum. Glucose and dextrose may be obtained through saccharification of starch based feedstocks including grains such as corn, wheat, rye, barley, and oats.

In addition, fermentable sugars may be obtained from cellulosic and lignocellulosic biomass through processes of pretreatment and saccharification, as described, for example, in co-owned and co-pending U.S. patent application US20070031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

In addition to an appropriate carbon source, fermentation media must contain suitable minerals, salts, cofactors, buffers and other components, known to those skilled in the art, suitable for the growth of the cultures and promotion of an enzymatic pathway necessary for 2-butanol or 2-butanone production.

Culture Conditions

Typically cells are grown at a temperature in the range of about 25° C. to about 40° C. in an appropriate medium. Suitable growth media in the present invention are common commercially prepared media such as Luria Bertani (LB) broth, Sabouraud Dextrose (SD) broth or Yeast Medium (YM) broth. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are between pH 5.0 to pH 9.0, where pH 6.0 to pH 8.0 is preferred as the initial condition.

Fermentations may be performed under aerobic or anaerobic conditions, where anaerobic or microaerobic conditions are preferred.

Industrial Batch and Continuous Fermentations

The present process employs a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.,* 36:227, (1992), herein incorporated by reference.

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the turbidity of the culture medium, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for 2-butanol or 2-butanone production.

Methods for 2-Butanol and 2-Butanone Isolation from the Fermentation Medium

The bioproduced 2-butanol may be isolated from the fermentation medium using methods known in the art for ABE fermentations (see for example, Durre, *Appl. Microbiol. Biotechnol.* 49:639-648 (1998), Groot et al., *Process Biochem.* 27:61-75 (1992), and references therein). For example, solids may be removed from the fermentation medium by centrifugation, filtration, decantation, or the like. Then, the 2-butanol may be isolated from the fermentation medium using methods such as distillation, azeotropic distillation, liquid-liquid extraction, adsorption, gas stripping, membrane evaporation, or pervaporation. These same methods may be adapted to isolate bioproduced 2-butanone from the fermentation medium.

EXAMPLES

The present invention is further defined in the following Examples. It should be understood that these Examples, while indicating a preferred embodiment of the invention, are given by way of illustration only. From the above discussion and these Examples, one skilled in the art can ascertain the essential characteristics of this invention, and, without departing from the spirit and scope thereof, can make various changes and modifications of the invention to adapt it to various uses and conditions.

General Methods

Standard recombinant DNA and molecular cloning techniques described in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, N.Y., (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N.

Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials described for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified. Bacterial strains are obtained from the American Type Culture Collection (ATCC, Manassas, Va.) unless otherwise noted.

Oligonucleotide primers described in the following Examples are given in Table 4. All oligonucleotide primers were synthesized by Sigma-Genosys

TABLE 4

All oligonucleotide primers were synthesized by Sigma-Geosys (Woodlands, TX).

Cloning and Screening Primers

| Gene | Primer Name | Sequence | SEQ ID NO: | Description |
|---|---|---|---|---|
| budB | B1 | CACCATGGACAAACAGTA TCCGGTACGCC | 15 | budB forward |
| budB | B2 | CGAAGGGCGATAGCTTTA CCAATCC | 16 | budB reverse |
| budA | B3 | CACCATGAATCATTCTGC TGAATGCACCTGCG | 17 | budA forward |
| budA | B4 | GATACTGTTTGTCCATGT GACC | 18 | budA reverse |
| budC | B5 | CACCATGAAAAAAGTCGC ACTTGTTACC | 19 | budC forward |
| budC | B6 | TTAGTTAAATACCAT | 20 | budC reverse |
| pddA | B7 | CACCATGAGATCGA AAAGATTTG | 21 | pddABC forward |
| pddC | B8 | CTTAGAGAAGTTAATCGT CGCC | 22 | pddABC reverse |
| sadh | B9 | CACCATGAAAGCCCTCCA GTACACC | 23 | sadh forward |

TABLE 4-continued

All oligonucleotide primers were synthesized by Sigma-Geosys (Woodlands, TX).

Cloning and Screening Primers

| Gene | Primer Name | Sequence | SEQ ID NO: | Description |
|---|---|---|---|---|
| sadh | B10 | CGTCGTGTCATGCCCGG G | 24 | sadh reverse |
| budA | B11 | GATCGAATTCGTTTAAACT TAGTTTTCTACCGCACG | 25 | budABC forward |
| budC | B12 | GATCGCATGCAAGCTTTC ATATAGTCGGAATTCC | 26 | budABC reverse |
| pddA | B13 | GATCGAATTCGTTTAAACA AAGGAGGTCTGATTCATG AGATCG | 27 | pddABC forward |
| pddC | B14 | GATCGGATTCTTAATCGT CGCC | 28 | pddABC reverse |
| sadh | B15 | GATCGGATCCAAAGGAGG TCGGGCGCATGAAAGCC C | 29 | sadh forward |
| sadh | B16 | GATCTCTAGAAAGCTTTC AGCCCGGGACGACC | 30 | sadh reverse |
| — | BenF | ACTTTCTTTCGCCTGTTTC AC | 31 | — |
| — | BenBPR | CATGAAGCTTGTTTAAACT CGGTGACCTTGAAAATAA TGAAAACTTATATTGTTTT GAAAATAATGAAAACTTAT ATTG | 32 | — |
| budAB | BABC F | GAGCTCGAATTCAAAGGA GGAAGTGTATATGAATCA TTC | 33 | budAB forward |
| budAB | BAB R | GGATCCTCTAGAATTAGT TAAATACCATCCCGCCG | 34 | budAB reverse |
| budC | BC Spe F | ACTAGTAAAGGAGGAAAG AGTATGAAGAAGGTCGCA CT | 40 | budC forward |
| budC | BC Xba R | TCTAGAAAGCAGGGGCAA GCCATGTC | 41 | budC reverse |
| pddAB C-ddrAB | DDo For | AAGCTTAAAGGAGGCTGA TTCATGAGATCGAAAAGA TT | 44 | pddABC-ddrAB forward |
| pddAB C-ddrAB | DDo Rev | TCTAGATTATTCATCCTGC TGTTCTCC | 45 | pddABC-ddrAB reverse |
| chnA | ChnA F | CATCAATTGACTACGTAG TCGTACGTGTAAGGAGGT TTGAAATGGAAAAAATTAT G | 54 | chnA forward |
| chnA | ChnA R | CATGCTAGCCCCGGGTAT CTTCTACTCATTTTTTATTT CG | 55 | chnA reverse |
| — | Top ter F1 | CTAGAAGTCAAAAGCCTC CGACCGGAGGCTTTTGA | 58 | forward |
| — | Top ter F2 | CTGCTCGAGTTGCTAGC AAGTTTAAACAAAAAAAA GCCCGCTCATTAGGCGG GCTGAGCT | 59 | forward |

TABLE 4-continued

All oligonucleotide primers were synthesized by Sigma-Geosys (Woodlands, TX).

Cloning and Screening Primers

| Gene | Primer Name | Sequence | SEQ ID NO: | Description |
|---|---|---|---|---|
| — | Bot ter R1 | CAGCCCGCCTAATGAGC GGGCTTTTTTTTGTTTAA AC | 60 | reverse |
| — | Bot ter R2 | TTGCTAGCAACTCGAGCA GTCAAAAGCCTCCGGTC GGAGGCTTTTGACTT | 61 | reverse |
| KA-AT | OT872 | CTCCGGAATTCATGTCTG ACGGACGACTCACCGCA | 127 | Aminoalcohol kinase/lyase operon forward |
| KA-AT | OT873 | TTCCAATGCATTGGCTGC AGTTATCTCTGTGCACGA GTGCCGATGA | 128 | Aminoalcohol kinase/lyase operon reverse |
| KA | OT879 | AACAGCCAAGCTTGGCT GCAGTCATCGCGCATTCT CCGGG | 129 | Aminoalcohol kinase reverse |
| AT | OT880 | TCTCCGGAATTCATGACG TCTGAAATGACAGCGACA GAAG | 130 | Aminoalcohol lyase forward |
| pBAD. HisB | OT909 | GCTAACAGGAGGAAGAA TTCATGGGGGGTTCTC | 131 | Adds EcoRI site to replace NcoI site |
| pBAD. HisB | OT910 | GAGAACCCCCCATGAATT CTTCCTCCTGTTAGC | 132 | Adds EcoRI site to replace NcoI site |
| BudAB | N84seqR3 | GGACCTGCTTCGCTTTAT CG | 159 | reverse |
| APT | APTfor | GCGCGCCCGGGAAGAAG GAGCTCTTCACCATGAAC AAACCACAGTCTTGG | 162 | APT forward |
| APT | APTrev | GCGCGCCCGGGTTCATG CCACCTCTGCG | 163 | APT reverse |

TABLE 5

Sequencing Primers

| Name | Sequence | Gene-specific | SEQ ID NO: |
|---|---|---|---|
| M13 Forward | GTAAAACGACGGCCAGT | — | 35 |
| M13 Reverse | AACAGCTATGACCATG | — | 36 |
| N83 SeqF2 | GCTGGATTACCAGCTCGACC | — | 37 |
| N83 SeqF3 | CGGACGCATTACCGGCAAAG | — | 38 |
| N84 Seq R2 | GCATCGAGATTATCGGGATG | — | 65 |
| N84 SeqR4 | CGAAGCGAGAGAAGTTATCC | — | 39 |
| Trc F | TTGACAATTAATCATCCGGC | all | 42 |
| Trc R | CTTCTCTCATCCGCCAAAAC | all | 43 |

TABLE 5-continued

Sequencing Primers

| Name | Sequence | Gene-specific | SEQ ID NO: |
|---|---|---|---|
| DDko seq F2 | GCATGGCGCGGATTTGACGAAC | pddABC-ddrAB | 46 |
| DDko seq F5 | CATTAAAGAGACCAAGTACGTG | pddABC-ddrAB | 47 |
| DDko seq F7 | ATATCCTGGTGGTGTCGTCGGC GT | pddABC-ddrAB | 48 |
| DDko seq F9 | TCTTTGTCACCAACGCCCTGCG | pddABC-ddrAB | 49 |
| DDko seq R1 | GCCCACCGCGCTCGCCGCCGCG | pddABC-ddrAB | 50 |

TABLE 5-continued

| Sequencing Primers | | | |
|---|---|---|---|
| Name | Sequence | Gene-specific | SEQ ID NO: |
| DDko seq R3 | CCCCCAGGATGGCGGCTTCGGC | pddABC-ddrAB | 51 |
| DDko seq R7 | GGGCCGACGGCGATAATCACTT | pddABC-ddrAB | 52 |
| DDko seq R10 | TTCTTCGATCCACTCCTTAACG | pddABC-ddrAB | 53 |
| chnSeq F1 | CTCAACAGGGTGTAAGTGTAGT | chnA | 56 |
| chnSeq R1 | CGTTTTGATATAGCCAGGATGT | chnA | 57 |
| pCL 1925 vec F | CGGTATCATCAACAGGCTTACC | all | 62 |
| pCL 1925 vec R1 | AGGGTTTTCCCAGTCACGACGT | all | 63 |
| pCL 1925 vec R2 | CGCAATAGTTGGCGAAGTAATC | all | 64 |
| APTseq Rev | GCTAGAGATGATAGC | APT | 160 |
| APTseq For | GGAAGAGACTATCCAGCG | APT | 161 |

Methods for Determining 2-Butanol and 2-Butanone Concentration in Culture Media

The concentration of 2-butanol and 2-butanone in the culture media can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. Under the conditions used, 2-butanone and 2-butanol had retention times of 39.5 and 44.3 min, respectively. Alternatively, gas chromatography (GC) methods are available. For example, a specific GC method utilized an HP-INNOWax column (30 m×0.53 mm id,1 μm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas.

The retention times of 2-butanone and 2-butanol were 3.61 and 5.03 min, respectively.

2-Butanone can also be detected by derivatization with 3-methyl-2-benzothiazolinone hydrazone (MBTH). An aqueous solution containing 2-butanone is mixed with an equal volume of an aqueous solution of 6 mg/mL MBTH in 375 mM glycine-HCl (pH 2.7) and incubated at 100° C. for 3 min. The resulting MBTH-derivatized samples are analyzed on a 25 cm×4.6 mm (id) Supelosil LC-18-D5 5 μm column (Supelco) using a mobile phase of 55% acetonitrile in water at a flow rate of 1 mL/min. The 2-butanone derivative appears as two peaks (cis and trans isomers) with retention times of approximately 12.3 and 13.3 min and absorbance maxima of 230 and 307 nm.

The meaning of abbreviations is as follows: "s" means second(s), "min" means minute(s), "h" means hour(s), "psi" means pounds per square inch, "nm" means nanometers, "d" means day(s), "μL" means microliter(s), "mL" means milliliter(s), "L" means liter(s), "mm" means millimeter(s), "nm" means nanometers, "mM" means millimolar, "M" means molar, "mmol" means millimole(s), "μmol" means micromole(s)", "g" means gram(s), "μg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "wt %" means percent by weight, "HPLC" means high performance liquid chromatography, and "GC" means gas chromatography. The term "molar selectivity" is the number of moles of product produced per mole of sugar substrate consumed and is reported as a percent.

Example 1

Cloning and Expression of Acetolactate Synthase

The purpose of this Example was to clone and express in *E. coli* the budB gene that encodes the enzyme acetolactate synthase. The budB gene was amplified from *Klebsiella pneumoniae* strain ATCC 25955 genomic DNA using PCR.

The budB sequence which encodes acetolactate synthase was amplified from *Klebsiella pneumoniae* (ATCC 25955) genomic DNA by PCR using the primer pair B1 (SEQ ID NO:15) and B2 (SEQ ID NO:16). Other PCR amplification reagents (e.g. Kod HiFi DNA Polymerase (Novagen Inc., Madison, Wis.; catalog no. 71805-3)) were supplied in manufacturers' kits and used according to the manufacturer's protocol. *Klebsiella pneumoniae* genomic DNA was prepared using the Gentra Puregene Puregene kit (Gentra Systems, Inc., Minneapolis, Minn.; catalog number D-5000A). Amplification was carried out in a DNA Thermocycler GeneAmp 9700 (PE Applied Biosystems, Foster city, Calif.). The nucleotide sequence of the open reading frame (ORF) and the predicted amino acid sequence of the enzyme are given as SEQ ID NO:3 and SEQ ID NO:4, respectively.

For expression studies the Gateway cloning technology (Invitrogen Corp., Carlsbad, Calif.) was used. The entry vector pENTR/SD/D-TOPO allows directional cloning and provided a Shine-Dalgarno sequence for the gene of interest. The destination vector pDEST14 used a T7 promoter for expression of the gene with no tag. The forward primer incorporated four bases (CACC) immediately adjacent to the translational start codon to allow directional cloning of the budB acetolactate synthase coding region PCR product into pENTR/SD/D-TOPO (Invitrogen), generating the plasmid pENTRSDD-TOPObudB. The PENTR construct was transformed into *E. coli* Top10 (Invitrogen) cells and plated according to the manufacturer's recommendations. Transformants were grown overnight and plasmid DNA was prepared using the QIAprep Spin Miniprep kit (Qiagen, Valencia, Calif.; catalog no. 27106) according to the manufacturer's recommendations. To create an expression clone, the budB coding region from PENTRSDD-TOPObudB was transferred to the PDEST 14 vector by in vitro recombination using the LR Clonase mix (Invitrogen, Corp., Carlsbad, Calif.). The resulting vector, pDEST14budB,was transformed into BL-21-AI cells (Invitrogen Corp.). BL-21-Al cells carry a chromosomal copy of the T7 RNA polymerase under control of the arabinose-inducible araBAD promoter.

Transformants are inoculated into LB medium supplemented with 50 μg/mL of ampicillin and grown overnight. An aliquot of the overnight culture is used to inoculate 50 mL of LB medium supplemented with 50 μg/mL of ampicillin. The culture is incubated at 37° C. with shaking until the $OD_{600}$ reaches 0.6-0.8. The culture is split into two 25-mL portions and arabinose is added to one of the flasks to a final concentration of 0.2% w/v. The negative control flask is not induced with arabinose. The flasks are incubated for 4 h at 37° C. with shaking. Cells are harvested by centrifugation and the cell pellets are resuspended in 50 mM MOPS, pH 7.0 buffer. The cells are disrupted either by sonication or by passage through a French Pressure Cell. Each cell lysate is centrifuged yielding the supernatant and the pellet or the insoluble fraction. An aliquot of each fraction (whole cell lysate, from induced and control cells, is resuspended in SDS (MES) loading buffer (Invitrogen), heated to 85° C. for 10 min and subjected to SDS-PAGE analysis (NuPAGE 4-12% Bis-Tris Gel, catalog no. NP0322Box, Invitrogen). A protein of the expected molecular weight, as deduced from the nucleic acid sequence, is present in the induced culture but not in the uninduced control.

Acetolactate synthase activity in the cell free extracts is measured using the method described by Bauerle et al. (Bauerle et al. (1964) *Biochim. Biophys.* Acta 92:142-149). Protein concentration is measured by either the Bradford method or by the Bicinchoninic Kit (Sigma, catalog no. BCA-1; St. Louis, Mo.) using Bovine serum albumin (BSA) (Bio-Rad, Hercules, Calif.) as the standard.

Example 2

Cloning and Expression of Acetolactate Decarboxylase

The purpose of this Example was to clone and express in *E. coli* the budA gene that encodes the enzyme acetolactate decarboxylase. The budA gene was amplified from *Klebsiella pneumoniae* strain ATCC 25955 genomic DNA using PCR.

The budA sequence which encodes acetolactate decarboxylase, was cloned in the same manner as described for budB in Example 1, except that the primers used for PCR amplification were B3 (SEQ ID NO:17) and B4 (SEQ ID NO:18). The nucleotide sequence of the open reading frame (ORF) and the predicted amino acid sequence of the enzyme are given as SEQ ID NO:1 and SEQ ID NO:2, respectively. The resulting plasmid was named pENTRSDD-TOPObudA.

Acetolactate decarboxylase activity in the cell free extracts is measured using the method described by Bauerle et al., supra.

Example 3

Prophetic

Cloning and Expression of Butanediol Dehydrogenase

The purpose of this prophetic Example is to describe how to clone and express in *E. coli* the budC gene that encodes the enzyme butanediol dehydrogenase. The budC gene is amplified from *Klebsiella pneumoniae* strain IAM1063 genomic DNA using PCR.

The budC sequence encoding butanediol dehydrogenase is cloned and expressed in the same manner as described for budA in Example 1, except that the primers used for PCR amplification are B5 (SEQ ID NO:19) and B6 (SEQ ID NO:20) and the genomic template DNA is from *Klebsiella. pneumoniae* IAM1063 (which is obtained from the Institute of Applied Microbiology Culture Collection, Tokyo, Japan).

*Klebsiella pneumoniae* IAM1063 genomic DNA is prepared using the Gentra Puregene Puregene kit (Gentra Systems, Inc., Minneapolis, Minn.; catalog number D-5000A). The nucleotide sequence of the open reading frame (ORF) and the predicted amino acid sequence of the enzyme are given as SEQ ID NO:5 and SEQ ID NO:6, respectively.

Butanediol dehydrogenase activity in the cell free extracts is measured spectrophotometrically by following NADH consumption at an absorbance of 340 nm.

Example 4

Prophetic

Cloning and Expression of Butanediol Dehydratase

The purpose of this prophetic Example is to describe how to clone and express in *E. coli* the pddA, pddB and pddC genes that encode butanediol dehydratase. The pddA, pddB and pddC genes are amplified from *Klebsiella oxytoca* ATCC 8724 genomic DNA using PCR.

The pddA, pddB and pddC sequences which encode butanediol dehydratase are cloned and expressed in the same manner as described for budA in Example 1, except that the genomic template DNA is from *Klebsiella oxytoca* ATCC 8724, and the primers are B7 (SEQ ID NO:21) and B8 (SEQ ID NO:22). *Klebsiella oxytoca* genomic DNA is prepared using the Gentra Puregene Puregene kit (Gentra Systems, Inc., Minneapolis, Minn.; catalog number D-5000A). A single PCR product including all three open reading frames (ORFs) is cloned, so that all three coding regions are expressed as an operon from a single promoter on the expression plasmid. The nucleotide sequences of the open reading frames for the three subunits are given as SEQ ID NOs:7, 9, and 11, respectively, and the predicted amino acid sequences of the three enzyme subunits are given as SEQ ID NOs:8, 10, and 12, respectively.

Butanediol dehydratase activity in the cell free extracts is measured by derivatizing the ketone product with 2,4-dinitrophenylhydrazine (DNPH). Briefly, 100 μL of reaction mixture, cell extract containing approximately 0.0005 units of enzyme, 40 mM potassium phosphate buffer (pH 8.0), 2 μg of adenosylcobalamin, 5 μg of 2,3,-butanediol, and 1 μg of bovine serum albumin, is quenched by addition of an equal volume of 0.05 wt % DNPH in 1.0 N HCl. After 15 min at room temperature, the color is developed by addition of 100 μL of 4 N NaOH. The amount of product is determined from the absorbance of the final solution at 550 nm compared to a standard curve prepared with 2-butanone. All reactions are carried out at 37° C. under dim red light.

Example 5

Prophetic

Cloning and Expression of Butanol Dehydrogenase

The purpose of this prophetic Example is to describe how to clone and express in *E. coli* the sadh gene that encodes butanol dehydrogenase. The sadh gene is amplified from *Rhodococcus ruber* strain 219 genomic DNA using PCR.

The sadh sequence encoding butanol dehydrogenase is cloned and expressed in the same manner as described for budA in Example 1, except that the genomic template DNA is from *Rhodococcus ruber* strain 219 (Meens, Institut fuer Mikrobiologie, Universitaet Hannover, Hannover, Germany) and the primers are B9 (SEQ ID NO:23) and B10 (SEQ ID NO:24). *Rhodococcus ruber* genomic DNA is prepared using the Ultra Clean™ Microbial DNA Isolation Kit (MO BIO Laboratories Inc., Carlsbad, Calif.), according to the manufacturer's protocol. The nucleotide sequence of the open reading frame (ORF) and the predicted amino acid sequence of the enzyme are given as SEQ ID NO:13 and SEQ ID NO:14, respectively.

Butanol dehydrogenase activity in cell free extracts is measured by following the increase in absorbance at 340 nm resulting from the conversion of NAD to NADH when the enzyme is incubated with NAD and 2-butanol.

Example 6

Prophetic

Construction of a Transformation Vector for the Genes in a 2-Butanol Biosynthetic Pathway The purpose of this prophetic Example is to describe the preparation of a transformation vector for the genes in a 2-butanol biosynthetic pathway (i.e., Pathway 3 as described above). Like most organisms, *E. coli* converts glucose initially to pyruvic acid. The enzymes required to convert pyruvic acid to 2-butanol following Pathway 3, i.e., acetolactate synthase, acetolactate decarboxylase, butanediol dehydrogenase, butanediol dehydratase, and butanol dehydrogenase, are encoded by the budA, budB, budC, pddA, pddB, pddC and sadh genes. To simplify building the 2-butanol biosynthetic pathway in a recombinant organism, the genes encoding the 5 steps in the pathway are divided into two operons. The upper pathway comprises the first three steps catalyzed by acetolactate synthase, acetolactate decarboxylase, and butanediol dehydrogenase. The lower pathway comprises the last two steps catalyzed by butanediol dehydratase and butanol dehydrogenase.

The coding sequences are amplified by PCR with primers that incorporate restriction sites for later cloning, and the forward primers contain an optimized *E. coli* ribosome binding site (AAAGGAGG). PCR products are TOPO cloned into the pCR4Blunt-TOPO vector and transformed into Top10 cells (Invitrogen). Plasmid DNA is prepared from the TOPO clones, and the sequence of the cloned PCR fragment is verified. Restriction enzymes and T4 DNA ligase (New England Biolabs, Beverly, Mass.) are used according to manufacturer's recommendations. For cloning experiments, restriction fragments are gel-purified using QIAquick Gel Extraction kit (Qiagen).

After confirmation of the sequence, the coding regions are subcloned into a modified pUC19 vector as a cloning platform. The pUC19 vector is modified by a HindIII/SapI digest, followed by treatment with Klenow DNA polymerase to fill in the ends. The 2.4 kB vector fragment is gel-puriifed and religated creating pUC19dHS. Alternatively the pUC19 vector is modified by a SphI/SapI digest, followed by treatment with Klenow DNA polymerase to blunt the ends. The 2.4 kB vector fragment is gel-purified and religated creating pUC19dSS. The digests remove the lac promoter adjacent to the MCS (multiple cloning sites), preventing transcription of the operons from the vector.

Upper Pathway:

The budABC coding regions are amplified from *Klebsiella pneumoniae* genomic DNA by PCR using primer pair B11 and B12 (Table 4), given as SEQ ID NOs:25 and 26, respectively. The forward primer incorporates an EcoRI restriction site and a ribosome binding site (RBS). The reverse primer incorporates an SphI restriction site. The PCR product is cloned into pCR4 Blunt-TOPO creating pCR4 Blunt-TOPO-budABC.

To construct the upper pathway operon pCR4 Blunt-TOPO-budABC is digested with EcoRI and SphI releasing a 3.2 kbp budABC fragment. The pUC19dSS vector is also digested with EcoRI and SphI, releasing a 2.0 kbp vector fragment. The budABC fragment and the vector fragment are ligated together using T4 DNA ligase (New England Biolabs) to form pUC1 9dSS-budABC.

Lower Pathway:

The pddABC coding regions are amplified from *Klebsiella oxytoca* ATCC 8724 genomic DNA by PCR using primers B13 and B14 (Table 4), given as SEQ ID NOs:27 and 28, respectively, creating a 2.9 kbp product. The forward primer incorporates EcoRI and PmeI restriction sites and a RBS. The reverse primer incorporates the BamHI restriction site. The PCR product is cloned into pCRBlunt II-TOPO creating pCRBIuntII-pdd.

The sadh gene is amplified from *Rhodococcus ruber* strain 219 genomic DNA by PCR using primers B15 and B16 (Table 4), given as SEQ ID NOs:29 and 30, respectively, creating a 1.0 kbp product. The forward primer incorporates a BamHI restriction site and a RBS. The reverse primer incorporates an XbaI restriction site. The PCR product is cloned into pCR-Blunt II-TOPO creating pCRBIuntII-sadh.

To construct the lower pathway operon, a 2.9 kbp EcoRI and BamHI fragment from pCRBIuntII-pdd, a 1.0 kbp BamHI and XbaI fragment from pCRBIuntII-sadh, and the large fragment from an EcoRI and XbaI digest of pUC19dHS are ligated together. The three-way ligation creates pUC19dHS-pdd-sadh.

The pUC19dSS-budABC vector is digested with PmeI and HindIII, releasing a 3.2 kbp fragment that is cloned into pBenBP, an *E. coli*-*B. subtilis* shuttle vector. Plasmid pBenBP is created by modification of the pBE93 vector, which is described by Nagarajan (WO 93/2463, Example 4). To generate pBenBP, the *Bacillus amyloliquefaciens* neutral protease promoter (NPR) signal sequence and the phoA gene are removed from pBE93 with an NcoI/HindIII digest. The NPR promoter is PCR amplified from pBE93 by primers BenF and BenBPR, given by SEQ ID NOs:31 and 32, respectively. Primer BenBPR incorporates BstEII, PmeI and HindIII sites downstream of the promoter. The PCR product is digested with NcoI and HindIII, and the fragment is cloned into the corresponding sites in the vector pBE93 to create pBenBP. The upper operon fragment is subcloned into the PmeI and HindIII sites in pBenBP creating pBen-budABC.

The pUC19dHS-pdd-sadh vector is digested with PmeI and HindIII releasing a 3.9 kbp fragment that is cloned into the PmeI and HindIII sites of pBenBP, creating pBen-pdd-sadh.

Example 7

Prophetic

Expression of a 2-Butanol Biosynthetic Pathway in *E. coli*

The purpose of this prophetic Example is to describe how to express a 2-butanol biosynthetic pathway in *E. coli.*

The plasmids pBen-budABC and pBen-pdd-sadh, prepared as described in Example 6, are separately transformed into *E. coli* NM522 (ATCC No. 47000), and expression of the genes in each operon is monitored by SDS-PAGE analysis and enzyme assay. After confirmation of expression of all genes, pBen-budABC is digested with EcoRI and HindIII to release the NPR promoter-budABC fragment. The fragment is blunt ended using the Klenow fragment of DNA polymerase (New England Biolabs, catalog no. M0210S). The plasmid pBen-pdd-sadh is digested with EcoRI and similarly blunted to create a linearized, blunt-ended vector fragment. The vector and NPR-budABC fragments are ligated, creating p2BOH. This plasmid is transformed into *E. coli* NM522 to give *E. coli* NM522/p2BOH, and expression of the genes is monitored as previously described.

*E. coli* NM522/p2BOH is inoculated into a 250 mL shake flask containing 50 mL of medium and shaken at 250 rpm and 35° C. The medium is composed of: dextrose, 5 g/L; MOPS, 0.05 M; ammonium sulfate, 0.01 M; potassium phosphate, monobasic, 0.005 M; S10 metal mix, 1% (v/v); yeast extract, 0.1% (w/v); casamino acids, 0.1% (w/v); thiamine, 0.1 mg/L; proline, 0.05 mg/L; and biotin 0.002 mg/L, and is titrated to pH 7.0 with KOH. S10 metal mix contains: $MgCl_2$, 200 mM; $CaCl_2$, 70 mM; $MnCl_2$, 5 mM; $FeCl_3$, 0.1 mM; $ZnCl_2$, 0.1 mM; thiamine hydrochloride, 0.2 mM; $CuSO_4$, 172 μM; $COCl_2$, 253 μM; and $Na_2MoO_4$, 242 μM. After 18 h, 2-butanol is detected by HPLC or GC analysis using methods that are well known in the art, for example, as described in the General Methods section above.

Example 8

Prophetic

Expression of a 2-Butanol Biosynthetic Pathway in *Bacillus subtilis*

The purpose of this prophetic Example is to describe how to express a 2-butanol biosynthetic pathway in *Bacillus subtilis.*

The plasmids pBen-budABC and pBen-pdd-sadh, prepared as described in Example 6, are separately transformed into *Bacillus subtilis* BE1010 (*J. Bacteriol.* 173:2278-2282 (1991)) and expression of the genes in each operon is monitored as described in Example 7. The plasmid pBen-budABC is digested with EcoRI and HindIII to release the NPR promoter-budABC fragment. The fragment is blunt ended using the Klenow fragment of DNA polymerase (New England Biolabs, catalog no. M0210S). The plasmid pBen-pdd-sadh is digested with EcoRI and similarly blunted to create a linearized, blunt-ended vector fragment. The vector and NPR-budABC fragments are ligated, creating p2BOH. This plasmid is transformed into *Bacillus subtilis* BE1010 to give *Bacillus subtilis* BE1010/p2BOH, and expression of the genes is monitored as previously described.

*Bacillus subtilis* BE1010/p2BOH is inoculated into a 250 mL shake flask containing 50 mL of medium and shaken at 250 rpm and 35° C. for 18 h. The medium is composed of: dextrose, 5 g/L; MOPS, 0.05 M; glutamic acid, 0.02 M; ammonium sulfate, 0.01 M; potassium phosphate, monobasic buffer, 0.005 M; S10 metal mix (as described in Example 7), 1% (v/v); yeast extract, 0.1% (w/v); casamino acids, 0.1% (w/v); tryptophan, 50 mg/L; methionine, 50 mg/L; and lysine, 50 mg/L, and is titrated to pH 7.0 with KOH. After 18 h, 2-butanol is detected by HPLC or GC analysis using methods that are well known in the art, for example, as described in the General Methods section above.

Example 9

Construction of a Transformation Vector for the Genes in a 2-Butanol Biosynthetic Pathway The purpose of this Example was to prepare a recombinant *E. coli* host carrying the genes in a 2-butanol biosynthetic pathway (i.e., Pathway 3 as described above). Like most organisms, *E. coli* converts glucose initially to pyruvic acid. The enzymes required to convert pyruvic acid to 2-butanone in Pathway 3, i.e., acetolactate synthase, acetolactate decarboxylase, butanediol dehydrogenase, and butanediol dehydratase are encoded by the budA, budB, budC, pddA, pddB, and pddC genes. In the last step of the pathway, a butanol dehydrogenase converts 2-butanone to 2-butanol. Dehydrogenases that carry out this last step are promiscuous and may be found in many organisms. To simplify building the 2-butanol biosynthetic pathway in a recombinant organism, the genes encoding the 5 steps in the pathway were divided into multiple operons. The upper pathway operon comprised the first three steps catalyzed by acetolactate synthase, acetolactate decarboxylase, and butanediol dehydrogenase and were cloned onto an expression vector. The lower pathway comprised the last two steps catalyzed by butanediol dehydratase including the reactivating factor (Mori et al., *J. Biol. Chem.* 272:32034 (1997)) and a butanol dehydrogenase. The diol dehydratase can undergo suicide inactivation during catalysis. The reactivating factor protein encoded by ddrA and ddrB (GenBank AF01 7781, SEQ ID NO:70) reactivates the inactive enzyme. The ddrA and ddrB genes flank the diol dehydratase operon. The operons for the dehydratase/reactivating factor and the butanol dehydrogenase were either cloned onto another expression vector or the dehydratase/reactivating factor operon was cloned singly onto another expression vector and the last step was provided by an endogenous activity in the demonstration host.

Construction of Vector pTrc99a-budABC:

The budAB coding regions were amplified from *K. pneumoniae* ATCC 25955 genomic DNA by PCR using primer pair BABC F and BAB R, given as SEQ ID NOs:33 and 34, respectively (see Table 4), creating a 2.5 kbp product. The forward primer incorporated SacI and EcoRI restriction sites and a ribosome binding site (RBS). The reverse primer incorporated a SpeI restriction site. The PCR product was cloned into pCR4 Blunt-TOPO creating pCR4 Blunt-TOPO-budAB. Plasmid DNA was prepared from the TOPO clones and the sequence of the genes was verified with primers M13 Forward (SEQ ID NO:35), M13 Reverse (SEQ ID NO:36), N83 SeqF2 (SEQ ID NO:37), N83 SeqF3 (SEQ ID NO:38) and N84 SeqR4 (SEQ ID NO:39) (see Table 5).

The budC coding region was amplified from *K. pneumoniae* ATCC 25955 genomic DNA by PCR using primer pair BC Spe F and BC Xba R given as SEQ ID NOs:40 and 41, respectively, creating a 0.8 kbp product. The forward primer incorporated a SpeI restriction site, a RBS and modified the CDS by changing the second and third codons from AAA to AAG. The reverse primer incorporated an XbaI restriction site. The PCR product was cloned into pCR4 Blunt-TOPO creating pCR4 Blunt-TOPO-budC. Plasmid DNA was prepared from the TOPO clones and the sequence of the genes was verified with primers M13 Forward (SEQ ID NO:35) and M13 Reverse (SEQ ID NO:36).

To construct the budABC operon, pCR4 Blunt-TOPO-budC was digested with SnaBI and XbaI releasing a 1.0 kbp budC fragment. The vector pTrc99a (Amann et al., *Gene* 69(2):301-315 (1988)) was digested with SmaI and XbaI creating a 4.2 kbp linearized vector fragment. The vector and the budC fragment were ligated to create pTrc99a-budC and transformed into *E. coli* Top 10 cells (Invitrogen). Transformants were analyzed by PCR amplification with primers Trc F (SEQ ID NO:42) and Trc R (SEQ ID NO:43) for a 1.2 kbp product to confirm the presence of the budC insert. The budAB genes were subcloned from pCR4 Blunt-TOPO-budAB as a 2.5 kbp EcoRI/SpeI fragment. Vector pTrc99a- budC was digested with EcoRI and SpeI and the resulting 5.0 kbp vector fragment was gel-purified. The purified vector and budAB insert were ligated and transformed into *E. coli* Top 10 cells. Transformants were screened by PCR amplification with primers Trc F (SEQ ID NO:42) and N84 Seq R2 (SEQ ID NO:65) to confirm creation of pTrc99a-budABC. In this plasmid, the bud A, B, and C coding regions are adjacent to each other, in this order, and between the Trc promoter and the rrnB termination sequence.

Results:

Three independent isolates of *E. coli* Top 10/pTrc99a-budABC were examined for the production of butanediol, using *E. coli* Top 10/pCL1925-Kodd-ddr (described below) as a negative control. The strains were grown in LB medium containing 100 μg/mL carbenicillin. The resulting cells were used to inoculate shake flasks (approximately 175 mL total volume) containing 125 mL of TM3a/glucose medium with 100 μg/mL carbenicillin. In addition, the flasks inoculated with strains carrying pTrc99a-budABC contained 0.4 mM isopropyl β-D-1-thiogalactopyranoside (IPTG). TM3a/glucose medium contains (per liter): 10 g glucose, 13.6 g $KH_2PO_4$, 2.0 g citric acid monohydrate, 3.0 g $(NH_4)_2SO_4$, 2.0 g $MgSO_4.7H_2O$, 0.2 g $CaCl_2.2H_2O$, 0.33 g ferric ammonium citrate, 1.0 mg thiamine HCl, 0.50 g yeast extract, and 10 mL trace elements solution, adjusted to pH 6.8 with $NH_4OH$. The solution of trace elements contained: citric acid $.H_2O$ (4.0 g/L), $MnSO_4.H_2O$ (3.0 g/L), NaCl (1.0 g/L), $FeSO_4.7H_2O$ (0.10 g/L), $CoCl_2.6H_2O$ (0.10 g/L), $ZnSO_4.7H_2O$ (0.10 g/L), $CuSO_4.5H_2O$ (0.010 g/L), $H_3BO_3$ (0.010 g/L), and $Na_2MoO_4.2H_2O$ (0.010 g/L). The flasks, capped with vented caps, were inoculated at a starting $OD_{600}$ of approximately 0.03 units and incubated at 34° C. with shaking at 300 rpm.

Approximately 23 h after induction, an aliquot of the broth was analyzed by HPLC (Shodex Sugar SH1011 column) and GC (HP-INNOWax), using the same methods described in the General Methods section for 2-butanol and 2-butanone. The results of the analysis are given in Table 6. The three *E. coli* clones converted glucose to acetoin and meso-2,3-butanediol, the desired intermediates of the pathway, with a molar selectivity of 14%. This selectivity was approximately 35-fold higher than that observed with the *E. coli* control strain lacking budABC.

TABLE 6

Production of Acetoin and meso-2,3-butanediol by *E. coli* Top 10/pTrc99a-budABC

| Strain | $OD_{600}$ | Acetoin, mM | Meso-2,3-Butanediol, mM | Molar Selectivity[a], % |
|---|---|---|---|---|
| Negative control | 1.4 | 0.07 | 0.03 | 0.4 |
| Isolate #1 | 1.5 | 0.64 | 1.3 | 14 |
| Isolate #2 | 1.4 | 0.70 | 1.2 | 14 |
| Isolate #3 | 1.4 | 0.74 | 1.3 | 15 |

[a]Molar selectivity is (acetoin + meso-2,3-butanendiol)/(glucose consumed).

Construction of Vector pCL1925-KoDD-ddr:

The diol dehydratase (GenBank D45071, SEQ ID NO:69) and reactivating factor (GenBank AF01 7781, SEQ ID NO:70) operons were PCR amplified from *Klebsiella oxytoca* ATCC 8724 as a single unit with primers DDo For (SEQ ID NO: 44) and DDo Rev (SEQ ID NO:45). The forward primer incorporated an optimized *E. coli* RBS and a HindIII restriction site. The reverse primer included an XbaI restriction site. The 5318 bp PCR product was cloned into pCR4Blunt-TOPO and clones of the resulting pCR4Blunt-TOPO-Kodd-ddr were sequenced with primers M13 Forward (SEQ ID NO:35), M13 Reverse (SEQ ID NO:36), DDko seq F2 (SEQ ID NO:46), DDko seq F5 (SEQ ID NO:47), DDko seq F7 (SEQ ID NO:48), DDko seq F9 (SEQ ID NO:49), DDko seq R1 (SEQ ID NO:50), DDko seq R3 (SEQ ID NO:51), DDko seq R7 (SEQ ID NO:52), and DDko seq R10 (SEQ ID NO:53). A clone having the insert with the expected sequence was identified.

For expression, the diol dehydratase/reactivating factor genes were subcloned into pCL1925 (U.S. Pat. No. 7,074,608), a low copy plasmid carrying the glucose isomerase promoter from Streptomcyes. pCR4Blunt-TOPO-Kodd-ddr was digested with HindIII and XbaI and the resulting 5.3 kbp Kodd-ddr fragment was gel-purified. Vector pCL1925 was digested with HindIII and XbaI and the resulting 4539 bp vector fragment was gel purified. The vector and Kodd-ddr fragment were ligated and transformed into *E. coli* Top10. Transformants were screened by PCR with primers DDko Seq F7 (SEQ ID NO:48) and DDko Seq R7 (SEQ ID NO: 52). Amplification of the plasmid (pCL1925-Kodd-ddr) carrying the insert resulted in a product of approximately 797 bp.

Activity of diol dehydratase towards meso-2,3-butanediol was measured by incubating cell extract (total protein~0.8 mg/mL) with 10 mM butanediol and 12 mM coenzyme $B_{12}$ in 80 mM HEPES (pH 8.2) for 17 h at room temperature. Formation of the expected product, 2-butanone, was determined by HPLC as described in the General Methods.

Construction of Vector pCL1925-KoDD-ddr::T5 chnA ter:

To provide a heterologous alcohol dehydrogenase activity, the chnA gene encoding cyclohexanol dehydrogenase from *Acinetobacter sp.* (Cheng et al., *J. Bacteriol.* 182:4744-4751 (2000)) was cloned into the pCL1925 vector with the diol dehydratase operon, pCL1925-Kodd-ddr. The chnA gene, given as SEQ ID NO:71 (Genbank No: AF282240, SEQ ID NO:73) was amplified from pDCQ2, a cosmid carrying the cyclohexanol gene cluster from Acinetobacter, with primers ChnA F (SEQ ID NO:54) and ChnA R (SEQ ID NO:55). The resulting 828 bp PCR product was cloned into pCR4Blunt-TOPO to create pCR4Blunt-TOPO-chnA and transformants were screened by colony PCR with primers M13 Forward (SEQ ID NO:35) and M13 Reverse (SEQ ID NO:36). Correct clones produced a PCR product of about 1 kbp and were sequenced with primers M13 Forward (SEQ ID NO:35) and M13 Reverse (SEQ ID NO:36).

After sequencing pCR4Blunt-TOPO-chnA to confirm the correct sequence, the chnA gene was subcloned from the plasmid as an 813 bp MfeI/SmaI fragment. The expression vector pQE30 (Qiagen) was digested with MfeI and SmaI and the resulting 3350 bp vector fragment was gel-purified. The chnA fragment and the purified vector were ligated and transformed into *E. coli* Top10 cells. Transformants were colony PCR screened with primers chnSeq F1 (SEQ ID NO:56) and chnseq R1 (SEQ ID NO:57) for a 494 bp PCR product. This cloning placed the chnA gene under the control of the T5 promoter in the plasmid, pQE30-chnA.

To prepare the pCL1925 vector to carry two operons, terminators were added to the vector. A tonB terminator-mcs-trpA terminator fragment was prepared by oligonucleotide annealing with primers Top ter F1 (SEQ ID NO:58), Top ter F2 (SEQ ID NO:59), Bot ter R1 (SEQ ID NO:60) and Bot ter R2 (SEQ ID NO:61). The annealed DNA was gel-purified on a 6% PAGE gel (Embi-tec, San Diego, Calif.). Vector pCL1925 was digested with SacI and XbaI and gel-purified. The annealed DNA and vector fragment were ligated to create pCL1925-ter. Transformants were screened by colony PCR amplification with primers pCL1925 vec F (SEQ ID NO:62) and pCL1925 vec R1 (SEQ ID NO:63) for the presence of a PCR product of approximately 400 bp. Positive clones from the PCR screen were sequenced with the same primers.

Vector pCL1925-ter was digested with XhoI and PmeI and the resulting 4622 bp fragment was gel-purified. pQE30-chnA was digested with NcoI and the DNA was treated with Klenow DNA polymerase to blunt the ends. pQE30-chnA was then digested with XhoI and the resulting 1.2 kbp T5 promoter-chnA fragment was gel-purified. The pCL1 925-ter vector and the chnA operon fragment were ligated together to give pCL1 925-ter-T5chnA and transformed into *E. coli* Top10. Transformants were screened by colony PCR amplification with primers pCL1925 vec F (SEQ ID NO:64) and chnseq R1 (SEQ ID NO:59) for a product of approximately 1 kbp.

To finish building the pathway vector, the pCL1925-KoDD-ddr plasmid was digested with XbaI and SacI and the resulting 9504 bp vector fragment was gel-purified. The chnA operon flanked by terminators, with the trpA terminator (Koichi et al. (1997) Volume 272, Number 51, pp. 32034-32041) 3' to the chnA coding sequence, from pCL1925-ter-T5chnA was gel-purified as a 1271 bp XbaI/SacI fragment. After ligation of the fragments and transformation into *E. coli* Top10, transformants were screened by colony PCR. Primers chnSeq F1 (SEQ ID NO:58) and pCL1925 vec R2 (SEQ ID NO:64) amplified the expected 1107 bp PCR product in the resulting plasmid, pCL1925-KoDD-ddr::ter-T5chnA .

Example 10

Expression of a 2-Butanol Biosynthetic Pathway in *E. coli* with Overexpressed Endogenous Alcohol Dehydrogenase The purpose of this Example was to express a 2-butanol biosynthetic pathway in several *E. coli* strains.

Construction of *E. coli* Strains Constitutively Expressing yqhD:

*E. coli* contains a native gene (yqhD) that was identified as a 1,3-propanediol dehydrogenase (U.S. Pat. No. 6,514,733). The yqhD gene, given as SEQ ID NO:74, has 40% identity to the gene adhB in Clostridium, a probable NADH-dependent butanol dehydrogenase. The yqhD gene was placed under the constitutive expression of a variant of the glucose isomerase promoter 1.6GI (SEQ ID NO:67) in *E. coli* strain MG1655 1.6yqhD::Cm (WO 2004/033646) using λ Red technology (Datsenko and Wanner, *Proc. Natl. Acad. Sci. U.S.A.* 97:6640 (2000)). Similarly, the native promoter was replaced by the 1.5GI promoter (WO 2003/089621) (SEQ ID NO:68), creating strain MG1655 1.5yqhD::Cm, thus, replacing the 1.6GI promoter of MG1655 1.6yqhD::Cm with the 1.5GI promoter. The 1.5GI and 1.6GI promoters differ by 1 bp in the −35 region, thereby altering the strength of the promoters (WO 2004/033646). While replacing the native yqhD promoter with either the 1.5GI or 1.6GI promoter, the yqhc gene encoding the putative transcriptional regulator for the yqh operon was deleted. Butanol dehydrogenase activity was confirmed by enzyme assay using methods that are well known in the art.

Transformation of *E. coli* Strains:

Pathway plasmids pCL1925-Kodd-ddr and pTrc99a-budABC, described in Example 9, were co-transformed into *E. coli* strains MG1655, MG1655 1.6yqhD, and MG1655 1.5yqhD. The two latter strains overexpress the 1,3-propanediol dehydrogenase, YqhD, which also has butanol dehydrogenase activity. Strains were examined for the production of 2-butanone and 2-butanol essentially as described above. Cells were inoculated into shake flasks (approximately 175 mL total volume) containing either 50 or 150 mL of TM3a/glucose medium (with 0.1 mg/L vitamin $B_{12}$, appropriate antibiotics and IPTG) to represent medium and low oxygen conditions, respectively. Spectinomycin (50 μg/mL) and carbenicillin (100 μg/mL) were used for plasmids pCL1925-Kodd-ddr and pTrc99a-budABC, respectively. The flasks were inoculated at a starting $OD_{600}$ of <0.04 units and incubated at 34° C. with shaking at 300 rpm. The flasks containing 50 mL of medium were capped with vented caps; the flasks containing 150 mL, were capped with non-vented caps to minimize air exchange. IPTG was present at time zero at a concentration of zero or 0.04 mM. Analytical results for 2-butanone and 2-butanol production are presented in Table 7. All the *E. coli* strains comprising a 2-butanol biosynthetic pathway produced 2-butanone under low and medium oxygen conditions and produced 2-butanol under low oxygen conditions.

TABLE 7

Production of 2-Butanone and 2-Butanol by *E. coli* MG1655 strains harboring pathway plasmids pCL1925-Kodd-ddr and pTrc99a-budABC

| Strain[a,b] | IPTG, mM | Volume of Medium, mL | 2-Butanone, mM | 2-Butanol, mM |
|---|---|---|---|---|
| MG1655 #1 | 0 | 50 | 0.08 | Not detected |
| MG1655 #2 | 0 | 50 | 0.11 | Not detected |
| MG1655 #1 | 0.04 | 50 | 0.12 | Not detected |
| MG1655 #2 | 0.04 | 50 | 0.11 | Not detected |
| MG1655 #1 | 0 | 150 | 0.15 | 0.047 |
| MG1655 #2 | 0 | 150 | 0.19 | 0.041 |
| MG1655 #1 | 0.04 | 150 | 0.10 | 0.015 |
| MG1655 #2 | 0.04 | 150 | 0.11 | 0.015 |
| MG1655 1.5yqhD #1 | 0 | 50 | 0.10 | Not detected |
| MG1655 1.5yqhD #2 | 0 | 50 | 0.07 | Not detected |
| MG1655 1.5yqhD #1 | 0.04 | 50 | 0.12 | Not detected |
| MG1655 1.5yqhD #2 | 0.04 | 50 | 0.18 | Not detected |
| MG1655 1.5yqhD #1 | 0 | 150 | 0.16 | 0.030 |
| MG1655 1.5yqhD #2 | 0 | 150 | 0.18 | 0.038 |
| MG1655 1.5yqhD #1 | 0.04 | 150 | 0.10 | 0.021 |
| MG1655 1.5yqhD #2 | 0.04 | 150 | 0.09 | 0.017 |
| MG1655 1.6yqhD #1 | 0 | 50 | 0.08 | Not detected |
| MG1655 1.6yqhD #2 | 0 | 50 | 0.07 | Not detected |
| MG1655 1.6yqhD #1 | 0.04 | 50 | 0.12 | Not detected |
| MG1655 1.6yqhD #2 | 0.04 | 50 | 0.15 | Not detected |
| MG1655 1.6yqhD #1 | 0 | 150 | 0.17 | 0.019 |
| MG1655 1.6yqhD #2 | 0 | 150 | 0.18 | 0.041 |
| MG1655 1.6yqhD #1 | 0.04 | 150 | 0.11 | 0.026 |
| MG1655 1.6yqhD #2 | 0.04 | 150 | 0.11 | 0.038 |
| Control (uninoculated medium) | | | Not detected | Not detected |

[a]#1 and #2 represent independent isolates.

[b]MG1655 is MG1655/pCL1925-Kodd-ddr/pTrc99a-budABC

MG1655 1.6yqhD is MG1655 1.6yqhD/pCL1925-Kodd-ddr/pTrc99a-budABC

MG1655 1.6yqhD is MG1655 1.5yqhD/pCL1925-Kodd-ddr/pTrc99a-budABC.

Example 11

Expression of a 2-Butanol Biosynthetic Pathway in *E. coli* with Heterologous Alcohol Dehydrogenase Plasmids pCL1925-KoDD-ddr::ter-T5chnA and pTrc99a-budABC, described in Example 9, were transformed into *E. coli* strains MG1655 and MG1655 ΔyqhCD for a demonstration of the production of 2-butanol.

MG1655 ΔyqhCD carries a yqhCD inactivation that was made using the method of Datsenko and Wanner (*Proc. Natl. Acad. Sci. U.S.A.* 97(12):6640-6645 (2000)). After replacement of the region with the FRT-CmR-FRT cassette of pKD3, the chloramphenicol resistance marker was removed using the FLP recombinase. The sequence of the deleted region is given as SEQ ID NO:66.

Strains MG1655/pTrc99a-budABC/pCL1925KoDD-ddr::ter-T5 chnA and MG1655 ΔyqhCD/pTrc99a-budABC/pCL1925KoDD-ddr::ter-T5 chnA were examined for the production of 2-butanone and 2-butanol essentially as described above. Strain MG1655 ΔyqhCD/pCL1925 was used as a negative control. Cells were inoculated into shake flasks (approximately 175 mL total volume) containing 50 or 150 mL of TM3a/glucose medium (with 0.1 mg/L vitamin $B_{12}$ and appropriate antibiotics) to represent medium and low oxygen conditions, respectively. Spectinomycin (50 μg/mL) and ampicillin (100 μg/mL) were used for selection of pCL1925 based plasmids and pTrc99a-budABC, respectively. Enzyme activity derived from pTrc99a-budABC was detected by enzyme assay in the absence of IPTG inducer, thus, IPTG was not added to the medium. The flasks were inoculated at a starting $OD_{600}$ of ≦0.01 units and incubated at 34° C. with shaking at 300 rpm for 24 h. The flasks containing 50 mL of medium were capped with vented caps; the flasks containing 150 mL, were capped with non-vented caps to minimize air exchange. Analytical results for 2-butanone and 2-butanol production are presented in Table 8. Both *E. coli* strains comprising a 2-butanol biosynthetic pathway produced 2-butanone under low and medium oxygen conditions and produced 2-butanol under low oxygen conditions, while the negative control strain did not produce detectable levels of either 2-butanone or 2-butanol.

TABLE 8

Production of 2-butanone and 2-butanol by *E. coli* strains

| Strain[a] | Volume, mL | 2-Butanone, mM | 2-Butanol, mM |
|---|---|---|---|
| Negative control, MG1655 ΔyqhCD/pCL1925 | 50 | Not detected | Not detected |
| MG1655/pTrc99a-budABC/pCL1925KoDD-ddr::T5 chnA ter | 50 | 0.33 | Not detected |
| MG1655 ΔyqhCD/pTrc99a-budABC/pCL1925KoDD-ddr::T5 chnA ter #1 | 50 | 0.23 | Not detected |
| MG1655 ΔyqhCD/pTrc99a-budABC/pCL1925KoDD-ddr::T5 chnA #2 | 50 | 0.19 | Not detected |
| Negative control, MG1655 ΔyqhCD/pCL1925 | 150 | Not detected | Not detected |
| MG1655/pTrc99a-budABC/pCL1925KoDD-ddr::T5 chnA ter | 150 | 0.41 | 0.12 |
| MG1655 ΔyqhCD/pTrc99a-budABC/pCL1925KoDD-ddr::T5 chnA #1 | 150 | 0.15 | 0.46 |
| MG1655 ΔyqhCD/pTrc99a-budABC/pCL1925KoDD-ddr::T5 chnA #2 | 150 | 0.44 | 0.14 |
| Medium | | Not detected | Not detected |

[a]#1 and #2 represent independent isolates.

Example 12

Cloning of Amino:Pyruvate Transaminase (APT)

An amino:pyruvate transaminase (APT) from *Vibrio Fluvialis JS*17 was identified by Shin et al. (Appl. Microbiol Biotechnol. ( 2003) 61:463-471). The amino acid sequence (SEQ ID NO:122) was found to have significant homology with co-amino acid:pyruvate transaminases (Shin and Kim (*J. Org. Chem.* 67:2848-2853 (2002)). It was shown that the *Vibrio Fluvialis* APT has transaminase activity towards acetoin.

For expression of the APT enzyme in *E. coli*, a codon optimized APT coding region (SEQ ID NO:144) was designed using the preferred *E. coli* codons with additional considerations such as codon balance and mRNA stability, and synthesized (by DNA2.0; Redwood City, Calif.). The coding region DNA fragment was subcloned into the pBAD.HisB vector (Invitrogen) between the NcoI and HindIII sites and the resulting plasmid, hereafter referred to as pBAD.APT1, was transformed into TOP10 cells.

Example 13

Characterization of *Vibrio Fluvialis* APT Alanine:Acetoin Aminotransferase Activity A 5 mL volume of LB broth +100 μg/mL ampicillin was inoculated with a fresh colony of TOP10/pBAD:APT1 cells. The culture was incubated at 37° C. for approximately 16 h with shaking (225 rpm). A 300 μL aliquot of this culture was used to inoculate 300 mL of the same medium, which was incubated at 37° C. with shaking (225 rpm). When the culture reached an $OD_{600}$ of 0.8, L-arabinose was added to a final concentration of 0.2% (w/v). The culture was incubated for an additional 16 h, then harvested. The cells were washed once with 100 mM potassium phosphate buffer (pH 7.8) and then frozen and stored at −80° C.

To isolate the enzyme, the cell pellet was thawed and resuspended in 8 mL of 100 mM potassium phosphate buffer (pH 7) containing 0.2 mM ethylenediaminetetraacetate, 1 mM dithiothreitol and 1 tablet of protease inhibitor cocktail (Roche; Indianapolis, Ind.). The cells were lysed by two passes through a French pressure cell at 900 psi, and the resulting lysate was clarified by centrifugation for 30 min at 17000×g. Ammonium sulfate was added to 35% saturation, and the solution was stirred for 30 min at room temperature, at which point precipitated solids were removed by centrifugation (30 min, 17000×g). Additional ammonium sulfate was added to the supernatant to give 55% saturation, and the solution was again stirred for 30 min at room temperature. The precipitated solids were removed by centrifugation (30 min, 17000×g) and then resuspended in 5 mL of 100 mM potassium phosphate buffer (pH 7) containing 10 μM pyridoxal 5'-phosphate and 1 mM dithiothreitol. This solution was desalted by passage through a PD10 column equilibrated with Buffer A (50 mM bis-tris propane buffer (pH 6) containing 10 μM pyridoxal 5'-phosphate and 1 mM dithiothreitol). The desalted extract was then loaded onto a 20 mL Q-Fast Flow column pre-equilibrated with Buffer A. APT was eluted with a linear gradient of 0-0.1 M NaCl in Buffer A. The enzyme was detected in eluted fractions by the presence of a protein band of size ~50 kD when analyzed by SDS-polyacrylamide gel electrophoresis and by the characteristic absorbance at 418 nm. Fractions containing the enzyme eluted at ~0.3 M NaCl. These fractions were pooled to yield a total of 6 mL of a 5.45 mg/mL solution of enzyme, which was >90% pure, as judged by SDS-polyacrylamide gel electrophoresis.

The alanine:acetoin aminotransferase activity of APT was assayed using a lactic dehydrogenase coupled assay. Reaction mixtures contained 100 mM bis-tris propane (pH 9.0), 10 μM pyridoxal 5'-phosphate, 0-50 mM acetoin, 0-5 mM L-alanine, 0.14 or 0.28 mg/mL purified enzyme, 200 μM NADH and 20 U/mL lactic dehydrogenase (Sigma; St. Louis, Mo.). The reaction was followed by measuring the change in absorbance at 340 nm, indicative of the oxidation of NADH. Under these conditions, the $k_{cat}/K_m$ for acetoin was 10 $M^{-1}$ $s^{-1}$ and that for L-alanine was 400 $M^{-1}$ $s^{-1}$.

The identity of the expected product 3-amino-2-butanol was confirmed by comparison to a synthetic standard. A mixture of (R,R)- and (S,S)-3-amino-2-butanol was synthesized by the method of Dickey et al. [*J Amer Chem Soc* 74:944 (1952)]: 5 g of trans-2,3-epoxybutane were slowly stirred into 150 mL of cold (4° C.) $NH_4OH$. The reaction was slowly warmed to room temperature, sealed and stirred at room temperature for an additional 10 days. At this time, excess ammonia and water and residual epoxybutane were removed by rotary evaporation under vacuum at 40° C. The resulting clear oil (2.9 g) was resuspended in water to a concentration of 10% (w/v). Production of the desired product was confirmed by NMR analysis and comparison of the spectrum to that reported by Levy et al. [*Org. Magnetic Resonance* 14:214 (1980)]. A mixture of the corresponding (2R,3S)- and (2S,3R)- isomers was produced using the identical method with the exception that the starting material was the cis-isomer of 2,3-epoxybutane.

An analytical method for detection of 3-amino-2-butanol was developed based on the o-phthaldialdehyde derivatization method for amino acid determination reported by Roth [*Anal. Chem.* 43:880 (1971)]. A 200 μL aliquot of 1 mM 3-amino-2-butanol (mixture of isomers) was mixed with 200 μL of a 50 mM solution of borate (pH 9.5), to which was added 10 μL of 5 μL/mL 2-mercaptoethanol in ethanol and 10 μL of 10 mg/mL o-phthaldialdehdye in ethanol. The solution was incubated at room temperature for 10 min, at which time the derivative was extracted into 200 μL hexane. The hexane was separated from the aqueous solution by decanting, and 10 μL were injected onto a Chiracel OD HPLC column (Daicel Chemical Industries; Fort Lee, N.J.). The column was run isocratically with a mobile phase of 90:10 hexane:isopropanol at a rate of 1 mL/min. The derivatized isomers of 3-amino-2-butanol were detected by absorbance at 340 nm with retention times of approximately 15.7 and 16.8 min [(2S,3S) and (2R,3R)], and 18.4 and 21.9 min [(2R,3S) and (2S,3R)]. To differentiate the enantiomers in the first mixture, the pure (2R,3R) isomer (Bridge Organics; Vicksburg, Mich.) was also run under the identical conditions and found to be the 16.8 min peak. To differentiate the enantiomers in the second mixture, the mixture was first kinetically resolved using the alanine:acetoin aminotransferase: 0.28 mg of purified enzyme was incubated with 10 mM pyruvate and 10 mM 3-amino-2-butanol [1:1 mixture of (2R,3S) and (2S,3R) isomers] in 1 mL of 100 mM bis-tris propane (pH 9.0). After 24 h at room temperature, an aliquot was removed and analyzed as described above. Analysis revealed that the 18.4 min peak was 95% depleted, while the 21.9 min peak was >90% retained. A 100 μL aliquot of the remaining reaction mixture was mixed with 50 μL of 20 mM NADH and 10 μL of extract from the TOP10/pTrc99a-BudC strain described in Example 9. The BudC enzyme is known to reduce (R)-acetoin to meso-2,3-butanediol and (S)-acetoin to (S,S)-2,3-butanediol [Ui et al. (2004) *Letters in Applied Microbiology* 39:533-537]. After 3 h, samples were taken from the reaction and analyzed as described above for acetoin and butanediol. The analysis indicated that the primary product of the reduction was meso-2,3-butanediol, indicating that the product of the aminotransferase reaction was (R)-acetoin, and therefore the consumed 3-amino-2-butanol isomer was the (2R,3S) isomer. Thus the retention time of 18.4 min can be assigned to this isomer and 21.9 to the (2S,3R) isomer.

To confirm that the product of the APT-catalyzed alanine: acetoin aminotransferase reaction was 3-amino-2-butanol, 0.28 mg of purified enzyme was incubated with 10 mM acetoin, 10 mM L-alanine, 50 U lactic dehydrogenase and 200 pM NADH in 1 mL of 100 mM bis-tris propane (pH 9.0). The reaction mixture was incubated at room temperature for 20 h, after which a 200 μL aliquot was removed and derivatized as described above. The retention times of the derivatized products were 15.8 min (major product) and 18.5 min (minor product), matching that of the (2S,3S)- and (2R,3S)-3-amino-2-butanol standards.

Example 14

Identification and Cloning of *Erwinia carotovora* subsp. *atroseptica* Amino Alcohol Kinase and Amino Alcohol O-Phosphate Lyase The purpose of this example is to describe the identification and cloning of sequences encoding an amino alcohol kinase and amino alcohol O-phosphate lyase from the bacterium *Erwinia carotovora.* These two enzymes are part of Pathway 1 for the conversion of 3-amino-2-butanol to 2-butanone via the intermediate 3-amino-2-butanol phosphate as shown in FIG. 1.

Prediction of the *Erwinia* Amino Alcohol Kinase and the Amino Alcohol O-phosphate Lyase ATP-dependent amino alcohol kinase and amino alcohol O-phosphate lyase activities have been detected in several *Pseudomonas* and *Erwinia* species, including *Pseudomonas* sp. P6 (NCIB10431), *Pseudomonas putida* NCIB 10558 (Jones et al. (1973) *Biochem. J.* 134:167-182), *Erwinia carotovora, Erwinia amanas, Erwina milletiae*, and *Erwinia atroseptica* (Jones et al. (1973) *Biochem. J.* 134:959-968). In these studies, the extracts of the above species were shown to have activity for the enzymatic conversion of aminopropanol through aminopropanol O-phosphate to propionaldehyde, and the conversion of ethanolamine through ethanolamine O-phosphate to acetaldehyde.

The genomic sequence of the *Erwinia atroseptica* strain in which these activities were reported to exist (now designated as *Erwinia carotovora* subsp. *atroseptica* strain SCRI1043 (ATCC BAA-672)) has been determined at the Sanger Institute (Bell et al. *Proc. Natl. Acad. Sci. USA* 101 (30): 11105-11110). Analysis of the putative kinases in the *Erwinia carotovora* subsp. *atroseptica* genome revealed an operon sequence (SEQ ID NO:164) encoding a putative protein (ECA2059; SEQ ID NO:124) that is 39% identical to a *Rhizobium loti* homoserine kinase and a putative class-IIII pyridoxal phosphate (PLP)-dependent aminotransferase (ECA2060; SEQ ID NO:126) that is 58% identical to a putative aminotransferase from Rhizobium meliloti. Based on the above it was expected that ECA2059 was an amino alcohol kinase and ECA2060 was an amino alcohol O-phosphate lyase which uses PLP as cofactor.

Cloning of the Putative Amino Alcohol Kinase and Putative Amino Alcohol O-phosphase Lyase from *Erwinia carotovora* subsp. *atroseptica*

Genomic DNA of *Erwinia carotovora* subsp. *atroseptica* (ATCC #: BAA-672D) was obtained from American Type Culture Collection (ATCC). The operon encoding the putative amino alcohol kinase (KA) and amino alcohol O-phosphate lyase (AT) was named KA-AT (SEQ ID NO:164. This operon was amplified from the *Erwinia* genomic DNA by Phusion DNA polymerase (Finnzymes; via New England Biolabs; Ipswich, Mass.) using primers OT872 (SEQ. ID. No.127) and OT873 (SEQ. ID. No128). A DNA fragment of 2.4 kb was obtained by the PCR reaction, which corresponds to the size of the KA-AT operon. The PCR product was digested with EcoRI and PstI restriction enzymes, and cloned into vector pKK223-3 (Amersham Biosciences; Piscataway, N.J.) which was digested with the same restriction enzymes. This produced plasmid pKK223.KA-AT, which contained the putative Erwinia amino alcohol kinase-lyase operon under control of the tac promoter. Similarly, plasmids pKK223.KA and pKK223.AT were made which placed the putative *Erwinia kinase* and the putative *Erwinia lyase* coding regions in separate vectors, each under the control of the tac promoter. For the PCR cloning of the KA coding region (SEQ ID NO:123), primers OT872 (SEQ. ID. No.127) and OT879 (SEQ. ID. No.129) were used; and for the PCR cloning of AT coding region (SEQ ID NO:125), primers OT873 (SEQ. ID. No.128) and OT880 (SEQ. ID. No.130) were used in the PCR amplifications, which generated PCR products of 1.1 kb and 1.3 kb respectively. The PCR products were each digested with EcoRI and PstI, and ligated into vector pKK223-3 to generate pKK223.KA and pKK223.AT.

In vivo Activity of the Putative Amino Alcohol Kinase and Putative Amino Alcohol O-phosphate Lyase from *Erwinia carotovora* subsp. *atroseptica*

Plasmids pKK223.KA-AT, pKK223.KA, pKK223.AT and pKK223-3 were transformed into the *E. coli* MG1655 strain. The transformants were restreaked onto a MOPS minimal media plate containing 1% glucose, 0.5% aminopropanol as a sole nitrogen source, 1 mM IPTG and 100 μg/mL ampicillin. Expression of KA-AT, KA and AT genes were induced by the IPTG. A control plate had no IPTG included. The plates were incubated at 37° C. for 7 days. On the plate with IPTG, only the strain MG1655/pKK223.KA-AT grew, while all the other three strains did not grow. On the plate without added IPTG, the strain MG1655/pKK223.KA-AT grew, but the colonies were significantly smaller than those on the IPTG-containing plate, which corresponds to the lower expression levels of KA and AT in the uninduced cells. None of the other three strains grew on this plate . This indicates that the co-expression of the putative *Erwinia* KA and AT genes provided sufficient enzyme activities that allowed the *E. coli* strain MG1655/pKK223.KA-AT to utilize aminopropanol as a sole nitrogen source. Expression of each individual enzyme of either KA or AT was not sufficient to provide such enzyme activity in vivo.

Example 15

In vitro Activity of *Erwinia* putative Amino Alcohol Kinase and Amino Alcohol O-Phosphate Lyase Subcloning of the *Erwinia* KA-AT Operon into the pBAD.HisB Vector and Induction of Protein Expression The protein expression levels of *Erwinia* putative KA and AT enzymes expressed in MG1655 cells from the pKK223.KA-AT vector were analyzed by SDS-PAGE analysis. The expression level of the *Erwinia* AT enzyme was relatively low, with a new protein band detected at the correct molecular weight of 46 kD in the soluble fraction of a cell extract, while no new protein band was detected at the size predicted for the KA enzyme.

In an effort to improve the expression of the *Erwinia* putative KA and AT genes, the KA-AT operon was subcloned into the EcoRI and HindIII sites of vector pBAD.HisB-EcoRI. pBAD.HisB-EcoRI was derived from the pBAD.HisB vector (Invitrogen), by replacing the NcoI site in pBAD.HisB with an EcoRI site via QuickChange site-directed mutagenesis (Stratagene, La Jolla, Calif.) using primers OT909 (SEQ ID.# 131) & OT910 (SEQ ID.# 132). In the constructed plasmid pBAD.KA-AT, the KA-AT operon was placed directly under control of the araB promoter (without His-tag).

The PBAD.KA-AT plasmid was transformed into the *E. coli* TOP10 strain. A 50 mL culture of TOP10/pBAD.KA-AT strain was grown to mid log phase ($OD_{600}$=0.6) in LB, 100 μg/mL ampicillin media at 37° C. with shaking at 250 rpm. The culture was induced by addition of L-arabinose to a final concentration of 0.1% (w/v), and it was further incubated at 37° C. for 5 h before harvesting by centrifugation. The cell pellet was resuspended in ice cold 50 mM Tris-HCl, pH 8.0, and disrupted by sonication on ice with a Fischer Sonic Model 300 Dismembrator (Fischer, Pittsburgh, Pa.) at 50% power, repeating four cycles of 30 seconds sonication with 60 seconds rest in-between each cycle. Each sonicated sample was centrifuged (15,000×g, 4 min, 4° C.). Clarified cell free extracts were analyzed for protein expression level and amino alcohol O-phosphate lyase activity.

Chemical Synthesis of Aminobutanol O-phoslphate and Aminolprolpanol O-phosphate

The substrate (R,R)-3-amino-2-butanol O-phosphate was synthesized by a method based on that reported by Ferrari and Ferrari (U.S. Pat. No. 2,730,542 [1956]) for phosphoethanolamine: 10 mmol of $H_3PO_4$ in a 50% (w/v) aqueous solution was mixed with a 50% (w/v) solution of 3-amino-2-butanol (~20:1 (R,R):(S,S) isomers; Bridge Organics; Vicksburg, Mich.) while stirring on ice. After mixing, the solution was slowly warmed to room temperature and then stirred under vacuum and heated to 70° C. After 1 h at 70° C., the temperature was slowly increased to 185° C. and maintained there for an additional 2 h. At that time, the reaction was cooled to room temperature and the vacuum released. The remaining material was dissolved in water, and analysis by NMR indicated that 80% of the starting material was converted to product with 20% remaining unreacted. No additional products were observed.

The additional substrates (2R,3S)-3-amino-2-butanol O-phosphate and (2S,3R)-3-amino-2-butanol O-phosphate were synthesized by the same procedure using a 1:1 mixture of (2R,3S)-3-amino-2-butanol and (2S,3R)-3-amino-2-butanol (synthesized as described in Example 13) as the starting material. DL -1-amino-2-propanol O-phosphate, (S)-2-amino-1-propanol O-phosphate, and (R)-2-amino-1-propanol O-phosphate were synthesized by the same procedure using DL-1-amino-2-propanol, (R)-2-amino-1-propanol, or (S)-2-amino-1-propanol as the starting material.

Analysis of the Aminopropanol O-phoshate Lyase Activity Encoded by the Putative *Erwinia* KA-AT Operon The aminopropanol O-phosphate lyase assay was performed as described by Jones et al. (1973, *Biochem. J.* 134: 167-182) and G. Gori et al. (1995, Chromatographia 40:336) The formation of propionaldehyde from aminopropanol O-phosphate was assayed calorimetrically with MBTH, which allows the detection of aldehyde formation. The reaction was performed as follows. In a 1 mL reaction, 100 μg cell free extract of *E. coli* TOP10/pBAD.KA-AT was added to 10 mM DL-1-amino-2-propanol O-phosphate in 100 mM Tris-HCl, pH 7.8, with 0.1 mM PLP. The reaction was incubated at 37° C. for 10 min and 30 min, with an aliquot of 100 μL reaction mixture removed at each time point and mixed with 100 μL of 6 mg/mL MBTH in 375 mM glycine-HCl, pH 2.7. This mixture was incubated at 100° C. for 3 min, cooled on ice for 15-30 s, and 1 mL of 3.3 mg/mL $FeCl_3.6H_2O$ (in 10 mM HCl) was added, followed by incubation for 30 min at room temperature. The absorbance of the reaction mixture which contains the aldehyde-MBTH adduct, was measured at 670 nm. The results of the assay are listed in Table 9. In the presence of the aminopropanol phosphate substrate, PLP and cell free extract, formation of aldehyde was detected, as indicated by an $Abs_{670}$ that was higher than the control background of up to 0.3. In the absence of either the substrate or the cell free extract, no aldehyde formation was detected. In the absence of added PLP, somewhat less amount aldehyde was detected, presumably due to the presence of PLP in the cell free extract. Cell free extract of the uninduced TOP10/pBAD.KA-AT culture did not produce any detectable aldehyde in the reaction. These results indicated that the putative *Erwinia* amino alcohol O-phosphate lyase does catalyze the conversion of aminopropanol O-phosphate to propionaldehyde.

TABLE 9

Aminopropanol O-phosphate lyase assay. Sample 1 was the cell free extract of a non-induced control of *E. coli* TOP10/pBAD.KA-AT. Samples 2-5 contained the cell free extract of the induced culture *E. coli* TOP10/pBAD.KA-AT.

| Sample Number | Induction by 0.1% arabinose | Aminopropanol O-phosphate | PLP | Enzyme extract (100 μg/mL) | $OD_{670}$, 10 min | $OD_{670}$, 30 min |
|---|---|---|---|---|---|---|
| 1 | uninduced | (+) | (+) | (+) | 0.262 | 0.255 |
| 2 | induced | (+) | (+) | (+) | 1.229 | 2.264 |
| 3 | induced | (−) | (+) | (+) | 0.303 | 0.223 |
| 4 | induced | (+) | (−) | (+) | 0.855 | 1.454 |
| 5 | induced | (+) | (+) | (−) | 0.156 | 0.065 |

Analysis of the Activity of the *Erwinia* Amino Alcohol O-phosphate Lyase towards Aminobutanol O-phosihate Substrate The activity of the amino alcohol O-phosphate lyase towards the aminobutanol O-phosphate substrates was studied under the same conditions as described above. The reaction was carried out at 37° C. overnight in a 1 mL reaction that contained 100 μg of cell free extract of *E. coli* TOP10/pBAD.KA-AT, 10 mM aminobutanol O-phosphate (either the mixture of (R,R)+(S,S) or the mixture of (R,S) +(S,R) isomers described in Example 15) in 100 mM Tris-HCI, pH 7.8, with 0.1 mM PLP. An aliquot of 100 μL reaction mixture was removed and the 2-butanone product was detected using the MBTH derivatization method described in the General Methods. The two peaks representing the derivatized 2-butanone isomers were observed. Therefore the *Erwinia* amino alcohol O-phosphate lyase is an aminobutanol phosphate phospho-lyase in addition to an aminopropanol phosphate phospho-lyase.

Analysis of the Activity of the *Erwinia* Amino Alcohol O-phosphate Lyase towards Stereoisomers of Aminopropanol O-phosphate and Aminobutanol O-phosphate The activity of the *Erwinia* amino alcohol O-phosphate lyase towards various stereoisomers of aminopropanol O-phosphate and aminobutanol O-phosphate was studied under the same conditions as described above. In the presence of the Erwinia amino alcohol O-phosphate lyase, both (R) and (S)-2-amino-1-propanol O-phosphate were converted to propanone by the enzyme, but the product yield was much higher with the (S) isomer. The enzyme also produced butanone from both mixtures of 3-amino)-2-butanol O-phosphate isomers, with a higher product yield found in the reaction containing the (R,S) and (S,R) substrate isomers. Both propanone and butanone products were derivatized by MBTH, and detected by HPLC as described in General Methods.

Optimization of the Gene Expression Level for the *Erwinia* Amino Alcohol Kinase and Amino Alcohol O-phosphate Lyase In order to improve the expression levels for the *Erwinia* amino alcohol kinase and the amino alcohol O-phosphate lyase in *E. coli*, codon optimized coding regions for both enzymes (named EKA: SEQ ID NO:155 and EAT: SEQ ID NO:156 respectively) were synthesized by DNA2.0 (Redwood City, Calif.). Each coding region was synthesized with 5' and 3' tails including restriction sites for cloning: EKA has 5' BbsI and 3' EcoRI, HindIII sites; EAT has 5' EcoRI and 3' HindIII sites. The EKA and EAT coding regions were provided from DNA2.0 as plasmids pEKA and pEAT, which were in the pJ51 vector of DNA2.0. The EKA optimized coding region was subcloned by ligating a BbsI and HindIII digested fragment of pEKA into the pBAD.HisB vector between the NcoI and HindIII sites, to generate plasmid PBAD.EKA. In the resulting plasmid the coding region is 5' to the His tag, so a coding region for an N-terminus $His_6$ tag fused to the *Erwinia* amino alcohol kinase was constructed by performing a QuickChange site-directed mutagenesis reaction using primers SEQ ID NO:157 and SEQ ID NO:158 to generate vector pBAD.His-EKA.

pBAD.His-EKA was transformed into *E. coli* strain BL21-AI (F ompT hsdSB ($rB^-$ $mB^-$) gal dcm araB::T7RNAP-tetA; Invitrogen to produce strain BL21-AI/pBAD.HisA-EKA. A 50 mL culture of BL21-AI/pBAD.HisA-EKA was grown to mid-log stage ($OD_{600}$=0.6), induced with 0.1% arabinose, and further incubated at 30° C. overnight. Cell free extracts were prepared by sonication. The $His_6$-tagged fusion protein of *Erwinia* amino alcohol kinase was purified using the ProBond™ Purification System (Invitrogen) under non-denaturing purification conditions following the manufacturer's instructions.

Prophetic Result

The kinase activity of the $His_6$-tagged *Erwinia* amino alcohol kinase is analyzed by the ADP Quest Assay (DiscoveRx, Fremont, Calif.) following the manufacture's instructions. This is a biochemical assay that measures the accumulation of ADP, a product of the amino alcohol kinase reaction using either aminopropanol or aminobutanol as substrate. 10 mM substrate is mixed with $His_6$-tagged *Erwinia* amino alcohol kinase, in 100 mM Tris-HCl, pH 7.8, 10 mM $MgCl_2$, 2 mM KCl, 0.1 mM ATP, and incubated at 37° C. for 1 h in a 0.2 mL reaction. ADP reagent A (100 μL) and ADP reagent B (200 μL) are added and the mixture is incubated at room temperature for 30 min. The fluorescence signal indicating activity is measured with excitation wavelength of 530 nm and emission wavelength of 590 nm.

Example 16

Expression of Entire Pathway 3

Construction of Vector pCLBudAB-ter-T5chnA

The vector pTrc99a::BudABC (described in Example 9) is digested with EcoRI, and the DNA is treated with Klenow DNA polymerase to blunt the ends. The blunted vector is subsequently digested with SpeI to yield a 2.5 kb fragment containing the budA and budB genes. The vector pCL1925-ter-T5chnA (described in Example 9) is digested with HindIII, and the DNA was treated with Klenow DNA polymerase to blunt the ends. The blunted vector is subsequently digested with XbaI to yield a 4.6 kb fragment which is then ligated to the budAB fragment from pTrc99a::BudABC. The resulting plasmid, designated pCLBudAB-ter-T5chnA, is used to transform *E. coli* Top10 cells, and single colonies are screened for proper plasmid structure by PCR using primers pCL1925vecF (SEQ ID NO:62) and N84seqR3 (SEQ ID NO:159). Plasmid is prepared from a single colony which yields a PCR product of the expected size of 1.4 kb.

Construction of Vector pKK223.KA-AT-APT

The APT gene is amplified from the vector PBAD.APT (described in Example 12) by PCR using primers APTfor (SEQ ID NO:162; 5' includes RBS and SmaI site) and APTrev (SEQ ID NO:163; 3' adds SmaI site). The product of expected size of 1.7 kbp is gel purified and digested with SmaI to yield blunt ends. The vector pKK223.KA-AT (described in Example 14) is digested with PstI, and the DNA is treated with Klenow DNA polymerase to blunt the ends. The resulting DNA fragment is ligated with the SmaI-digested PCR product, and the ligation product is used to transform *E. coli* Top10 cells. Individual ampicillin resistant colonies are screened by PCR using primers OT872 (SEQ ID NO:127) and APTrev (SEQ ID NO:163). The presence of a PCR product of the expected size of 4.1 kbp indicates that the gene encoding APT is present and oriented in the same direction as the genes encoding KA and AT. The sequence of the insert is verified using the primers APTseqRev (SEQ ID NO:160) and APTseqFor (SEQ ID NO:161). This plasmid is named pKK223.KA-AT-APT. Proper expression of all three genes is verified by growing a 5 mL culture of Top10/pKK223.KA-AT-APT in LB +100 μg/mL ampicillin at 37° C. with shaking. When the $OD_{600}$ reaches ~0.8, expression of the genes on the plasmid is induced by addition of IPTG to 0.4 mM. The expression is evaluated by SDS PAGE and activity assays as described above.

Construction of 2-butanol Production Strain and Production of 2-butanone and 2-butanol

*E. coli* strain MG1655 is transformed with both pKK223.KA-AT-APT and pCLBudAB-ter-T5chnA, and transformants selected for ampicillin and spectinomycin resistance, indicative of the presence of the plasmids. The cells are inoculated into shake flasks (approximately 175 mL total volume) containing 50 or 150 mL of TM3a/glucose medium (with appropriate antibiotics) to represent medium and low oxygen conditions, respectively. IPTG is added to 0.4 mM to induce expression of genes from pKK223.KA-AT-APT. As a negative control, MG1655 cells are grown in the same medium lacking antibiotics. The flasks are inoculated at a starting $OD_{600}$ of $\leqq$0.01 and incubated at 34° C. with shaking at 300 rpm for 24 h. The flasks containing 50 mL of medium are capped with vented caps; the flasks containing 150 mL are capped with non-vented caps to minimize air exchange. The MG1655/pKK223.KA-AT-APT/pCLBudAB-ter-T5chnA strain comprising a 2-butanol biosynthetic pathway produces both 2-butanone and 2-butanol under low and medium oxygen conditions while the negative control strain does not produce detectable levels of either 2-butanone or 2-butanol.

Example 17

Characterization of Glycerol Dehydratase Butanediol Dehydratase Activity

Glycerol dehydratase (E.C. 4.2.1.30) and diol dehydratase (E.C. 4.2.1.28), while structurally related, are often distinguished in the art based on various differences that include substrate specificity. This example demonstrates that glycerol dehydratase converts meso-2,3-butanediol to 2-butanone. The recombinant *E. coli* strain KLP23/pSYCO1 2, comprising *Klebsiella pneumoniae* genes encoding the multiple subunits of glycerol dehydratase (alpha: SEQ ID NO:145 (coding region) and 146 (protein); beta: SEQ ID NO: 147 (coding region) and 148 (protein); and gamma: SEQ ID NO: 149 (coding region) and 150 (protein)) and *Klebsiella pneumoniae* genes encoding the multiple subunits of glycerol dehydratase reactivase (large subunit, SEQ ID NO: 151 (coding region) and 152 (protein); and small subunit, SEQ ID NO: 153 (coding region) and 154 (protein)), is described in Emptage et al. U.S. Pat. No. 6,514,733 and in WO 2003089621, which are herein incorporated by reference. A crude, cell free extract of KLP23/pSYCO12 was prepared by methods known to one skilled in the art. Enzyme assay was performed in the absence of light in 80 mM HEPES buffer, pH 8.2 at 37° C. with 12 μM coenzyme $B_{12}$ and 10 mM meso-2,3-butanediol. The formation of 2-butanone was monitored by HPLC (Shodex SH-1011 column and SH-G guard column with refractive index detection; 0.01 M $H_2SO_4$ as the mobile phase at a flow rate of 0.5 mL/min and a column temperature of 50° C.; 2-butanone retention time=40.2 min). The rate of 2-butanone formation by the glycerol dehydratase preparation was determined to be 0.4 nmol/min/mg of crude protein.

What is claimed is:

1. A recombinant microbial host cell comprising at least one heterologous DNA molecule encoding a polypeptide that catalyzes a substrate to product conversion of 3-amino-2-butanol phosphate to 2-butanone and at least one heteroloqous DNA molecule encoding a polypeptide that catalyzes a substrate to product conversion of 3-amino-2-butanol to 3-amino-2-butanol phosphate;

wherein said microbial host cell produces 2-butanol by the conversion of 3-amino-2butanol phosphate to 2-butanone; and wherein the polypeptide that catalyzes a substrate to product conversion of 3-amino-2-butanol phosphate to 2-butanone is aminobutanol phosphate phospho-lyase having the amino acid sequence that has at least 95% identity to the amino acid sequence of SEQ ID NO:126 based on the Clustal W method of alignment using the default parameters of GAP PENALTY=10, GAP LENGTH PENALTY=0.1, and Gonnet 250 series of protein weight matrix.

2. A recombinant microbial host cell comprising at least one heteroloqous DNA molecule encoding a polypeptide that catalyzes a substrate to product conversion of 3-amino-2-butanol phosphate to 2-butanone and at least one heterologous DNA molecule encoding a polypeptide that catalyzes a substrate to product conversion of 3-amino-2-butanol to 3-amino-2-butanol phosphate;

wherein said microbial host cell produces 2-butanone by the conversion of 3-amino-2-butanol phosphate to 2-butanone; and wherein the polypeptide that catalyzes a substrate to product conversion of 3-amino-2-butanol phosphate to 2-butanone is aminobutanol phosphate phospho-lyase having the amino acid sequence that has at least 95% identity to the amino acid sequence of SEQ ID NO:126 based on the Clustal W method of alignment using the default parameters of GAP PENALTY=10, GAP LENGTH PENALTY=0.1, and Gonnet 250 series of protein weight matrix.

3. A host cell according to claim 1 or 2 wherein the cell is a member of a genus selected from the group consisting of *Clostridium, Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Brevibacterium, Pichia, Candida, Hansenula* and *Saccharomyces*.

4. The recombinant host cell of claim 1 wherein the at least one heterologous DNA molecule encoding a polypeptide that catalyzes a substrate to product conversion of 3-amino-2-butanol to 3-amino-2-butanol phosphate has at least 80% identity to SEQ ID NO: 124 based on the Clustal W method of alignment using the default parameters of GAP PENALTY=10, GAP LENGTH PENALTY=0.1, and Gonnet 250 series of protein weight matrix.

5. The recombinant host cell of claim 2 wherein the at least one heterologous DNA molecule encoding a polypeptide that catalyzes a substrate to product conversion of 3-amino-2-butanol to 3-amino-2-butanol phosphate has at least 80% identity to SEQ ID NO: 124 based on the Clustal W method of alignment using the default parameters of GAP PENALTY=10, GAP LENGTH PENALTY=0.1, and Gonnet 250 series of protein weight matrix.

6. The recombinant host cell of claim 1 further comprising heterologous DNA molecules encoding polypeptides that catalyze the following substrate to product conversions:

(a) pyruvate to alpha-acetolactate;

(b) alpha-acetolactate to acetoin; and (c) acetoin to 3-amino-2-butanol.

7. The recombinant host cell of claim 2 further comprising heterologous DNA molecules encoding polypeptides that catalyze the following substrate to product conversions:

(a) pyruvate to alpha-acetolactate;

(b) alpha-acetolactate to acetoin; and (c) acetoin to 3-amino-2-butanol.

8. The recombinant host cell of claim 1, further comprising at least one heterologous DNA molecule encoding a polypeptide that catalyzes a substrate to product conversion selected from the group consisting of:

(a) pyruvate to alpha-acetolactate;

(b) alpha-acetolactate to acetoin;

(c) acetoin to 3-amino-2-butanol; and (d) 2-butanone to 2-butanol.

9. The recombinant host cell of claim 2, further comprising at least one heterologous DNA molecule encoding a polypeptide that catalyzes a substrate to product conversion selected from the group consisting of:

(a) pyruvate to alpha-acetolactate;

(b) alpha-acetolactate to acetoin; and (c) acetoin to 3-amino-2-butanol.

10. The recombinant host cell of claim 1 wherein the polypeptide that catalyzes a substrate to product conversion of 3-amino-2-butanol phosphate to 2-butanone is aminobutanol phosphate phospho-lyase having the amino acid sequence of SEQ ID NO:126.

11. The recombinant host cell of claim 1, wherein the at least one heterologous DNA molecule encoding a polypeptide that catalyzes a substrate to product conversion of 3-amino-2-butanol to 3-amino-2-butanol phosphate has at least 95% identity to SEQ ID NO: 124 based on the Clustal W method of alignment using the default parameters of GAP PENALTY=10, GAP LENGTH PENALTY=0.1, and Gonnet 250 series of protein weight matrix.

12. The recombinant host cell of claim 2 wherein the polypeptide that catalyzes a substrate to product conversion of 3-amino-2-butanol phosphate to 2-butanone is aminobutanol phosphate phospho-lyase having the amino acid sequence of SEQ ID NO:126.

13. The recombinant host cell of claim 2, wherein the at least one heterologous DNA molecule encoding a polypeptide that catalyzes a substrate to product conversion of 3-amino-2-butanol to 3-amino-2-butanol phosphate has at least 95% identity to SEQ ID NO: 124 based on the Clustal W method of alignment using the default parameters of GAP PENALTY=10, GAP LENGTH PENALTY=0.1, and Gonnet 250 series of protein weight matrix.

* * * * *

SEQUENCE LISTING

<160> NUMBER OF SEQ ID NOS: 164

<210> SEQ ID NO 1
<211> LENGTH: 780
<212> TYPE: DNA
<213> ORGANISM: Klebsiella pneumoniae

<400> SEQUENCE: 1
atgaatcatt ctgctgaatg cacctgcgaa gagagtctat gcgaaaccct gcgggcgttt 60

```
tccgcgcagc atcccgagag cgtgctctat cagacatcgc tcatgagcgc cctgctgagc    120

ggggtttacg aaggcagcac caccatcgcg gacctgctga aacacggcga tttcggcctc    180

ggcaccttta atgagctgga cggggagctg atcgccttca gcagtcaggt ctatcagctg    240

cgcgccgacg gcagcgcgcg caaagcccag ccggagcaga aaacgccgtt cgcggtgatg    300

acctggttcc agccgcagta ccggaaaacc tttgaccatc cggtgagccg ccagcagctg    360

cacgaggtga tcgaccagca aatcccctct gacaacctgt tctgcgccct gcgcatcgac    420

ggccatttcc gccatgccca tacccgcacc gtgccgcgcc agacgccgcc gtaccgggcg    480

atgaccgacg tcctcgacga tcagccggtg ttccgcttta accagcgcga aggggtgctg    540

gtcggcttcc ggaccccgca gcatatgcag gggatcaacg tcgccgggta tcacgagcac    600

tttattaccg atgaccgcaa aggcggcggt cacctgctgg attaccagct cgaccatggg    660

gtgctgacct tcggcgaaat tcacaagctg atgatcgacc tgcccgccga cagcgcgttc    720

ctgcaggcta atctgcatcc cgataatctc gatgccgcca tccgttccgt agaaagttaa    780
```

<210> SEQ ID NO 2
<211> LENGTH: 259
<212> TYPE: PRT
<213> ORGANISM: Klebsiella pneumoniae

<400> SEQUENCE: 2

```
Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Lys His Gly Asp Phe Gly Leu Gly Thr Phe Asn
    50                  55                  60

Glu Leu Asp Gly Glu Leu Ile Ala Phe Ser Ser Gln Val Tyr Gln Leu
65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255
```

Val Glu Ser

<210> SEQ ID NO 3
<211> LENGTH: 1680
<212> TYPE: DNA
<213> ORGANISM: Klebsiella pneumoniae

<400> SEQUENCE: 3

```
atggacaaac agtatccggt acgccagtgg gcgcacggcg ccgatctcgt cgtcagtcag     60
ctggaagctc agggagtacg ccaggtgttc ggcatccccg gcgccaaaat tgacaaggtc    120
ttcgactcac tgctggattc ctcgattcgc attattccgg tacgccacga agccaacgcc    180
gcgtttatgg ccgccgccgt cggacgcatt accggcaaag cgggcgtggc gctggtcacc    240
tccggtccgg gctgttccaa cctgatcacc ggcatggcca ccgcgaacag cgaaggcgac    300
ccggtggtgg ccctgggcgg cgcggtaaaa cgcgccgata aagcgaagca ggtccaccag    360
agtatggata cggtggcgat gttcagcccg gtcaccaaat acgccgtcga ggtgacggcg    420
ccggatgcgc tggcggaagt ggtctccaac gccttccgcg ccgccgagca gggccggccg    480
ggcagcgcgt tcgttagcct gccgcaggat gtggtcgatg gcccggtcag cggcaaagtg    540
ctgccggcca gcggggcccc gcagatgggc gccgcgccgg atgatgccat cgaccaggtg    600
gcgaagctta tcgcccaggc gaagaacccg atcttcctgc tcggcctgat ggccagccag    660
ccggaaaaca gcaaggcgct gcgccgtttg ctggagacca gccatattcc agtcaccagc    720
acctatcagg ccgccggagc ggtgaatcag gataacttct ctcgcttcgc cggccgggtt    780
gggctgttta acaaccaggc cggggaccgt ctgctgcagc tcgccgacct ggtgatctgc    840
atcggctaca gcccggtgga atacgaaccg gcgatgtgga acagcggcaa cgcgacgctg    900
gtgcacatcg acgtgctgcc cgcctatgaa gagcgcaact acaccccgga tgtcgagctg    960
gtgggcgata tcgccggcac tctcaacaag ctggcgcaaa atatcgatca tcggctggtg   1020
ctctccccgc aggcggcgga gatcctccgc gaccgccagc accagcgcga gctgctggac   1080
cgccgcggcg cgcagctgaa ccagtttgcc ctgcatccgc tgcgcatcgt tcgcgccatg   1140
caggacatcg tcaacagcga cgtcacgttg accgtggaca tgggcagctt ccatatctgg   1200
attgcccgct acctgtacag cttccgcgcc cgtcaggtga tgatctccaa cggccagcag   1260
accatgggcg tcgccctgcc ctgggctatc ggcgcctggc tggtcaatcc tgagcgaaaa   1320
gtggtctccg tctccggcga cggcggcttc ctgcagtcga gcatggagct ggagaccgcc   1380
gtccgcctga aagccaacgt actgcacctg atctgggtcg ataacggcta caacatggtg   1440
gccattcagg aagagaaaaa ataccagcgc ctgtccggcg tcgagttcgg gccgatggat   1500
tttaaagcct atgccgaatc cttcggcgcg aaagggtttg ccgtggaaag cgccgaggcg   1560
ctggagccga ccctgcacgc ggcgatggac gtcgacggcc cggcggtggt ggccattccg   1620
gtggattatc gcgataaccc gctgctgatg ggccagctgc atctgagtca gattctgtaa   1680
```

<210> SEQ ID NO 4
<211> LENGTH: 559
<212> TYPE: PRT
<213> ORGANISM: Klebsiella pneumoniae

<400> SEQUENCE: 4

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30
```

```
Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Val Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285

Glu Pro Ala Met Trp Asn Ser Gly Asn Ala Thr Leu Val His Ile Asp
    290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
        355                 360                 365

Phe Ala Leu His Pro Leu Arg Ile Val Arg Ala Met Gln Asp Ile Val
    370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
        435                 440                 445

Gly Phe Leu Gln Ser Ser Met Glu Leu Glu Thr Ala Val Arg Leu Lys
```

```
    450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu His Ala Ala
        515                 520                 525

Met Asp Val Asp Gly Pro Ala Val Val Ala Ile Pro Val Asp Tyr Arg
    530                 535                 540

Asp Asn Pro Leu Leu Met Gly Gln Leu His Leu Ser Gln Ile Leu
545                 550                 555


<210> SEQ ID NO 5
<211> LENGTH: 771
<212> TYPE: DNA
<213> ORGANISM: Klebsiella pneumoniae

<400> SEQUENCE: 5

atgaaaaaag tcgcacttgt taccggcgcc ggccagggga ttggtaaagc tatcgccctt      60

cgtctggtga aggatggatt tgccgtggcc attgccgatt ataacgacgc caccgccaaa     120

gcggtcgcct cggaaatcaa ccaggccggc ggacacgccg tggcggtgaa agtggatgtc     180

tccgaccgcg atcaggtatt tgccgccgtt gaacaggcgc gcaaaaacgct gggcggcttc     240

gacgtcatcg tcaataacgc cggtgtggca ccgtctacgc cgatcgagtc cattaccccg     300

gagattgtcg acaaagtcta caacatcaac gtcaaagggg tgatctgggg tattcaggcg     360

gcggtcgagg cctttaagaa agaggggcac ggcgggaaaa tcatcaacgc ctgttcccag     420

gccggccacg tcggcaaccc ggagctggcg gtgtatagct ccagtaaatt cgcggtacgc     480

ggcttaaccc agaccgccgc tcgcgacctc gcgccgctgg gcatcacggt caacggctac     540

tgcccgggga ttgtcaaaac gccaatgtgg gccgaaattg accgccaggt gtccgaagcc     600

gccggtaaac cgctgggcta cggtaccgcc gagttcgcca aacgcatcac tctcggtcgt     660

ctgtccgagc cggaagatgt cgccgcctgc gtctcctatc ttgccagccc ggattctgat     720

tacatgaccg gtcagtcgtt gctgatcgac ggcgggatgg tatttaacta a              771


<210> SEQ ID NO 6
<211> LENGTH: 256
<212> TYPE: PRT
<213> ORGANISM: Klebsiella pneumoniae

<400> SEQUENCE: 6

Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Lys Ala Val Ala Ser Glu Ile Asn Gln
        35                  40                  45

Ala Gly Gly His Ala Val Ala Val Lys Val Asp Val Ser Asp Arg Asp
    50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95
```

```
Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
                245                 250                 255
```

<210> SEQ ID NO 7
<211> LENGTH: 1665
<212> TYPE: DNA
<213> ORGANISM: Klebsiella oxytoca

<400> SEQUENCE: 7

```
atgagatcga aaagatttga agcactggcg aaacgccctg tgaatcagga cggcttcgtt     60

aaggagtgga tcgaagaagg ctttatcgcg atggaaagcc cgaacgaccc aaaaccgtcg    120

attaaaatcg ttaacggcgc ggtgaccgag ctggacggga aaccggtaag cgattttgac    180

ctgatcgacc actttatcgc ccgctacggt atcaacctga accgcgccga agaagtgatg    240

gcgatggatt cggtcaagct ggccaacatg ctgtgcgatc cgaacgttaa acgcagcgaa    300

atcgtcccgc tgaccaccgc gatgacgccg gcgaaaattg tcgaagtggt ttcgcatatg    360

aacgtcgtcg agatgatgat ggcgatgcag aaaatgcgcg cccgccgcac cccgtcccag    420

caggcgcacg tcaccaacgt caaagataac ccggtacaga ttgccgccga cgccgccgaa    480

ggggcatggc gcggatttga cgaacaggaa accaccgttg cggtagcgcg ctatgcgccg    540

ttcaacgcca tcgcgctgct ggtgggctcg caggtaggcc gtccgggcgt gctgacgcag    600

tgctcgctgg aagaagccac cgagctgaag ctcggcatgc tgggccacac ctgctacgcc    660

gaaaccatct ccgtctacgg caccgagccg gtctttaccg acggcgacga cacgccgtgg    720

tcgaagggct tcctcgcctc gtcctacgcc tctcgcgggc tgaaaatgcg ctttacctcc    780

ggctccggct cggaagtgca gatgggctac gccgaaggca aatccatgct ttatctggaa    840

gcgcgctgca tctacatcac caaagccgcg ggcgtacagg gtctgcaaaa cggttccgta    900

agctgcatcg gcgtgccgtc tgcggtgcct tccggcattc gcgcggtgct ggcggaaaac    960

ctgatctgtt cgtcgctgga tctggagtgc gcctccagca acgaccagac cttcacccac   1020

tccgatatgc gtcgtaccgc gcgcctgctg atgcagttcc tgccgggcac cgactttatc   1080

tcctccggtt attccgcggt gccgaactac gacaacatgt tcgccggctc caacgaagat   1140

gccgaagact ttgacgacta caacgtcatc cagcgcgacc tgaaggtgga cggcggtttg   1200

cgtccggttc gcgaagagga cgtcatcgcc atccgtaaca aagccgcccg cgcgctgcag   1260
```

```
gccgtgtttg ccggaatggg gctgccgccg attaccgatg aagaagttga agccgcgacc   1320

tacgcccacg gttcgaaaga tatgccggag cgcaacatcg tcgaagacat caagttcgcc   1380

caggaaatca tcaataaaaa ccgcaacggt ctggaagtgg tgaaagcgct ggcgcagggc   1440

ggattcaccg acgtggccca ggacatgctc aacatccaga aagctaagct gaccggggac   1500

tacctgcata cctccgcgat tatcgtcggc gacgggcagg tgctgtcagc cgtcaacgac   1560

gtcaacgact atgccggtcc ggcaacgggc tatcgcctgc agggcgaacg ctgggaagag   1620

attaaaaaca tccctggcgc tcttgatccc aacgagattg attaa                   1665


<210> SEQ ID NO 8
<211> LENGTH: 554
<212> TYPE: PRT
<213> ORGANISM: Klebsiella oxytoca

<400> SEQUENCE: 8

Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Asp Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
    290                 295                 300

Val Pro Ser Ala Val Pro Ser Gly Ile Arg Ala Val Leu Ala Glu Asn
```

```
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Leu Leu Met Gln
            340                 345                 350

Phe Leu Pro Gly Thr Asp Phe Ile Ser Ser Gly Tyr Ser Ala Val Pro
        355                 360                 365

Asn Tyr Asp Asn Met Phe Ala Gly Ser Asn Glu Asp Ala Glu Asp Phe
    370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
        435                 440                 445

Pro Glu Arg Asn Ile Val Glu Asp Ile Lys Phe Ala Gln Glu Ile Ile
    450                 455                 460

Asn Lys Asn Arg Asn Gly Leu Glu Val Val Lys Ala Leu Ala Gln Gly
465                 470                 475                 480

Gly Phe Thr Asp Val Ala Gln Asp Met Leu Asn Ile Gln Lys Ala Lys
                485                 490                 495

Leu Thr Gly Asp Tyr Leu His Thr Ser Ala Ile Ile Val Gly Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Glu Ile Lys Asn Ile
    530                 535                 540

Pro Gly Ala Leu Asp Pro Asn Glu Ile Asp
545                 550
```

<210> SEQ ID NO 9
<211> LENGTH: 675
<212> TYPE: DNA
<213> ORGANISM: Klebsiella oxytoca

<400> SEQUENCE: 9

```
atggaaatta atgaaaaatt gctgcgccag ataattgaag acgtgctcag cgagatgaag     60

ggcagcgata aaccggtctc gtttaatgcg ccggcggcct ccgcggcgcc ccaggccacg    120

ccgcccgccg gcgacggctt cctgacggaa gtgggcgaag cgcgtcaggg aacccagcag    180

gacgaagtga ttatcgccgt cggcccggct ttcggcctgg cgcagaccgt caatatcgtc    240

ggcatcccgc ataagagcat tttgcgcgaa gtcattgccg gtattgaaga agaaggcatt    300

aaggcgcgcg tgattcgctg ctttaaatcc tccgacgtgg ccttcgtcgc cgttgaaggt    360

aatcgcctga gcggctccgg catctctatc ggcatccagt cgaaaggcac cacggtgatc    420

caccagcagg ggctgccgcc gctctctaac ctggagctgt tcccgcaggc gccgctgctg    480

accctggaaa cctatcgcca gatcggcaaa aacgccgccc gctatgcgaa acgcgaatcg    540

ccgcagccgg tcccgacgct gaatgaccag atggcgcggc cgaagtacca ggcgaaatcg    600

gccattttgc acattaaaga gaccaagtac gtggtgacgg gcaaaaaccc gcaggaactg    660

cgcgtggcgc tttga                                                      675
```

<210> SEQ ID NO 10
<211> LENGTH: 224
<212> TYPE: PRT
<213> ORGANISM: Klebsiella oxytoca

<400> SEQUENCE: 10

```
Met Glu Ile Asn Glu Lys Leu Leu Arg Gln Ile Ile Glu Asp Val Leu
1               5                   10                  15

Ser Glu Met Lys Gly Ser Asp Lys Pro Val Ser Phe Asn Ala Pro Ala
            20                  25                  30

Ala Ser Ala Ala Pro Gln Ala Thr Pro Pro Ala Gly Asp Gly Phe Leu
        35                  40                  45

Thr Glu Val Gly Glu Ala Arg Gln Gly Thr Gln Gln Asp Glu Val Ile
    50                  55                  60

Ile Ala Val Gly Pro Ala Phe Gly Leu Ala Gln Thr Val Asn Ile Val
65                  70                  75                  80

Gly Ile Pro His Lys Ser Ile Leu Arg Glu Val Ile Ala Gly Ile Glu
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220
```

<210> SEQ ID NO 11
<211> LENGTH: 522
<212> TYPE: DNA
<213> ORGANISM: Klebsiella oxytoca

<400> SEQUENCE: 11

```
atgaataccg acgcaattga atcgatggta cgcgacgtat tgagccgcat gaacagcctg      60

cagggcgagg cgcctgcggc ggctccggcg gctggcggcg cgtcccgtag cgccagggtc     120

agcgactacc cgctggcgaa caagcacccg gaatgggtga aaaccgccac caataaaacg     180

ctggacgact ttacgctgga aaacgtgctg agcaataaag tcaccgccca ggatatgcgt     240

attaccccgg aaaccctgcg cttacaggct tctattgcca aagacgcggg ccgcgaccgg     300

ctggcgatga acttcgagcg cgccgccgag ctgaccgcgg taccggacga tcgcattctt     360

gaaatctaca acgccctccg cccctatcgc tcgacgaaag aggagctgct ggcgatcgcc     420

gacgatctcg aaagccgcta tcaggcgaag atttgcgccg ctttcgttcg cgaagcggcc     480

acgctgtacg tcgagcgtaa aaaactcaaa ggcgacgatt aa                        522
```

<210> SEQ ID NO 12
<211> LENGTH: 173
<212> TYPE: PRT
<213> ORGANISM: Klebsiella oxytoca

<400> SEQUENCE: 12

```
Met Asn Thr Asp Ala Ile Glu Ser Met Val Arg Asp Val Leu Ser Arg
1               5                   10                  15

Met Asn Ser Leu Gln Gly Glu Ala Pro Ala Ala Ala Pro Ala Ala Gly
            20                  25                  30

Gly Ala Ser Arg Ser Ala Arg Val Ser Asp Tyr Pro Leu Ala Asn Lys
        35                  40                  45

His Pro Glu Trp Val Lys Thr Ala Thr Asn Lys Thr Leu Asp Asp Phe
    50                  55                  60

Thr Leu Glu Asn Val Leu Ser Asn Lys Val Thr Ala Gln Asp Met Arg
65                  70                  75                  80

Ile Thr Pro Glu Thr Leu Arg Leu Gln Ala Ser Ile Ala Lys Asp Ala
                85                  90                  95

Gly Arg Asp Arg Leu Ala Met Asn Phe Glu Arg Ala Ala Glu Leu Thr
            100                 105                 110

Ala Val Pro Asp Asp Arg Ile Leu Glu Ile Tyr Asn Ala Leu Arg Pro
        115                 120                 125

Tyr Arg Ser Thr Lys Glu Glu Leu Leu Ala Ile Ala Asp Asp Leu Glu
    130                 135                 140

Ser Arg Tyr Gln Ala Lys Ile Cys Ala Ala Phe Val Arg Glu Ala Ala
145                 150                 155                 160

Thr Leu Tyr Val Glu Arg Lys Lys Leu Lys Gly Asp Asp
                165                 170
```

<210> SEQ ID NO 13
<211> LENGTH: 1041
<212> TYPE: DNA
<213> ORGANISM: Rhodococcus ruber

<400> SEQUENCE: 13

```
atgaaagccc tccagtacac cgagatcggc tccgagccgg tcgtcgtcga cgtccccacc     60

ccggcgcccg ggccgggtga gatcctgctg aaggtcaccg cggccggctt gtgccactcg    120

gacatcttcg tgatggacat gccggcagag cagtacatct acggtcttcc cctcaccctc    180

ggccacgagg gcgtcggcac cgtcgccgaa ctcggcgccg gcgtcaccgg attcgagacg    240

ggggacgccg tcgccgtgta cgggccgtgg gggtgcggtg cgtgccacgc gtgcgcgcgc    300

ggccgggaga actactgcac ccgcgccgcc gagctgggca tcaccccgcc cggtctcggc    360

tcgcccgggt cgatggccga gtacatgatc gtcgactcgg cgcgccacct cgtcccgatc    420

ggggacctcg accccgtcgc ggcggttccg ctcaccgacg cgggcctgac gccgtaccac    480

gcgatctcgc gggtcctgcc cctgctggga cccggctcga ccgcggtcgt catcggggtc    540

ggcggactcg ggcacgtcgg catccagatc ctgcgcgccg tcagcgcggc ccgcgtgatc    600

gccgtcgatc tcgacgacga ccgactcgcg ctcgcccgcg aggtcggcgc cgacgcggcg    660

gtgaagtcgg gcgccggggc ggcggacgcg atccgggagc tgaccggcgg tgagggcgcg    720

acggcggtgt tcgacttcgt cggcgcccag tcgacgatcg acacggcgca gcaggtggtc    780

gcgatcgacg ggcacatctc ggtggtcggc atccatgccg gcgcccacgc caaggtcggc    840

ttcttcatga tcccgttcgg cgcgtccgtc gtgacgccgt actggggcac gcggtccgag    900

ctgatggacg tcgtggacct ggcccgtgcc ggccggctcg acatccacac cgagacgttc    960

accctcgacg agggacccac ggcctaccgg cggctacgcg agggcagcat ccgcggccgc   1020

ggggtggtcg tcccgggctg a                                                1041
```

<210> SEQ ID NO 14
<211> LENGTH: 346
<212> TYPE: PRT
<213> ORGANISM: Klebsiella oxytoca

<400> SEQUENCE: 14

```
Met Lys Ala Leu Gln Tyr Thr Glu Ile Gly Ser Glu Pro Val Val Val
1               5                   10                  15

Asp Val Pro Thr Pro Ala Pro Gly Pro Gly Glu Ile Leu Leu Lys Val
            20                  25                  30

Thr Ala Ala Gly Leu Cys His Ser Asp Ile Phe Val Met Asp Met Pro
        35                  40                  45

Ala Glu Gln Tyr Ile Tyr Gly Leu Pro Leu Thr Leu Gly His Glu Gly
    50                  55                  60

Val Gly Thr Val Ala Glu Leu Gly Ala Gly Val Thr Gly Phe Glu Thr
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Glu Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
    130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Asp Arg
        195                 200                 205

Leu Ala Leu Ala Arg Glu Val Gly Ala Asp Ala Ala Val Lys Ser Gly
    210                 215                 220

Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255

Gln Gln Val Val Ala Ile Asp Gly His Ile Ser Val Val Gly Ile His
            260                 265                 270

Ala Gly Ala His Ala Lys Val Gly Phe Phe Met Ile Pro Phe Gly Ala
        275                 280                 285

Ser Val Val Thr Pro Tyr Trp Gly Thr Arg Ser Glu Leu Met Asp Val
    290                 295                 300

Val Asp Leu Ala Arg Ala Gly Arg Leu Asp Ile His Thr Glu Thr Phe
305                 310                 315                 320

Thr Leu Asp Glu Gly Pro Thr Ala Tyr Arg Arg Leu Arg Glu Gly Ser
                325                 330                 335

Ile Arg Gly Arg Gly Val Val Val Pro Gly
            340                 345
```

<210> SEQ ID NO 15
<211> LENGTH: 29
<212> TYPE: DNA
<213> ORGANISM: Artificial Sequence
<220> FEATURE:

<223> OTHER INFORMATION: Primer

<400> SEQUENCE: 15
caccatggac aaacagtatc cggtacgcc 29

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
cgaagggcga tagctttacc aatcc 25

<210> SEQ ID NO 17
<211> LENGTH: 32
<212> TYPE: DNA
<213> ORGANISM: Artificial Sequence
<220> FEATURE:
<223> OTHER INFORMATION: Primer

<400> SEQUENCE: 17
caccatgaat cattctgctg aatgcacctg cg 32

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
gatactgttt gtccatgtga cc 22

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
caccatgaaa aaagtcgcac ttgttacc 28

<210> SEQ ID NO 20
<211> LENGTH: 15
<212> TYPE: DNA
<213> ORGANISM: Artificial Sequence
<220> FEATURE:
<223> OTHER INFORMATION: Primer

<400> SEQUENCE: 20
ttagttaaat accat 15

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
caccatgaga tcgaaaagat ttg 23

<210> SEQ ID NO 22

<211> LENGTH: 22
<212> TYPE: DNA
<213> ORGANISM: Artificial Sequence
<220> FEATURE:
<223> OTHER INFORMATION: Primer

<400> SEQUENCE: 22
cttagagaag ttaatcgtcg cc 22

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
caccatgaaa gccctccagt acacc 25

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
cgtcgtgtca tgcccggg 18

<210> SEQ ID NO 25
<211> LENGTH: 36
<212> TYPE: DNA
<213> ORGANISM: Artificial Sequence
<220> FEATURE:
<223> OTHER INFORMATION: Primer

<400> SEQUENCE: 25
gatcgaattc gtttaaactt agttttctac cgcacg 36

<210> SEQ ID NO 26
<211> LENGTH: 34
<212> TYPE: DNA
<213> ORGANISM: Artificial Sequence
<220> FEATURE:
<223> OTHER INFORMATION: Primer

<400> SEQUENCE: 26
gatcgcatgc aagctttcat atagtcggaa ttcc 34

<210> SEQ ID NO 27
<211> LENGTH: 43
<212> TYPE: DNA
<213> ORGANISM: Artificial Sequence
<220> FEATURE:
<223> OTHER INFORMATION: Primer

<400> SEQUENCE: 27
gatcgaattc gtttaaacaa aggaggtctg attcatgaga tcg 43

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28

```
gatcggattc ttaatcgtcg cc                                              22


<210> SEQ ID NO 29
<211> LENGTH: 36
<212> TYPE: DNA
<213> ORGANISM: Artificial Sequence
<220> FEATURE:
<223> OTHER INFORMATION: Primer

<400> SEQUENCE: 29

gatcggatcc aaaggaggtc gggcgcatga aagccc                               36


<210> SEQ ID NO 30
<211> LENGTH: 32
<212> TYPE: DNA
<213> ORGANISM: Artificial Sequence
<220> FEATURE:
<223> OTHER INFORMATION: Primer

<400> SEQUENCE: 30

gatctctaga aagctttcag cccgggacga cc                                   32


<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31

actttctttc gcctgtttca c                                               21


<210> SEQ ID NO 32
<211> LENGTH: 79
<212> TYPE: DNA
<213> ORGANISM: Artificial Sequence
<220> FEATURE:
<223> OTHER INFORMATION: Primer

<400> SEQUENCE: 32

catgaagctt gtttaaactc ggtgaccttg aaaataatga aaacttatat tgttttgaaa     60

ataatgaaaa cttatattg                                                  79


<210> SEQ ID NO 33
<211> LENGTH: 39
<212> TYPE: DNA
<213> ORGANISM: Artificial Sequence
<220> FEATURE:
<223> OTHER INFORMATION: Primer BABC F

<400> SEQUENCE: 33

gagctcgaat tcaaaggagg aagtgtatat gaatcattc                            39


<210> SEQ ID NO 34
<211> LENGTH: 35
<212> TYPE: DNA
<213> ORGANISM: Artificial Sequence
<220> FEATURE:
<223> OTHER INFORMATION: Primer BAB R

<400> SEQUENCE: 34

ggatcctcta gaattagtta aataccatcc cgccg                                35


<210> SEQ ID NO 35
<211> LENGTH: 17
<212> TYPE: DNA
```

```
<213> ORGANISM: Artificial Sequence
<220> FEATURE:
<223> OTHER INFORMATION: Primer M13 Forward

<400> SEQUENCE: 35

gtaaaacgac ggccagt                                                    17


<210> SEQ ID NO 36
<211> LENGTH: 16
<212> TYPE: DNA
<213> ORGANISM: Artificial Sequence
<220> FEATURE:
<223> OTHER INFORMATION: Primer M13 Reverse

<400> SEQUENCE: 36

aacagctatg accatg                                                     16


<210> SEQ ID NO 37
<211> LENGTH: 20
<212> TYPE: DNA
<213> ORGANISM: Artificial Sequence
<220> FEATURE:
<223> OTHER INFORMATION: Primer N83 SeqF2

<400> SEQUENCE: 37

gctggattac cagctcgacc                                                 20


<210> SEQ ID NO 38
<211> LENGTH: 20
<212> TYPE: DNA
<213> ORGANISM: Artificial Sequence
<220> FEATURE:
<223> OTHER INFORMATION: Primer N83SeqF3

<400> SEQUENCE: 38

cggacgcatt accggcaaag                                                 20


<210> SEQ ID NO 39
<211> LENGTH: 20
<212> TYPE: DNA
<213> ORGANISM: Artificial Sequence
<220> FEATURE:
<223> OTHER INFORMATION: Primer N84 SeqR4

<400> SEQUENCE: 39

cgaagcgaga gaagttatcc                                                 20


<210> SEQ ID NO 40
<211> LENGTH: 38
<212> TYPE: DNA
<213> ORGANISM: Artificial Sequence
<220> FEATURE:
<223> OTHER INFORMATION: Primer BC Spe F

<400> SEQUENCE: 40

actagtaaag gaggaaagag tatgaagaag gtcgcact                             38


<210> SEQ ID NO 41
<211> LENGTH: 26
<212> TYPE: DNA
<213> ORGANISM: Artificial Sequence
<220> FEATURE:
<223> OTHER INFORMATION: Primer BC Xba R

<400> SEQUENCE: 41

tctagaaagc aggggcaagc catgtc                                          26
```

<210> SEQ ID NO 42
<211> LENGTH: 20
<212> TYPE: DNA
<213> ORGANISM: Artificial Sequence
<220> FEATURE:
<223> OTHER INFORMATION: Primer Trc F

<400> SEQUENCE: 42
ttgacaatta atcatccggc 20

<210> SEQ ID NO 43
<211> LENGTH: 20
<212> TYPE: DNA
<213> ORGANISM: Artificial Sequence
<220> FEATURE:
<223> OTHER INFORMATION: Primer Trc R

<400> SEQUENCE: 43
cttctctcat ccgccaaaac 20

<210> SEQ ID NO 44
<211> LENGTH: 38
<212> TYPE: DNA
<213> ORGANISM: Artificial Sequence
<220> FEATURE:
<223> OTHER INFORMATION: Primer DDo For

<400> SEQUENCE: 44
aagcttaaag gaggctgatt catgagatcg aaaagatt 38

<210> SEQ ID NO 45
<211> LENGTH: 27
<212> TYPE: DNA
<213> ORGANISM: Artificial Sequence
<220> FEATURE:
<223> OTHER INFORMATION: Primer DDo Rev

<400> SEQUENCE: 45
tctagattat tcatcctgct gttctcc 27

<210> SEQ ID NO 46
<211> LENGTH: 22
<212> TYPE: DNA
<213> ORGANISM: Artificial Sequence
<220> FEATURE:
<223> OTHER INFORMATION: Primer DDko seq F2

<400> SEQUENCE: 46
gcatggcgcg gatttgacga ac 22

<210> SEQ ID NO 47
<211> LENGTH: 22
<212> TYPE: DNA
<213> ORGANISM: Artificial Sequence
<220> FEATURE:
<223> OTHER INFORMATION: Primer DDko seq F5

<400> SEQUENCE: 47
cattaaagag accaagtacg tg 22

<210> SEQ ID NO 48
<211> LENGTH: 24
<212> TYPE: DNA
<213> ORGANISM: Artificial Sequence
<220> FEATURE:
<223> OTHER INFORMATION: Primer DDko seq F7

<400> SEQUENCE: 48
atatcctggt ggtgtcgtcg gcgt 24

<210> SEQ ID NO 49
<211> LENGTH: 22
<212> TYPE: DNA
<213> ORGANISM: Artificial Sequence
<220> FEATURE:
<223> OTHER INFORMATION: Primer DDko seq F9

<400> SEQUENCE: 49
tctttgtcac caacgccctg cg 22

<210> SEQ ID NO 50
<211> LENGTH: 22
<212> TYPE: DNA
<213> ORGANISM: Artificial Sequence
<220> FEATURE:
<223> OTHER INFORMATION: Primer DDko seq R1

<400> SEQUENCE: 50
gcccaccgcg ctcgccgccg cg 22

<210> SEQ ID NO 51
<211> LENGTH: 22
<212> TYPE: DNA
<213> ORGANISM: Artificial Sequence
<220> FEATURE:
<223> OTHER INFORMATION: Primer DDko seq R3

<400> SEQUENCE: 51
cccccaggat ggcggcttcg gc 22

<210> SEQ ID NO 52
<211> LENGTH: 22
<212> TYPE: DNA
<213> ORGANISM: Artificial Sequence
<220> FEATURE:
<223> OTHER INFORMATION: Primer DDko seq R7

<400> SEQUENCE: 52
gggccgacgg cgataatcac tt 22

<210> SEQ ID NO 53
<211> LENGTH: 22
<212> TYPE: DNA
<213> ORGANISM: Artificial Sequence
<220> FEATURE:
<223> OTHER INFORMATION: Primer DDko seq R10

<400> SEQUENCE: 53
ttcttcgatc cactccttaa cg 22

<210> SEQ ID NO 54
<211> LENGTH: 56
<212> TYPE: DNA
<213> ORGANISM: Artificial Sequence
<220> FEATURE:
<223> OTHER INFORMATION: Primer ChnA F

<400> SEQUENCE: 54
catcaattga ctacgtagtc gtacgtgtaa ggaggtttga aatggaaaaa attatg 56

<210> SEQ ID NO 55
<211> LENGTH: 40
<212> TYPE: DNA

<213> ORGANISM: Artificial Sequence
<220> FEATURE:
<223> OTHER INFORMATION: Primer ChnA R

<400> SEQUENCE: 55
catgctagcc ccgggtatct tctactcatt ttttatttcg 40

<210> SEQ ID NO 56
<211> LENGTH: 22
<212> TYPE: DNA
<213> ORGANISM: Artificial Squence
<220> FEATURE:
<223> OTHER INFORMATION: Primer chnSeq F1

<400> SEQUENCE: 56
ctcaacaggg tgtaagtgta gt 22

<210> SEQ ID NO 57
<211> LENGTH: 22
<212> TYPE: DNA
<213> ORGANISM: Artificial Sequence
<220> FEATURE:
<223> OTHER INFORMATION: Primer chnSeq R1

<400> SEQUENCE: 57
cgttttgata tagccaggat gt 22

<210> SEQ ID NO 58
<211> LENGTH: 35
<212> TYPE: DNA
<213> ORGANISM: Artificial Sequence
<220> FEATURE:
<223> OTHER INFORMATION: Primer Top ter F1

<400> SEQUENCE: 58
ctagaagtca aaagcctccg accggaggct tttga 35

<210> SEQ ID NO 59
<211> LENGTH: 60
<212> TYPE: DNA
<213> ORGANISM: Artificial Sequence
<220> FEATURE:
<223> OTHER INFORMATION: Primer Top ter F2

<400> SEQUENCE: 59
ctgctcgagt tgctagcaag tttaaacaaa aaaaagcccg ctcattaggc gggctgagct 60

<210> SEQ ID NO 60
<211> LENGTH: 37
<212> TYPE: DNA
<213> ORGANISM: Artificial Sequence
<220> FEATURE:
<223> OTHER INFORMATION: Primer Bot ter R1

<400> SEQUENCE: 60
cagcccgcct aatgagcggg cttttttttg tttaaac 37

<210> SEQ ID NO 61
<211> LENGTH: 50
<212> TYPE: DNA
<213> ORGANISM: Artificial Sequence
<220> FEATURE:
<223> OTHER INFORMATION: Primer Bot ter R2

<400> SEQUENCE: 61
ttgctagcaa ctcgagcagt caaaagcctc cggtcggagg cttttgactt 50

<210> SEQ ID NO 62
<211> LENGTH: 22
<212> TYPE: DNA
<213> ORGANISM: Artificial Sequence
<220> FEATURE:
<223> OTHER INFORMATION: Primer pCL1925 vec F

<400> SEQUENCE: 62
cggtatcatc aacaggctta cc 22

<210> SEQ ID NO 63
<211> LENGTH: 22
<212> TYPE: DNA
<213> ORGANISM: Artificial Sequence
<220> FEATURE:
<223> OTHER INFORMATION: Primer pCL1925 vec R1

<400> SEQUENCE: 63
agggttttcc cagtcacgac gt 22

<210> SEQ ID NO 64
<211> LENGTH: 22
<212> TYPE: DNA
<213> ORGANISM: Artificial Sequence
<220> FEATURE:
<223> OTHER INFORMATION: Primer pCL1925 vec R2

<400> SEQUENCE: 64
cgcaatagtt ggcgaagtaa tc 22

<210> SEQ ID NO 65
<211> LENGTH: 20
<212> TYPE: DNA
<213> ORGANISM: Artificial Sequence
<220> FEATURE:
<223> OTHER INFORMATION: Primer N84 Seq R2

<400> SEQUENCE: 65
gcatcgagat tatcgggatg 20

<210> SEQ ID NO 66
<211> LENGTH: 208
<212> TYPE: DNA
<213> ORGANISM: Escherichia coli

<400> SEQUENCE: 66
atcgcccgca ttcttgccgc atcttccccc ggcgtcacac cgaagtaacg tttaaactca 60
cggctgtgta ggctggagct gcttcgaagt tcctatactt tctagagaat aggaacttcg 120
gaataggaac taaggaggat attcatatga ttacgttgga tgtcagccgc cgtatatacg 180
aagccgcccg ctaagctttt tacgcctc 208

<210> SEQ ID NO 67
<211> LENGTH: 42
<212> TYPE: DNA
<213> ORGANISM: Artificial Squence
<220> FEATURE:
<223> OTHER INFORMATION: Promoter 1.6GI Variant

<400> SEQUENCE: 67
gcccttgaca atgccacatc ctgagcaaat aattcaacca ct 42

<210> SEQ ID NO 68
<211> LENGTH: 42
<212> TYPE: DNA

<213> ORGANISM: Artificial Sequence
<220> FEATURE:
<223> OTHER INFORMATION: Promoter 1.5 GI

<400> SEQUENCE: 68
gcccttgact atgccacatc ctgagcaaat aattcaacca ct 42

<210> SEQ ID NO 69
<211> LENGTH: 3240
<212> TYPE: DNA
<213> ORGANISM: Klebsiella oxytoca

<400> SEQUENCE: 69
ggcgcggtcc gccaggcggt cacctccgcg cgcgaaatcg gcaaaaccgt ccttgcgacc 60
ctcggtgctg aaccgaaaaa cgatcgcccg tcctacatct gatacccacg aggctgattc 120
atgagatcga aaagatttga agcactggcg aaacgccctg tgaatcagga cggcttcgtt 180
aaggagtgga tcgaagaagg ctttatcgcg atggaaagcc cgaacgaccc aaaaccgtcg 240
attaaaatcg ttaacggcgc ggtgaccgag ctggacggga aaccggtaag cgattttgac 300
ctgatcgacc actttatcgc ccgctacggt atcaacctga accgcgccga agaagtgatg 360
gcgatggatt cggtcaagct ggccaacatg ctgtgcgatc cgaacgttaa acgcagcgaa 420
atcgtcccgc tgaccaccgc gatgacgccg gcgaaaattg tcgaagtggt ttcgcatatg 480
aacgtcgtcg agatgatgat ggcgatgcag aaaatgcgcg cccgccgcac cccgtcccag 540
caggcgcacg tcaccaacgt caaagataac ccggtacaga ttgccgccga cgccgccgaa 600
ggggcatggc gcggatttga cgaacaggaa accaccgttg cggtagcgcg ctatgcgccg 660
ttcaacgcca tcgcgctgct ggtgggctcg caggtaggcc gtccgggcgt gctgacgcag 720
tgctcgctgg aagaagccac cgagctgaag ctcggcatgc tgggccacac ctgctacgcc 780
gaaaccatct ccgtctacgg caccgagccg gtctttaccg acggcgacga cacgccgtgg 840
tcgaagggct tcctcgcctc gtcctacgcc tctcgcgggc tgaaaatgcg ctttacctcc 900
ggctccggct cggaagtgca gatgggctac gccgaaggca aatccatgct ttatctggaa 960
gcgcgctgca tctacatcac caaagccgcg ggcgtacagg gtctgcaaaa cggttccgta 1020
agctgcatcg gcgtgccgtc tgcggtgcct tccggcattc gcgcggtgct ggcggaaaac 1080
ctgatctgtt cgtcgctgga tctggagtgc gcctccagca acgaccagac cttcacccac 1140
tccgatatgc gtcgtaccgc gcgcctgctg atgcagttcc tgccgggcac cgactttatc 1200
tcctccggtt attccgcggt gccgaactac gacaacatgt tcgccggctc caacgaagat 1260
gccgaagact ttgacgacta caacgtcatc cagcgcgacc tgaaggtgga cggcggtttg 1320
cgtccggttc gcgaagagga cgtcatcgcc atccgtaaca aagccgcccg cgcgctgcag 1380
gccgtgtttg ccggaatggg gctgccgccg attaccgatg aagaagttga agccgcgacc 1440
tacgcccacg gttcgaaaga tatgccggag cgcaacatcg tcgaagacat caagttcgcc 1500
caggaaatca tcaataaaaa ccgcaacggt ctggaagtgg tgaaagcgct ggcgcagggc 1560
ggattcaccg acgtggccca ggacatgctc aacatccaga aagctaagct gaccggggac 1620
tacctgcata cctccgcgat tatcgtcggc gacgggcagg tgctgtcagc cgtcaacgac 1680
gtcaacgact atgccggtcc ggcaacgggc tatcgcctgc agggcgaacg ctgggaagag 1740
attaaaaaca tccctggcgc tcttgatccc aacgagattg attaaggggt gagaaatgga 1800
aattaatgaa aaattgctgc gccagataat tgaagacgtg ctcagcgaga tgaagggcag 1860
cgataaaccg gtctcgttta atgcgccggc ggcctccgcg gcgccccagg ccacgccgcc 1920

```
cgccggcgac ggcttcctga cggaagtggg cgaagcgcgt cagggaaccc agcaggacga   1980

agtgattatc gccgtcggcc cggctttcgg cctggcgcag accgtcaata tcgtcggcat   2040

cccgcataag agcattttgc gcgaagtcat tgccggtatt gaagaagaag gcattaaggc   2100

gcgcgtgatt cgctgcttta aatcctccga cgtggccttc gtcgccgttg aaggtaatcg   2160

cctgagcggc tccggcatct ctatcggcat ccagtcgaaa ggcaccacgg tgatccacca   2220

gcaggggctg ccgccgctct ctaacctgga gctgttcccg caggcgccgc tgctgaccct   2280

ggaaacctat cgccagatcg gcaaaaacgc cgcccgctat gcgaaacgcg aatcgccgca   2340

gccggtcccg acgctgaatg accagatggc gcggccgaag taccaggcga aatcggccat   2400

tttgcacatt aaagagacca agtacgtggt gacgggcaaa aacccgcagg aactgcgcgt   2460

ggcgctttga taaaggataa ctccatgaat accgacgcaa ttgaatcgat ggtacgcgac   2520

gtattgagcc gcatgaacag cctgcagggc gaggcgcctg cggcggctcc ggcggctggc   2580

ggcgcgtccc gtagcgccag ggtcagcgac tacccgctgg cgaacaagca cccggaatgg   2640

gtgaaaaccg ccaccaataa aacgctggac gactttacgc tggaaaacgt gctgagcaat   2700

aaagtcaccg cccaggatat gcgtattacc ccggaaaccc tgcgcttaca ggcttctatt   2760

gccaaagacg cgggccgcga ccggctggcg atgaacttcg agcgcgccgc cgagctgacc   2820

gcggtaccgg acgatcgcat tcttgaaatc tacaacgccc tccgccccta tcgctcgacg   2880

aaagaggagc tgctggcgat cgccgacgat ctcgaaagcc gctatcaggc gaagatttgc   2940

gccgctttcg ttcgcgaagc ggccacgctg tacgtcgagc gtaaaaaact caaaggcgac   3000

gattaacttc tctaagtaat tcgagatgca ttgaggcggc aagtgagtga caaattcgtc   3060

tggaacgaat ttgaacagcc ataggctggc tttagtgagg gacagggatg tccctcataa   3120

ccccgatgag cttactgtag taagtgattc gggtgaaaga acgcagccaa caaaaaggca   3180

gtttgaagta cgacgagaaa aggggcatgt gatgcgatat atagctggca ttgatatcgg   3240
```

<210> SEQ ID NO 70
<211> LENGTH: 2640
<212> TYPE: DNA
<213> ORGANISM: Klebsiella oxytoca

<400> SEQUENCE: 70

```
acgtcgagcg taaaaaactc aaaggcgacg attaacttct ctaagtaatt cgagatgcat     60

tgaggcggca agtgagtgac aaattcgtct ggaacgaatt tgaacagcca taggctggct    120

ttagtgaggg acagggatgt ccctcataac cccgatgagc ttactgtagt aagtgattcg    180

ggtgaaagaa cgcagccaac aaaaaggcag tttgaagtac gacgagaaaa ggggcatgtg    240

atgcgatata tagctggcat tgatatcggc aactcatcga cggaagtcgc cctggcgacc    300

ctggatgagg ctggcgcgct gacgatcacc cacagcgcgc tggcggaaac caccggaatc    360

aaaggcacgt tgcgtaacgt gttcgggatt caggaggcgc tcgccctcgt cgccagaggc    420

gccgggatcg ccgtcagcga tatttcgctc atccgcatca acgaagcgac gccggtgatt    480

ggcgatgtgg cgatggaaac cattaccgaa accatcatca ccgaatcgac catgatcggc    540

cataacccga aaacgcccgg cggcgcgggg cttggcacag gcatcaccat tacgccgcag    600

gagctgctaa cccgcccggc ggacgcgccc tatatcctgg tggtgtcgtc ggcgttcgat    660

tttgccgata tcgccagcgt gattaacgct tccctgcgcg ccgggtatca gattaccggc    720

gtcattttac agcgcgacga tggcgtgctg gtcagcaacc ggctggaaaa accgctgccg    780

atcgttgacg aagtgctgta catcgaccgc attccgctgg ggatgctggc ggcgattgag    840
```

-continued

```
gtcgccgttc cggggaaggt catcgaaacc ctctctaacc cttacggcat cgccaccgtc    900

tttaacctca gccccgagga gacgaagaac atcgtcccga tggcccgggc gctgattggc    960

aaccgttccg ccgtggtggt caaaacgcca tccggcgacg tcaaagcgcg cgcgataccc   1020

gccggtaatc ttgagctgct ggcccagggc cgtagcgtgc gcgtggatgt ggccgccggc   1080

gccgaagcca tcatgaaagc ggtcgacggc tgcggcaggc tcgataacgt caccggcgaa   1140

tccggcacca atatcggcgg catgctggaa cacgtgcgcc agaccatggc cgagctgacc   1200

aacaagccga gcagcgaaat atttattcag gacctgctgg ccgttgatac ctcggtaccg   1260

gtgagcgtta ccggcggtct ggccggggag ttctcgctgg agcaggccgt gggcatcgcc   1320

tcgatggtga aatcggatcg cctgcagatg gcaatgatcg cccgcgaaat cgagcagaag   1380

ctcaatatcg acgtgcagat cggcggcgca gaggccgaag ccgccatcct gggggcgctg   1440

accacgccgg gcaccacccg accgctggcg atcctcgacc tcggcgcggg ctccaccgat   1500

gcctccatca tcaaccccaa aggcgacatc atcgccaccc atctcgccgg cgcaggcgac   1560

atggtgacga tgattattgc ccgcgagctg gggctggaag accgctatct ggcggaagag   1620

atcaagaagt acccgctggc taaggtggaa agcctgttcc atttacgcca cgaggacggc   1680

agcgtgcagt tcttctccac gccgctgccg cccgccgtgt tcgcccgcgt ctgcgtggtg   1740

aaagcggacg aactggtgcc gctgcccggc gatttagcgc tggaaaaagt gcgcgccatt   1800

cgccgcagcg ccaaagagcg ggtctttgtc accaacgccc tgcgcgcgct gcgtcaggtc   1860

agccccaccg gcaacattcg cgatattccg ttcgtggtgc tggtcggcgg ttcgtcgctg   1920

gatttcgaag tcccgcagct ggtcaccgat gcgctggcgc actaccgcct ggttgccgga   1980

cggggaaata ttcgcggcag cgagggcccc cgaaacgcgg tggccaccgg cctgattctc   2040

tcctggcata aggagtttgc gcatgaacgg taatcacagc gccccggcca tcgcgatcgc   2100

cgtcatcgac ggctgcgacg gcctgtggcg cgaagtgctg ctgggtatcg aagaggaagg   2160

tatccctttc cggctccagc atcacccggc cggagaggtc gtggacagcg cctggcaggc   2220

ggcgcgcagc tcgccgctgc tggtgggcat cgcctgcgac cgccatatgc tggtcgtgca   2280

ctacaagaat ttacccgcat cggcgccgct ttttacgctg atgcatcatc aggacagtca   2340

ggcccatcgc aacaccggta ataacgcggc acggctggtc aaggggatcc ctttccggga   2400

tctgaatagc gaagcaacag gagaacagca ggatgaataa cgcactggga ctggttgaaa   2460

caaaagggtt agtgggcgcc attgaggccg ccgatgcgat ggtgaaatcc gccaacgtgc   2520

agctggtcgg ctacgaaaaa attggctcgg gcctcgtcac cgtgatggtg cgcggcgacg   2580

tcggcgcggt caaagcggcg gtagacgcgg gcagcgcggc ggcgagcgcg gtgggcgaag   2640
```

<210> SEQ ID NO 71
<211> LENGTH: 756
<212> TYPE: DNA
<213> ORGANISM: Acinetobacter sp.

<400> SEQUENCE: 71

```
atggaaaaaa ttatgtcaaa taaattcaac aataaagtcg ctttaattac tggcgctggt     60

tcaggtattg gtaaaagcac cgcactgctt ttggctcaac agggtgtaag tgtagtggtt    120

tcagatatta acctggaagc agcacagaaa gttgtggacg aaattgtcgc tttaggcggg    180

aaagcggctg cgaataaggc caatactgct gagcctgaag acatgaaagc tgcagtcgag    240

tttgcggtca gcacttttgg tgcactgcat ttggccttca ataatgcggg aattctgggt    300

gaagttaact ccaccgaaga attgagcatt gaaggatggc gtcgtgtgat tgatgtgaac    360
```

```
ttgaatgcgg ttttctacag catgcattat gaagttcctg caatcttggc cgcagggggc    420

ggagcgattg tcaataccgc ttctattgca ggcttgatcg ggattcaaaa tatttcaggc    480

tatgtcgctg caaaacatgg cgtaacgggt ctaacgaaag cggcggcatt ggaatatgca    540

gataaaggga ttcgcattaa ttcagtacat cctggctata tcaaaacgcc tttgattgca    600

gaatttgaag aagcagaaat ggtaaaacta catccgattg gtcgtttggg acagccggaa    660

gaagttgctc aggttgttgc cttcctactt tctgatgatg cttcatttgt gaccggtagt    720

cagtatgtgg tcgatggtgc atatacctcg aaataa                              756
```

<210> SEQ ID NO 72
<211> LENGTH: 251
<212> TYPE: PRT
<213> ORGANISM: Acinetobacter sp.

<400> SEQUENCE: 72

```
Met Glu Lys Ile Met Ser Asn Lys Phe Asn Asn Lys Val Ala Leu Ile
1               5                   10                  15

Thr Gly Ala Gly Ser Gly Ile Gly Lys Ser Thr Ala Leu Leu Leu Ala
            20                  25                  30

Gln Gln Gly Val Ser Val Val Val Ser Asp Ile Asn Leu Glu Ala Ala
        35                  40                  45

Gln Lys Val Val Asp Glu Ile Val Ala Leu Gly Gly Lys Ala Ala Ala
    50                  55                  60

Asn Lys Ala Asn Thr Ala Glu Pro Glu Asp Met Lys Ala Ala Val Glu
65                  70                  75                  80

Phe Ala Val Ser Thr Phe Gly Ala Leu His Leu Ala Phe Asn Asn Ala
                85                  90                  95

Gly Ile Leu Gly Glu Val Asn Ser Thr Glu Glu Leu Ser Ile Glu Gly
            100                 105                 110

Trp Arg Arg Val Ile Asp Val Asn Leu Asn Ala Val Phe Tyr Ser Met
        115                 120                 125

His Tyr Glu Val Pro Ala Ile Leu Ala Ala Gly Gly Gly Ala Ile Val
    130                 135                 140

Asn Thr Ala Ser Ile Ala Gly Leu Ile Gly Ile Gln Asn Ile Ser Gly
145                 150                 155                 160

Tyr Val Ala Ala Lys His Gly Val Thr Gly Leu Thr Lys Ala Ala Ala
                165                 170                 175

Leu Glu Tyr Ala Asp Lys Gly Ile Arg Ile Asn Ser Val His Pro Gly
            180                 185                 190

Tyr Ile Lys Thr Pro Leu Ile Ala Glu Phe Glu Glu Ala Glu Met Val
        195                 200                 205

Lys Leu His Pro Ile Gly Arg Leu Gly Gln Pro Glu Glu Val Ala Gln
    210                 215                 220

Val Val Ala Phe Leu Leu Ser Asp Asp Ala Ser Phe Val Thr Gly Ser
225                 230                 235                 240

Gln Tyr Val Val Asp Gly Ala Tyr Thr Ser Lys
                245                 250
```

<210> SEQ ID NO 73
<211> LENGTH: 17417
<212> TYPE: DNA
<213> ORGANISM: Acinetobacter sp.

<400> SEQUENCE: 73

```
ctagcattta cgcgtgaggt aggtgggtag gtctgtaatg tgaagatcta cgaggaaatc     60
```

-continued

```
ggcgtcatga cgtgaggtcc agcgaaccgt cttgcgtaat ccgtcattca tggtgagtaa    120
cattgcccgt atttcgcgtt cagtatatag cagaccagca tgattaacga gatcctgggt    180
attttagtcc ggacacccaa agtcccatgc ggtcgccaga tccagtaagt cgactacgac    240
ttgctcatct gtagccaacc ccgcaatcac ttccacaatt ttcatcagtg gaaccggatt    300
gaagaaatgg aaacctgcga tacggccctg atgctgacac gcagatgcaa ttgaggtcac    360
agatagtgag gatgtatttg aaaccagaat agtttcttca gccacaatcc tttcaagctg    420
tttaaacaaa gtttgcttga tttccagatt ttcaataatt gcttctacga ccagatcaac    480
gccagcaacc tcttcaatgc tttccaagat aatcaatcgg gctaaggtat ccacaagctg    540
ctgttcggtt aactttcctt tagcagctag tttgtgcaag gttactttta atttttccaa    600
gccttgctca gcagcgccgg gtttagcatc aaataaacgg acctcaacac ccgcctgtgc    660
tgcaatttgc gcaataccca ttcccattac gcctgtgcca atcaaggcca tttttttgaat    720
cgtcatgact tattttcctt gatattgagg gcttcgcttt tcgaaaaagg cattgacgcc    780
ttctttttga tcttgtgtat caaataaaat ttggaaggct ttacgctcta atgccaaagc    840
accatcgagt ggcatattgg cacctagtgt tgtgacttct ttgatctgtt caacggcaat    900
cggtgagagt tgggcaatct gtgtcgcaat ttcaaccgct ttagcaaggg tttgatcatc    960
ctcaaccact tcggaaacca accccatttt gtcagcttct tctgcagaaa agatctttcc   1020
tgttaacact atttgcatgg ctttaaactt ccctaccgca cgcagtaagc gttgggtacc   1080
accagcacct ggcatcagcc ccaatttgac ttcaggctga ccaaactggg ctgattttcc   1140
ggcaataatg atgtctgcat gcattgcaag ttcacaccca ccacccaatg catatccatt   1200
cacagcagcc acaatcggtt tagggcaatc aataatggcc cgccagtact gttccgtatg   1260
gcgtaaatac atgtctacgg tttttgcagt ggtgaagtcc cggatatccg cacctgctgc   1320
aaatactttt tcaccaccag taatgacaat tgcgcggact gtatcagatg cagcgagctg   1380
ctcaaacatt gctgcgagct gttggcgcag ttccagattc aatgcatttc tagtatctgg   1440
acgatgtagt tcaacaatgg ccacaccatt actttgaata tctaaattca atatttcatt   1500
ttccataaca acctacatgt ttcgcatagc ggtttattta aaccaaatat acctgttttt   1560
ttgcaacaat aaagcccaca ggaacatagt tttaaattaa aaattggcta aaaatattta   1620
aaaaacacaa ataaaatacc gcacagcggt atttgatatc aatattattg catttatttt   1680
tccattctgt catattattt tcattccaaa gcattagatc accccctgcat gaagcagaga   1740
tggctaaatt tacctatcta atacaagggc ttaaaaatga ttcgcgatca agacacatta   1800
aatcagctgg ttgacatgat ccgtcagttt gtcgatggcg ttcttattcc caatgaagaa   1860
attgttgcgg aaaccgatga aattccagct gaaatcgtgc agcaaatgaa agaactgggt   1920
ctttttggtc tcaccattcc tgaggaatat gagggtcttg gcctgaccat ggaggaagag   1980
gtttacattg catttgaact gggacgtacc tctcctgctt tccgttcact gatcggcact   2040
aacaatggga tcggttcatc aggcttaatt attgatggct ccgaagagca gaaacagtat   2100
tttttgccac gtctggcaag tggtgaaatt attggttcat tctgtttaac tgaacctgat   2160
tccggttcag atgctgcctc tttaaaaacc acagcggtga aagatggtga tcattacatt   2220
ttaaatggca ctaagcgtta catcaccaat gcaccgcatg cgggtgtctt tactgtcatg   2280
gcacgtacca gtaccgaaat taaaggtaca ggtggaattt cagcctttat cgtggacagt   2340
aaaactcctg gtatttcctt gggtaaacgt gataagaaga tgggccaaaa aggtgcacat   2400
acctgtgatg tgatttttga aaactgtcgt attcctgcat ctgcactcat tggtggtgtt   2460
```

```
gaaggtgtag gttttaaaac tgcaatgaag gtacttgata aaggccgtat tcatattgct   2520
gcattaagtg taggtgctgc tacgcgtatg ctggaagatt ccctacaata tgccgttgag   2580
cgcaaacagt ttggtcaagc gattgcgaac ttccagttga ttcaaggtat gttagccgat   2640
tctaaagctg aaatttacgc agcaaaatgt atggtattag atgctgcccg acttcgtgat   2700
gctggacaga atgtcagcac ggaagcatct tgtgccaaga tgtttgccac tgaaatgtgt   2760
ggccgtgtcg cagatcgtgg cgtacagatc catggtggtg cgggttatat cagtgaatat   2820
gctattgagc gtttttaccg tgatgtacgt ttattccgtt tgtatgaagg tacaacgcaa   2880
atccaacagg tcattattgc ccgcaatatg atccgtgaag cgactcaata attgtataac   2940
aggtattgag tgtatctaaa aggacgggat tagtgattta agctataact tgaatactaa   3000
tcctgacttt ttgatggcaa ggctataaaa cctcctagct cattttatct ctaagctaat   3060
cacagctgaa agatattttc agtcttcatc cttaccagac agttcacaat acaaaattgg   3120
attttatgaa tatgcaagaa caagaaatcg aacgcgaatc aatggagttt gacgtcgtga   3180
ttgtcggcgc aggaccggcc ggtctttctg cagcgatcaa gatccgtcaa cttgcaattg   3240
aaaacaacct gaacgatctg tcggtttgtg tggtggaaaa aggctctgaa gtcggtgcgc   3300
acatcttgtc cggtgcggta ctggaaccac gtgccatgaa tgagctgttc ccgaactgga   3360
aggaagaagg tgcaccttta aatgttccag tgaccgaaga caagacctat ttcctgctct   3420
cggatgaaaa atcacaagaa gcgccacact ggatggtgcc taaaaccatg cataacgatg   3480
gcaactatgt tatctcgctc ggcaacgtag tgcgctggtt gggtcaaaaa gcggaagagc   3540
tggaagtatc tattttcccg ggctttgccg ctgctgaaat tctgtaccat gcagatggtt   3600
cggtgaaagg cattcaaacc ggtgacatgg gcattggcaa ggatggcgaa ccgacccata   3660
actttactcc gggctatgaa ctgcatgcca aatacaccct gtttgctgaa ggctgccgtg   3720
gccacctcgg caagcgttta attgccaaat acaacctcga taaagattca gatccacaac   3780
attacggtat cggtatcaaa gagctgtggg aaatcgaccc ggcgaaacac aagccaggtc   3840
tggtgatgca cggtgccggc tggccattgt ctgaaaccgg ttcttcaggc ggctggtggt   3900
tgtatcatgc ggaaaacaat caggtgactt tgggcatgat cgtcgatctg tcttacacca   3960
acccgcatat gtatccgttt atggaaatgc agcgctggaa aacccatccg ctgatcaagc   4020
agtatctgga aggtggcaaa cgtatttctt atggcgcgcg tgcggtaacc aaaggcggct   4080
ttaactcgct accgaaattt accttcccgg gcggatcgct gattggtgac gatgccggct   4140
tcctgaactt tgccaaaatc aagggctcac ataccgcgat gaaatccggc atgctctgcg   4200
gtgaagcagt gtttgaagcc attgctgccg gtgtggaaaa aggtggtgac cttgcggttg   4260
cgcgtgtgac ggaaggcgaa gacttgtttg ccaaaaaact gacttcttac accgacaagt   4320
tcaataatag ctggctgaaa gaagagctgt acaactcgcg taactttggc ccggccatgc   4380
acaagtttgg tcagtggctc ggtggtgcgt ttaactttat cgaccagaac gtgtttaagg   4440
tgccgtttac cctgcatgac ctggtgacgg atttcggtgc gctgaaaacc gtcgatgcgg   4500
tgaacttcaa gccgaattat ccaaaaccgg atggcaaact gacctttgac cgtctgtctt   4560
cggtgtttgt atccaacacg gtgcatgaag aaaaccagcc agcgcattta aaactgactg   4620
acacttcgat tccggtgaat gtcaacctgc caaaatggga tgaaccggcg cagcgctact   4680
gccccgcggg tgtatacgaa atcatggaaa atgatgacgg ttcgaaacgc ttccagatca   4740
atgcagccaa ctgtgtgcac tgcaagacct gtgacatcaa ggatccttca cagaacatca   4800
cctgggtaac accggaaggt ggtggtggtc caaactatcc gaatatgtaa gtctaatcac   4860
```

-continued

```
ttcaaggaag aggtttccca tttcccttct ttctagcaga tgaagaagct tgcaactaaa   4920
agagattgtt tggatcagtt acccaaaatc gttgaaaaga ttttaactct tcgattttta   4980
tttttaggt aatcctagcc ctctcggggg ctaggattaa aaattttaag ttattccaac   5040
acgaatgaca aattgttcaa tgcaaaataa aaacatacaa tatataaata tattttttaa   5100
ttaaaacata agattacaat aaaataagaa tttttatttg gagtttgttt tttttctaca   5160
atgatcatta tgtacaattt ttaggttcac cccatccaag ccttgtgatt gcattcctgc   5220
gattctttat tcaatgaata agcaatgcta ttaatcagca atgaataacc agcactgcag   5280
attttgaata aattcacatg tcgtaatgga gattatcatg tcacaaaaaa tggattttga   5340
tgctatcgtg attggtggtg gttttggcgg actttatgca gtcaaaaaat taagagacga   5400
gctcgaactt aaggttcagg cttttgataa agccacggat gtcgcaggta cttggtactg   5460
gaaccgttac ccaggtgcat tgtcggatac agaaacccac ctctactgct attcttggga   5520
taaagaatta ctacaatcgc tagaaatcaa gaaaaaatat gtgcaaggcc ctgatgtacg   5580
caagtattta cagcaagtgg ctgaaaagca tgatttaaag aagagctatc aattcaatac   5640
cgcggttcaa tcggctcatt acaacgaagc agatgccttg tgggaagtca ccactgaata   5700
tggtgataag tacacggcgc gtttcctcat cactgcttta ggcttattgt ctgcgcctaa   5760
cttgccaaac atcaaaggca ttaatcagtt taaaggtgag ctgcatcata ccagccgctg   5820
gccagatgac gtaagttttg aaggtaaacg tgtcggcgtg attggtacgg gttccaccgg   5880
tgttcaggtt attacggctg tggcacctct ggctaaacac ctcactgtct tccagcgttc   5940
tgcacaatac agcgttccaa ttggcaatga tccactgtct gaagaagatg ttaaaaagat   6000
caaagacaat tatgacaaaa tttgggatgg tgtatggaat tcagcccttg cctttggcct   6060
gaatgaaagc acagtgccag caatgagcgt atcagctgaa gaacgcaagg cagtttttga   6120
aaaggcatgg caaacaggtg gcggtttccg tttcatgttt gaaactttcg gtgatattgc   6180
caccaatatg gaagccaata tcgaagcgca aaatttcatt aagggtaaaa ttgctgaaat   6240
cgtcaaagat ccagccattg cacagaagct tatgccacag gatttgtatg caaaacgtcc   6300
gttgtgtgac agtggttact acaacacctt taaccgtgac aatgtccgtt tagaagatgt   6360
gaaagccaat ccgattgttg aaattaccga aaacggtgtg aaactcgaaa atggcgattt   6420
cgttgaatta gacatgctga tatgtgccac aggttttgat gccgtcgatg gcaactatgt   6480
gcgcatggac attcaaggta aaaacggctt ggccatgaaa gactactgga aagaaggtcc   6540
gtcgagctat atgggtgtca ccgtaaataa ctatccaaac atgttcatgg tgcttggacc   6600
gaatggcccg tttaccaacc tgccgccatc aattgaatca caggtggaat ggatcagtga   6660
taccattcaa tacacggttg aaaacaatgt tgaatccatt gaagcgacaa aagaagcgga   6720
agaacaatgg actcaaactt gcgccaatat tgcggaaatg accttattcc ctaaagcgca   6780
atcctggatt tttggtgcga atatcccggg caagaaaaac acggtttact tctatctcgg   6840
tggtttaaaa gaatatcgca gtgcgctagc caactgcaaa aaccatgcct atgaaggttt   6900
tgatattcaa ttacaacgtt cagatatcaa gcaacctgcc aatgcctaaa tatatggggg   6960
gcatccccca tattccattt tgtttaacat cagtcatatg ccagggatgt cttatcatga   7020
actatccaaa tatacottta tatatcaacg gtgagtttct agatcatacc aatagagacg   7080
tcaaagaagt ttttaatcca gtgaaccatg aatgtattgg actcatggcc tgtgcatcac   7140
aagcagacct ggactacgca cttgaaagtt cacaacaggc ttttctaagg tggaaaaaaa   7200
cttctcctat cacccgtagt gaaatcctca gaacctttgc gaaactagcg cgtgaaaaag   7260
```

```
cagcagaaat cgggcgcaat attacccttg atcaaggtaa gcccctgaaa gaagccattg   7320

cagaagtcac tgtctgtgca gaacatgcag aatggcatgc agaagaatgc cgacgcattt   7380

atggccgtgt tattccaccg cgtaacccaa atgtacagca actagtagtc agagaaccgc   7440

tgggcgtatg tctggcattt tcaccgtgga atttcccgtt taatcaggca attcgtaaaa   7500

tttctgctgc aattgctgcc ggctgcacca tcattgtgaa aggttctggc gacacaccaa   7560

gcgcggtata tgcgattgcc cagctatttc atgaggcggg tttgccgaat ggtgtgctga   7620

atgtgatttg gggtgactca aacttcattt ctgattacat gatcaaatcg ccgatcatcc   7680

aaaagatttc attcacaggc tcaaccccgg tgggtaaaaa attagcctcg caagcgagtc   7740

tgtatatgaa gccttgcacc atggaattgg gtggtcatgc accggtcatc gtctgtgatg   7800

atgctgatat tgatgccgct gttgaacatc tggtcggtta taaattccgt aatgcaggac   7860

aggtctgtgt atcaccaacc cgtttttatg tgcaggaagg tatttataag gaattttctg   7920

agaaagtggt gttaagagcc aaacagatca aagtgggttg tggcttagac gcatcctcag   7980

atatgggacc attggctcaa gctcgccgca tgcatgcaat gcaacaaatt gttgaagatg   8040

cggttcataa aggctcaaaa ttactgcttg gcggaaataa aatttctgac aaaggcaatt   8100

tttttgaacc aacggtactc ggtgacttgt gcaatgacac ccagtttatg aatgacgagc   8160

catttggtcc gatcattggt ttgatacctt ttgacacaat agaccatgtc ctggaagaag   8220

caaatcgatt accatttgga ttagcctctt acgcttttac cacatccagc aaaaatgcgc   8280

atcaaatctc atacggactg gaggctggca tggtttcgat taaccacatg ggattggcgc   8340

tcgctgaaac accttttggt ggtattaagg atagcggttt tggtagtgaa gggggtatcg   8400

aaacctttga cggttacctc agaaccaaat ttattacgca actcaattag aaatggatct   8460

tggtgtgcgt aggcacacca attctctttt gactttaagg atgaaagtta aatgagcaca   8520

gacaaagcaa atacgctgat caaacccgaa gatgtcgtgt tatggattcc gggtaatgtc   8580

acaattgaca gcatgaatgc cggttgggaa aacattgcaa tcagagggta cgaatatacc   8640

aacctcgatg tgcatattcc tgccatgcgt gactacatga tcgtcaacta taaaaaaagt   8700

gcggcggaaa tgcgtagaaa aggcgatgcc tcttgggata cccaagtggt taagccgggt   8760

tatgtctcct tgttgacctg tggtgaagat tcccgctggg cgtggaatga ccatattgcc   8820

gtcacccatg tctacatttc gcatgactcc atcacctcaa tggcgaataa ggtgtttgat   8880

tatgatatcg cttcgatccg aatcagagac gaagtcggtg tggaagatca tgttttacct   8940

gctctgactt cacttttaga actagaatta aagcaaggtg gtttaggtgg aaacctgtat   9000

ttagagagca ttaaaaacca gatcgccctg catttactcc gtcagtatgc caaattagat   9060

tttaaggaag gacagtgccg ttctggtttt actcccctac aacgcagact gttattagaa   9120

tttatcaatg aaaacatgag cattaaaatt accctcgaag atttagcggg attagtcaag   9180

atgagcgtgc ctcatttaat gagaaaattt aaagtcgatt ttggtaattc ccctgctgcc   9240

tacatcatga atctcagggt gcaatttgct aaacgtttgc tcacttcaaa aaaagaaatt   9300

ccactgaaag tgattgccag tgaagccggt tttgcgatc agagccatat gacccgagta   9360

tttcaaaaat tttttgggaa aacacccatc gaaatcagac aggaacacac caatctcgtg   9420

tctgaaaatt cagtctcctc tattgttttt tgagtactaa gagccacgca agaacctgat   9480

tttcaataaa gcatccactg aaaaccagtg tggacttaca tgcattattt atgcaaaata   9540

acaaatgtca tgtgagtatc aagatatact ttctatcgct atcaagaact tgccagtaca   9600

ggcaatatgg atgcactcat caaccagagt cgcagaactc caaatttaaa aaaccgagtg   9660
```

```
gatgagcaaa ctgaataagc tgttgttgat tttgcaatcc aatatccagc ttatggtcag   9720
catcggacca gtaatgagct acgtcagatt ggcatcttcg tatctggcag cggtgtgcgc   9780
tctatctggc ttagacacaa tcttgagaat ttcaaaaagc gattaaaggc acttgaaatt   9840
aaagttgctc aagaaggcat tcagttgaat gatcagcaga ttgccgcatt agaacgtaaa   9900
catgaagatg atgttgcttg tggtgaaatt gaaacacatc atccaggtta ccttggagca   9960
caagatactt tttatgtcgg aaatctaaaa ggtgttgggc atatttatca gcaaactttt  10020
attgatactt atagcaaagt ggttcactgc aagctgtaca caaccaagac accaatcaca  10080
gccgcagatt tattgaatga ccgcgtgtta ccattctatg agtcacaagg attgccaatg  10140
cttcgcattt tgaccgacag aggcaccgaa tattgcggta aagttgaaca tcacgattat  10200
gagctttatt tggctctgaa tgatattgat cacactaaaa ctaaagcagc atcaccacaa  10260
acaaatggga tctgtgagcg cttccataag acgatcttgc aggagtttta tcagattact  10320
tttcgaaaga aactctatag ctcattagaa gagttacagc ttgatctaga cggttggctg  10380
aaattctata atactgaacg aacccatcag ggtaaggtgt gtaatggcag atgagcagca  10440
ttgctgcgca agattgcaac attacttgat ggaaaacgta tttgggctga aaagaattta  10500
gttcaaattt aacctgacag tcttaagcaa atatcggtaa ctatcagatc aggtttgaga  10560
taccgtctga aacgtcaagt aaatgattga gaattcatgc tcaataatct gcttgataag  10620
gctgttggtg tttgagcaca ccataacaaa gatgaatcaa cttcctcatc gcggctccaa  10680
tcgctatcat cttggtttta ccattcgcca ataaacgttc attcattgcc ctgatgtgag  10740
ggttatgccg agttgcgaca atggctgcca tatataaacc agcacgtatt ttggaagagc  10800
ccgctttgga taaacggctt ctgccatgaa tggaactacc cgattgcttt tgaatgggga  10860
ccaaaccgac aaaggcagcc gcttgactag ccctttcaaa agtatggctg cgcaagaaac  10920
tgagcattaa taaactggtt cgatctgcaa tggctggaat actgctgagc agttctttat  10980
catttttaa atcaggattc tgattaatgt gatcatcaat ttgctggtcg ataccctgaa  11040
tgtgtttgtt taactgttca atactcttgt ggatagactg aagtacaggt tccatcgtga  11100
aggtcgactc tgctttttcc aaacgattct tttcacgttg taaatcttca caaagaatag  11160
ctcttctatc cagcaaagca ttcagcaatt gaatatgttt aggtaaaggt tgccaaaaat  11220
gtagatcggc agtcatcgca aatcgagcta ggacctcact atccaccttg tctgttttat  11280
tcagcttaga catactctga gcaaaatatc gagctctggc aggattggtt acacagactt  11340
gatagcccgc atcaaataaa tatttaacca agagttcatg ataaatagat gttgcttcca  11400
ttaaaataat ggtctgcgta gaagttgcag catgctgctt tagccaggtt tgaagttgct  11460
caaaaccttt tggtgtattt gaaaaagttt tggttttctt tttatttgca gaattttcta  11520
aaattaaaca gcaatcaatt ttagctttag caacatcaat accaagataa aacataatct  11580
ttacctgctt tatttatcca attattgttt tagcataacc accgtctttt cttgtgaatg  11640
cagcatcaaa gtgcttgtta ccgtccagag ttgtgcaagt ggttagggca aattacaggt  11700
tttatctcaa actctaactt tatgttttgc tagtacacga aactctgcaa tttgcaatat  11760
agtgatagct aatcactatg aatggtaaga tacaagctag tacacataag aagatattac  11820
ttcttctcag gcagattcgc agcaaagaaa aattttccct tacaacaata gataaaagaa  11880
aagagggtat cacccctctt tcctctttat atgggggtat cttctactca tttttattt  11940
cgaggtatat gcaccatcga ccacatactg actaccggtc acaaatgaag catcatcaga  12000
aagtaggaag gcaacaacct gagcaacttc ttccggctgt cccaaacgac caatcggatg  12060
```

-continued

```
tagttttacc atttctgctt cttcaaattc tgcaatcaaa ggcgttttga tatagccagg  12120
atgtactgaa ttaatgcgaa tccctttatc tgcatattcc aatgccgccg ctttcgttag  12180
acccgttacg ccatgttttg cagcgacata gcctgaaata ttttgaatcc cgatcaagcc  12240
tgcaatagaa gcggtattga caatcgctcc gccccctgcg gccaagattg caggaacttc  12300
ataatgcatg ctgtagaaaa ccgcattcaa gttcacatca atcacacgac gccatccttc  12360
aatgctcaat tcttcggtgg agttaacttc acccagaatt cccgcattat tgaaggccaa  12420
atgcagtgca ccaaaagtgc tgaccgcaaa ctcgactgca gctttcatgt cttcaggctc  12480
agcagtattg gccttattcg cagccgcttt cccgcctaaa gcgacaattt cgtccacaac  12540
tttctgtgct gcttccaggt taatatctga aaccactaca cttacaccct gttgagccaa  12600
aagcagtgcg gtgcttttac caatacctga accagcgcca gtaattaaag cgactttatt  12660
gttgaattta tttgacataa ttttttccat ttcaaatttt aagcatcaaa gcttgtttca  12720
tattttaaga ttcaagaaac cagatccggt agatgactcg tctgccaagc gacaacccgt  12780
ctgatatcag gcttgcgatt caccctgtag acggttttca ttcctaaatt ctgtatttcc  12840
aagttatata aacaaaagtg ctaatctatg gggaattccc aggatccaaa caaatagaat  12900
gccatgaaag catcttttgc caagcgctgt gctgtatgtt tcctagacaa accaccaacg  12960
ataactgcaa ctttttgaac tccttacaat ttccttattt tctttcccct tcatcgcata  13020
aaaatagttt ttgcattcac aacaaaatca gcatgaatag tttttaaact cactgtacat  13080
attttctata ttgatgacca agctggatat tgaattgcaa aattctatac agcctgttca  13140
acatgatcga tttagaaggc atacagtaaa cgtgactgaa gtccagaaat ttccaagcca  13200
ttttcaacat tcacatcttg tcgccattgt aataatagct gcagattcgg cttgatattg  13260
gtagaagcag aaacgacaaa ggtatctttt ctatcactgc cacgttcagt gacaccattc  13320
accttttctt taccgccatc ggtatgtctc caggtgacag ccaaattgga tttatcggtc  13380
actttataga gtgcggagaa atctgtctgg aaaaaaacct ctttctcaat gttggtatat  13440
ttttgctcgc tataaagttc aaactgcccc accccctcaa gcgcaaattt atcagttaaa  13500
gcatggtaat aaccggcctg aacattatat tgatagcgat cattactgat ggcaaaaccc  13560
ttcgtttcat tactgccggt aggtacggtc aaaaaaccac cgaaaccaaa atagcgccct  13620
ttttcagcat catgcaatgg ccaggcgata ccacccacaa ttaaatcacc gacacccgag  13680
atatcatcag cgccattcat cttttgcttg gcaaaaggca agaggaattg aggatctaca  13740
atccaatccc ctacttcaat aaaacgaacg taacgcaata ttcccaaatc aatgcttaaa  13800
tcgagatcat cagcgacttt atcaccattt gcatacgcct tatccgcttc cgtatgctgg  13860
taataggcaa ccgctaagtt ggttccccct ggaagtgctt gataatcccc ggcatcagaa  13920
ctcacccctg cggcttgcag gtccaaagcg gcagttaaag caaagaccaa agcagctatt  13980
ttttgatttg aacgatgata gaaatagttt ttcatttgtt tcatttttaa ctctccgttg  14040
ttttgactca tttttttaaa atgagtcttc ctagcacaaa gaccactcag gtctttgcgc  14100
aatttcttga ttttgatttg ggtattaaat atggaaaaac gttgggtgat cagttttcgt  14160
gcataagcac aatacgcccg atgacgttgc catctttcaa gtctccaaat gcggaattga  14220
tctgcgaaat tggcagtttt ttcacgggaa tggctgacat gtgggtttct ttcaccagct  14280
ccaccagctc tcttaattcc tctaccgtcc ctacataact gccctggatt gtgagtggtc  14340
tcattggaat caccggaatg gaaagcttaa tttctccccc catcaatccg cagatcacaa  14400
tatgcccacc acgtgcagca ctcgccaagg caaggctcaa tgttggatta ctgccaacca  14460
```

```
gatcaaggat cagacgtgca ccaccgtcag ttgcctgaat cagctgttga gcagcatcct  14520
cacttcggct attgatgacc gataatgcac cggcagcacg tgctgcttcc agtttgctgt  14580
catcaatatc aactacgatt gcgcctttgg cttgcatagc tttgagcaac tcgagtgcca  14640
tcagccctaa accaccggca ccaatgatca ccaccggctc gctttgaatc aaatcaccga  14700
atttttttcag tgcactgtat gttgtcacgc ctgcacatgc caaaggtgca gcttcagcca  14760
gatccagacc tgcaatatcc accagatatc gtggatgcgg cacgatgata tattcggcaa  14820
aaccacccgg cttggcgatg cctaactgtt gcggtttggc acacaggttt tcttcgccac  14880
gtttacagta gttgcattca ccgcaaccaa tccatggatg aaccaagctg accatgccga  14940
ccttgactga ttccgcatct ggaccgacag caaccacctg acctgtaatt tcatgactta  15000
aggttaaggg tggcttcagc ccacgatctg caagggataa acgcttgccc ccacctagat  15060
cataataacc ttcccataag tgtaaatccg tatggcatag acctgcggct tttacatgga  15120
gtaaaacttc agtacctttc ggttgcggaa tttctttctc aacgtcttcg agtggttgtc  15180
catgatgcgt cacgcagtaa cagtgcatga atctctcctt tgaaacaata aaatagacgg  15240
ccttgtagtg aacaaagtct tttattcact aagttttata cgccgtgtgg gcactgattt  15300
atgctttaaa ccactgcgca attttcgcta attcttgatc agcttcactt gcacgcccag  15360
ctaggaaagg aaaaacgtgc tgcatgttgt ccaccacaga taaagtcaca tcaacaccct  15420
cttttttgc aatatcagca agacgtgttg cattgtctac aagtgattca actgatccgg  15480
cattgatata caaacgtggg aaaacctgat aattggcttt taacggattc gccaatggat  15540
ttgccggatc accatgttca cccaagaaca tttgtgacat gcctttaagc agatccactg  15600
taatcaaggc atcagtggca tcgttgctga tcagggtttc acctttgtgc tccatatcca  15660
gccaaggaga gaatgcaatc actgctcctg gcaactcaat cccttcattt cgtagattga  15720
gtacggttga tatcgccaga ttccccccg cagaatcccc tgcggtcagc atattttttg  15780
cagtaaagcc acgctggagt agttctttat atactgctgt cacgtcctga atttgtgccg  15840
ggaagacatg ttctggtgaa cgtcggtaat caaccacaaa tgcggatacc cctaaatact  15900
tggccaaatg ccccaccagc ttacggtgac tggccgaaga accgaccgca aatccaccgc  15960
catgggtata aatgatgact ttggataagt cagcatcttt cggataaatc caaagacctt  16020
ctacacctgc cacaacatcg aatttataag acacttcttc cggttccaat gtaggttgat  16080
gccattcatc aaacatactg cgaaagtctt caatggtcat attcggattt tcctgcatcc  16140
gtcttgacca gttcgcatat aaatcgaaaa gaaattgagt attgctttgt gtgctattca  16200
ttttaaaatc cttgatttga tatttaagga ataaatccta gttttattcc atgaagatat  16260
aaaaacttga gtgccatcac tcatggctag acactcagaa gatccaaatc taaagagtgg  16320
ctttgcatca ctggtttgat acaatttttt gcatgactaa gtaatctacg gataatctaa  16380
ccgtttcaaa ttagtatttt aaaatgtaaa aaatacatac cagcgaatgt tttctgcaaa  16440
atcgcatcct gttcaatata gcttttgatc ctacttattc tcttttctat tccagtccgt  16500
tataaaaaag ctttcattca ttttcatgca atcatgagct atgaatgttc ttaaacatta  16560
aacgattgtg tgtatggctg acttgtacat tcttgtactt atttttgtat aaaatgatca  16620
ggctcatcaa tttatgggaa aaattacaat tcgggtacaa tatctttcct gtttcatgaa  16680
tctattcaac tcattaaact tacgaccctc aactgcccaa aatcatagga tctgccgatc  16740
cacttgcaga attagcaatg ctaaaacatg aactccaaag agttactaaa aaaagagcat  16800
attaaaaaaa agccgtggca tatttcgcaa gccagttcaa gtcaggtatg tctttattca  16860
```

```
gtacctcagt taaactttag attttcataa cgatggttat tctgcatggc taaatacgct  16920

aatcagcaaa aaactctcca aaagataggc acagaaacac atatcaacca taaaaaccat  16980

ctcagacagt atatttacaa gcctctaatt caccgcactc acacttctct gcaagccttt  17040

ttaaataccc tgtacaaagt tctcagcctg atgaagcttc accttggact tagctttcag  17100

ttcagcctgt acttggtcag tttctgaatt ttcatttgca taaaactcct ccaccacatc  17160

cataccctcc tcaatgtcag tttcaaaatg tgcattgtca tagccttgcc gtgccatttg  17220

aatggcttat tgaagattaa tggcatcacg taaagttaaa tccacgtaat acacaggtgt  17280

tcgatagctt tgcgtcgtag actttctcga agagtcaatt gcagcggtag gcatgacagc  17340

aagccattca atgccgcatg gtaataactc agccgtgcgg ccaacgttcg tatgctgtta  17400

aaacccggtt attctaa                                                 17417
```

<210> SEQ ID NO 74
<211> LENGTH: 1164
<212> TYPE: DNA
<213> ORGANISM: Escherichia coli

<400> SEQUENCE: 74

```
atgaacaact ttaatctgca caccccaacc cgcattctgt ttggtaaagg cgcaatcgct     60

ggtttacgcg aacaaattcc tcacgatgct cgcgtattga ttacctacgg cggcggcagc    120

gtgaaaaaaa ccggcgttct cgatcaagtt ctggatgccc tgaaaggcat ggacgtgctg    180

gaatttggcg gtattgagcc aaacccggct tatgaaacgc tgatgaacgc cgtgaaactg    240

gttcgcgaac agaaagtgac tttcctgctg gcggttggcg gcggttctgt actggacggc    300

accaaattta tcgccgcagc ggctaactat ccggaaaata tcgatccgtg gcacattctg    360

caaacgggcg gtaaagagat taaaagcgcc atcccgatgg gctgtgtgct gacgctgcca    420

gcaaccggtt cagaatccaa cgcaggcgcg gtgatctccc gtaaaaccac aggcgacaag    480

caggcgttcc attctgccca tgttcagccg gtatttgccg tgctcgatcc ggtttatacc    540

tacaccctgc cgccgcgtca ggtggctaac ggcgtagtgg acgcctttgt acacaccgtg    600

gaacagtatg ttaccaaacc ggttgatgcc aaaattcagg accgtttcgc agaaggcatt    660

ttgctgacgc taatcgaaga tggtccgaaa gccctgaaag agccagaaaa ctacgatgtg    720

cgcgccaacg tcatgtgggc ggcgactcag gcgctgaacg gtttgattgg cgctggcgta    780

ccgcaggact gggcaacgca tatgctgggc cacgaactga ctgcgatgca cggtctggat    840

cacgcgcaaa cactggctat cgtcctgcct gcactgtgga atgaaaaacg cgataccaag    900

cgcgctaagc tgctgcaata tgctgaacgc gtctggaaca tcactgaagg ttccgatgat    960

gagcgtattg acgccgcgat tgccgcaacc cgcaatttct ttgagcaatt aggcgtgccg   1020

acccacctct ccgactacgg tctggacggc agctccatcc cggctttgct gaaaaaactg   1080

gaagagcacg gcatgaccca actgggcgaa aatcatgaca ttacgttgga tgtcagccgc   1140

cgtatatacg aagccgcccg ctaa                                          1164
```

<210> SEQ ID NO 75
<211> LENGTH: 387
<212> TYPE: PRT
<213> ORGANISM: Escherichia coli

<400> SEQUENCE: 75

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
```

```
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 76
<211> LENGTH: 1623
<212> TYPE: DNA
<213> ORGANISM: Bacillus subtilis

<400> SEQUENCE: 76

atgtatttgg cattccaggt gcaaaaattg atgcggtatt tgacgcttta caagataaag      60
```

```
gacctgaaat tatcgttgcc cggcacgaac aaaacgcagc aattcatggc ccaagcagtc    120
ggccgtttaa ctggaaaacc gggagtcgtg ttagtcacat caggaccggg tgcctctaac    180
ttggcaacag gcctgctgac agcgaacact gaaggagacc ctgtcgttgc gcttgctgga    240
aacgtgatcc gtgcatatcg tttaaaacgg acacatcaat ctttggataa tgcggcgcta    300
ttccagccga ttacaaaata cagtgtagaa gttcaagatg taaaaaatat accggaagct    360
gttacaaatg catttaggat agcgtcagca gggcaggctg gggccgcttt tgtgagcttt    420
ccgcaagatg ttgtgaatga agtcacaaat acgaaaaacg tgcgtgctgt tgcagcgcca    480
aaactcggtc ctgcagcaga tgatgcaatc agtgcggcca tagcaaaaat ccaaacagca    540
aaacttcctg tcgttttggt cggcatgaaa ggcggaagac cggaagcaat taaagcggtt    600
cgcaagcttt tgaaaaaggt tcagcttcca tttgttgaaa catatcaagc tgccggtacc    660
ctttctagag atttagagga tcaatatttt ggccgtatcg gtttgttccg caaccagcct    720
ggcgatttac tgctagagca ggcagatgtt gttctgacga tcggctatga cccgattgaa    780
tatgatccga aattctggaa tatcaatgga gaccggacaa ttatccattt agacgagatt    840
atcgctgaca ttgatcatgc ttaccagcct gatcttgaat tgatcggtga cattccgtcc    900
acgatcaatc atatcgaaca cgatgctgtg aaagtggaat ttgcagagcg tgagcagaaa    960
atcctttctg atttaaaaca atatatgcat gaaggtgagc aggtgcctgc agattggaaa   1020
tcagacagag cgcaccctct tgaaatcgtt aaagagttgc gtaatgcagt cgatgatcat   1080
gttacagtaa cttgcgatat cggttcgcac tccatttgga tgtcacgtta tttccgcagc   1140
tacgagccgt taacattaat gatcagtaac ggtatgcaaa cactcggcgt tgcgcttcct   1200
tgggcaatcg gcgcttcatt ggtgaaaccg ggagaaaaag tggtttctgt ctctggtgac   1260
ggcggtttct tattctcagc aatggaatta gagacagcag ttcgactaaa agcaccaatt   1320
gtacacattg tatggaacga cagcacatat gacatggtgc atttccagca attgaaaaaa   1380
tataaccgta catctgcggt cgatttcgga aatatcgata tcgtgaaata tgcggaaagc   1440
ttcggagcaa ctgcgttgcg cgtagaatca ccagaccagc tggcagatgt tctgcgtcaa   1500
ggcatgaacg ctgaaggtcc tgtcatcatc gatgtcccgg ttgactacag tgataacatt   1560
aatttagcaa gtgacaagct tccgaaagaa ttcggggaac tcatgaaaac gaaagctctc   1620
tag                                                                 1623
```

<210> SEQ ID NO 77
<211> LENGTH: 540
<212> TYPE: PRT
<213> ORGANISM: Bacillus subtilis

<400> SEQUENCE: 77

```
Met Tyr Leu Ala Phe Gln Val Gln Lys Leu Met Arg Tyr Leu Thr Leu
1               5                   10                  15

Tyr Lys Ile Lys Asp Leu Lys Leu Ser Leu Pro Gly Thr Asn Lys Thr
            20                  25                  30

Gln Gln Phe Met Ala Gln Ala Val Gly Arg Leu Thr Gly Lys Pro Gly
        35                  40                  45

Val Val Leu Val Thr Ser Gly Pro Gly Ala Ser Asn Leu Ala Thr Gly
    50                  55                  60

Leu Leu Thr Ala Asn Thr Glu Gly Asp Pro Val Val Ala Leu Ala Gly
65                  70                  75                  80

Asn Val Ile Arg Ala Tyr Arg Leu Lys Arg Thr His Gln Ser Leu Asp
                85                  90                  95
```

```
Asn Ala Ala Leu Phe Gln Pro Ile Thr Lys Tyr Ser Val Glu Val Gln
            100                 105                 110

Asp Val Lys Asn Ile Pro Glu Ala Val Thr Asn Ala Phe Arg Ile Ala
        115                 120                 125

Ser Ala Gly Gln Ala Gly Ala Ala Phe Val Ser Phe Pro Gln Asp Val
    130                 135                 140

Val Asn Glu Val Thr Asn Thr Lys Asn Val Arg Ala Val Ala Ala Pro
145                 150                 155                 160

Lys Leu Gly Pro Ala Ala Asp Asp Ala Ile Ser Ala Ala Ile Ala Lys
                165                 170                 175

Ile Gln Thr Ala Lys Leu Pro Val Val Leu Val Gly Met Lys Gly Gly
            180                 185                 190

Arg Pro Glu Ala Ile Lys Ala Val Arg Lys Leu Leu Lys Lys Val Gln
        195                 200                 205

Leu Pro Phe Val Glu Thr Tyr Gln Ala Ala Gly Thr Leu Ser Arg Asp
    210                 215                 220

Leu Glu Asp Gln Tyr Phe Gly Arg Ile Gly Leu Phe Arg Asn Gln Pro
225                 230                 235                 240

Gly Asp Leu Leu Leu Glu Gln Ala Asp Val Val Leu Thr Ile Gly Tyr
                245                 250                 255

Asp Pro Ile Glu Tyr Asp Pro Lys Phe Trp Asn Ile Asn Gly Asp Arg
            260                 265                 270

Thr Ile Ile His Leu Asp Glu Ile Ile Ala Asp Ile Asp His Ala Tyr
        275                 280                 285

Gln Pro Asp Leu Glu Leu Ile Gly Asp Ile Pro Ser Thr Ile Asn His
    290                 295                 300

Ile Glu His Asp Ala Val Lys Val Glu Phe Ala Glu Arg Glu Gln Lys
305                 310                 315                 320

Ile Leu Ser Asp Leu Lys Gln Tyr Met His Glu Gly Glu Gln Val Pro
                325                 330                 335

Ala Asp Trp Lys Ser Asp Arg Ala His Pro Leu Glu Ile Val Lys Glu
            340                 345                 350

Leu Arg Asn Ala Val Asp Asp His Val Thr Val Thr Cys Asp Ile Gly
        355                 360                 365

Ser His Ser Ile Trp Met Ser Arg Tyr Phe Arg Ser Tyr Glu Pro Leu
    370                 375                 380

Thr Leu Met Ile Ser Asn Gly Met Gln Thr Leu Gly Val Ala Leu Pro
385                 390                 395                 400

Trp Ala Ile Gly Ala Ser Leu Val Lys Pro Gly Glu Lys Val Val Ser
                405                 410                 415

Val Ser Gly Asp Gly Gly Phe Leu Phe Ser Ala Met Glu Leu Glu Thr
            420                 425                 430

Ala Val Arg Leu Lys Ala Pro Ile Val His Ile Val Trp Asn Asp Ser
        435                 440                 445

Thr Tyr Asp Met Val His Phe Gln Gln Leu Lys Lys Tyr Asn Arg Thr
    450                 455                 460

Ser Ala Val Asp Phe Gly Asn Ile Asp Ile Val Lys Tyr Ala Glu Ser
465                 470                 475                 480

Phe Gly Ala Thr Ala Leu Arg Val Glu Ser Pro Asp Gln Leu Ala Asp
                485                 490                 495

Val Leu Arg Gln Gly Met Asn Ala Glu Gly Pro Val Ile Ile Asp Val
            500                 505                 510

Pro Val Asp Tyr Ser Asp Asn Ile Asn Leu Ala Ser Asp Lys Leu Pro
```

```
        515                 520                 525

Lys Glu Phe Gly Glu Leu Met Lys Thr Lys Ala Leu
    530                 535                 540
```

<210> SEQ ID NO 78
<211> LENGTH: 1680
<212> TYPE: DNA
<213> ORGANISM: Klebsiella terrigena

<400> SEQUENCE: 78

```
atggacaaac cgcgtcacga acgtcaatgg gcccacggtg ccgacttaat cgtcagccag     60

cttgaggccc agggcgtacg ccaggtcttc ggcatccccg gtgccaaaat cgacaaggtg    120

tttgattccc tcctcgactc ctcaatccgc attattccgg tgcgccacga ggctaacgcc    180

gcctttatgg ccgcggcggt cgggcggatt accggtaaag cgggcgtcgc gctggtgacc    240

tccggtcccg gctgctcaaa cctgattacc ggcatggcca ccgccaatag cgaaggcgac    300

ccggtggtgg cgctgggcgg cgcggtgaag cgcgcggata aggccaagct ggttcaccaa    360

agcatggaca ccgtggcgat gttcagcccg gtcaccaaat acgccgtcga ggtgaccgcc    420

tccgacgcgc tggccgaggt ggtctccaac gcctttcgcg ccgccgaaca ggggcgtccg    480

gggagcgcgt ttgtcagcct gccgcaggat atcgttgacg gccccgccag cggcagcacg    540

ctgcccgcca gcagagcgcc gcagatgggc gccgcgccgg atggcgccgt tgacagcgtg    600

gcgcaggcga tcgccgcggc gaagaaccct atcttcctgc tcgggctgat ggccagccag    660

ccggaaaaca gccgcgccct gcaccgccat gctggaaaaa agccatattc cggtcaccag    720

cacctatcag gcgccggggc ggtaaatcag gataacttcg cccgcttcgc cggccgggta    780

ggcctgttta ataaccaggc gggcgatcgc ctgctgcgtc aggcggacct gatcatctgc    840

atcggctata gcccggttga gtacgaaccg gcgatgtgga acagcggcac ggcaaccctg    900

gtgcatatcg acgtgctgcc ggcctatgaa gagcggaact acgtcccgga tatcgagctg    960

gtgggcgaca tcgccgccac cctcgagaag ctggcccagc gcattgaaca tcggctggtg   1020

ttaactccgc aggcggcgga catcctcgcc gaccgccagc gccagcggga gctgcttgac   1080

cgccgcgggg cgcagctgaa tcagtttgcg ctccacccgc tgcgcatcgt gcgggcgatg   1140

caggatatcg tcaatagcga cgtcaccttg accgtcgata tgggcagttt ccatatctgg   1200

attgcccgct acctctacag cttccgcgcc cgccaggtga tgatctccaa cggtcagcaa   1260

acgatgggcg tcgcgctgcc gtgggcaatc ggcgcgtggc tggtcaatcc gcagcgcaag   1320

gtggtctcgg tatccggcga tggcggcttc ctgcagtcga gcatggagct ggagaccgcc   1380

gtgcgcctgc acgccaatat tctgcacatc atctgggtcg ataacggcta caacatggtg   1440

gcgattcagg aacagaagaa atatcagcgc ctctccggcg tggagttcgg cccggtcgat   1500

ttcaaagtct acgccgaagc gttcggggcc tgcgggtttg cggtagagag cgccgaggcc   1560

ctggagccga ccctgcgcgc ggcgatggat gtcgacggcc cggcggtggt cgccattccg   1620

gtcgattacc gcgataaccc tctgctgatg ggccagctcc atctcagcca aatactgtga   1680
```

<210> SEQ ID NO 79
<211> LENGTH: 559
<212> TYPE: PRT
<213> ORGANISM: Klebsiella terrigena

<400> SEQUENCE: 79

```
Met Asp Lys Pro Arg His Glu Arg Gln Trp Ala His Gly Ala Asp Leu
1               5                   10                  15
```

```
Ile Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Leu Val His Gln Ser Met Asp Thr Val Ala Met Phe
        115                 120                 125

Ser Pro Val Thr Lys Tyr Ala Val Glu Val Thr Ala Ser Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Ile Val Asp Gly Pro Ala
                165                 170                 175

Ser Gly Ser Thr Leu Pro Ala Ser Arg Ala Pro Gln Met Gly Ala Ala
            180                 185                 190

Pro Asp Gly Ala Val Asp Ser Val Ala Gln Ala Ile Ala Ala Ala Lys
        195                 200                 205

Asn Pro Ile Phe Leu Leu Gly Leu Met Ala Ser Gln Pro Glu Asn Ser
    210                 215                 220

Arg Ala Leu His Arg His Ala Gly Lys Lys Pro Tyr Ser Gly His Gln
225                 230                 235                 240

His Leu Ser Gly Ala Gly Ala Val Asn Gln Asp Asn Phe Ala Arg Phe
                245                 250                 255

Ala Gly Arg Val Gly Leu Phe Asn Asn Gln Ala Gly Asp Arg Leu Leu
            260                 265                 270

Arg Gln Ala Asp Leu Ile Ile Cys Ile Gly Tyr Ser Pro Val Glu Tyr
        275                 280                 285

Glu Pro Ala Met Trp Asn Ser Gly Thr Ala Thr Leu Val His Ile Asp
    290                 295                 300

Val Leu Pro Ala Tyr Glu Glu Arg Asn Tyr Val Pro Asp Ile Glu Leu
305                 310                 315                 320

Val Gly Asp Ile Ala Ala Thr Leu Glu Lys Leu Ala Gln Arg Ile Glu
                325                 330                 335

His Arg Leu Val Leu Thr Pro Gln Ala Ala Asp Ile Leu Ala Asp Arg
            340                 345                 350

Gln Arg Gln Arg Glu Leu Leu Asp Arg Arg Gly Ala Gln Leu Asn Gln
        355                 360                 365

Phe Ala Leu His Pro Leu Arg Ile Val Arg Ala Met Gln Asp Ile Val
    370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Gln Arg Lys Val Val Ser Val Ser Gly Asp Gly
        435                 440                 445
```

```
Gly Phe Leu Gln Ser Ser Met Glu Leu Glu Thr Ala Val Arg Leu His
    450                 455                 460

Ala Asn Ile Leu His Ile Ile Trp Val Asp Asn Gly Tyr Asn Met Val
465                 470                 475                 480

Ala Ile Gln Glu Gln Lys Lys Tyr Gln Arg Leu Ser Gly Val Glu Phe
                485                 490                 495

Gly Pro Val Asp Phe Lys Val Tyr Ala Glu Ala Phe Gly Ala Cys Gly
            500                 505                 510

Phe Ala Val Glu Ser Ala Glu Ala Leu Glu Pro Thr Leu Arg Ala Ala
        515                 520                 525

Met Asp Val Asp Gly Pro Ala Val Val Ala Ile Pro Val Asp Tyr Arg
    530                 535                 540

Asp Asn Pro Leu Leu Met Gly Gln Leu His Leu Ser Gln Ile Leu
545                 550                 555


<210> SEQ ID NO 80
<211> LENGTH: 768
<212> TYPE: DNA
<213> ORGANISM: Bacillus subtilis

<400> SEQUENCE: 80

atgaaacgag aaagcaacat tcaagtgctc agccgtggtc aaaaagatca gcctgtgagc      60

cagatttatc aagtatcaac aatgacttct ctattagacg gagtatatga cggagatttt     120

gaactgtcag agattccgaa atatggagac ttcggtatcg gaacctttaa caagcttgac     180

ggagagctga ttgggtttga cggcgaattt taccgtcttc gctcagacgg aaccgcgaca     240

ccggtccaaa atggagaccg ttcaccgttc tgttcattta cgttctttac accggacatg     300

acgcacaaaa ttgatgcgaa aatgacacgc gaagactttg aaaaagagat caacagcatg     360

ctgccaagca gaaacttatt ttatgcaatt cgcattgacg gattgtttaa aaaggtgcag     420

acaagaacag tagaacttca agaaaaacct tacgtgccaa tggttgaagc ggtcaaaaca     480

cagccgattt tcaacttcga caacgtgaga ggaacgattg taggtttctt gacaccagct     540

tatgcaaacg gaatcgccgt ttctggctat cacctgcact tcattgacga aggacgcaat     600

tcaggcggac acgtttttga ctatgtgctt gaggattgca cggttacgat ttctcaaaaa     660

atgaacatga atctcagact tccgaacaca gcggatttct ttaatgcgaa tctggataac     720

cctgattttg cgaaagatat cgaaacaact gaaggaagcc ctgaataa                  768


<210> SEQ ID NO 81
<211> LENGTH: 255
<212> TYPE: PRT
<213> ORGANISM: Bacillus subtilis

<400> SEQUENCE: 81

Met Lys Arg Glu Ser Asn Ile Gln Val Leu Ser Arg Gly Gln Lys Asp
1               5                   10                  15

Gln Pro Val Ser Gln Ile Tyr Gln Val Ser Thr Met Thr Ser Leu Leu
            20                  25                  30

Asp Gly Val Tyr Asp Gly Asp Phe Glu Leu Ser Glu Ile Pro Lys Tyr
        35                  40                  45

Gly Asp Phe Gly Ile Gly Thr Phe Asn Lys Leu Asp Gly Glu Leu Ile
    50                  55                  60

Gly Phe Asp Gly Glu Phe Tyr Arg Leu Arg Ser Asp Gly Thr Ala Thr
65                  70                  75                  80

Pro Val Gln Asn Gly Asp Arg Ser Pro Phe Cys Ser Phe Thr Phe Phe
```

```
                85                  90                  95

Thr Pro Asp Met Thr His Lys Ile Asp Ala Lys Met Thr Arg Glu Asp
            100                 105                 110

Phe Glu Lys Glu Ile Asn Ser Met Leu Pro Ser Arg Asn Leu Phe Tyr
        115                 120                 125

Ala Ile Arg Ile Asp Gly Leu Phe Lys Lys Val Gln Thr Arg Thr Val
    130                 135                 140

Glu Leu Gln Glu Lys Pro Tyr Val Pro Met Val Glu Ala Val Lys Thr
145                 150                 155                 160

Gln Pro Ile Phe Asn Phe Asp Asn Val Arg Gly Thr Ile Val Gly Phe
                165                 170                 175

Leu Thr Pro Ala Tyr Ala Asn Gly Ile Ala Val Ser Gly Tyr His Leu
            180                 185                 190

His Phe Ile Asp Glu Gly Arg Asn Ser Gly Gly His Val Phe Asp Tyr
        195                 200                 205

Val Leu Glu Asp Cys Thr Val Thr Ile Ser Gln Lys Met Asn Met Asn
    210                 215                 220

Leu Arg Leu Pro Asn Thr Ala Asp Phe Phe Asn Ala Asn Leu Asp Asn
225                 230                 235                 240

Pro Asp Phe Ala Lys Asp Ile Glu Thr Thr Glu Gly Ser Pro Glu
                245                 250                 255


<210> SEQ ID NO 82
<211> LENGTH: 780
<212> TYPE: DNA
<213> ORGANISM: Klebsiella terrigena

<400> SEQUENCE: 82

gtgaatcatt atcctgaatg cacctgccag gagagcctgt gcgaaaccgt acgcggcttc     60

tccgcccacc accctgatag cgttatctat cagacctctc tgatgagcgc gctgctgagc    120

ggggtctatg agggtagcac caccatcgcc gacctgctga cccacggcga cttcggtctc    180

ggcaccttta acgaactcga tggcgaactg attgccttta gcagcgaggt ctaccagctg    240

cgcgctgacg gcagcgcgcg taaagcccgg gcggatcaaa aaacgccctt cgcggtgatg    300

acctggttca gaccgcagta ccgtaaaacc tttgaccacc cggtcagccg ccagcagctg    360

cacgacgtta tcgaccagca aatcccctcc gataacctgt tctgcgccct gcatattgat    420

ggtcactttc gccacgccca cacccgcacc gtgccgcggc agacgccgcc ctatcgggcg    480

atgaccgacg tgctcgatga ccagccggtt ttccgcttca accagcgcaa ggggacgctg    540

gtcggctttc gcaccccgca gcatatgcag ggccttaacg ttgccggcta ccacgagcac    600

tttattaccg acgatcgcca gggcggcggc catctgctgg actaccagct cgatagcggc    660

gtgctgacct tcggcgagat ccacaagctg atgattgacc tcccggccga cagcgctttc    720

ctgcaggccg acctgcatcc tgacaatctc gatgccgcta ttcgtgcggt agaaaactaa    780


<210> SEQ ID NO 83
<211> LENGTH: 259
<212> TYPE: PRT
<213> ORGANISM: Klebsiella terrigena

<400> SEQUENCE: 83

Met Asn His Tyr Pro Glu Cys Thr Cys Gln Glu Ser Leu Cys Glu Thr
1               5                   10                  15

Val Arg Gly Phe Ser Ala His His Pro Asp Ser Val Ile Tyr Gln Thr
            20                  25                  30
```

```
Ser Leu Met Ser Ala Leu Leu Ser Gly Val Tyr Glu Gly Ser Thr Thr
        35                  40                  45

Ile Ala Asp Leu Leu Thr His Gly Asp Phe Gly Leu Gly Thr Phe Asn
    50                  55                  60

Glu Leu Asp Gly Glu Leu Ile Ala Phe Ser Ser Glu Val Tyr Gln Leu
65                  70                  75                  80

Arg Ala Asp Gly Ser Ala Arg Lys Ala Arg Ala Asp Gln Lys Thr Pro
                85                  90                  95

Phe Ala Val Met Thr Trp Phe Arg Pro Gln Tyr Arg Lys Thr Phe Asp
            100                 105                 110

His Pro Val Ser Arg Gln Gln Leu His Asp Val Ile Asp Gln Gln Ile
        115                 120                 125

Pro Ser Asp Asn Leu Phe Cys Ala Leu His Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Lys Gly Thr Leu Val Gly Phe Arg Thr Pro Gln His Met Gln Gly Leu
            180                 185                 190

Asn Val Ala Gly Tyr His Glu His Phe Ile Thr Asp Asp Arg Gln Gly
        195                 200                 205

Gly Gly His Leu Leu Asp Tyr Gln Leu Asp Ser Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asp Leu His Pro Asp Asn Leu Asp Ala Ala Ile Arg Ala
                245                 250                 255

Val Glu Asn


<210> SEQ ID NO 84
<211> LENGTH: 1053
<212> TYPE: DNA
<213> ORGANISM: Bacillus cereus

<400> SEQUENCE: 84

atgaaagcac tactttggca taatcaacgt gatgtacgag tagaagaagt accagaacca      60

acagtaaaac caggaacagt gaaaatcaaa gttaaatggt gtggtatttg tgggacagac     120

ttgcatgaat atttagcagg gcctattttt attccaacag aagaacatcc attaacacat     180

gtgaaagcac ctgttatttt aggtcatgag tttagtggtg aggtaataga gattggtgaa     240

ggagttacat ctcataaagt gggagaccgc gttgttgtag agccaattta ttcttgtggt     300

aaatgtgaag cttgtaaaca tggacattac aatgtttgtg aacaacttgt tttccacggt     360

cttggcggag aaggcggcgg tttctctgaa tatacagtag taccagaaga tatggttcat     420

cacattccag atgaaatgac gtatgaacaa ggtgcgcttg tagaaccagc agcagtagca     480

gttcatgcag tacgtcaaag taaattaaaa gaaggggaag ctgtagcggt atttggttgc     540

ggtccaattg gacttcttgt tatccaagca gctaaagcag caggagcaac tcctgttatt     600

gcagttgaac tttctaaaga acgtcaagag ttagcgaaat tagcaggtgc ggattatgta     660

ttaaatccag caactcaaga tgtgttagct gaaattcgta acttaacaaa tggtttaggt     720

gtaaatgtta gctttgaagt aacaggtgtt gaagttgtac tacgccaagc gattgaaagt     780

acaagcttcg aaggacaaac tgtaattgtt agtgtatggg aaaaagacgc aacaattact     840
```

```
ccaaataact tagtattaaa agaaaaagaa gttattggta ttttaggata ccgtcacatc    900

ttcccagctg ttattaaatt gattagctcc ggtcaaattc aagcagagaa attaattacg    960

aaaaaaatta cagtggatca agttgttgaa gaaggatttg aagcacttgt aaaagataaa   1020

acacaagtga aaattcttgt ttcacctaaa taa                                1053


<210> SEQ ID NO 85
<211> LENGTH: 350
<212> TYPE: PRT
<213> ORGANISM: Bacillus cereus

<400> SEQUENCE: 85

Met Lys Ala Leu Leu Trp His Asn Gln Arg Asp Val Arg Val Glu Glu
1               5                   10                  15

Val Pro Glu Pro Thr Val Lys Pro Gly Thr Val Lys Ile Lys Val Lys
            20                  25                  30

Trp Cys Gly Ile Cys Gly Thr Asp Leu His Glu Tyr Leu Ala Gly Pro
        35                  40                  45

Ile Phe Ile Pro Thr Glu Glu His Pro Leu Thr His Val Lys Ala Pro
    50                  55                  60

Val Ile Leu Gly His Glu Phe Ser Gly Glu Val Ile Glu Ile Gly Glu
65                  70                  75                  80

Gly Val Thr Ser His Lys Val Gly Asp Arg Val Val Val Glu Pro Ile
                85                  90                  95

Tyr Ser Cys Gly Lys Cys Glu Ala Cys Lys His Gly His Tyr Asn Val
            100                 105                 110

Cys Glu Gln Leu Val Phe His Gly Leu Gly Gly Glu Gly Gly Gly Phe
        115                 120                 125

Ser Glu Tyr Thr Val Val Pro Glu Asp Met Val His His Ile Pro Asp
    130                 135                 140

Glu Met Thr Tyr Glu Gln Gly Ala Leu Val Glu Pro Ala Ala Val Ala
145                 150                 155                 160

Val His Ala Val Arg Gln Ser Lys Leu Lys Glu Gly Glu Ala Val Ala
                165                 170                 175

Val Phe Gly Cys Gly Pro Ile Gly Leu Leu Val Ile Gln Ala Ala Lys
            180                 185                 190

Ala Ala Gly Ala Thr Pro Val Ile Ala Val Glu Leu Ser Lys Glu Arg
        195                 200                 205

Gln Glu Leu Ala Lys Leu Ala Gly Ala Asp Tyr Val Leu Asn Pro Ala
    210                 215                 220

Thr Gln Asp Val Leu Ala Glu Ile Arg Asn Leu Thr Asn Gly Leu Gly
225                 230                 235                 240

Val Asn Val Ser Phe Glu Val Thr Gly Val Glu Val Val Leu Arg Gln
                245                 250                 255

Ala Ile Glu Ser Thr Ser Phe Glu Gly Gln Thr Val Ile Val Ser Val
            260                 265                 270

Trp Glu Lys Asp Ala Thr Ile Thr Pro Asn Asn Leu Val Leu Lys Glu
        275                 280                 285

Lys Glu Val Ile Gly Ile Leu Gly Tyr Arg His Ile Phe Pro Ala Val
    290                 295                 300

Ile Lys Leu Ile Ser Ser Gly Gln Ile Gln Ala Glu Lys Leu Ile Thr
305                 310                 315                 320

Lys Lys Ile Thr Val Asp Gln Val Val Glu Glu Gly Phe Glu Ala Leu
                325                 330                 335

Val Lys Asp Lys Thr Gln Val Lys Ile Leu Val Ser Pro Lys
```

340 345 350

<210> SEQ ID NO 86
<211> LENGTH: 1053
<212> TYPE: DNA
<213> ORGANISM: Bacillus cereus

<400> SEQUENCE: 86

```
atgaaagcac tactttggca taatcaacgt gatgtacgag tagaagaagt accagaacca      60

acagtaaaac caggaacagt gaaaatcaaa gttaaatggt gtggtatttg tgggacagac     120

ttgcatgaat atttagcagg gcctattttt attccaacag aagaacatcc attaacacat     180

gtgaaagcac ctgttatttt aggtcatgag tttagtggtg aggtaataga gattggtgaa     240

ggagttacat ctcataaagt gggagaccgc gttgttgtag agccaattta ttcttgtggt     300

aaatgtgaag cttgtaaaca tggacattac aatgtttgtg aacaacttgt tttccacggt     360

cttggcggag aaggcggcgg tttctctgaa tatacagtag taccagaaga tatggttcat     420

cacattccag atgaaatgac gtatgaacaa ggtgcgcttg tagaaccagc agcagtagca     480

gttcatgcag tacgtcaaag taaattaaaa gaaggggaag ctgtagcggt atttggttgc     540

ggtccaattg gacttcttgt tatccaagca gctaaagcag caggagcaac tcctgttatt     600

gcagttgaac tttctaaaga acgtcaagag ttagcgaaat tagcaggtgc ggattatgta     660

ttaaatccag caactcaaga tgtgttagct gaaattcgta acttaacaaa tggtttaggt     720

gtaaatgtta gctttgaagt aacaggtgtt gaagttgtac tacgccaagc gattgaaagt     780

acaagcttcg aaggacaaac tgtaattgtt agtgtatggg aaaaagacgc aacaattact     840

ccaaataact tagtattaaa agaaaaagaa gttattggta ttttaggata ccgtcacatc     900

ttcccagctg ttattaaatt gattagctcc ggtcaaattc aagcagagaa attaattacg     960

aaaaaaatta cagtggatca agttgttgaa gaaggatttg aagcacttgt aaaagataaa    1020

acacaagtga aaattcttgt ttcacctaaa taa                                 1053
```

<210> SEQ ID NO 87
<211> LENGTH: 350
<212> TYPE: PRT
<213> ORGANISM: Bacillus cereus

<400> SEQUENCE: 87

```
Met Lys Ala Leu Leu Trp His Asn Gln Arg Asp Val Arg Val Glu Glu
1               5                   10                  15

Val Pro Glu Pro Thr Val Lys Pro Gly Thr Val Lys Ile Lys Val Lys
            20                  25                  30

Trp Cys Gly Ile Cys Gly Thr Asp Leu His Glu Tyr Leu Ala Gly Pro
        35                  40                  45

Ile Phe Ile Pro Thr Glu Glu His Pro Leu Thr His Val Lys Ala Pro
    50                  55                  60

Val Ile Leu Gly His Glu Phe Ser Gly Glu Val Ile Glu Ile Gly Glu
65                  70                  75                  80

Gly Val Thr Ser His Lys Val Gly Asp Arg Val Val Val Glu Pro Ile
                85                  90                  95

Tyr Ser Cys Gly Lys Cys Glu Ala Cys Lys His Gly His Tyr Asn Val
            100                 105                 110

Cys Glu Gln Leu Val Phe His Gly Leu Gly Gly Glu Gly Gly Gly Phe
        115                 120                 125

Ser Glu Tyr Thr Val Val Pro Glu Asp Met Val His His Ile Pro Asp
    130                 135                 140
```

```
Glu Met Thr Tyr Glu Gln Gly Ala Leu Val Glu Pro Ala Ala Val Ala
145                 150                 155                 160

Val His Ala Val Arg Gln Ser Lys Leu Lys Glu Gly Glu Ala Val Ala
                165                 170                 175

Val Phe Gly Cys Gly Pro Ile Gly Leu Leu Val Ile Gln Ala Ala Lys
            180                 185                 190

Ala Ala Gly Ala Thr Pro Val Ile Ala Val Glu Leu Ser Lys Glu Arg
        195                 200                 205

Gln Glu Leu Ala Lys Leu Ala Gly Ala Asp Tyr Val Leu Asn Pro Ala
    210                 215                 220

Thr Gln Asp Val Leu Ala Glu Ile Arg Asn Leu Thr Asn Gly Leu Gly
225                 230                 235                 240

Val Asn Val Ser Phe Glu Val Thr Gly Val Glu Val Val Leu Arg Gln
                245                 250                 255

Ala Ile Glu Ser Thr Ser Phe Glu Gly Gln Thr Val Ile Val Ser Val
            260                 265                 270

Trp Glu Lys Asp Ala Thr Ile Thr Pro Asn Asn Leu Val Leu Lys Glu
        275                 280                 285

Lys Glu Val Ile Gly Ile Leu Gly Tyr Arg His Ile Phe Pro Ala Val
    290                 295                 300

Ile Lys Leu Ile Ser Ser Gly Gln Ile Gln Ala Glu Lys Leu Ile Thr
305                 310                 315                 320

Lys Lys Ile Thr Val Asp Gln Val Val Glu Glu Gly Phe Glu Ala Leu
                325                 330                 335

Val Lys Asp Lys Thr Gln Val Lys Ile Leu Val Ser Pro Lys
            340                 345                 350
```

<210> SEQ ID NO 88
<211> LENGTH: 1113
<212> TYPE: DNA
<213> ORGANISM: Lactococcus lactis

<400> SEQUENCE: 88

```
ttgcctgaaa cgacaaccat cctatataga ggaggcgttt ttatgcgcgc agcacgtttt     60

tacgaccgcg gggatatccg cattgatgaa attaatgaac caatagtaaa agctggccaa    120

gttggcattg atgtggcttg gtgtggaatt tgtggaacag atctccatga atttttagat    180

ggcccaattt tttgtccgtc agcagaacat cctaatccaa ttactggaga agtaccacca    240

gtcactcttg gacatgaaat gtctggggtt gtaaatttta taggtgaagg agtaagcgga    300

cttaaagtag gtgaccatgt cgttgtcgaa ccttatatcg ttcccgaagg gactgataca    360

agtgaaactg gacattataa cctctcagaa ggctcaaact ttattggttt gggcggaaat    420

ggtggaggtt tggctgaaaa aatttctgtt gatgaacgtt gggttcacaa aattcctgat    480

aacttaccat tggatgaagc tgctctaatt gagccactat cagtcggcta tcacgctgtt    540

gaacgagcaa atttaagtga aaagagtacg gtattagttg ttggtgctgg accaattgga    600

ctattaactg ctgccgttgc aaaagcgcaa ggacatactg ttatcatcag tgaacctagt    660

ggacttcgtc gtaaaaaagc acaagaagca caagttgctg attatttctt caatccaatt    720

gaagatgaca ttcaagctaa agttcatgaa attaatgaaa aaggagtgga cgcagccttt    780

gaatgtacct ctgtccaacc gggatttgac gcttgtctag atgcgattcg tatgggtgga    840

acagttgtca ttgtcgcaat ttggggcaag cctgctagtg ttgatatggc aaaattagta    900

atcaaagaag ctaacctttt aggaacgatt gcttataata acactcatcc aaaaacaatt    960
```

```
gatttagtat caacaggtaa aataaaattg gaccaattca tcacagctaa aatcggtttg   1020

gatgatttga ttgataaagg attcgatacg ctgattcatc ataatgaaac agctgttaaa   1080

attttagttt caccaactgg taaaggtcta taa                                1113


<210> SEQ ID NO 89
<211> LENGTH: 370
<212> TYPE: PRT
<213> ORGANISM: Lactococcus lactis

<400> SEQUENCE: 89

Met Pro Glu Thr Thr Thr Ile Leu Tyr Arg Gly Gly Val Phe Met Arg
1               5                   10                  15

Ala Ala Arg Phe Tyr Asp Arg Gly Asp Ile Arg Ile Asp Glu Ile Asn
            20                  25                  30

Glu Pro Ile Val Lys Ala Gly Gln Val Gly Ile Asp Val Ala Trp Cys
        35                  40                  45

Gly Ile Cys Gly Thr Asp Leu His Glu Phe Leu Asp Gly Pro Ile Phe
    50                  55                  60

Cys Pro Ser Ala Glu His Pro Asn Pro Ile Thr Gly Glu Val Pro Pro
65                  70                  75                  80

Val Thr Leu Gly His Glu Met Ser Gly Val Val Asn Phe Ile Gly Glu
                85                  90                  95

Gly Val Ser Gly Leu Lys Val Gly Asp His Val Val Val Glu Pro Tyr
            100                 105                 110

Ile Val Pro Glu Gly Thr Asp Thr Ser Glu Thr Gly His Tyr Asn Leu
        115                 120                 125

Ser Glu Gly Ser Asn Phe Ile Gly Leu Gly Gly Asn Gly Gly Gly Leu
    130                 135                 140

Ala Glu Lys Ile Ser Val Asp Glu Arg Trp Val His Lys Ile Pro Asp
145                 150                 155                 160

Asn Leu Pro Leu Asp Glu Ala Ala Leu Ile Glu Pro Leu Ser Val Gly
                165                 170                 175

Tyr His Ala Val Glu Arg Ala Asn Leu Ser Glu Lys Ser Thr Val Leu
            180                 185                 190

Val Val Gly Ala Gly Pro Ile Gly Leu Leu Thr Ala Ala Val Ala Lys
        195                 200                 205

Ala Gln Gly His Thr Val Ile Ile Ser Glu Pro Ser Gly Leu Arg Arg
    210                 215                 220

Lys Lys Ala Gln Glu Ala Gln Val Ala Asp Tyr Phe Phe Asn Pro Ile
225                 230                 235                 240

Glu Asp Asp Ile Gln Ala Lys Val His Glu Ile Asn Glu Lys Gly Val
                245                 250                 255

Asp Ala Ala Phe Glu Cys Thr Ser Val Gln Pro Gly Phe Asp Ala Cys
            260                 265                 270

Leu Asp Ala Ile Arg Met Gly Gly Thr Val Val Ile Val Ala Ile Trp
        275                 280                 285

Gly Lys Pro Ala Ser Val Asp Met Ala Lys Leu Val Ile Lys Glu Ala
    290                 295                 300

Asn Leu Leu Gly Thr Ile Ala Tyr Asn Asn Thr His Pro Lys Thr Ile
305                 310                 315                 320

Asp Leu Val Ser Thr Gly Lys Ile Lys Leu Asp Gln Phe Ile Thr Ala
                325                 330                 335

Lys Ile Gly Leu Asp Asp Leu Ile Asp Lys Gly Phe Asp Thr Leu Ile
            340                 345                 350
```

```
His His Asn Glu Thr Ala Val Lys Ile Leu Val Ser Pro Thr Gly Lys
        355                 360                 365

Gly Leu
    370


<210> SEQ ID NO 90
<211> LENGTH: 705
<212> TYPE: DNA
<213> ORGANISM: Pyrococcus furiosus

<400> SEQUENCE: 90

atgaaggttg ccgtaattac tggggcatcc cgtggaatcg ggaagctat agcaaaggcc      60

cttgctgaag atggatattc ccttgcctta ggggctagaa gtgttgatag gttagagaag    120

attgccaagg aactcagcga aaaacatggg gtggaggtat tttacgacta cctcgatgta    180

tcaaaaccag aaagcgttga agagtttgca aggaaaacgc tagctcactt tggagatgtg    240

gacgttgttg tggccaatgc ggggcttggt tactttggta ggcttgaaga gcttacagaa    300

gagcagttcc acgaaatgat tgaagtaaac cttttgggag tttggagaac aataaaagct    360

ttcttaaact ccttaaagcg gactggagga gtggctattg ttgttacttc agatgtttct    420

gcaaggctac ttccatacgg tggaggttat gtggcaacta aatgggctgc aagagcattg    480

gtaaggacct tccagattga gaatccagat gtgaggttct tcgagctaag acctggagca    540

gtagatacat attttggagg gagcaaagct gggaagccaa aggagcaagg gtatttaaaa    600

cctgaggaag ttgctgaggc agtaaaatac ctcctaagac ttccaaagga tgttagggtt    660

gaggaattaa tgttgcgctc aatttatcaa aaacctgagt attga                    705


<210> SEQ ID NO 91
<211> LENGTH: 234
<212> TYPE: PRT
<213> ORGANISM: Pyrococcus furiosus

<400> SEQUENCE: 91

Met Lys Val Ala Val Ile Thr Gly Ala Ser Arg Gly Ile Gly Glu Ala
1               5                   10                  15

Ile Ala Lys Ala Leu Ala Glu Asp Gly Tyr Ser Leu Ala Leu Gly Ala
            20                  25                  30

Arg Ser Val Asp Arg Leu Glu Lys Ile Ala Lys Glu Leu Ser Glu Lys
        35                  40                  45

His Gly Val Glu Val Phe Tyr Asp Tyr Leu Asp Val Ser Lys Pro Glu
    50                  55                  60

Ser Val Glu Glu Phe Ala Arg Lys Thr Leu Ala His Phe Gly Asp Val
65                  70                  75                  80

Asp Val Val Val Ala Asn Ala Gly Leu Gly Tyr Phe Gly Arg Leu Glu
                85                  90                  95

Glu Leu Thr Glu Glu Gln Phe His Glu Met Ile Glu Val Asn Leu Leu
            100                 105                 110

Gly Val Trp Arg Thr Ile Lys Ala Phe Leu Asn Ser Leu Lys Arg Thr
        115                 120                 125

Gly Gly Val Ala Ile Val Val Thr Ser Asp Val Ser Ala Arg Leu Leu
    130                 135                 140

Pro Tyr Gly Gly Gly Tyr Val Ala Thr Lys Trp Ala Ala Arg Ala Leu
145                 150                 155                 160

Val Arg Thr Phe Gln Ile Glu Asn Pro Asp Val Arg Phe Phe Glu Leu
                165                 170                 175

Arg Pro Gly Ala Val Asp Thr Tyr Phe Gly Gly Ser Lys Ala Gly Lys
```

```
            180                 185                 190

Pro Lys Glu Gln Gly Tyr Leu Lys Pro Glu Glu Val Ala Glu Ala Val
        195                 200                 205

Lys Tyr Leu Leu Arg Leu Pro Lys Asp Val Arg Val Glu Glu Leu Met
    210                 215                 220

Leu Arg Ser Ile Tyr Gln Lys Pro Glu Tyr
225                 230


<210> SEQ ID NO 92
<211> LENGTH: 1665
<212> TYPE: DNA
<213> ORGANISM: Salmonella typhimurium

<400> SEQUENCE: 92

atgagatcga aaagatttga agcactggcg aaacgccctg tgaatcagga cggctttgtt      60

aaggagtgga tcgaagaagg ctttatcgcg atggaaagcc cgaacgaccc aaaaccgtcg     120

ataaaaatcg ttaacggcgc ggtaaccgag ctggacggaa aaccggttag cgaattcgac     180

ctgatcgacc actttatcgc ccgctacggc atcaacctga accgcgccga agaagtgatg     240

gcgatggatt cggtcaagct ggctaacatg ctgtgcgatc cgaacgtcaa gcgcagcgaa     300

atcgttccgc taaccaccgc gatgacccca gcgaaaattg tcgaagtggt ttcgcatatg     360

aacgtggttg agatgatgat ggcgatgcag aaaatgcgcg cccgccgtac tccatctcaa     420

caggcgcacg tcaccaacgt taaagacaac ccggtgcaaa ttgccgccga tgccgccgaa     480

ggcgcatggc gcgggtttga cgaacaagag acgacggttg cggtagcgcg ctatgcgccg     540

ttcaacgcca tcgcgctgct ggttggttct caggtaggtc gtccgggggt actgactcaa     600

tgctcgctgg aagaagccac cgagctgaag ctcggcatgc tgggccacac ctgctacgcc     660

gaaaccatct ccgtttacgg caccgagccg gtcttcaccg acggtgacga taccccatgg     720

tcgaagggct tcttagcctc ttcctacgcc tctcgcggcc tgaaaatgcg cttcacctcc     780

ggctccggct ccgaagtgca gatgggctac gccgaaggca aatccatgct gtatctggaa     840

gcgcgctgca tctatatcac caaagccgcg ggcgttcagg ggctgcaaaa cggctccgta     900

agcagcatcg gcgtaccgtc tgccgtgccg tcaggcattc gtgccgtgct ggcggaaaac     960

ctgatctgct cttcgctgga tctggaatgc gcctccagta acgaccagac cttcacccac    1020

tccgatatgc gtcgtaccgc tcgcctgctg atgcagttcc tgccgggtac cgactttatc    1080

tcctccggtt attccgcggt gccgaactac gacaacatgt tcgccggttc caacgaagat    1140

gcggaagact ttgacgacta caacgttatc cagcgtgacc tgaaagtgga cggcggtctg    1200

cgcccggttc gcgaagagga cgttatcgcc atccgtaaca aagccgcccg cgcgctgcag    1260

gccgtgtttg ccggaatggg actgccgccg attaccgatg aagaagttga agccgcgacc    1320

tatgcccacg gttcgaaaga tatgccggag cgcaacatcg tcgaagacat caagttcgcc    1380

caggaaatca tcaataaaaa ccgcaacggt ctggaagttg tgaaagcgct ggctcagggc    1440

gggtttaccg acgtggccca ggacatgctc aacatccaga aagccaagct aaccggcgac    1500

tatttgcaca cctccgccat tatcgtcggc gacggacaag tgctctctgc ggttaatgac    1560

gtcaatgact atgccggtcc ggcaacaggt tatcgcctgc agggagaacg ctgggaagag    1620

attaaaaaca tccctggcgc tcttgatccc aacgagattg attaa                    1665


<210> SEQ ID NO 93
<211> LENGTH: 554
<212> TYPE: PRT
<213> ORGANISM: Salmonella typhimurium
```

<400> SEQUENCE: 93

```
Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Glu Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Ser Ile Gly
    290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Leu Leu Met Gln
            340                 345                 350

Phe Leu Pro Gly Thr Asp Phe Ile Ser Ser Gly Tyr Ser Ala Val Pro
        355                 360                 365

Asn Tyr Asp Asn Met Phe Ala Gly Ser Asn Glu Asp Ala Glu Asp Phe
    370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415
```

```
Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
        435                 440                 445

Pro Glu Arg Asn Ile Val Glu Asp Ile Lys Phe Ala Gln Glu Ile Ile
    450                 455                 460

Asn Lys Asn Arg Asn Gly Leu Glu Val Val Lys Ala Leu Ala Gln Gly
465                 470                 475                 480

Gly Phe Thr Asp Val Ala Gln Asp Met Leu Asn Ile Gln Lys Ala Lys
                485                 490                 495

Leu Thr Gly Asp Tyr Leu His Thr Ser Ala Ile Ile Val Gly Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Glu Ile Lys Asn Ile
    530                 535                 540

Pro Gly Ala Leu Asp Pro Asn Glu Ile Asp
545                 550


<210> SEQ ID NO 94
<211> LENGTH: 675
<212> TYPE: DNA
<213> ORGANISM: Salmonella typhimurium

<400> SEQUENCE: 94

atggaaatta atgaaaaatt gctgcgccag ataattgaag acgtactccg cgatatgaag      60

ggcagcgata aacccgtctc gtttaatgcg cctgcggcat ccacagcacc acagaccgct     120

gcgcctgcgg gcgacggctt tctgaccgaa gtgggcgaag cgcgccaggg cactcagcag     180

gacgaagtca ttatcgccgt cggcccggca tttggcctgg cgcaaaccgt caatatcgtc     240

ggcttaccgc ataagagcat tctgcgcgaa gtcattgccg gtattgaaga agaaggcatc     300

aaggcgcgcg tgattcgctg ctttaaatct tccgacgtgg cgttcgtcgc cgttgaaggt     360

aaccgcctga gcggatccgg catctccatc ggcatccagt cgaaaggtac tacggttatc     420

caccagcagg ggctaccgcc gctctccaac ctggagctgt tcccgcaggc accgctgctg     480

acgctggaaa cctaccgtca gattggtaaa aacgccgccc gctatgcgaa acgagaatca     540

ccgcagccgg tccctacgct caatgaccag atggcacgcc cgaagtacca ggcaaagtcg     600

gccattttgc atattaaaga gaccaagtac gtcgtgacgg gcaaaaaccc gcaggaactg     660

cgcgtggcgc tttga                                                      675


<210> SEQ ID NO 95
<211> LENGTH: 224
<212> TYPE: PRT
<213> ORGANISM: Salmonella typhimurium

<400> SEQUENCE: 95

Met Glu Ile Asn Glu Lys Leu Leu Arg Gln Ile Ile Glu Asp Val Leu
1               5                   10                  15

Arg Asp Met Lys Gly Ser Asp Lys Pro Val Ser Phe Asn Ala Pro Ala
            20                  25                  30

Ala Ser Thr Ala Pro Gln Thr Ala Ala Pro Ala Gly Asp Gly Phe Leu
        35                  40                  45

Thr Glu Val Gly Glu Ala Arg Gln Gly Thr Gln Gln Asp Glu Val Ile
    50                  55                  60
```

```
Ile Ala Val Gly Pro Ala Phe Gly Leu Ala Gln Thr Val Asn Ile Val
65                  70                  75                  80

Gly Leu Pro His Lys Ser Ile Leu Arg Glu Val Ile Ala Gly Ile Glu
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220
```

<210> SEQ ID NO 96
<211> LENGTH: 522
<212> TYPE: DNA
<213> ORGANISM: Salmonella typhimurium

<400> SEQUENCE: 96

```
atgaataccg acgcaattga atcgatggtc cgggacgtat tgagccgcat gaacagcctg      60

cagggcgatg cgccagcagc ggctcctgcg gcaggcggca cgtcccgcag cgcaaaggtc     120

agcgactacc cgctggcgaa caaacacccg gaatgggtga aaaccgccac caataaaacg     180

ctggacgact ttacgctgga aaacgtgctg agcaataaag tcaccgctca ggatatgcgt     240

attaccccgg aaaccctgcg cttacaggcc tctatcgcca aagatgcggg tcgcgaccgg     300

ctggcgatga acttcgaacg cgccgccgaa ctgaccgcgg taccggacga tcgcattctt     360

gaaatctaca acgcccttcg tccgtatcgt tcaacgaaag aagagctgct cgctatcgcc     420

gacgatctcg aaaaccgtta tcaggcaaag atttgcgcag ctttcgttcg tgaagcggca     480

gggctgtacg ttgagcgtaa aaaactcaaa ggcgacgatt aa                        522
```

<210> SEQ ID NO 97
<211> LENGTH: 173
<212> TYPE: PRT
<213> ORGANISM: Salmonella typhimurium

<400> SEQUENCE: 97

```
Met Asn Thr Asp Ala Ile Glu Ser Met Val Arg Asp Val Leu Ser Arg
1               5                   10                  15

Met Asn Ser Leu Gln Gly Asp Ala Pro Ala Ala Ala Pro Ala Ala Gly
            20                  25                  30

Gly Thr Ser Arg Ser Ala Lys Val Ser Asp Tyr Pro Leu Ala Asn Lys
        35                  40                  45

His Pro Glu Trp Val Lys Thr Ala Thr Asn Lys Thr Leu Asp Asp Phe
    50                  55                  60

Thr Leu Glu Asn Val Leu Ser Asn Lys Val Thr Ala Gln Asp Met Arg
65                  70                  75                  80

Ile Thr Pro Glu Thr Leu Arg Leu Gln Ala Ser Ile Ala Lys Asp Ala
```

```
                85                  90                  95

Gly Arg Asp Arg Leu Ala Met Asn Phe Glu Arg Ala Ala Glu Leu Thr
            100                 105                 110

Ala Val Pro Asp Asp Arg Ile Leu Glu Ile Tyr Asn Ala Leu Arg Pro
        115                 120                 125

Tyr Arg Ser Thr Lys Glu Glu Leu Leu Ala Ile Ala Asp Asp Leu Glu
    130                 135                 140

Asn Arg Tyr Gln Ala Lys Ile Cys Ala Ala Phe Val Arg Glu Ala Ala
145                 150                 155                 160

Gly Leu Tyr Val Glu Arg Lys Lys Leu Lys Gly Asp Asp
                165                 170


<210> SEQ ID NO 98
<211> LENGTH: 1677
<212> TYPE: DNA
<213> ORGANISM: Lactobacillus collinoides

<400> SEQUENCE: 98

ttggaacgtc aaaaaagatt tgaaaaatta gagaaacgtc cagtgcattt agatgggttc      60

gttaagaact gggacgacga aggtttagtt gcccttaacg gtaagaacga tccaaagcca     120

agcattacga tcgaaaacgg tgttgttact gaaatggatg gtaagaagaa ggcagacttc     180

gaccttatcg acaagtacat cgctgaatac gggatcaact tggacaatgc tgaaaagact     240

ttaaacacag attcagttaa gatcgccaac atgatgtgtg atcctaacgt ctcccgtgct     300

gaaattattg aatatacaac tgctatgaca ccagccaagg ctgctgaagt tatcagccag     360

ttaaacttcg ctgaaatgat catggcaact caaaagatgc ggccacgtcg gacccctatg     420

actcaagtcc acgctaccaa cactttggat aacccagttg aaatcgctgc tgatgctgcc     480

gaagctgcat tacgtggggt tcctgaagaa gaaaccacca ctgccattgc tcggtatgcg     540

ccaatgaacg ctatttcaat catggttggg gcccaagcag gccgtcctgg tgttatcacc     600

caatgttcag ttgaagaagc tgacgaattg agtttgggga tgcgtgggtt tactgcctat     660

gctgaaacca tttcagttta tgggactgac cgggtcttca ctgatggtga tgatacccct     720

tggtcaaaag gtttcttagc ttcttgctac gcttcacgtg gtttgaagat gcggtttact     780

tcaggtgccg gttcagaagc tatgatgggc tacactgaag gtaaatcaat gctttacctt     840

gaagctcgtt gtatctacat taccaaggcg tcaggtgttc aaggtctgca aaacggtggt     900

gttagttgta tcgggatgcc aggtgccgtc gttggtggta tccgtgaagt cttaggtgaa     960

aacttactat gtatgtcact tgatgttgaa tgtgcttctg gttgtgacca agccttctct    1020

cactctgaca ttcgtcggac tggccggatg attggccaat tcatcgctgg tactgattac    1080

ctgtcatcag gttacgctgc cgaagaaaac atggataaca ccttcgctgg ttcaaacatg    1140

gatgttctgg actacgatga ttacatcact ttggaacgtg atatggctat taacggtggt    1200

atcatgccaa ttaccgaaga ggaatctatt aagattcgtc acaaggctgc ggttgctatc    1260

caagctgtct ttgatggctt aggcctacca cagatcactg atgaagaagt tgaagccgca    1320

acttatggca gcaattcaaa cgacatgcca aaacgtgaca tggttcaaga tatgaaagct    1380

gctcaaggtc tgatgactcg tggcattact gttgttgacg ttatcaaggc cttatatgac    1440

catgatatta aagacgtcgc tgaggctgtg cttaagttag cgcaacaaaa ggtttgtggt    1500

gattacctgc aaacatctgc tgtcttcttg gatggttgga agtgtacttc agctattaac    1560

aacgctaacg attacaaagg cccaggtact ggttaccgtc tatgggaaga caaagacaaa    1620

tgggatcgtc tagaaaacgt tccgtgggct ttggatcctc agaagttgga attctaa       1677
```

<210> SEQ ID NO 99
<211> LENGTH: 558
<212> TYPE: PRT
<213> ORGANISM: Lactobacillus collinoides

<400> SEQUENCE: 99

```
Met Glu Arg Gln Lys Arg Phe Glu Lys Leu Glu Lys Arg Pro Val His
1               5                   10                  15

Leu Asp Gly Phe Val Lys Asn Trp Asp Asp Glu Gly Leu Val Ala Leu
            20                  25                  30

Asn Gly Lys Asn Asp Pro Lys Pro Ser Ile Thr Ile Glu Asn Gly Val
        35                  40                  45

Val Thr Glu Met Asp Gly Lys Lys Lys Ala Asp Phe Asp Leu Ile Asp
    50                  55                  60

Lys Tyr Ile Ala Glu Tyr Gly Ile Asn Leu Asp Asn Ala Glu Lys Thr
65                  70                  75                  80

Leu Asn Thr Asp Ser Val Lys Ile Ala Asn Met Met Cys Asp Pro Asn
                85                  90                  95

Val Ser Arg Ala Glu Ile Ile Glu Tyr Thr Thr Ala Met Thr Pro Ala
            100                 105                 110

Lys Ala Ala Glu Val Ile Ser Gln Leu Asn Phe Ala Glu Met Ile Met
        115                 120                 125

Ala Thr Gln Lys Met Arg Pro Arg Arg Thr Pro Met Thr Gln Val His
    130                 135                 140

Ala Thr Asn Thr Leu Asp Asn Pro Val Glu Ile Ala Ala Asp Ala Ala
145                 150                 155                 160

Glu Ala Ala Leu Arg Gly Val Pro Glu Glu Glu Thr Thr Thr Ala Ile
                165                 170                 175

Ala Arg Tyr Ala Pro Met Asn Ala Ile Ser Ile Met Val Gly Ala Gln
            180                 185                 190

Ala Gly Arg Pro Gly Val Ile Thr Gln Cys Ser Val Glu Glu Ala Asp
        195                 200                 205

Glu Leu Ser Leu Gly Met Arg Gly Phe Thr Ala Tyr Ala Glu Thr Ile
    210                 215                 220

Ser Val Tyr Gly Thr Asp Arg Val Phe Thr Asp Gly Asp Asp Thr Pro
225                 230                 235                 240

Trp Ser Lys Gly Phe Leu Ala Ser Cys Tyr Ala Ser Arg Gly Leu Lys
                245                 250                 255

Met Arg Phe Thr Ser Gly Ala Gly Ser Glu Ala Met Met Gly Tyr Thr
            260                 265                 270

Glu Gly Lys Ser Met Leu Tyr Leu Glu Ala Arg Cys Ile Tyr Ile Thr
        275                 280                 285

Lys Ala Ser Gly Val Gln Gly Leu Gln Asn Gly Gly Val Ser Cys Ile
    290                 295                 300

Gly Met Pro Gly Ala Val Val Gly Gly Ile Arg Glu Val Leu Gly Glu
305                 310                 315                 320

Asn Leu Leu Cys Met Ser Leu Asp Val Glu Cys Ala Ser Gly Cys Asp
                325                 330                 335

Gln Ala Phe Ser His Ser Asp Ile Arg Arg Thr Gly Arg Met Ile Gly
            340                 345                 350

Gln Phe Ile Ala Gly Thr Asp Tyr Leu Ser Ser Gly Tyr Ala Ala Glu
        355                 360                 365

Glu Asn Met Asp Asn Thr Phe Ala Gly Ser Asn Met Asp Val Leu Asp
    370                 375                 380
```

```
Tyr Asp Asp Tyr Ile Thr Leu Glu Arg Asp Met Ala Ile Asn Gly Gly
385                 390                 395                 400

Ile Met Pro Ile Thr Glu Glu Glu Ser Ile Lys Ile Arg His Lys Ala
                405                 410                 415

Ala Val Ala Ile Gln Ala Val Phe Asp Gly Leu Gly Leu Pro Gln Ile
            420                 425                 430

Thr Asp Glu Glu Val Glu Ala Ala Thr Tyr Gly Ser Asn Ser Asn Asp
        435                 440                 445

Met Pro Lys Arg Asp Met Val Gln Asp Met Lys Ala Ala Gln Gly Leu
    450                 455                 460

Met Thr Arg Gly Ile Thr Val Val Asp Val Ile Lys Ala Leu Tyr Asp
465                 470                 475                 480

His Asp Ile Lys Asp Val Ala Glu Ala Val Leu Lys Leu Ala Gln Gln
                485                 490                 495

Lys Val Cys Gly Asp Tyr Leu Gln Thr Ser Ala Val Phe Leu Asp Gly
            500                 505                 510

Trp Lys Cys Thr Ser Ala Ile Asn Asn Ala Asn Asp Tyr Lys Gly Pro
        515                 520                 525

Gly Thr Gly Tyr Arg Leu Trp Glu Asp Lys Asp Lys Trp Asp Arg Leu
    530                 535                 540

Glu Asn Val Pro Trp Ala Leu Asp Pro Gln Lys Leu Glu Phe
545                 550                 555
```

<210> SEQ ID NO 100
<211> LENGTH: 693
<212> TYPE: DNA
<213> ORGANISM: Lactobacillus collinoides

<400> SEQUENCE: 100

```
gtgagttcag aaatcgatga aacattgctt agaaatatca ttaaaggcgt tttaaatgaa      60

gttcaaaact ctgatacgcc aatttccttt ggtggccaag atgcagcccc agttgccggt     120

gccaaggaag gtgccgcacc agaaaagaag ttggattggt tccaacacgt tggaatcgcc     180

aaaccaggtt tgtcaaagga tgaagttgta attggtgttg ccccagcatt tgctgaagtg     240

ttgacgcaaa ctatgacgaa gatccaacac aaagacatcc tgcgtcaaat cattgccgga     300

gttgaagaag aaggtctcaa ggcccgtgtc gttaaggttt atcggacttc agacgtttcc     360

ttcgtttccg ctgatgttga caagttgtca ggttcaggaa tttcagttgc cgttcaatca     420

aaggggacaa cgattattca ccaaaaggat caagcaccgt tgtcaaacct tgaattgttc     480

ccacaggctc cagttttgac attggacgct taccgtcaaa tcggtaagaa cgctgcccag     540

tatgctaagg gtatgtcacc aaccccagtg ccaacaatta acgaccagat ggcacgtgtg     600

caatatcaag cactttctgc tttgatgcac atcaaggaaa caaaacaggt tgttgttggg     660

aagcctgctg aagaaattaa ggtaaccttt tag                                  693
```

<210> SEQ ID NO 101
<211> LENGTH: 230
<212> TYPE: PRT
<213> ORGANISM: Lactobacillus collinoides

<400> SEQUENCE: 101

```
Met Ser Ser Glu Ile Asp Glu Thr Leu Leu Arg Asn Ile Ile Lys Gly
1               5                   10                  15

Val Leu Asn Glu Val Gln Asn Ser Asp Thr Pro Ile Ser Phe Gly Gly
            20                  25                  30
```

```
Gln Asp Ala Ala Pro Val Ala Gly Ala Lys Glu Gly Ala Ala Pro Glu
        35                  40                  45

Lys Lys Leu Asp Trp Phe Gln His Val Gly Ile Ala Lys Pro Gly Leu
    50                  55                  60

Ser Lys Asp Glu Val Val Ile Gly Val Ala Pro Ala Phe Ala Glu Val
65                  70                  75                  80

Leu Thr Gln Thr Met Thr Lys Ile Gln His Lys Asp Ile Leu Arg Gln
                85                  90                  95

Ile Ile Ala Gly Val Glu Glu Glu Gly Leu Lys Ala Arg Val Val Lys
            100                 105                 110

Val Tyr Arg Thr Ser Asp Val Ser Phe Val Ser Ala Asp Val Asp Lys
        115                 120                 125

Leu Ser Gly Ser Gly Ile Ser Val Ala Val Gln Ser Lys Gly Thr Thr
    130                 135                 140

Ile Ile His Gln Lys Asp Gln Ala Pro Leu Ser Asn Leu Glu Leu Phe
145                 150                 155                 160

Pro Gln Ala Pro Val Leu Thr Leu Asp Ala Tyr Arg Gln Ile Gly Lys
                165                 170                 175

Asn Ala Ala Gln Tyr Ala Lys Gly Met Ser Pro Thr Pro Val Pro Thr
            180                 185                 190

Ile Asn Asp Gln Met Ala Arg Val Gln Tyr Gln Ala Leu Ser Ala Leu
        195                 200                 205

Met His Ile Lys Glu Thr Lys Gln Val Val Val Gly Lys Pro Ala Glu
    210                 215                 220

Glu Ile Lys Val Thr Phe
225                 230


<210> SEQ ID NO 102
<211> LENGTH: 522
<212> TYPE: DNA
<213> ORGANISM: Lactobacillus collinoides

<400> SEQUENCE: 102

atgagtgaag tagatgactt agtagctaga attgctgctc agctacaaca aagtggaaac      60

gcttctagtg cctcaactag tgccggtact tctgctggtt ccgagaaaga attaggcgca     120

gcagattacc cactatttga aaagcaccca gatcaaatca agacgccatc aggtaaaaat     180

gttgaagaaa tcaccttgga aaatgttatt aacggcaagg tagacgcaaa ggatatgcgg     240

attacgcccg caaccctgaa gttacaaggt gaaattgctg ccaacgcagg tcggccagca     300

atccaacgga acttccagcg ggcttctgaa ttaacttcag ttcccgatga tgttgttttg     360

gacttatata attcattacg gccattccgt tcaaccaagc aagaattatt ggataccgcc     420

aaggagcttc gtgacaagta tcacgcacct atctgtgccg gctggttcga agaagcagcc     480

gaaaactacg aagtcaacaa gaagttgaag ggcgataact ag                        522


<210> SEQ ID NO 103
<211> LENGTH: 173
<212> TYPE: PRT
<213> ORGANISM: Lactobacillus collinoides

<400> SEQUENCE: 103

Met Ser Glu Val Asp Asp Leu Val Ala Arg Ile Ala Ala Gln Leu Gln
1               5                   10                  15

Gln Ser Gly Asn Ala Ser Ser Ala Ser Thr Ser Ala Gly Thr Ser Ala
            20                  25                  30

Gly Ser Glu Lys Glu Leu Gly Ala Ala Asp Tyr Pro Leu Phe Glu Lys
```

```
        35                  40                  45

His Pro Asp Gln Ile Lys Thr Pro Ser Gly Lys Asn Val Glu Glu Ile
    50                  55                  60

Thr Leu Glu Asn Val Ile Asn Gly Lys Val Asp Ala Lys Asp Met Arg
65                  70                  75                  80

Ile Thr Pro Ala Thr Leu Lys Leu Gln Gly Glu Ile Ala Ala Asn Ala
                85                  90                  95

Gly Arg Pro Ala Ile Gln Arg Asn Phe Gln Arg Ala Ser Glu Leu Thr
            100                 105                 110

Ser Val Pro Asp Asp Val Val Leu Asp Leu Tyr Asn Ser Leu Arg Pro
        115                 120                 125

Phe Arg Ser Thr Lys Gln Glu Leu Leu Asp Thr Ala Lys Glu Leu Arg
    130                 135                 140

Asp Lys Tyr His Ala Pro Ile Cys Ala Gly Trp Phe Glu Glu Ala Ala
145                 150                 155                 160

Glu Asn Tyr Glu Val Asn Lys Lys Leu Lys Gly Asp Asn
                165                 170
```

<210> SEQ ID NO 104
<211> LENGTH: 1665
<212> TYPE: DNA
<213> ORGANISM: Klebsiella pneumoniae

<400> SEQUENCE: 104

```
atgagatcga aaagatttga agcactggcg aaacgccctg tgaatcagga tggtttcgtt     60

aaggagtgga ttgaagaggg ctttatcgcg atggaaagtc ctaacgatcc caaaccttct    120

atccgcatcg tcaacggcgc ggtgaccgaa ctcgacggta aaccggttga cgagttcgac    180

ctgattgacc actttatcgc gcgctacggc attaatctcg cccgggccga agaagtgatg    240

gccatggatt cggttaagct cgccaacatg ctctgcgacc cgaacgttaa acgcagcgac    300

atcgtgccgc tcactaccgc gatgaccccg gcgaaaatcg tggaagtggt gtcgcatatg    360

aacgtggtcg agatgatgat ggcgatgcaa aaaatgcgcg cccgccgcac gccgtcccag    420

caggcgcatg tcactaatat caaagataat ccggtacaga ttgccgccga cgccgctgaa    480

ggcgcatggc gcggctttga cgaacaggag accaccgtcg ccgtggcgcg ctacgcgcgg    540

ttcaacgcca tcgccctgct ggtgggttca caggttggcc gccccggcgt cctcacccag    600

tgttcgctgg aagaagccac cgagctgaaa ctgggcatgc tgggccacac ctgctatgcc    660

gaaaccattt cggtatacgg tacggaaccg gtgtttaccg atggcgatga cactccatgg    720

tcgaaaggct tcctcgcctc ctcctacgcc tcgcgcggcc tgaaaatgcg ctttacctcc    780

ggttccggtt ctgaagtaca gatgggctat gccgaaggca aatcgatgct ttatctcgaa    840

gcgcgctgca tctacatcac caaagccgcc ggggtgcaag gcctgcagaa tggctccgtc    900

agctgtatcg gcgtaccgtc cgccgtgccg tccgggatcc gcgccgtact ggcggaaaac    960

ctgatctgct cagcgctgga tctggagtgc gcctccagca acgatcaaac ctttacccac   1020

tcggatatgc ggcgtaccgc gcgtctgctg atgcagttcc tgccaggcac cgacttcatc   1080

tcctccggtt actcggcggt gcccaactac gacaacatgt tcgccggttc caacgaagat   1140

gccgaagact tcgatgacta caacgtgatc cagcgcgacc tgaaggtcga tgggggtctg   1200

cggccggtgc gtgaagagga cgtgatcgcc attcgcaaca aagccgcccg cgcgctgcag   1260

gcggtatttg ccggcatggg tttgccgcct attacggatg aagaggtaga agccgccacc   1320

tacgcccacg gttcaaaaga tatgcctgag cgcaatatcg tcgaggacat caagtttgct   1380
```

```
caggagatca tcaacaagaa ccgcaacggc ctggaggtgg tgaaagccct ggcgaaaggc   1440

ggcttccccg atgtcgccca ggacatgctc aatattcaga aagccaagct caccggcgac   1500

tacctgcata cctccgccat cattgttggc gagggccagg tgctctcggc cgtgaatgac   1560

gtgaacgatt atgccggtcc ggcaacaggc taccgcctgc aaggcgagcg ctgggaagag   1620

attaaaaata tcccgggcgc gctcgatccc aatgaacttg gctaa                   1665
```

<210> SEQ ID NO 105
<211> LENGTH: 554
<212> TYPE: PRT
<213> ORGANISM: Klebsiella pneumoniae

<400> SEQUENCE: 105

```
Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Arg Ile Val Asn Gly Ala Val
        35                  40                  45

Thr Glu Leu Asp Gly Lys Pro Val Asp Glu Phe Asp Leu Ile Asp His
    50                  55                  60

Phe Ile Ala Arg Tyr Gly Ile Asn Leu Ala Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Asp Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Ile Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Arg Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
    290                 295                 300

Val Pro Ser Ala Val Pro Ser Gly Ile Arg Ala Val Leu Ala Glu Asn
305                 310                 315                 320

Leu Ile Cys Ser Ala Leu Asp Leu Glu Cys Ala Ser Ser Asn Asp Gln
                325                 330                 335
```

```
Thr Phe Thr His Ser Asp Met Arg Arg Thr Ala Arg Leu Leu Met Gln
            340                 345                 350

Phe Leu Pro Gly Thr Asp Phe Ile Ser Ser Gly Tyr Ser Ala Val Pro
        355                 360                 365

Asn Tyr Asp Asn Met Phe Ala Gly Ser Asn Glu Asp Ala Glu Asp Phe
    370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
        435                 440                 445

Pro Glu Arg Asn Ile Val Glu Asp Ile Lys Phe Ala Gln Glu Ile Ile
    450                 455                 460

Asn Lys Asn Arg Asn Gly Leu Glu Val Val Lys Ala Leu Ala Lys Gly
465                 470                 475                 480

Gly Phe Pro Asp Val Ala Gln Asp Met Leu Asn Ile Gln Lys Ala Lys
                485                 490                 495

Leu Thr Gly Asp Tyr Leu His Thr Ser Ala Ile Ile Val Gly Glu Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Glu Ile Lys Asn Ile
    530                 535                 540

Pro Gly Ala Leu Asp Pro Asn Glu Leu Gly
545                 550
```

<210> SEQ ID NO 106
<211> LENGTH: 687
<212> TYPE: DNA
<213> ORGANISM: Klebsiella pneumoniae

<400> SEQUENCE: 106

```
atggaaatta acgaaacgct gctgcgccag attatcgaag aggtgctgtc ggagatgaaa      60

tcaggcgcag ataagccggt ctcctttagc gcgccggcgt ctgtcgcctc tgccgcgccg     120

gtcgccgttg cgcctgtgtc cggcgacagc ttcctgacgg aaatcggcga agccaaaccc     180

ggcacgcagc aggatgaagt cattattgcc gtcgggccag cgtttggtct ggcgcaaacc     240

gccaatatcg tcggcattcc gcataaaaat attctgcgcg aagtgatcgc cggcattgag     300

gaagaaggca tcaaagcccg ggtgatccgc tgctttaagt catctgacgt cgccttcgtg     360

gcagtggaag gcaaccgcct gagcggctcc ggcatctcga tcggtattca gtcgaaaggc     420

accaccgtca tccaccagcg cggcctgccg ccgctttcca atctggaact cttcccgcag     480

gcgccgctgt taacgctgga aacctaccgt cagattggca aaaacgccgc gcgctacgcc     540

aaacgcgagt cgccgcagcc ggtgccgacg cttaacgatc agatggctcg tcccaaatac     600

caggcgaagt cggccatttt gcacattaaa gagaccaaat acgtggtgac gggcaaaaac     660

ccgcaggaac tgcgcgtggc gctttaa                                         687
```

<210> SEQ ID NO 107
<211> LENGTH: 228
<212> TYPE: PRT
<213> ORGANISM: Klebsiella pneumoniae

<400> SEQUENCE: 107

```
Met Glu Ile Asn Glu Thr Leu Leu Arg Gln Ile Ile Glu Glu Val Leu
1               5                   10                  15

Ser Glu Met Lys Ser Gly Ala Asp Lys Pro Val Ser Phe Ser Ala Pro
            20                  25                  30

Ala Ser Val Ala Ser Ala Ala Pro Val Ala Val Ala Pro Val Ser Gly
        35                  40                  45

Asp Ser Phe Leu Thr Glu Ile Gly Glu Ala Lys Pro Gly Thr Gln Gln
    50                  55                  60

Asp Glu Val Ile Ile Ala Val Gly Pro Ala Phe Gly Leu Ala Gln Thr
65                  70                  75                  80

Ala Asn Ile Val Gly Ile Pro His Lys Asn Ile Leu Arg Glu Val Ile
                85                  90                  95

Ala Gly Ile Glu Glu Glu Gly Ile Lys Ala Arg Val Ile Arg Cys Phe
            100                 105                 110

Lys Ser Ser Asp Val Ala Phe Val Ala Val Glu Gly Asn Arg Leu Ser
        115                 120                 125

Gly Ser Gly Ile Ser Ile Gly Ile Gln Ser Lys Gly Thr Thr Val Ile
    130                 135                 140

His Gln Arg Gly Leu Pro Pro Leu Ser Asn Leu Glu Leu Phe Pro Gln
145                 150                 155                 160

Ala Pro Leu Leu Thr Leu Glu Thr Tyr Arg Gln Ile Gly Lys Asn Ala
                165                 170                 175

Ala Arg Tyr Ala Lys Arg Glu Ser Pro Gln Pro Val Pro Thr Leu Asn
            180                 185                 190

Asp Gln Met Ala Arg Pro Lys Tyr Gln Ala Lys Ser Ala Ile Leu His
        195                 200                 205

Ile Lys Glu Thr Lys Tyr Val Val Thr Gly Lys Asn Pro Gln Glu Leu
    210                 215                 220

Arg Val Ala Leu
225
```

<210> SEQ ID NO 108
<211> LENGTH: 525
<212> TYPE: DNA
<213> ORGANISM: Klebsiella pneumoniae

<400> SEQUENCE: 108

```
atgaataccg acgcaattga atccatggta cgcgacgtgc tgagccggat gaacagccta     60

caggacgggg taacgcccgc gccagccgcg ccgacaaacg acaccgttcg ccagccaaaa    120

gttagcgact acccgttagc gacctgccat ccggagtggg tcaaaaccgc taccaataaa    180

acgctcgatg acctgacgct ggagaacgta ttaagcgatc gcgttacggc gcaggacatg    240

cgcatcactc cggaaacgct gcgtatgcag gcggcgatcg cccaggatgc cggacgcgat    300

cggctggcga tgaactttga gcgggccgca gagctcaccg cggttcccga cgaccgaatc    360

cttgagatct acaacgccct gcgcccatac cgttccaccc aggcggagct actggcgatc    420

gctgatgacc tcgagcatcg ctaccaggca cgactctgtg ccgcctttgt tcgggaagcg    480

gccgggctgt acatcgagcg taagaagctg aaaggcgacg attaa                    525
```

<210> SEQ ID NO 109
<211> LENGTH: 174
<212> TYPE: PRT
<213> ORGANISM: Klebsiella pneumoniae

<400> SEQUENCE: 109

Met Asn Thr Asp Ala Ile Glu Ser Met Val Arg Asp Val Leu Ser Arg
1 5 10 15

Met Asn Ser Leu Gln Asp Gly Val Thr Pro Ala Pro Ala Ala Pro Thr
20 25 30

Asn Asp Thr Val Arg Gln Pro Lys Val Ser Asp Tyr Pro Leu Ala Thr
35 40 45

Cys His Pro Glu Trp Val Lys Thr Ala Thr Asn Lys Thr Leu Asp Asp
50 55 60

Leu Thr Leu Glu Asn Val Leu Ser Asp Arg Val Thr Ala Gln Asp Met
65 70 75 80

Arg Ile Thr Pro Glu Thr Leu Arg Met Gln Ala Ala Ile Ala Gln Asp
85 90 95

Ala Gly Arg Asp Arg Leu Ala Met Asn Phe Glu Arg Ala Ala Glu Leu
100 105 110

Thr Ala Val Pro Asp Asp Arg Ile Leu Glu Ile Tyr Asn Ala Leu Arg
115 120 125

Pro Tyr Arg Ser Thr Gln Ala Glu Leu Leu Ala Ile Ala Asp Asp Leu
130 135 140

Glu His Arg Tyr Gln Ala Arg Leu Cys Ala Ala Phe Val Arg Glu Ala
145 150 155 160

Ala Gly Leu Tyr Ile Glu Arg Lys Lys Leu Lys Gly Asp Asp
165 170

<210> SEQ ID NO 110
<211> LENGTH: 1833
<212> TYPE: DNA
<213> ORGANISM: Klebsiella oxytoca

<400> SEQUENCE: 110
atgcgatata tagctggcat tgatatcggc aactcatcga cggaagtcgc cctggcgacc 60
ctggatgagg ctggcgcgct gacgatcacc cacagcgcgc tggcggaaac caccggaatc 120
aaaggcacgt tgcgtaacgt gttcgggatt caggaggcgc tcgccctcgt cgccagaggc 180
gccgggatcg ccgtcagcga tatttcgctc atccgcatca acgaagcgac gccggtgatt 240
ggcgatgtgg cgatggaaac cattaccgaa accatcatca ccgaatcgac catgatcggc 300
cataacccga aaacgcccgg cggcgcgggg cttggcacag gcatcaccat tacgccgcag 360
gagctgctaa cccgcccggc ggacgcgccc tatatcctgg tggtgtcgtc ggcgttcgat 420
tttgccgata tcgccagcgt gattaacgct tccctgcgcg ccgggtatca gattaccggc 480
gtcattttac agcgcgacga tggcgtgctg gtcagcaacc ggctggaaaa accgctgccg 540
atcgttgacg aagtgctgta catcgaccgc attccgctgg ggatgctggc ggcgattgag 600
gtcgccgttc cggggaaggt catcgaaacc ctctctaacc cttacggcat cgccaccgtc 660
tttaacctca gccccgagga gacgaagaac atcgtcccga tggcccgggc gctgattggc 720
aaccgttccg ccgtggtggt caaaacgcca tccggcgacg tcaaagcgcg cgcgataccc 780
gccggtaatc ttgagctgct ggcccagggc cgtagcgtgc gcgtggatgt ggccgccggc 840
gccgaagcca tcatgaaagc ggtcgacggc tgcggcaggc tcgataacgt caccggcgaa 900
tccggcacca atatcggcgg catgctggaa cacgtgcgcc agaccatggc cgagctgacc 960
aacaagccga gcagcgaaat atttattcag gacctgctgg ccgttgatac ctcggtaccg 1020
gtgagcgtta ccggcggtct ggccggggag ttctcgctgg agcaggccgt gggcatcgcc 1080
tcgatggtga aatcggatcg cctgcagatg gcaatgatcg cccgcgaaat cgagcagaag 1140

```
ctcaatatcg acgtgcagat cggcggcgca gaggccgaag ccgccatcct gggggcgctg   1200

accacgccgg gcaccacccg accgctggcg atcctcgacc tcggcgcggg ctccaccgat   1260

gcctccatca tcaaccccaa aggcgacatc atcgccaccc atctcgccgg cgcaggcgac   1320

atggtgacga tgattattgc ccgcgagctg gggctggaag accgctatct ggcggaagag   1380

atcaagaagt acccgctggc taaggtggaa agcctgttcc atttacgcca cgaggacggc   1440

agcgtgcagt tcttctccac gccgctgccg cccgccgtgt tcgcccgcgt ctgcgtggtg   1500

aaagcggacg aactggtgcc gctgcccggc gatttagcgc tggaaaaagt gcgcgccatt   1560

cgccgcagcg ccaaagagcg ggtctttgtc accaacgccc tgcgcgcgct gcgtcaggtc   1620

agccccaccg gcaacattcg cgatattccg ttcgtggtgc tggtcggcgg ttcgtcgctg   1680

gatttcgaag tcccgcagct ggtcaccgat gcgctggcgc actaccgcct ggttgccgga   1740

cggggaaata ttcgcggcag cgagggcccc cgaaacgcgg tggccaccgg cctgattctc   1800

tcctggcata aggagtttgc gcatgaacgg taa                                1833
```

<210> SEQ ID NO 111
<211> LENGTH: 610
<212> TYPE: PRT
<213> ORGANISM: Klebsiella oxytoca

<400> SEQUENCE: 111

```
Met Arg Tyr Ile Ala Gly Ile Asp Ile Gly Asn Ser Ser Thr Glu Val
1               5                   10                  15

Ala Leu Ala Thr Leu Asp Glu Ala Gly Ala Leu Thr Ile Thr His Ser
            20                  25                  30

Ala Leu Ala Glu Thr Thr Gly Ile Lys Gly Thr Leu Arg Asn Val Phe
        35                  40                  45

Gly Ile Gln Glu Ala Leu Ala Leu Val Ala Arg Gly Ala Gly Ile Ala
    50                  55                  60

Val Ser Asp Ile Ser Leu Ile Arg Ile Asn Glu Ala Thr Pro Val Ile
65                  70                  75                  80

Gly Asp Val Ala Met Glu Thr Ile Thr Glu Thr Ile Ile Thr Glu Ser
                85                  90                  95

Thr Met Ile Gly His Asn Pro Lys Thr Pro Gly Gly Ala Gly Leu Gly
            100                 105                 110

Thr Gly Ile Thr Ile Thr Pro Gln Glu Leu Leu Thr Arg Pro Ala Asp
        115                 120                 125

Ala Pro Tyr Ile Leu Val Val Ser Ser Ala Phe Asp Phe Ala Asp Ile
    130                 135                 140

Ala Ser Val Ile Asn Ala Ser Leu Arg Ala Gly Tyr Gln Ile Thr Gly
145                 150                 155                 160

Val Ile Leu Gln Arg Asp Asp Gly Val Leu Val Ser Asn Arg Leu Glu
                165                 170                 175

Lys Pro Leu Pro Ile Val Asp Glu Val Leu Tyr Ile Asp Arg Ile Pro
            180                 185                 190

Leu Gly Met Leu Ala Ala Ile Glu Val Ala Val Pro Gly Lys Val Ile
        195                 200                 205

Glu Thr Leu Ser Asn Pro Tyr Gly Ile Ala Thr Val Phe Asn Leu Ser
    210                 215                 220

Pro Glu Glu Thr Lys Asn Ile Val Pro Met Ala Arg Ala Leu Ile Gly
225                 230                 235                 240

Asn Arg Ser Ala Val Val Val Lys Thr Pro Ser Gly Asp Val Lys Ala
                245                 250                 255
```

```
Arg Ala Ile Pro Ala Gly Asn Leu Glu Leu Leu Ala Gln Gly Arg Ser
            260                 265                 270

Val Arg Val Asp Val Ala Ala Gly Ala Glu Ala Ile Met Lys Ala Val
        275                 280                 285

Asp Gly Cys Gly Arg Leu Asp Asn Val Thr Gly Glu Ser Gly Thr Asn
    290                 295                 300

Ile Gly Gly Met Leu Glu His Val Arg Gln Thr Met Ala Glu Leu Thr
305                 310                 315                 320

Asn Lys Pro Ser Ser Glu Ile Phe Ile Gln Asp Leu Leu Ala Val Asp
                325                 330                 335

Thr Ser Val Pro Val Ser Val Thr Gly Gly Leu Ala Gly Glu Phe Ser
            340                 345                 350

Leu Glu Gln Ala Val Gly Ile Ala Ser Met Val Lys Ser Asp Arg Leu
        355                 360                 365

Gln Met Ala Met Ile Ala Arg Glu Ile Glu Gln Lys Leu Asn Ile Asp
    370                 375                 380

Val Gln Ile Gly Gly Ala Glu Ala Glu Ala Ala Ile Leu Gly Ala Leu
385                 390                 395                 400

Thr Thr Pro Gly Thr Thr Arg Pro Leu Ala Ile Leu Asp Leu Gly Ala
                405                 410                 415

Gly Ser Thr Asp Ala Ser Ile Ile Asn Pro Lys Gly Asp Ile Ile Ala
            420                 425                 430

Thr His Leu Ala Gly Ala Gly Asp Met Val Thr Met Ile Ile Ala Arg
        435                 440                 445

Glu Leu Gly Leu Glu Asp Arg Tyr Leu Ala Glu Glu Ile Lys Lys Tyr
    450                 455                 460

Pro Leu Ala Lys Val Glu Ser Leu Phe His Leu Arg His Glu Asp Gly
465                 470                 475                 480

Ser Val Gln Phe Phe Ser Thr Pro Leu Pro Pro Ala Val Phe Ala Arg
                485                 490                 495

Val Cys Val Val Lys Ala Asp Glu Leu Val Pro Leu Pro Gly Asp Leu
            500                 505                 510

Ala Leu Glu Lys Val Arg Ala Ile Arg Arg Ser Ala Lys Glu Arg Val
        515                 520                 525

Phe Val Thr Asn Ala Leu Arg Ala Leu Arg Gln Val Ser Pro Thr Gly
    530                 535                 540

Asn Ile Arg Asp Ile Pro Phe Val Val Leu Val Gly Gly Ser Ser Leu
545                 550                 555                 560

Asp Phe Glu Val Pro Gln Leu Val Thr Asp Ala Leu Ala His Tyr Arg
                565                 570                 575

Leu Val Ala Gly Arg Gly Asn Ile Arg Gly Ser Glu Gly Pro Arg Asn
            580                 585                 590

Ala Val Ala Thr Gly Leu Ile Leu Ser Trp His Lys Glu Phe Ala His
        595                 600                 605

Glu Arg
    610
```

```
<210> SEQ ID NO 112
<211> LENGTH: 378
<212> TYPE: DNA
<213> ORGANISM: Klebsiella oxytoca

<400> SEQUENCE: 112

atgaacggta atcacagcgc cccggccatc gcgatcgccg tcatcgacgg ctgcgacggc      60
```

```
ctgtggcgcg aagtgctgct gggtatcgaa gaggaaggta tccctttccg gctccagcat    120

cacccggccg gagaggtcgt ggacagcgcc tggcaggcgg cgcgcagctc gccgctgctg    180

gtgggcatcg cctgcgaccg ccatatgctg gtcgtgcact acaagaattt acccgcatcg    240

gcgccgcttt ttacgctgat gcatcatcag gacagtcagg cccatcgcaa caccggtaat    300

aacgcggcac ggctggtcaa ggggatccct ttccgggatc tgaatagcga agcaacagga    360

gaacagcagg atgaataa                                                  378
```

<210> SEQ ID NO 113
<211> LENGTH: 125
<212> TYPE: PRT
<213> ORGANISM: Klebsiella oxytoca

<400> SEQUENCE: 113

```
Met Asn Gly Asn His Ser Ala Pro Ala Ile Ala Ile Ala Val Ile Asp
1               5                   10                  15

Gly Cys Asp Gly Leu Trp Arg Glu Val Leu Leu Gly Ile Glu Glu Glu
            20                  25                  30

Gly Ile Pro Phe Arg Leu Gln His His Pro Ala Gly Glu Val Val Asp
        35                  40                  45

Ser Ala Trp Gln Ala Ala Arg Ser Ser Pro Leu Leu Val Gly Ile Ala
    50                  55                  60

Cys Asp Arg His Met Leu Val Val His Tyr Lys Asn Leu Pro Ala Ser
65                  70                  75                  80

Ala Pro Leu Phe Thr Leu Met His His Gln Asp Ser Gln Ala His Arg
                85                  90                  95

Asn Thr Gly Asn Asn Ala Ala Arg Leu Val Lys Gly Ile Pro Phe Arg
            100                 105                 110

Asp Leu Asn Ser Glu Ala Thr Gly Glu Gln Gln Asp Glu
        115                 120                 125
```

<210> SEQ ID NO 114
<211> LENGTH: 1833
<212> TYPE: DNA
<213> ORGANISM: Salmonella typhimurium

<400> SEQUENCE: 114

```
atgcgatata tagctggcat tgacatcggt aactcatcaa cggaagtcgc actggcgcgg     60

caagatgaga ctggcgcact gacgattaca cacagcgcgc tggcggaaac caccgggatc    120

aaaggcacgt tgcgtaacgt gttcggcatt caggaagcgc tcgccctcgt cgcaaagcgc    180

gcggggatca atgtcagaga tatttcgctc atccgcatta acgaagccac gccggtgatt    240

ggcgatgtgg cgatggaaac cattaccgaa accatcatca ccgaatcgac aatgatcggc    300

cataacccaa aaacgccggg cggagcaggc cttggtgtgg gtatcacgat tacgccggag    360

gagctgttaa cccgcccggc ggactcgtcc tatattctgg tggtatcgtc agcctttgat    420

tttgctgata tcgccaatgt tatcaacgcc tcaatgcgcg ccggatacca gattaccggc    480

gtcattttgc agcgcgacga tggcgtactg gtcagcaacc ggctggaaaa atcgctaccg    540

attgtcgatg aagttctgta catcgaccgc attccgctgg ggatgctggc ggcgattgaa    600

gtcgccgtgc cgggaaaggt tatcgaaacc ctctctaacc cttacggcat cgccaccgta    660

tttaatctca acgccgatga gacaaaaaac atcgtcccga tggcgcgcgc gctgattggc    720

aaccgttccg ccgtggtggt taaaacgcca tccggcgacg tcaaagcgcg cgcaataccc    780

gccggtaacc tggagctgca ggctcagggt cgtaccgtgc gcgtggatgt tgccgccggt    840
```

```
gccgaagcca tcatgaaagc ggtggacggt tgcggcaagc tcgacaacgt caccggcgag    900

gccgggacca atatcggcgg catgctggag cacgtgcgcc agaccatggc cgaactgacc    960

aacaagccga gcagtgagat tttcattcag gatctactgg ccgttgacac ctcggttccg   1020

gtgagcgtca ccggcggtct ggccggggag ttctcgctgg agcaggccgt cggcatcgcc   1080

tcgatggtga aatcagaccg tctgcagatg gcgatgattg cccgtgaaat tgagcagaag   1140

cttaatatcg acgtgcagat cggcggcgct gaggctgaag ccgccattct gggcgcgctg   1200

accacgccgg gtaccacccg accgctggcg atcctcgacc tcggcgcggg ctccaccgat   1260

gcctccatca tcaaccctaa aggcgaaatc atcgccaccc atctcgccgg ggcaggcgac   1320

atggtcacga tgattattgc ccgcgaactg ggctggaag accgctatct ggcggaagag   1380

atcaaaaaat acccgctggc taaggtcgaa agcctgttcc acttacgcca cgaggacggc   1440

agcgtccagt tcttcccgac gccgctgcct cccgccgtgt tcgcccgcgt ctgcgtggtg   1500

aaaccggacg aactggtgcc gcttcccggc gacttagcgc tggaaaaagt gcgcgccatt   1560

cgccgcagcg ctaaagaacg cgtctttgtc accaacgccc tgcgcgcgct gcgccaggtc   1620

agtccaaccg gcaacattcg cgatattccg ttcgtggtgc tggtcggcgg ctcgtcgctg   1680

gatttcgaag ttccgcagct ggtcaccgat gcgctggcgc actaccgcct ggtcgccggg   1740

cgaggaaata ttcgcggcag cgaaggccca agaaacgcgg tggccaccgg cctgattctc   1800

tcctggcata aggagtttgc gcatggacag taa                                1833
```

<210> SEQ ID NO 115
<211> LENGTH: 610
<212> TYPE: PRT
<213> ORGANISM: Salmonella typhimurium

<400> SEQUENCE: 115

```
Met Arg Tyr Ile Ala Gly Ile Asp Ile Gly Asn Ser Ser Thr Glu Val
1               5                   10                  15

Ala Leu Ala Arg Gln Asp Glu Thr Gly Ala Leu Thr Ile Thr His Ser
            20                  25                  30

Ala Leu Ala Glu Thr Thr Gly Ile Lys Gly Thr Leu Arg Asn Val Phe
        35                  40                  45

Gly Ile Gln Glu Ala Leu Ala Leu Val Ala Lys Arg Ala Gly Ile Asn
    50                  55                  60

Val Arg Asp Ile Ser Leu Ile Arg Ile Asn Glu Ala Thr Pro Val Ile
65                  70                  75                  80

Gly Asp Val Ala Met Glu Thr Ile Thr Glu Thr Ile Ile Thr Glu Ser
                85                  90                  95

Thr Met Ile Gly His Asn Pro Lys Thr Pro Gly Gly Ala Gly Leu Gly
            100                 105                 110

Val Gly Ile Thr Ile Thr Pro Glu Glu Leu Leu Thr Arg Pro Ala Asp
        115                 120                 125

Ser Ser Tyr Ile Leu Val Val Ser Ser Ala Phe Asp Phe Ala Asp Ile
    130                 135                 140

Ala Asn Val Ile Asn Ala Ser Met Arg Ala Gly Tyr Gln Ile Thr Gly
145                 150                 155                 160

Val Ile Leu Gln Arg Asp Asp Gly Val Leu Val Ser Asn Arg Leu Glu
                165                 170                 175

Lys Ser Leu Pro Ile Val Asp Glu Val Leu Tyr Ile Asp Arg Ile Pro
            180                 185                 190

Leu Gly Met Leu Ala Ala Ile Glu Val Ala Val Pro Gly Lys Val Ile
        195                 200                 205
```

```
Glu Thr Leu Ser Asn Pro Tyr Gly Ile Ala Thr Val Phe Asn Leu Asn
    210                 215                 220

Ala Asp Glu Thr Lys Asn Ile Val Pro Met Ala Arg Ala Leu Ile Gly
225                 230                 235                 240

Asn Arg Ser Ala Val Val Val Lys Thr Pro Ser Gly Asp Val Lys Ala
                245                 250                 255

Arg Ala Ile Pro Ala Gly Asn Leu Glu Leu Gln Ala Gln Gly Arg Thr
            260                 265                 270

Val Arg Val Asp Val Ala Ala Gly Ala Glu Ala Ile Met Lys Ala Val
        275                 280                 285

Asp Gly Cys Gly Lys Leu Asp Asn Val Thr Gly Glu Ala Gly Thr Asn
    290                 295                 300

Ile Gly Gly Met Leu Glu His Val Arg Gln Thr Met Ala Glu Leu Thr
305                 310                 315                 320

Asn Lys Pro Ser Ser Glu Ile Phe Ile Gln Asp Leu Leu Ala Val Asp
                325                 330                 335

Thr Ser Val Pro Val Ser Val Thr Gly Gly Leu Ala Gly Glu Phe Ser
            340                 345                 350

Leu Glu Gln Ala Val Gly Ile Ala Ser Met Val Lys Ser Asp Arg Leu
        355                 360                 365

Gln Met Ala Met Ile Ala Arg Glu Ile Glu Gln Lys Leu Asn Ile Asp
    370                 375                 380

Val Gln Ile Gly Gly Ala Glu Ala Glu Ala Ala Ile Leu Gly Ala Leu
385                 390                 395                 400

Thr Thr Pro Gly Thr Thr Arg Pro Leu Ala Ile Leu Asp Leu Gly Ala
                405                 410                 415

Gly Ser Thr Asp Ala Ser Ile Ile Asn Pro Lys Gly Glu Ile Ile Ala
            420                 425                 430

Thr His Leu Ala Gly Ala Gly Asp Met Val Thr Met Ile Ile Ala Arg
        435                 440                 445

Glu Leu Gly Leu Glu Asp Arg Tyr Leu Ala Glu Glu Ile Lys Lys Tyr
    450                 455                 460

Pro Leu Ala Lys Val Glu Ser Leu Phe His Leu Arg His Glu Asp Gly
465                 470                 475                 480

Ser Val Gln Phe Phe Pro Thr Pro Leu Pro Pro Ala Val Phe Ala Arg
                485                 490                 495

Val Cys Val Val Lys Pro Asp Glu Leu Val Pro Leu Pro Gly Asp Leu
            500                 505                 510

Ala Leu Glu Lys Val Arg Ala Ile Arg Arg Ser Ala Lys Glu Arg Val
        515                 520                 525

Phe Val Thr Asn Ala Leu Arg Ala Leu Arg Gln Val Ser Pro Thr Gly
    530                 535                 540

Asn Ile Arg Asp Ile Pro Phe Val Val Leu Val Gly Gly Ser Ser Leu
545                 550                 555                 560

Asp Phe Glu Val Pro Gln Leu Val Thr Asp Ala Leu Ala His Tyr Arg
                565                 570                 575

Leu Val Ala Gly Arg Gly Asn Ile Arg Gly Ser Glu Gly Pro Arg Asn
            580                 585                 590

Ala Val Ala Thr Gly Leu Ile Leu Ser Trp His Lys Glu Phe Ala His
        595                 600                 605

Gly Gln
    610
```

<210> SEQ ID NO 116
<211> LENGTH: 372
<212> TYPE: DNA
<213> ORGANISM: Salmonella typhimurium

<400> SEQUENCE: 116

```
atggacagta atcacagcgc cccggctatc gtcattaccg ttatcaacga ctgcgccagc     60

ctctggcacg aagtgctgct gggcattgaa gaggaaggca tccctttcct gcttcagcat    120

cacccggctg gagatatcgt tgacagcgcc tggcaggcgg cgcgcagctc gccgctgctg    180

gtcggcattg cctgcgatcg acactcgctg gtcgtgcatt acaagaattt acccgcatcg    240

gcgccgcttt ttacgctgat gcatcatcag gacagtcagg cccaacgcaa caccggtaat    300

aacgcggcac ggctggtcaa agggatccct ttcgggatct ccatgcttaa tcacaggaga    360

acggcagtat ga                                                        372
```

<210> SEQ ID NO 117
<211> LENGTH: 123
<212> TYPE: PRT
<213> ORGANISM: Salmonella typhimurium

<400> SEQUENCE: 117

```
Met Asp Ser Asn His Ser Ala Pro Ala Ile Val Ile Thr Val Ile Asn
1               5                   10                  15

Asp Cys Ala Ser Leu Trp His Glu Val Leu Leu Gly Ile Glu Glu Glu
            20                  25                  30

Gly Ile Pro Phe Leu Leu Gln His His Pro Ala Gly Asp Ile Val Asp
        35                  40                  45

Ser Ala Trp Gln Ala Ala Arg Ser Ser Pro Leu Leu Val Gly Ile Ala
    50                  55                  60

Cys Asp Arg His Ser Leu Val Val His Tyr Lys Asn Leu Pro Ala Ser
65                  70                  75                  80

Ala Pro Leu Phe Thr Leu Met His His Gln Asp Ser Gln Ala Gln Arg
                85                  90                  95

Asn Thr Gly Asn Asn Ala Ala Arg Leu Val Lys Gly Ile Pro Phe Gly
            100                 105                 110

Ile Ser Met Leu Asn His Arg Arg Thr Ala Val
        115                 120
```

<210> SEQ ID NO 118
<211> LENGTH: 1833
<212> TYPE: DNA
<213> ORGANISM: Lactobacillus collinoides

<400> SEQUENCE: 118

```
atgacacgtg taattggtgt tgatatcggg aattcctcta cagaagttgc gcttgctgat     60

gtgtctgaca gtggtgaagt aaatttcatt aattctggaa tttccgatac aactggcatt    120

aaaggtacta aacaaaattt gatcggggtg cgtaaatcca tccagatcgt tttgaaaaag    180

tcgaatatgc aaatttccga tgttgacctg attcggatca acgaagcaac gcccgttatc    240

ggtgatgttg ccatggagac catcaccgaa acggtgatta ctgaatcgac gatgatcggc    300

cacaacccag ggactcctgg gggtgtcggt actggttctg gttacacggt gaatttgctt    360

gatttgttga gccaaacgga taaggatcgt ccttatatcg ttatcatctc gaaagaaatc    420

gattttgctg acgcagctaa gctgatcaac gcttatgtgg cttctggtta taatattacc    480

gctgccattc tgcaaagtga tgatggggtg ctgatcaata atcggttgac ccataagatt    540

cccatcgtgg atgaagtctc acagatcgac aaggtaccgt tgaacatgct tgccgcagtg    600
```

```
gaagttgcac cgcctggcaa agtaattgct caactttcca acccgtatgg cattgccaca    660

ctgttcgaac tttcctctga agaaaccaag aacattgtgc cagttgcccg agccttaatc    720

ggaaaccggt cagcggttgt tattaaaacc cctgccggtg atgttaaagc tcgtgttatc    780

ccagccggga aaatcttgat caatggccaa ccgaatggtc atggtgaagt taacgttgcg    840

gctggtgccg atgccatcat gaaaaaggtg aacgagttcg atagtgtcga tgacattacc    900

ggtgaatcgg gcactaacgt tggtgggatg cttgaaaaag ttcgtcaaac aatggctgag    960

ttgaccgaca agcaaaatag cgacattgcc attcaagatt tattagctgt caatacgtcc   1020

gttccagtaa cggtgcgtgg tggtctggct ggtgaattct caatggaaca agccgttggg   1080

attgctgcta tggtcaaatc tgatcacttg caaatgcaag cgattgcaga cctgatgaaa   1140

gatgaatttc acgttcaagt cgaaatcggc ggtgctgaag ctgaatcagc catcctcggt   1200

gcgctaacaa cgccagggac gacaaaacca attgccatcc ttgatttggg ggctggttca   1260

acggatgcat caattatcaa ccaaaaggac gaaaaggtcg ctattcactt ggctggtgcc   1320

ggtgatatgg ttaccatgat catcaattct gaacttgggt tggaagaccc atatttagct   1380

gaggatatta agaaatatcc gctggctaaa gttgataatc tattccagct acggcatgaa   1440

gatggtgccg ttcaattctt tgaagatcca ttacctgctg atttatttgc cagagttgtg   1500

gctgttaaac cagatggtta cgaaccactt cctggtaatt tgagtatcga gaaagttaaa   1560

atcgtccgtc aaactgctaa gaagcgggtg ttcgtaacga acgcaattcg tgccttacac   1620

cacgttagcc caacaggtaa tatccgagat atcccatttg tggtcattgt cggcggctca   1680

gccctcgatt ttgaaattcc acaattggtc accgatgaat tatcacactt taacttagtt   1740

gcaggtcgtg gtaatattcg gggaattgaa ggtccacgga acgccgtggc aactggtttg   1800

attctttcat acgcgagtga gaagagggga tag                                 1833
```

```
<210> SEQ ID NO 119
<211> LENGTH: 610
<212> TYPE: PRT
<213> ORGANISM: Lactobacillus collinoides

<400> SEQUENCE: 119

Met Thr Arg Val Ile Gly Val Asp Ile Gly Asn Ser Ser Thr Glu Val
1               5                   10                  15

Ala Leu Ala Asp Val Ser Asp Ser Gly Glu Val Asn Phe Ile Asn Ser
            20                  25                  30

Gly Ile Ser Asp Thr Thr Gly Ile Lys Gly Thr Lys Gln Asn Leu Ile
        35                  40                  45

Gly Val Arg Lys Ser Ile Gln Ile Val Leu Lys Lys Ser Asn Met Gln
    50                  55                  60

Ile Ser Asp Val Asp Leu Ile Arg Ile Asn Glu Ala Thr Pro Val Ile
65                  70                  75                  80

Gly Asp Val Ala Met Glu Thr Ile Thr Glu Thr Val Ile Thr Glu Ser
                85                  90                  95

Thr Met Ile Gly His Asn Pro Gly Thr Pro Gly Gly Val Gly Thr Gly
            100                 105                 110

Ser Gly Tyr Thr Val Asn Leu Leu Asp Leu Leu Ser Gln Thr Asp Lys
        115                 120                 125

Asp Arg Pro Tyr Ile Val Ile Ile Ser Lys Glu Ile Asp Phe Ala Asp
    130                 135                 140

Ala Ala Lys Leu Ile Asn Ala Tyr Val Ala Ser Gly Tyr Asn Ile Thr
145                 150                 155                 160
```

```
Ala Ala Ile Leu Gln Ser Asp Asp Gly Val Leu Ile Asn Asn Arg Leu
                165                 170                 175

Thr His Lys Ile Pro Ile Val Asp Glu Val Ser Gln Ile Asp Lys Val
            180                 185                 190

Pro Leu Asn Met Leu Ala Ala Val Glu Val Ala Pro Pro Gly Lys Val
        195                 200                 205

Ile Ala Gln Leu Ser Asn Pro Tyr Gly Ile Ala Thr Leu Phe Glu Leu
    210                 215                 220

Ser Ser Glu Glu Thr Lys Asn Ile Val Pro Val Ala Arg Ala Leu Ile
225                 230                 235                 240

Gly Asn Arg Ser Ala Val Val Ile Lys Thr Pro Ala Gly Asp Val Lys
                245                 250                 255

Ala Arg Val Ile Pro Ala Gly Lys Ile Leu Ile Asn Gly Gln Pro Asn
            260                 265                 270

Gly His Gly Glu Val Asn Val Ala Ala Gly Ala Asp Ala Ile Met Lys
        275                 280                 285

Lys Val Asn Glu Phe Asp Ser Val Asp Asp Ile Thr Gly Glu Ser Gly
    290                 295                 300

Thr Asn Val Gly Gly Met Leu Glu Lys Val Arg Gln Thr Met Ala Glu
305                 310                 315                 320

Leu Thr Asp Lys Gln Asn Ser Asp Ile Ala Ile Gln Asp Leu Leu Ala
                325                 330                 335

Val Asn Thr Ser Val Pro Val Thr Val Arg Gly Gly Leu Ala Gly Glu
            340                 345                 350

Phe Ser Met Glu Gln Ala Val Gly Ile Ala Ala Met Val Lys Ser Asp
        355                 360                 365

His Leu Gln Met Gln Ala Ile Ala Asp Leu Met Lys Asp Glu Phe His
    370                 375                 380

Val Gln Val Glu Ile Gly Gly Ala Glu Ala Glu Ser Ala Ile Leu Gly
385                 390                 395                 400

Ala Leu Thr Thr Pro Gly Thr Thr Lys Pro Ile Ala Ile Leu Asp Leu
                405                 410                 415

Gly Ala Gly Ser Thr Asp Ala Ser Ile Ile Asn Gln Lys Asp Glu Lys
            420                 425                 430

Val Ala Ile His Leu Ala Gly Ala Gly Asp Met Val Thr Met Ile Ile
        435                 440                 445

Asn Ser Glu Leu Gly Leu Glu Asp Pro Tyr Leu Ala Glu Asp Ile Lys
    450                 455                 460

Lys Tyr Pro Leu Ala Lys Val Asp Asn Leu Phe Gln Leu Arg His Glu
465                 470                 475                 480

Asp Gly Ala Val Gln Phe Phe Glu Asp Pro Leu Pro Ala Asp Leu Phe
                485                 490                 495

Ala Arg Val Val Ala Val Lys Pro Asp Gly Tyr Glu Pro Leu Pro Gly
            500                 505                 510

Asn Leu Ser Ile Glu Lys Val Lys Ile Val Arg Gln Thr Ala Lys Lys
        515                 520                 525

Arg Val Phe Val Thr Asn Ala Ile Arg Ala Leu His His Val Ser Pro
    530                 535                 540

Thr Gly Asn Ile Arg Asp Ile Pro Phe Val Val Ile Val Gly Gly Ser
545                 550                 555                 560

Ala Leu Asp Phe Glu Ile Pro Gln Leu Val Thr Asp Glu Leu Ser His
                565                 570                 575

Phe Asn Leu Val Ala Gly Arg Gly Asn Ile Arg Gly Ile Glu Gly Pro
```

```
            580                 585                 590

Arg Asn Ala Val Ala Thr Gly Leu Ile Leu Ser Tyr Ala Ser Glu Lys
        595                 600                 605

Arg Gly
    610


<210> SEQ ID NO 120
<211> LENGTH: 351
<212> TYPE: DNA
<213> ORGANISM: Lactobacillus collinoides

<400> SEQUENCE: 120

atggcatttg attctgaacg tccgtcaatt ctattggcga caccaacggg ttctaatggc      60

caacttccag aagttctaaa accaatgctc aatggtattg aagaagaaca gattcctttt     120

cagattctcg atatggaagg cggttcagca gttgagcggg cttataacgc gtcagttgct     180

tcacgattat cagtgggcgt tgggtttgat gatgcacata tcattgtgca ttataaaaac     240

ttgaaaccag aaaaaccgct gtttgatgtt gccatcactg atgcagcatc cattcgtaaa     300

gttggcgcaa acgccgctcg acttgtaaag ggagttccat tcaagaagta a              351


<210> SEQ ID NO 121
<211> LENGTH: 116
<212> TYPE: PRT
<213> ORGANISM: Lactobacillus collinoides

<400> SEQUENCE: 121

Met Ala Phe Asp Ser Glu Arg Pro Ser Ile Leu Leu Ala Thr Pro Thr
1               5                   10                  15

Gly Ser Asn Gly Gln Leu Pro Glu Val Leu Lys Pro Met Leu Asn Gly
            20                  25                  30

Ile Glu Glu Glu Gln Ile Pro Phe Gln Ile Leu Asp Met Glu Gly Gly
        35                  40                  45

Ser Ala Val Glu Arg Ala Tyr Asn Ala Ser Val Ala Ser Arg Leu Ser
    50                  55                  60

Val Gly Val Gly Phe Asp Asp Ala His Ile Ile Val His Tyr Lys Asn
65                  70                  75                  80

Leu Lys Pro Glu Lys Pro Leu Phe Asp Val Ala Ile Thr Asp Ala Ala
                85                  90                  95

Ser Ile Arg Lys Val Gly Ala Asn Ala Ala Arg Leu Val Lys Gly Val
            100                 105                 110

Pro Phe Lys Lys
        115


<210> SEQ ID NO 122
<211> LENGTH: 453
<212> TYPE: PRT
<213> ORGANISM: Vibrio fluvialis

<400> SEQUENCE: 122

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60
```

```
His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 123
<211> LENGTH: 1122
<212> TYPE: DNA
<213> ORGANISM: Erwinia caratovora subsp. atroseptica

<400> SEQUENCE: 123

```
atgtctgacg gacgactcac cgcacttttt cctgcattcc cacacccggc gtccaatcag      60
cccgtatttg ccgaggcttc accgcacgac gacgagttaa tgacgcaggc cgtaccgcag     120
gtttcctgtc agcaggcgtt ggcgattgcg cagcaagaat atggcttgtc tgggcagatg     180
tcgctgcttc agggcgagcg tgatgtgaat ttctgtctga cggtgacgcc agatgaacgc     240
tacatgctga aagtcatcaa tgcggcagaa cctgccgacg tcagcaattt ccaaaccgcg     300
ctgctgctgc atcttgcccg tcaggcacct gaactgcccg taccgcgtat caggtcgaca     360
aaagcgggtc agtcggaaac aggcgttgag atcgatggtg tactgctgcg tgtgcggctt     420
gtgagctatc tggcaggaat gccgcagtat ctggcctcac cgtcaacggc gctgatgccg     480
cagttggggg gaacgctggc gcagttggat aacgcgcttc acagctttac gcatccggcg     540
gcaaaccgtg cgctgctgtg ggatatcagc cgggcagagc aggtgcgtcc ttacctcgat     600
ttcgtttctg aaccgcagca gtatcagcat cttcagcgta tttttgaccg ttatgacagt     660
aacgttgctc ctctgttgac gacgctacgt cgtcaggtca ttcataacga tctgaatccg     720
cataacgtgc tggtggatgg atcgtcgccg acgcgggtta ctggcattat cgattttggc     780
gatgccgtat ttgccccgtt aatttgcgaa gtcgcgacgg cactggcgta tcagatcggc     840
gatggaaccg atttgttgga gcatgttgtg ccgtttgttg cggcctatca ccaacgcatt     900
ccgttagcac cggaggagat tgcgctgtta cccgatctga tagcgacccg tatggcgctg     960
accctgacca ttgcgcagtg gcgagcatcg cgttatcccg acaatcggga gtatctgctg    1020
cgtaacgtgc cgcgctgttg gcacagtttg cagcgcattg cgacctattc ccatgcgcaa    1080
tttttgactc gcctacagca ggtttgcccg gagaatgcgc ga                       1122
```

<210> SEQ ID NO 124
<211> LENGTH: 374
<212> TYPE: PRT
<213> ORGANISM: Erwinia caratovora subsp. atroseptica

<400> SEQUENCE: 124

```
Met Ser Asp Gly Arg Leu Thr Ala Leu Phe Pro Ala Phe Pro His Pro
1               5                   10                  15

Ala Ser Asn Gln Pro Val Phe Ala Glu Ala Ser Pro His Asp Asp Glu
            20                  25                  30

Leu Met Thr Gln Ala Val Pro Gln Val Ser Cys Gln Gln Ala Leu Ala
        35                  40                  45

Ile Ala Gln Gln Glu Tyr Gly Leu Ser Gly Gln Met Ser Leu Leu Gln
    50                  55                  60

Gly Glu Arg Asp Val Asn Phe Cys Leu Thr Val Thr Pro Asp Glu Arg
65                  70                  75                  80

Tyr Met Leu Lys Val Ile Asn Ala Ala Glu Pro Ala Asp Val Ser Asn
                85                  90                  95

Phe Gln Thr Ala Leu Leu Leu His Leu Ala Arg Gln Ala Pro Glu Leu
            100                 105                 110

Pro Val Pro Arg Ile Arg Ser Thr Lys Ala Gly Gln Ser Glu Thr Gly
        115                 120                 125

Val Glu Ile Asp Gly Val Leu Leu Arg Val Arg Leu Val Ser Tyr Leu
    130                 135                 140

Ala Gly Met Pro Gln Tyr Leu Ala Ser Pro Ser Thr Ala Leu Met Pro
145                 150                 155                 160

Gln Leu Gly Gly Thr Leu Ala Gln Leu Asp Asn Ala Leu His Ser Phe
```

```
                165                 170                 175

Thr His Pro Ala Ala Asn Arg Ala Leu Leu Trp Asp Ile Ser Arg Ala
            180                 185                 190

Glu Gln Val Arg Pro Tyr Leu Asp Phe Val Ser Glu Pro Gln Gln Tyr
        195                 200                 205

Gln His Leu Gln Arg Ile Phe Asp Arg Tyr Asp Ser Asn Val Ala Pro
    210                 215                 220

Leu Leu Thr Thr Leu Arg Arg Gln Val Ile His Asn Asp Leu Asn Pro
225                 230                 235                 240

His Asn Val Leu Val Asp Gly Ser Ser Pro Thr Arg Val Thr Gly Ile
                245                 250                 255

Ile Asp Phe Gly Asp Ala Val Phe Ala Pro Leu Ile Cys Glu Val Ala
            260                 265                 270

Thr Ala Leu Ala Tyr Gln Ile Gly Asp Gly Thr Asp Leu Leu Glu His
        275                 280                 285

Val Val Pro Phe Val Ala Ala Tyr His Gln Arg Ile Pro Leu Ala Pro
    290                 295                 300

Glu Glu Ile Ala Leu Leu Pro Asp Leu Ile Ala Thr Arg Met Ala Leu
305                 310                 315                 320

Thr Leu Thr Ile Ala Gln Trp Arg Ala Ser Arg Tyr Pro Asp Asn Arg
                325                 330                 335

Glu Tyr Leu Leu Arg Asn Val Pro Arg Cys Trp His Ser Leu Gln Arg
            340                 345                 350

Ile Ala Thr Tyr Ser His Ala Gln Phe Leu Thr Arg Leu Gln Gln Val
        355                 360                 365

Cys Pro Glu Asn Ala Arg
    370
```

<210> SEQ ID NO 125
<211> LENGTH: 1272
<212> TYPE: DNA
<213> ORGANISM: Erwinia caratovora subsp. atroseptica

<400> SEQUENCE: 125

```
atgacagcga cagaagcttt gctggcgcgc cgtcagcgag tgttgggcgg cggttatcgc      60

ctgttttatg aagagccgct gcatgtcgcg cgcggcgagg gcgtgtggct gttcgatcac     120

caagggaaac gttatctgga tgtctacaat aatgtggctt cggtcggaca ttgccacccc     180

gcggtggttg aagccgtggc gcgacagagc gcacaactca atacccacac gcgctatttg     240

caccacgcga ttgtcgattt tgcggaagat ttgctgagcg aatttcccgc cgaattgaac     300

aatgtaatgc tgacctgtac cggcagtgag gctaacgatc tggcgctgcg tatcgcccga     360

catgtcacgg gcgggacggg gatgttggtg acgcgctggg cgtatcacgg cgtgaccagc     420

gcgctggcgg aactgtctcc gtcgctgggg gatggcgttg tgcgcggtag ccatgtgaag     480

ctgatcgacg cgccagacac ttatcgtcag cccggtgcat ttcttaccag cattcgtgaa     540

gcgctggcgc agatgcaacg ggaaggtatt cgtcctgcgg cgctgctggt agataccatt     600

ttttccagcg atggcgtgtt ctgtgcgccg gaaggcgaaa tggcacaggc ggcggcgttg     660

atccgtcagg cgggcgggct gtttattgcg gatgaagtgc agccgggctt cgggcgcacc     720

ggggaatcac tgtggggctt tgcgcgccac aatgtcgtcc ctgatttggt gagtctaggg     780

aaaccgatgg gcaacggaca tcccatcgct ggattggtgg ggcgttccgc tctgttcgac     840

gcatttgggc gcgatgtgcg ctatttcaat acctttggcg gcaatccggt ttcctgtcag     900

gcggcgcacg cggtgctgcg ggtgattcgg gaagagcagt tgcagcagaa tgcccagcgg     960
```

```
gtcggtgatt atctgcggca agggttgcag caactggcgc agcatttccc gctgattggt   1020

gatattcggg cttacggcct gtttattggt gcggagctgg tcagcgatcg cgaaagtaaa   1080

acgccggcaa gtgaatccgc gttgcaggtg gtgaatgcga tgcgccaacg tggtgtgctc   1140

atcagcgcga cggggccagc ggcgaacata ctgaaaattc gcccgccgct ggtgtttctg   1200

gaagaacacg ccgatgtgtt cttaaccacg ctgagtgacg ttttagcgct catcggcact   1260

cgtgcacaga ga                                                       1272
```

<210> SEQ ID NO 126
<211> LENGTH: 424
<212> TYPE: PRT
<213> ORGANISM: Erwinia caratovora subsp. atroseptica

<400> SEQUENCE: 126

```
Met Thr Ala Thr Glu Ala Leu Leu Ala Arg Arg Gln Arg Val Leu Gly
1               5                   10                  15

Gly Gly Tyr Arg Leu Phe Tyr Glu Glu Pro Leu His Val Ala Arg Gly
            20                  25                  30

Glu Gly Val Trp Leu Phe Asp His Gln Gly Lys Arg Tyr Leu Asp Val
        35                  40                  45

Tyr Asn Asn Val Ala Ser Val Gly His Cys His Pro Ala Val Val Glu
    50                  55                  60

Ala Val Ala Arg Gln Ser Ala Gln Leu Asn Thr His Thr Arg Tyr Leu
65                  70                  75                  80

His His Ala Ile Val Asp Phe Ala Glu Asp Leu Leu Ser Glu Phe Pro
                85                  90                  95

Ala Glu Leu Asn Asn Val Met Leu Thr Cys Thr Gly Ser Glu Ala Asn
            100                 105                 110

Asp Leu Ala Leu Arg Ile Ala Arg His Val Thr Gly Gly Thr Gly Met
        115                 120                 125

Leu Val Thr Arg Trp Ala Tyr His Gly Val Thr Ser Ala Leu Ala Glu
    130                 135                 140

Leu Ser Pro Ser Leu Gly Asp Gly Val Val Arg Gly Ser His Val Lys
145                 150                 155                 160

Leu Ile Asp Ala Pro Asp Thr Tyr Arg Gln Pro Gly Ala Phe Leu Thr
                165                 170                 175

Ser Ile Arg Glu Ala Leu Ala Gln Met Gln Arg Glu Gly Ile Arg Pro
            180                 185                 190

Ala Ala Leu Leu Val Asp Thr Ile Phe Ser Ser Asp Gly Val Phe Cys
        195                 200                 205

Ala Pro Glu Gly Glu Met Ala Gln Ala Ala Ala Leu Ile Arg Gln Ala
    210                 215                 220

Gly Gly Leu Phe Ile Ala Asp Glu Val Gln Pro Gly Phe Gly Arg Thr
225                 230                 235                 240

Gly Glu Ser Leu Trp Gly Phe Ala Arg His Asn Val Val Pro Asp Leu
                245                 250                 255

Val Ser Leu Gly Lys Pro Met Gly Asn Gly His Pro Ile Ala Gly Leu
            260                 265                 270

Val Gly Arg Ser Ala Leu Phe Asp Ala Phe Gly Arg Asp Val Arg Tyr
        275                 280                 285

Phe Asn Thr Phe Gly Gly Asn Pro Val Ser Cys Gln Ala Ala His Ala
    290                 295                 300

Val Leu Arg Val Ile Arg Glu Glu Gln Leu Gln Gln Asn Ala Gln Arg
305                 310                 315                 320
```

```
Val Gly Asp Tyr Leu Arg Gln Gly Leu Gln Gln Leu Ala Gln His Phe
                325                 330                 335

Pro Leu Ile Gly Asp Ile Arg Ala Tyr Gly Leu Phe Ile Gly Ala Glu
            340                 345                 350

Leu Val Ser Asp Arg Glu Ser Lys Thr Pro Ala Ser Glu Ser Ala Leu
        355                 360                 365

Gln Val Val Asn Ala Met Arg Gln Arg Gly Val Leu Ile Ser Ala Thr
    370                 375                 380

Gly Pro Ala Ala Asn Ile Leu Lys Ile Arg Pro Pro Leu Val Phe Leu
385                 390                 395                 400

Glu Glu His Ala Asp Val Phe Leu Thr Thr Leu Ser Asp Val Leu Ala
                405                 410                 415

Leu Ile Gly Thr Arg Ala Gln Arg
            420


<210> SEQ ID NO 127
<211> LENGTH: 35
<212> TYPE: DNA
<213> ORGANISM: Artificial Seqquence
<220> FEATURE:
<223> OTHER INFORMATION: Primer

<400> SEQUENCE: 127

ctccggaatt catgtctgac ggacgactca ccgca                              35


<210> SEQ ID NO 128
<211> LENGTH: 46
<212> TYPE: DNA
<213> ORGANISM: Artificial Seqquence
<220> FEATURE:
<223> OTHER INFORMATION: Primer

<400> SEQUENCE: 128

ttccaatgca ttggctgcag ttatctctgt gcacgagtgc cgatga                  46


<210> SEQ ID NO 129
<211> LENGTH: 40
<212> TYPE: DNA
<213> ORGANISM: Artificial Seqquence
<220> FEATURE:
<223> OTHER INFORMATION: Primer

<400> SEQUENCE: 129

aacagccaag cttggctgca gtcatcgcgc attctccggg                        40


<210> SEQ ID NO 130
<211> LENGTH: 40
<212> TYPE: DNA
<213> ORGANISM: Artificial Seqquence
<220> FEATURE:
<223> OTHER INFORMATION: Primer

<400> SEQUENCE: 130

tctccggaat tcatgacgtc tgaaatgaca gcgacagaag                        40


<210> SEQ ID NO 131
<211> LENGTH: 33
<212> TYPE: DNA
<213> ORGANISM: Artificial Sequence
<220> FEATURE:
<223> OTHER INFORMATION: Primer

<400> SEQUENCE: 131
```

```
gctaacagga ggaagaattc atggggggtt ctc                                33


<210> SEQ ID NO 132
<211> LENGTH: 33
<212> TYPE: DNA
<213> ORGANISM: Artificial Sequence
<220> FEATURE:
<223> OTHER INFORMATION: Primer

<400> SEQUENCE: 132

gagaaccccc catgaattct tcctcctgtt agc                                33


<210> SEQ ID NO 133
<211> LENGTH: 723
<212> TYPE: DNA
<213> ORGANISM: Klebsiella terrigena

<400> SEQUENCE: 133

atgcaaaaag tcgcacttgt caccggcgcc ggtcagggca tcggtaaagc tatcgccctg     60

cgtctggtga aggatggatt tgccgtggca atcgccgatt acaacgacgc tacggccaca    120

gcggtagccg ctgaaatcaa ccaggccggc ggccgcgcgg tggccattaa ggtcgacgtc    180

tcgcgccggg accaggtttt cgccgccgtt gagcaggcgc gtaaagccct gggcggattc    240

aacgttatcg tcaacaacgc cggcatcgcg ccgtcaacgc cgatcgagtc catcaccgag    300

gagatcgtcg accgggtcta taacatcaac gttaagggcg tcatctgggg gatgcaggcg    360

gcggtggagg ccttcaaaaa agaggggcac ggcgggaaga tcgtcaacgc ctgctcccag    420

gccggccacg tcggcaaccc ggagctggcg gtctacagtt cgagtaaatt cgccgtgcgc    480

ggcctgacgc aaaccgccgc ccgcgatctg gcgccgctgg gcatcaccgt taacggcttc    540

tgcccaggga tcgttaagac gccaatgtgg gcggagattg accgtcagtg tcggaagcgg    600

cgggcaaacc gctgggctac ggcacggctg aatttgccaa acgcatcacc cttggccgcc    660

tgtcggagcc tgaagacgtc gccgcctgcg tgtcgttcct cgccagcccg gattccgact    720

ata                                                                  723


<210> SEQ ID NO 134
<211> LENGTH: 241
<212> TYPE: PRT
<213> ORGANISM: Klebsiella terrigena

<400> SEQUENCE: 134

Met Gln Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Thr Ala Val Ala Ala Glu Ile Asn Gln
        35                  40                  45

Ala Gly Gly Arg Ala Val Ala Ile Lys Val Asp Val Ser Arg Arg Asp
    50                  55                  60

Gln Val Phe Ala Ala Val Glu Gln Ala Arg Lys Ala Leu Gly Gly Phe
65                  70                  75                  80

Asn Val Ile Val Asn Asn Ala Gly Ile Ala Pro Ser Thr Pro Ile Glu
                85                  90                  95

Ser Ile Thr Glu Glu Ile Val Asp Arg Val Tyr Asn Ile Asn Val Lys
            100                 105                 110

Gly Val Ile Trp Gly Met Gln Ala Ala Val Glu Ala Phe Lys Lys Glu
        115                 120                 125
```

```
Gly His Gly Gly Lys Ile Val Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Phe Cys Pro Gly Ile Val Lys Thr Pro Met Trp Ala Glu
            180                 185                 190

Ile Asp Arg Gln Cys Arg Lys Arg Arg Ala Asn Arg Trp Ala Thr Ala
        195                 200                 205

Arg Leu Asn Leu Pro Asn Ala Ser Pro Leu Ala Ala Cys Arg Ser Leu
    210                 215                 220

Lys Thr Ser Pro Pro Ala Cys Arg Ser Ser Pro Ala Arg Ile Pro Thr
225                 230                 235                 240

Ile


<210> SEQ ID NO 135
<211> LENGTH: 554
<212> TYPE: PRT
<213> ORGANISM: Clostridium pasteurianum

<400> SEQUENCE: 135

Met Lys Ser Lys Arg Phe Gln Val Leu Ser Glu Arg Pro Val Asn Lys
1               5                   10                  15

Asp Gly Phe Ile Gly Glu Trp Pro Glu Glu Gly Leu Ile Ala Met Ser
            20                  25                  30

Ser Pro Asn Asp Pro Lys Pro Ser Ile Lys Ile Lys Glu Gly Lys Val
        35                  40                  45

Ile Glu Leu Asp Gly Lys Asn Arg Glu Asp Phe Asp Met Ile Asp Arg
    50                  55                  60

Phe Ile Ala Asn Tyr Gly Ile Asn Leu Asn Arg Ala Glu Asp Val Ile
65                  70                  75                  80

Lys Met Asp Ser Val Lys Leu Ala Lys Met Leu Val Asp Ile Asn Val
                85                  90                  95

Asp Arg Lys Thr Ile Val Glu Leu Thr Thr Ala Met Thr Pro Ala Lys
            100                 105                 110

Ile Val Glu Val Val Gly Asn Met Asn Val Val Glu Met Met Met Ala
        115                 120                 125

Leu Gln Lys Met Arg Ala Arg Lys Thr Pro Ser Asn Gln Cys His Val
    130                 135                 140

Thr Asn Leu Lys Asp Asn Pro Val Gln Ile Ala Ala Asp Ala Ala Glu
145                 150                 155                 160

Ala Ala Ile Arg Gly Phe Asp Glu Gln Glu Thr Thr Val Gly Ile Val
                165                 170                 175

Arg Tyr Ala Pro Phe Asn Ala Leu Ala Leu Leu Val Gly Ala Gln Val
            180                 185                 190

Gly Arg Gly Gly Val Leu Thr Gln Cys Ala Ile Glu Glu Ala Thr Glu
        195                 200                 205

Leu Glu Leu Gly Met Arg Gly Leu Thr Ser Tyr Ala Glu Thr Val Ser
    210                 215                 220

Val Tyr Gly Thr Glu Asn Val Phe Thr Asp Gly Asp Asp Thr Pro Trp
225                 230                 235                 240

Ser Lys Ala Phe Leu Ala Ser Ala Tyr Ala Ser Arg Gly Leu Lys Met
                245                 250                 255

Arg Phe Thr Ser Gly Ser Gly Ser Glu Ala Leu Met Gly Tyr Ala Glu
```

```
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
    290                 295                 300

Met Thr Gly Ala Leu Pro Ser Gly Ile Arg Ala Val Leu Gly Glu Asn
305                 310                 315                 320

Leu Ile Thr Thr Met Leu Asp Ile Glu Val Ala Ser Ala Asn Asp Gln
                325                 330                 335

Thr Phe Ser His Ser Asp Ile Arg Arg Thr Ala Arg Met Leu Met Gln
            340                 345                 350

Met Leu Pro Gly Thr Asp Phe Ile Phe Ser Gly Tyr Ser Ser Val Pro
        355                 360                 365

Asn Tyr Asp Asn Met Phe Ala Gly Ser Asn Phe Asp Ala Glu Asp Phe
    370                 375                 380

Asp Asp Tyr Asn Val Ile Gln Arg Asp Leu Met Val Asp Gly Gly Leu
385                 390                 395                 400

Arg Pro Val Ser Glu Glu Glu Val Ile Thr Ile Arg Asn Lys Ala Ala
                405                 410                 415

Arg Ala Ile Gln Ala Val Phe Glu Gly Leu Lys Leu Pro Ala Ile Thr
            420                 425                 430

Asp Glu Glu Val Glu Ala Val Thr Tyr Ser His Gly Ser Lys Asp Val
        435                 440                 445

Pro Glu Arg Asn Val Val Glu Asp Leu Lys Ala Ala Glu Glu Met Ile
    450                 455                 460

Asn Arg Gly Ile Thr Gly Ile Asp Val Val Lys Ala Leu Ser Lys His
465                 470                 475                 480

Gly Phe Asp Asp Ile Ala Glu Asn Ile Leu Asn Met Leu Lys Gln Arg
                485                 490                 495

Ile Ser Gly Asp Tyr Leu Gln Thr Ser Ala Ile Ile Asp Lys Asn Phe
            500                 505                 510

Asn Val Val Ser Ala Val Asn Asp Cys Asn Asp Tyr Met Gly Pro Gly
        515                 520                 525

Thr Gly Tyr Arg Leu Ser Lys Glu Arg Trp Asp Glu Ile Lys Asn Ile
    530                 535                 540

Pro Asn Ala Met Lys Pro Glu Asp Ile Lys
545                 550


<210> SEQ ID NO 136
<211> LENGTH: 179
<212> TYPE: PRT
<213> ORGANISM: Clostridium pasteurianum

<400> SEQUENCE: 136

Met Glu Leu Lys Glu Lys Asp Ile Ala Leu Ser Gly Asn Gln Ser Asn
1               5                   10                  15

Glu Val Val Ile Gly Ile Ala Pro Ala Phe Gly Lys Tyr Gln His Gln
            20                  25                  30

Ser Ile Val Gly Val Pro His Asp Lys Ile Leu Arg Glu Leu Ile Ala
        35                  40                  45

Gly Ile Glu Glu Glu Gly Leu Lys Ser Arg Val Val Arg Ile Ile Arg
    50                  55                  60

Thr Ser Asp Val Ser Phe Ile Ala His Asp Ala Ala Val Leu Ser Gly
65                  70                  75                  80

Ser Gly Ile Gly Ile Gly Ile Gln Ser Lys Gly Thr Thr Val Ile His
```

```
                85                  90                  95

Gln Lys Asp Leu Leu Pro Leu Asn Asn Leu Glu Leu Phe Pro Gln Ala
            100                 105                 110

Pro Leu Leu Asp Leu Asp Ile Phe Arg Leu Ile Gly Lys Asn Ala Ala
        115                 120                 125

Lys Tyr Ala Lys Gly Glu Ser Pro Asn Pro Val Pro Thr Arg Asn Asp
    130                 135                 140

Gln Met Val Arg Pro Lys Phe Gln Ala Lys Ala Ala Leu Leu His Ile
145                 150                 155                 160

Lys Glu Thr Lys His Val Val Gln Asn Ala Lys Pro Ile Glu Leu Glu
                165                 170                 175

Ile Ile Ser


<210> SEQ ID NO 137
        <211> LENGTH: 146
<212> TYPE: PRT
<213> ORGANISM: Clostridium pasteurianum

<400> SEQUENCE: 137

Met Ser Asp Ile Thr Asn Asn Ile Lys Val Asp Tyr Glu Asn Asp Tyr
1               5                   10                  15

Pro Leu Ala Ala Lys Arg Ser Glu Trp Ile Lys Thr Pro Thr Gly Lys
            20                  25                  30

Asn Leu Lys Asp Ile Thr Leu Glu Ala Val Ile Asp Glu Asn Val Lys
        35                  40                  45

Ala Glu Asp Val Arg Ile Ser Arg Asp Thr Leu Glu Leu Gln Ala Gln
    50                  55                  60

Val Ala Glu Gly Ser Gly Arg Cys Ala Ile Ala Arg Asn Phe Arg Arg
65                  70                  75                  80

Ala Ala Glu Leu Ile Ser Ile Ser Asp Glu Arg Ile Leu Glu Ile Tyr
                85                  90                  95

Asn Ala Leu Arg Pro Tyr Arg Ser Thr Lys Asn Glu Leu Leu Ala Ile
            100                 105                 110

Ala Asp Glu Leu Glu Glu Lys Tyr Asp Ala Lys Val Asn Ala Asp Phe
        115                 120                 125

Ile Arg Glu Ala Ala Glu Val Tyr Ser Lys Arg Asn Lys Val Arg Ile
    130                 135                 140

Glu Asp
145


<210> SEQ ID NO 138
<211> LENGTH: 555
<212> TYPE: PRT
<213> ORGANISM: Escherichia blattae

<400> SEQUENCE: 138

Met Arg Arg Ser Lys Arg Phe Glu Val Leu Glu Lys Arg Pro Val Asn
1               5                   10                  15

Gln Asp Gly Leu Ile Gly Glu Trp Pro Glu Glu Gly Leu Ile Ala Met
            20                  25                  30

Gly Ser Pro Trp Asp Pro Pro Ser Ser Val Lys Val Glu Gln Gly Arg
        35                  40                  45

Ile Val Glu Leu Asp Gly Lys Ala Arg Ala Asp Phe Asp Met Ile Asp
    50                  55                  60

Arg Phe Ile Ala Asp Tyr Ala Ile Asn Ile Glu Glu Thr Glu His Ala
65                  70                  75                  80
```

```
Met Gly Leu Asp Ala Leu Thr Ile Ala Arg Met Leu Val Asp Ile Asn
                85                  90                  95

Val Ser Arg Ala Glu Ile Ile Lys Val Thr Thr Ala Ile Thr Pro Ala
            100                 105                 110

Lys Ala Val Glu Val Met Ser His Met Asn Val Val Glu Met Met Met
        115                 120                 125

Ala Leu Gln Lys Met Arg Ala Arg Arg Thr Pro Ser Asn Gln Cys His
    130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Thr Val Gly Ile
                165                 170                 175

Ala Arg Tyr Ala Pro Phe Asn Ala Leu Ala Leu Leu Ile Gly Ser Gln
            180                 185                 190

Ser Gly Arg Pro Gly Val Leu Thr Gln Cys Ser Val Glu Glu Ala Thr
        195                 200                 205

Glu Leu Glu Leu Gly Met Arg Gly Phe Thr Ser Tyr Ala Glu Thr Val
    210                 215                 220

Ser Val Tyr Gly Thr Glu Ala Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ala
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
    290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
            340                 345                 350

Gln Met Leu Pro Gly Thr Asp Phe Ile Phe Ser Gly Tyr Ser Ala Val
        355                 360                 365

Pro Asn Tyr Asp Asn Met Phe Ala Gly Ser Asn Phe Asp Ala Glu Asp
    370                 375                 380

Phe Asp Asp Tyr Asn Ile Leu Gln Arg Asp Leu Met Val Asp Gly Gly
385                 390                 395                 400

Leu Arg Pro Val Ser Glu Glu Glu Thr Ile Ala Ile Arg Asn Lys Ala
                405                 410                 415

Ala Arg Ala Val Gln Ala Val Phe Arg Glu Leu Gly Leu Pro Pro Val
            420                 425                 430

Thr Asp Glu Glu Val Thr Ala Ala Thr Tyr Ala His Gly Ser Lys Asp
        435                 440                 445

Met Pro Pro Arg Asn Val Val Glu Asp Leu Ser Ala Val Glu Glu Met
    450                 455                 460

Met Lys Arg Asn Ile Thr Gly Leu Asp Ile Val Arg Ala Leu Ser Val
465                 470                 475                 480

Asn Gly Phe Asp Asp Val Ala Asn Asn Ile Leu Asn Met Leu Arg Gln
                485                 490                 495

Arg Val Thr Gly Asp Tyr Leu Gln Thr Ser Ala Ile Leu Asp Arg Glu
            500                 505                 510
```

```
Phe Glu Val Val Ser Ala Val Asn Asp Ile Asn Asp Tyr Gln Gly Pro
        515                 520                 525

Gly Thr Gly Tyr Arg Ile Ser Pro Gln Arg Trp Glu Glu Ile Lys Asn
    530                 535                 540

Ile Ala Thr Val Ile Gln Pro Asp Ser Ile Glu
545                 550                 555


<210> SEQ ID NO 139
<211> LENGTH: 196
<212> TYPE: PRT
<213> ORGANISM: Escherichia blattae

<400> SEQUENCE: 139

Met Glu Thr Thr Gln Lys Lys Ala Pro Val Phe Thr Leu Asn Leu Val
1               5                   10                  15

Glu Ser Gly Val Ala Lys Pro Gly Glu Arg Ser Asp Glu Val Val Ile
            20                  25                  30

Gly Val Gly Pro Ala Phe Asp Lys Tyr Gln His Lys Thr Leu Ile Asp
        35                  40                  45

Met Pro His Lys Ala Ile Ile Lys Glu Leu Val Ala Gly Val Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Ala Asp Ala Lys Pro Val Thr Leu Asn Ile Glu Ile Thr
            180                 185                 190

Arg Glu Glu Ala
        195


<210> SEQ ID NO 140
<211> LENGTH: 141
<212> TYPE: PRT
<213> ORGANISM: Escherichia blattae

<400> SEQUENCE: 140

Met Thr Thr Thr Lys Met Ser Ala Ala Asp Tyr Pro Leu Ala Ser Arg
1               5                   10                  15

Cys Pro Glu Arg Ile Gln Thr Pro Thr Gly Lys Pro Leu Thr Asp Ile
            20                  25                  30

Thr Leu Glu Asn Val Leu Ala Gly Lys Val Gly Pro Gln Asp Val Arg
        35                  40                  45

Ile Ser Arg Glu Thr Leu Glu Tyr Gln Ala Gln Ile Ala Glu Gln Met
    50                  55                  60

His Arg His Ala Ile Ala Arg Asn Leu Arg Arg Ala Gly Glu Leu Ile
65                  70                  75                  80
```

```
Ala Ile Pro Asp Ala Arg Ile Leu Glu Ile Tyr Asn Ala Leu Arg Pro
                85                  90                  95

Tyr Arg Ser Ser Val Glu Glu Leu Leu Ala Ile Ala Asp Glu Leu Glu
            100                 105                 110

Thr Arg Tyr Gln Ala Thr Val Asn Ala Ala Phe Ile Arg Glu Ala Ala
        115                 120                 125

Glu Val Tyr Arg Gln Arg Asp Lys Leu Arg Lys Glu Ala
    130                 135                 140


<210> SEQ ID NO 141
<211> LENGTH: 555
<212> TYPE: PRT
<213> ORGANISM: Citrobacter freundii

<400> SEQUENCE: 141

Met Arg Arg Ser Lys Arg Phe Glu Val Leu Ala Gln Arg Pro Val Asn
1               5                   10                  15

Gln Asp Gly Leu Ile Gly Glu Trp Pro Glu Glu Gly Leu Ile Ala Met
            20                  25                  30

Glu Ser Pro Tyr Asp Pro Ala Ser Ser Val Lys Val Glu Asn Gly Arg
        35                  40                  45

Ile Val Glu Leu Asp Gly Lys Ser Arg Ala Glu Phe Asp Met Ile Asp
    50                  55                  60

Arg Phe Ile Ala Asp Tyr Ala Ile Asn Val Pro Glu Ala Glu Arg Ala
65                  70                  75                  80

Met Gln Leu Asp Ala Leu Glu Ile Ala Arg Met Leu Val Asp Ile His
                85                  90                  95

Val Ser Arg Glu Glu Ile Ile Ala Ile Thr Thr Ala Ile Thr Pro Ala
            100                 105                 110

Lys Arg Leu Glu Val Met Ala Gln Met Asn Val Val Glu Met Met Met
        115                 120                 125

Ala Leu Gln Lys Met Arg Ala Arg Arg Thr Pro Ser Asn Gln Cys His
    130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Thr Val Gly Ile
                165                 170                 175

Ala Arg Tyr Ala Pro Phe Asn Ala Leu Ala Leu Leu Val Gly Ser Gln
            180                 185                 190

Cys Gly Ala Pro Gly Val Leu Thr Gln Cys Ser Val Glu Glu Ala Thr
        195                 200                 205

Glu Leu Glu Leu Gly Met Arg Gly Leu Thr Ser Tyr Ala Glu Thr Val
    210                 215                 220

Ser Val Tyr Gly Thr Glu Ser Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ser
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
    290                 295                 300

Gly Met Thr Gly Ala Val Pro Ser Gly Ile Arg Ala Val Leu Ala Glu
305                 310                 315                 320
```

```
Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
            340                 345                 350

Gln Met Leu Pro Gly Thr Asp Phe Ile Phe Ser Gly Tyr Ser Ala Val
        355                 360                 365

Pro Asn Tyr Asp Asn Met Phe Ala Gly Ser Asn Phe Asp Ala Glu Asp
    370                 375                 380

Phe Asp Asp Tyr Asn Ile Leu Gln Arg Asp Leu Met Val Asp Gly Gly
385                 390                 395                 400

Leu Arg Pro Val Thr Glu Glu Glu Thr Ile Ala Ile Arg Asn Lys Ala
                405                 410                 415

Ala Arg Ala Ile Gln Ala Val Phe Arg Glu Leu Gly Leu Pro Leu Ile
            420                 425                 430

Ser Asp Glu Glu Val Asp Ala Ala Thr Tyr Ala His Gly Ser Lys Asp
        435                 440                 445

Met Pro Ala Arg Asn Val Val Glu Asp Leu Ala Ala Val Glu Glu Met
    450                 455                 460

Met Lys Arg Asn Ile Thr Gly Leu Asp Ile Val Gly Ala Leu Ser Ser
465                 470                 475                 480

Ser Gly Phe Glu Asp Ile Ala Ser Asn Ile Leu Asn Met Leu Arg Gln
                485                 490                 495

Arg Val Thr Gly Asp Tyr Leu Gln Thr Ser Ala Ile Leu Asp Arg Gln
            500                 505                 510

Phe Asp Val Val Ser Ala Val Asn Asp Ile Asn Asp Tyr Gln Gly Pro
        515                 520                 525

Gly Thr Gly Tyr Arg Ile Ser Ala Glu Arg Trp Ala Glu Ile Lys Asn
    530                 535                 540

Ile Ala Gly Val Val Gln Pro Gly Ser Ile Glu
545                 550                 555


<210> SEQ ID NO 142
<211> LENGTH: 194
<212> TYPE: PRT
<213> ORGANISM: Citrobacter freundii

<400> SEQUENCE: 142

Met Glu Cys Thr Thr Glu Arg Lys Pro Val Phe Thr Leu Gln Val Ser
1               5                   10                  15

Glu Gly Glu Ala Ala Lys Ala Asp Glu Arg Val Asp Glu Val Val Ile
            20                  25                  30

Gly Val Gly Pro Ala Phe Asp Lys Tyr Gln His Lys Thr Leu Ile Asp
        35                  40                  45

Met Pro His Lys Ala Ile Leu Lys Glu Leu Val Ala Gly Ile Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140
```

```
Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Arg Ala Pro Val Thr Leu His Ile Ala Leu Val
            180                 185                 190

Arg Glu


<210> SEQ ID NO 143
<211> LENGTH: 142
<212> TYPE: PRT
<213> ORGANISM: Citrobacter freundii

<400> SEQUENCE: 143

Met Asn Asp Asn Ile Met Thr Ala Gln Asp Tyr Pro Leu Ala Thr Arg
1               5                   10                  15

Cys Pro Glu Lys Ile Gln Thr Pro Thr Gly Lys Pro Leu Thr Glu Ile
            20                  25                  30

Thr Leu Glu Asn Val Leu Ala Gly Arg Val Gly Pro Gln Asp Val Arg
        35                  40                  45

Ile Ser Gln Gln Thr Leu Glu Tyr Gln Ala Gln Ile Ala Glu Gln Met
    50                  55                  60

Gln Arg His Ala Val Ala Arg Asn Phe Arg Arg Ala Ala Glu Leu Ile
65                  70                  75                  80

Ala Ile Pro Asp Ala Arg Ile Leu Glu Ile Tyr Asn Ala Leu Arg Pro
                85                  90                  95

Phe Arg Ser Ser Phe Ala Glu Leu Gln Ala Ile Ala Asp Glu Leu Glu
            100                 105                 110

His Thr Trp His Ala Thr Val Asn Ala Gly Phe Val Arg Glu Ser Ala
        115                 120                 125

Glu Val Tyr Leu Gln Arg Asn Lys Leu Arg Lys Gly Ser Gln
    130                 135                 140


<210> SEQ ID NO 144
<211> LENGTH: 1359
<212> TYPE: DNA
<213> ORGANISM: Artificial sequence
<220> FEATURE:
<223> OTHER INFORMATION: Codon optimized Vibrio fluvialis amine:pyruvate
      transaminase

<400> SEQUENCE: 144

atgaacaaac cacagtcttg ggaagctcgt gcagaaacct attctctgta cggcttcact      60

gacatgccgt ccctgcacca gcgtggtact gttgttgtca cgcacggcga aggtccgtac     120

attgttgacg tcaatggtcg ccgttatctg gacgctaatt ctggcctgtg gaatatggtt     180

gcaggttttg accataaggg tctgatcgac gcagctaagg ctcagtacga gcgttttccg     240

ggctaccatg cgttcttcgg tcgtatgagc gatcagacgg tgatgctgtc cgaaaaactg     300

gtagaagtct ctccgttcga cagcggccgt gtgttctata cgaacagcgg tagcgaagca     360

aacgacacta tggttaagat gctgtggttc ctgcatgcgg cggaaggtaa gccacaaaag     420

cgcaaaattc tgacccgttg gaacgcgtat cacggcgtta ctgcagttag cgcctccatg     480

accggtaaac cgtacaacag cgttttcggt ctgccgctgc caggtttcgt tcacctgact     540

tgccctcact actggcgtta cggtgaagaa ggcgagacgg aagaacaatt cgttgcacgc     600

ctggcacgcg aactggaaga gactatccag cgtgagggtg ctgacactat cgctggcttc     660

tttgctgagc cggttatggg tgcaggtggt gttattccgc ctgctaaagg ttattttcag     720
```

```
gctattctgc caatcctgcg taaatatgac atcccggtta tctctgacga agttatctgt    780
ggttttggtc gcactggcaa cacctggggt tgcgtaactt atgattttac tccggatgct    840
atcatctcta gcaaaaacct gaccgccggt ttcttcccga tgggcgcagt gatcctgggt    900
ccagaactga gcaagcgcct ggaaaccgca attgaagcaa tcgaggaatt tccgcacggc    960
tttaccgcgt ccggccatcc ggtaggctgt gcaatcgcgc tgaaagcgat cgatgttgtt   1020
atgaacgaag gcctggcgga aaacgttcgc cgtctggcac cgcgcttcga agaacgtctg   1080
aaacatatcg cggaacgtcc gaacattggt gaatatcgtg gtatcggttt tatgtgggct   1140
ctggaggcag tcaaagacaa agcgtctaaa actccgttcg atggcaatct gagcgtgagc   1200
gaacgtatcg ccaacacttg caccgacctg ggtctgatct gccgtccact gggccaaagc   1260
gtagtgctgt gtccgccgtt tatcctgacc gaagcgcaaa tggacgaaat gttcgacaaa   1320
ctggagaaag cactggataa agtgttcgca gaggtggca                          1359
```

```
<210> SEQ ID NO 145
<211> LENGTH: 1668
<212> TYPE: DNA
<213> ORGANISM: Klebsiella pneumoniae

<400> SEQUENCE: 145
```

```
atgaaaagat caaaacgatt tgcagtactg gcccagcgcc ccgtcaatca ggacgggctg     60
attggcgagt ggcctgaaga ggggctgatc gccatggaca gcccctttga cccggtctct    120
tcagtaaaag tggacaacgg tctgatcgtc gaactggacg gcaaacgccg ggaccagttt    180
gacatgatcg accgatttat cgccgattac gcgatcaacg ttgagcgcac agagcaggca    240
atgcgcctgg aggcggtgga aatagcccgt atgctggtgg atattcacgt cagccgggag    300
gagatcattg ccatcactac cgccatcacg ccggccaaag cggtcgaggt gatggcgcag    360
atgaacgtgg tggagatgat gatggcgctg cagaagatgc gtgcccgccg gacccccctcc    420
aaccagtgcc acgtcaccaa tctcaaagat aatccggtgc agattgccgc tgacgccgcc    480
gaggccggga tccgcggctt ctcagaacag gagaccacgg tcggtatcgc gcgctacgcg    540
ccgtttaacg ccctggcgct gttggtcggt tcgcagtgcg gccgccccgg cgtgttgacg    600
cagtgctcgg tggaagaggc caccgagctg gagctgggca tgcgtggctt aaccagctac    660
gccgagacgg tgtcggtcta cggcaccgaa gcggtattta ccgacggcga tgatacgccg    720
tggtcaaagg cgttcctcgc ctcggcctac gcctcccgcg ggttgaaaat gcgctacacc    780
tccggcaccg gatccgaagc gctgatgggc tattcggaga gcaagtcgat gctctacctc    840
gaatcgcgct gcatcttcat tactaaaggc gccggggttc agggactgca aaacggcgcg    900
gtgagctgta tcggcatgac cggcgctgtg ccgtcgggca ttcgggcggt gctggcggaa    960
aacctgatcg cctctatgct cgacctcgaa gtggcgtccg ccaacgacca gactttctcc   1020
cactcggata ttcgccgcac cgcgcgcacc ctgatgcaga tgctgccggg caccgacttt   1080
attttctccg gctacagcgc ggtgccgaac tacgacaaca tgttcgccgg ctcgaacttc   1140
gatgcggaag attttgatga ttacaacatc ctgcagcgtg acctgatggt tgacggcggc   1200
ctgcgtccgg tgaccgaggc ggaaaccatt gccattcgcc agaaagcggc gcgggcgatc   1260
caggcggttt tccgcgagct ggggctgccg ccaatcgccg acgaggaggt ggaggccgcc   1320
acctacgcgc acggcagcaa cgagatgccg ccgcgtaacg tggtggagga tctgagtgcg   1380
gtggaagaga tgatgaagcg caacatcacc ggcctcgata ttgtcggcgc gctgagccgc   1440
agcggctttg aggatatcgc cagcaatatt ctcaatatgc tgcgccagcg ggtcaccggc   1500
```

```
gattacctgc agacctcggc cattctcgat cggcagttcg aggtggtgag tgcggtcaac   1560

gacatcaatg actatcaggg gccgggcacc ggctatcgca tctctgccga acgctgggcg   1620

gagatcaaaa atattccggg cgtggttcag cccgacacca ttgaataa                1668


<210> SEQ ID NO 146
<211> LENGTH: 555
<212> TYPE: PRT
<213> ORGANISM: Klebsiella pneumoniae

<400> SEQUENCE: 146

Met Lys Arg Ser Lys Arg Phe Ala Val Leu Ala Gln Arg Pro Val Asn
1               5                   10                  15

Gln Asp Gly Leu Ile Gly Glu Trp Pro Glu Glu Gly Leu Ile Ala Met
            20                  25                  30

Asp Ser Pro Phe Asp Pro Val Ser Ser Val Lys Val Asp Asn Gly Leu
        35                  40                  45

Ile Val Glu Leu Asp Gly Lys Arg Arg Asp Gln Phe Asp Met Ile Asp
    50                  55                  60

Arg Phe Ile Ala Asp Tyr Ala Ile Asn Val Glu Arg Thr Glu Gln Ala
65                  70                  75                  80

Met Arg Leu Glu Ala Val Glu Ile Ala Arg Met Leu Val Asp Ile His
                85                  90                  95

Val Ser Arg Glu Glu Ile Ile Ala Ile Thr Thr Ala Ile Thr Pro Ala
            100                 105                 110

Lys Ala Val Glu Val Met Ala Gln Met Asn Val Val Glu Met Met Met
        115                 120                 125

Ala Leu Gln Lys Met Arg Ala Arg Arg Thr Pro Ser Asn Gln Cys His
    130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Thr Val Gly Ile
                165                 170                 175

Ala Arg Tyr Ala Pro Phe Asn Ala Leu Ala Leu Leu Val Gly Ser Gln
            180                 185                 190

Cys Gly Arg Pro Gly Val Leu Thr Gln Cys Ser Val Glu Glu Ala Thr
        195                 200                 205

Glu Leu Glu Leu Gly Met Arg Gly Leu Thr Ser Tyr Ala Glu Thr Val
    210                 215                 220

Ser Val Tyr Gly Thr Glu Ala Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ser
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
    290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
            340                 345                 350
```

```
Gln Met Leu Pro Gly Thr Asp Phe Ile Phe Ser Gly Tyr Ser Ala Val
        355                 360                 365

Pro Asn Tyr Asp Asn Met Phe Ala Gly Ser Asn Phe Asp Ala Glu Asp
    370                 375                 380

Phe Asp Asp Tyr Asn Ile Leu Gln Arg Asp Leu Met Val Asp Gly Gly
385                 390                 395                 400

Leu Arg Pro Val Thr Glu Ala Glu Thr Ile Ala Ile Arg Gln Lys Ala
                405                 410                 415

Ala Arg Ala Ile Gln Ala Val Phe Arg Glu Leu Gly Leu Pro Pro Ile
            420                 425                 430

Ala Asp Glu Glu Val Glu Ala Ala Thr Tyr Ala His Gly Ser Asn Glu
        435                 440                 445

Met Pro Pro Arg Asn Val Val Glu Asp Leu Ser Ala Val Glu Glu Met
    450                 455                 460

Met Lys Arg Asn Ile Thr Gly Leu Asp Ile Val Gly Ala Leu Ser Arg
465                 470                 475                 480

Ser Gly Phe Glu Asp Ile Ala Ser Asn Ile Leu Asn Met Leu Arg Gln
                485                 490                 495

Arg Val Thr Gly Asp Tyr Leu Gln Thr Ser Ala Ile Leu Asp Arg Gln
            500                 505                 510

Phe Glu Val Val Ser Ala Val Asn Asp Ile Asn Asp Tyr Gln Gly Pro
        515                 520                 525

Gly Thr Gly Tyr Arg Ile Ser Ala Glu Arg Trp Ala Glu Ile Lys Asn
    530                 535                 540

Ile Pro Gly Val Val Gln Pro Asp Thr Ile Glu
545                 550                 555


<210> SEQ ID NO 147
<211> LENGTH: 585
<212> TYPE: DNA
<213> ORGANISM: Klebsiella pneumoniae

<400> SEQUENCE: 147

gtgcaacaga caacccaaat tcagccctct tttaccctga aaacccgcga gggcggggta      60

gcttctgccg atgaacgcgc cgatgaagtg gtgatcggcg tcggccctgc cttcgataaa     120

caccagcatc acactctgat cgatatgccc catggcgcga tcctcaaaga gctgattgcc     180

ggggtggaag aagaggggct tcacgcccgg gtggtgcgca ttctgcgcac gtccgacgtc     240

tcctttatgg cctgggatgc ggccaacctg agcggctcgg ggatcggcat cggtatccag     300

tcgaagggga ccacggtcat ccatcagcgc gatctgctgc cgctcagcaa cctggagctg     360

ttctcccagg cgccgctgct gacgctggag acctaccggc agattggcaa aaacgctgcg     420

cgctatgcgc gcaaagagtc accttcgccg gtgccggtgg tgaacgatca gatggtgcgg     480

ccgaaattta tggccaaagc cgcgctattt catatcaaag agaccaaaca tgtggtgcag     540

gacgccgagc ccgtcaccct gcacatcgac ttagtaaggg agtga                     585


<210> SEQ ID NO 148
<211> LENGTH: 194
<212> TYPE: PRT
<213> ORGANISM: Klebsiella pneumoniae

<400> SEQUENCE: 148

Met Gln Gln Thr Thr Gln Ile Gln Pro Ser Phe Thr Leu Lys Thr Arg
1               5                   10                  15

Glu Gly Gly Val Ala Ser Ala Asp Glu Arg Ala Asp Glu Val Val Ile
```

```
            20                  25                  30

Gly Val Gly Pro Ala Phe Asp Lys His Gln His His Thr Leu Ile Asp
        35                  40                  45

Met Pro His Gly Ala Ile Leu Lys Glu Leu Ile Ala Gly Val Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Ala Glu Pro Val Thr Leu His Ile Asp Leu Val
            180                 185                 190

Arg Glu


<210> SEQ ID NO 149
<211> LENGTH: 426
<212> TYPE: DNA
<213> ORGANISM: Klebsiella pneumoniae

<400> SEQUENCE: 149

atgagcgaga aaaccatgcg cgtgcaggat tatccgttag ccacccgctg cccggagcat     60

atcctgacgc ctaccggcaa accattgacc gatattaccc tcgagaaggt gctctctggc    120

gaggtgggcc cgcaggatgt gcggatctcc cgccagaccc ttgagtacca ggcgcagatt    180

gccgagcaga tgcagcgcca tgcggtggcg cgcaatttcc gccgcgcggc ggagcttatc    240

gccattcctg acgagcgcat tctggctatc tataacgcgc tgcgcccgtt ccgctcctcg    300

caggcggagc tgctggcgat cgccgacgag ctggagcaca cctggcatgc gacagtgaat    360

gccgcctttg tccgggagtc ggcggaagtg tatcagcagc ggcataagct gcgtaaagga    420

agctaa                                                               426


<210> SEQ ID NO 150
<211> LENGTH: 141
<212> TYPE: PRT
<213> ORGANISM: Klebsiella pneumoniae

<400> SEQUENCE: 150

Met Ser Glu Lys Thr Met Arg Val Gln Asp Tyr Pro Leu Ala Thr Arg
1               5                   10                  15

Cys Pro Glu His Ile Leu Thr Pro Thr Gly Lys Pro Leu Thr Asp Ile
            20                  25                  30

Thr Leu Glu Lys Val Leu Ser Gly Glu Val Gly Pro Gln Asp Val Arg
        35                  40                  45

Ile Ser Arg Gln Thr Leu Glu Tyr Gln Ala Gln Ile Ala Glu Gln Met
    50                  55                  60

Gln Arg His Ala Val Ala Arg Asn Phe Arg Arg Ala Ala Glu Leu Ile
65                  70                  75                  80
```

```
Ala Ile Pro Asp Glu Arg Ile Leu Ala Ile Tyr Asn Ala Leu Arg Pro
                85                  90                  95

Phe Arg Ser Ser Gln Ala Glu Leu Leu Ala Ile Ala Asp Glu Leu Glu
            100                 105                 110

His Thr Trp His Ala Thr Val Asn Ala Ala Phe Val Arg Glu Ser Ala
        115                 120                 125

Glu Val Tyr Gln Gln Arg His Lys Leu Arg Lys Gly Ser
    130                 135                 140


<210> SEQ ID NO 151
<211> LENGTH: 1824
<212> TYPE: DNA
<213> ORGANISM: Klebsiella pneumoniae

<400> SEQUENCE: 151

atgccgttaa tagccgggat tgatatcggc aacgccacca ccgaggtggc gctggcgtcc      60

gactacccgc aggcgagggc gtttgttgcc agcgggatcg tcgcgacgac gggcatgaaa     120

gggacgcggg acaatatcgc cgggaccctc gccgcgctgg agcaggccct ggcgaaaaca     180

ccgtggtcga tgagcgatgt ctctcgcatc tatcttaacg aagccgcgcc ggtgattggc     240

gatgtggcga tggagaccat caccgagacc attatcaccg aatcgaccat gatcggtcat     300

aacccgcaga cgccgggcgg ggtgggcgtt ggcgtgggga cgactatcgc cctcgggcgg     360

ctggcgacgc tgccggcggc gcagtatgcc gaggggtgga tcgtactgat tgacgacgcc     420

gtcgatttcc ttgacgccgt gtggtggctc aatgaggcgc tcgaccgggg gatcaacgtg     480

gtggcggcga tcctcaaaaa ggacgacggc gtgctggtga acaaccgcct gcgtaaaacc     540

ctgccggtgg tggatgaagt gacgctgctg gagcaggtcc ccgagggggt aatggcggcg     600

gtggaagtgg ccgcgccggg ccaggtggtg cggatcctgt cgaatcccta cgggatcgcc     660

accttcttcg ggctaagccc ggaagagacc caggccatcg tccccatcgc ccgcgccctg     720

attggcaacc gttccgcggt ggtgctcaag accccgcagg gggatgtgca gtcgcgggtg     780

atcccggcgg gcaacctcta cattagcggc gaaaagcgcc gcggagaggc cgatgtcgcc     840

gagggcgcgg aagccatcat gcaggcgatg agcgcctgcg ctccggtacg cgacatccgc     900

ggcgaaccgg gcacccacgc cggcggcatg cttgagcggg tgcgcaaggt aatggcgtcc     960

ctgaccggcc atgagatgag cgcgatatac atccaggatc tgctggcggt ggatacgttt    1020

attccgcgca aggtgcaggg cgggatggcc ggcgagtgcg ccatggagaa tgccgtcggg    1080

atggcggcga tggtgaaagc ggatcgtctg caaatgcagg ttatcgcccg cgaactgagc    1140

gcccgactgc agaccgaggt ggtggtgggc ggcgtggagg ccaacatggc catcgccggg    1200

gcgttaacca ctcccggctg tgcggcgccg ctggcgatcc tcgacctcgg cgccggctcg    1260

acggatgcgg cgatcgtcaa cgcggagggg cagataacgg cggtccatct cgccgggggcg    1320

gggaatatgg tcagcctgtt gattaaaacc gagctgggcc tcgaggatct ttcgctggcg    1380

gaagcgataa aaaaataccc gctggccaaa gtggaaagcc tgttcagtat tcgtcacgag    1440

aatggcgcgg tggagttctt tcgggaagcc ctcagcccgg cggtgttcgc caaagtggtg    1500

tacatcaagg agggcgaact ggtgccgatc gataacgcca gcccgctgga aaaaattcgt    1560

ctcgtgcgcc ggcaggcgaa agagaaagtg tttgtcacca actgcctgcg cgcgctgcgc    1620

caggtctcac ccggcggttc cattcgcgat atcgcctttg tggtgctggt gggcggctca    1680

tcgctggact ttgagatccc gcagcttatc acggaagcct tgtcgcacta tggcgtggtc    1740

gccgggcagg gcaatattcg gggaacagaa gggccgcgca atgcggtcgc caccgggctg    1800
```

```
ctactggccg gtcaggcgaa ttaa                                            1824


<210> SEQ ID NO 152
<211> LENGTH: 607
<212> TYPE: PRT
<213> ORGANISM: Klebsiella pneumoniae

<400> SEQUENCE: 152

Met Pro Leu Ile Ala Gly Ile Asp Ile Gly Asn Ala Thr Thr Glu Val
1               5                   10                  15

Ala Leu Ala Ser Asp Tyr Pro Gln Ala Arg Ala Phe Val Ala Ser Gly
            20                  25                  30

Ile Val Ala Thr Thr Gly Met Lys Gly Thr Arg Asp Asn Ile Ala Gly
        35                  40                  45

Thr Leu Ala Ala Leu Glu Gln Ala Leu Ala Lys Thr Pro Trp Ser Met
    50                  55                  60

Ser Asp Val Ser Arg Ile Tyr Leu Asn Glu Ala Ala Pro Val Ile Gly
65                  70                  75                  80

Asp Val Ala Met Glu Thr Ile Thr Glu Thr Ile Ile Thr Glu Ser Thr
                85                  90                  95

Met Ile Gly His Asn Pro Gln Thr Pro Gly Gly Val Gly Val Gly Val
            100                 105                 110

Gly Thr Thr Ile Ala Leu Gly Arg Leu Ala Thr Leu Pro Ala Ala Gln
        115                 120                 125

Tyr Ala Glu Gly Trp Ile Val Leu Ile Asp Asp Ala Val Asp Phe Leu
    130                 135                 140

Asp Ala Val Trp Trp Leu Asn Glu Ala Leu Asp Arg Gly Ile Asn Val
145                 150                 155                 160

Val Ala Ala Ile Leu Lys Lys Asp Asp Gly Val Leu Val Asn Asn Arg
                165                 170                 175

Leu Arg Lys Thr Leu Pro Val Val Asp Glu Val Thr Leu Leu Glu Gln
            180                 185                 190

Val Pro Glu Gly Val Met Ala Ala Val Glu Val Ala Ala Pro Gly Gln
        195                 200                 205

Val Val Arg Ile Leu Ser Asn Pro Tyr Gly Ile Ala Thr Phe Phe Gly
    210                 215                 220

Leu Ser Pro Glu Glu Thr Gln Ala Ile Val Pro Ile Ala Arg Ala Leu
225                 230                 235                 240

Ile Gly Asn Arg Ser Ala Val Val Leu Lys Thr Pro Gln Gly Asp Val
                245                 250                 255

Gln Ser Arg Val Ile Pro Ala Gly Asn Leu Tyr Ile Ser Gly Glu Lys
            260                 265                 270

Arg Arg Gly Glu Ala Asp Val Ala Glu Gly Ala Glu Ala Ile Met Gln
        275                 280                 285

Ala Met Ser Ala Cys Ala Pro Val Arg Asp Ile Arg Gly Glu Pro Gly
    290                 295                 300

Thr His Ala Gly Gly Met Leu Glu Arg Val Arg Lys Val Met Ala Ser
305                 310                 315                 320

Leu Thr Gly His Glu Met Ser Ala Ile Tyr Ile Gln Asp Leu Leu Ala
                325                 330                 335

Val Asp Thr Phe Ile Pro Arg Lys Val Gln Gly Gly Met Ala Gly Glu
            340                 345                 350

Cys Ala Met Glu Asn Ala Val Gly Met Ala Ala Met Val Lys Ala Asp
        355                 360                 365
```

```
Arg Leu Gln Met Gln Val Ile Ala Arg Glu Leu Ser Ala Arg Leu Gln
    370                 375                 380

Thr Glu Val Val Val Gly Gly Val Glu Ala Asn Met Ala Ile Ala Gly
385                 390                 395                 400

Ala Leu Thr Thr Pro Gly Cys Ala Ala Pro Leu Ala Ile Leu Asp Leu
                405                 410                 415

Gly Ala Gly Ser Thr Asp Ala Ala Ile Val Asn Ala Glu Gly Gln Ile
            420                 425                 430

Thr Ala Val His Leu Ala Gly Ala Gly Asn Met Val Ser Leu Leu Ile
        435                 440                 445

Lys Thr Glu Leu Gly Leu Glu Asp Leu Ser Leu Ala Glu Ala Ile Lys
    450                 455                 460

Lys Tyr Pro Leu Ala Lys Val Glu Ser Leu Phe Ser Ile Arg His Glu
465                 470                 475                 480

Asn Gly Ala Val Glu Phe Phe Arg Glu Ala Leu Ser Pro Ala Val Phe
                485                 490                 495

Ala Lys Val Val Tyr Ile Lys Glu Gly Glu Leu Val Pro Ile Asp Asn
            500                 505                 510

Ala Ser Pro Leu Glu Lys Ile Arg Leu Val Arg Arg Gln Ala Lys Glu
        515                 520                 525

Lys Val Phe Val Thr Asn Cys Leu Arg Ala Leu Arg Gln Val Ser Pro
    530                 535                 540

Gly Gly Ser Ile Arg Asp Ile Ala Phe Val Val Leu Val Gly Gly Ser
545                 550                 555                 560

Ser Leu Asp Phe Glu Ile Pro Gln Leu Ile Thr Glu Ala Leu Ser His
                565                 570                 575

Tyr Gly Val Val Ala Gly Gln Gly Asn Ile Arg Gly Thr Glu Gly Pro
            580                 585                 590

Arg Asn Ala Val Ala Thr Gly Leu Leu Leu Ala Gly Gln Ala Asn
        595                 600                 605
```

<210> SEQ ID NO 153
<211> LENGTH: 354
<212> TYPE: DNA
<213> ORGANISM: Klebsiella pneumoniae

<400> SEQUENCE: 153

```
atgtcgcttt caccgccagg cgtacgcctg ttttacgatc cgcgcgggca ccatgccggc      60

gccatcaatg agctgtgctg ggggctggag gagcaggggg tcccctgcca gaccataacc     120

tatgacggag gcggtgacgc cgctgcgctg ggcgccctgg cggccagaag ctcgcccctg     180

cgggtgggta tcgggctcag cgcgtccggc gagatagccc tcactcatgc ccagctgccg     240

gcggacgcgc cgctggctac cggacacgtc accgatagcg acgatcaact gcgtacgctc     300

ggcgccaacg ccgggcagct ggttaaagtc ctgccgttaa gtgagagaaa ctga           354
```

<210> SEQ ID NO 154
<211> LENGTH: 117
<212> TYPE: PRT
<213> ORGANISM: Klebsiella pneumoniae

<400> SEQUENCE: 154

```
Met Ser Leu Ser Pro Pro Gly Val Arg Leu Phe Tyr Asp Pro Arg Gly
1               5                   10                  15

His His Ala Gly Ala Ile Asn Glu Leu Cys Trp Gly Leu Glu Glu Gln
            20                  25                  30

Gly Val Pro Cys Gln Thr Ile Thr Tyr Asp Gly Gly Gly Asp Ala Ala
```

```
        35                  40                  45

Ala Leu Gly Ala Leu Ala Ala Arg Ser Ser Pro Leu Arg Val Gly Ile
    50                  55                  60

Gly Leu Ser Ala Ser Gly Glu Ile Ala Leu Thr His Ala Gln Leu Pro
65                  70                  75                  80

Ala Asp Ala Pro Leu Ala Thr Gly His Val Thr Asp Ser Asp Asp Gln
                85                  90                  95

Leu Arg Thr Leu Gly Ala Asn Ala Gly Gln Leu Val Lys Val Leu Pro
            100                 105                 110

Leu Ser Glu Arg Asn
        115


<210> SEQ ID NO 155
<211> LENGTH: 1125
<212> TYPE: DNA
<213> ORGANISM: artificial sequence
<220> FEATURE:
<223> OTHER INFORMATION: Codon optimized amino alcohol kinase from
      Erwinia caratovora subsp. atroseptica

<400> SEQUENCE: 155

atgagcgatg gccgtctgac cgcactgttt cctgcatttc cacatccggc atccaaccag     60

ccagtgtttg cggaggcttc cccgcacgac gatgaactga tgacgcaggc ggtgccgcag    120

gtttcctgcc agcaagccct ggcaattgcc cagcaggaat atggcctgag cggtcagatg    180

agcctgctgc agggcgaacg tgacgttaat ttctgtctga ccgtaacgcc agatgaacgc    240

tatatgctga aagtcatcaa cgctgctgaa ccggcagatg tgagcaactt tcagactgcg    300

ctgctgctgc acctggcacg tcaggcgcca gaactgccag tccctcgtat ccgctccacg    360

aaggctggtc agtctgaaac gggcgtcgaa attgatggtg ttctgctgcg tgtgcgtctg    420

gtttcctacc tggctggcat gccgcagtac ctggcgtctc cgagcacggc actgatgcca    480

cagctgggcg gtactctggc gcagctggac aacgctctgc actctttcac ccatccggcg    540

gctaaccgtg ctctgctgtg ggacatctcc cgcgcagagc aggtccgccc gtacctggac    600

ttcgttagcg agccgcagca gtatcagcac ctgcagcgca tctttgatcg ctatgactct    660

aacgtggcac cgctgctgac gacgctgcgc cgccaggtta tccacaacga cctgaacccg    720

cataacgtcc tggtcgatgg ttccagcccg acgcgcgtca cgggtatcat cgacttcggc    780

gatgcagtgt tcgcgccgct gatctgtgag gttgcgaccg ctctggcgta ccaaattggc    840

gacggcacgg atctgctgga acatgtggta ccgtttgtcg cagcgtatca ccagcgtatt    900

ccgctggcgc cggaggaaat cgccctgctg ccagatctga tcgcgacccg catggcactg    960

actctgacca tcgctcagtg gcgtgcgtct cgctacccag ataaccgcga atacctgctg   1020

cgcaacgtgc cgcgctgctg gcactccctg cagcgtatcg caacttacag ccacgcacaa   1080

tttctgacgc gcctgcagca ggtttgccca gaaaacgctc gttga                   1125


<210> SEQ ID NO 156
<211> LENGTH: 1275
<212> TYPE: DNA
<213> ORGANISM: artificial sequence
<220> FEATURE:
<223> OTHER INFORMATION: Codon optimized amino alcohol O-phosphate lyase
      from Erwinia caratovora subsp. atroseptica

<400> SEQUENCE: 156

atgactgcaa ctgaagctct gctggcacgt cgtcagcgcg ttctgggcgg tggctaccgt     60

ctgttctacg aagaaccgct gcatgttgca cgcggcgaag gtgtatggct gttcgatcat    120
```

```
cagggtaaac gttacctgga cgtatataac aacgtagcta gcgtaggtca ctgtcacccg    180

gccgttgtag aagcggtcgc gcgtcaatct gcgcaactga acacccatac gcgctacctg    240

catcacgcga tcgtagattt tgctgaagat ctgctgtctg agttcccggc agaactgaac    300

aacgtcatgc tgacctgtac tggctccgaa gcgaacgacc tggccctgcg cattgcgcgt    360

cacgttacgg gtggtaccgg catgctggtg acccgttggg cctaccatgg tgttacgtcc    420

gctctggcgg agctgtcccc gtccctgggc gacggcgtag tacgcggttc ccacgtaaag    480

ctgatcgatg ctccggatac ctaccgtcag ccgggtgctt tcctgacctc tatccgcgaa    540

gcgctggcac agatgcagcg tgaaggtatt cgtccggcgg ctctgctggt tgatactatc    600

ttctcctccg acggtgtatt ctgtgcgccg gaaggtgaga tggcccaggc agccgcactg    660

atccgtcagg ccggtggcct gttcattgcg gacgaagtgc agccgggctt tggtcgtacc    720

ggtgaatccc tgtggggttt cgcacgtcat aacgtggttc cagatctggt ttctctgggc    780

aaaccgatgg gtaacggcca tccgattgct ggtctggtag gtcgctccgc actgttcgac    840

gcttttggtc gtgatgttcg ctactttaat actttcggcg gtaacccagt atcctgccag    900

gcggcacatg ctgttctgcg cgttatccgt gaagaacagc tgcagcagaa cgcgcagcgt    960

gttggtgatt atctgcgcca aggtctgcag cagctggcac aacacttccc gctgatcggt   1020

gacattcgtg catatggtct gtttatcggt gctgaactgg tttccgaccg tgaatccaaa   1080

accccagcga gcgagtctgc actgcaggtt gttaacgcga tgcgtcagcg tggtgtactg   1140

atctccgcaa ccggcccggc ggcgaacatt ctgaagatcc gtcctccgct ggtattcctg   1200

gaggaacacg cggacgtgtt cctgactacc ctgtccgacg tgctggcgct gatcggtact   1260

cgtgcacagc gttaa                                                    1275
```

<210> SEQ ID NO 157
<211> LENGTH: 77
<212> TYPE: DNA
<213> ORGANISM: artificial sequence
<220> FEATURE:
<223> OTHER INFORMATION: Primer

<400> SEQUENCE: 157

```
caggaggaat taaccatggg gggttctcat catcatcatc atcatggtga cgatgacgat     60

aagatgagcg atggccg                                                    77
```

<210> SEQ ID NO 158
<211> LENGTH: 77
<212> TYPE: DNA
<213> ORGANISM: artificial sequence
<220> FEATURE:
<223> OTHER INFORMATION: Primer

<400> SEQUENCE: 158

```
cggccatcgc tcatcttatc gtcatcgtca ccatgatgat gatgatgatg agaacccccc     60

atggttaatt cctcctg                                                    77
```

<210> SEQ ID NO 159
<211> LENGTH: 20
<212> TYPE: DNA
<213> ORGANISM: artificial sequence
<220> FEATURE:
<223> OTHER INFORMATION: Primer

<400> SEQUENCE: 159

```
ggacctgctt cgctttatcg                                                 20
```

<210> SEQ ID NO 160
<211> LENGTH: 15
<212> TYPE: DNA
<213> ORGANISM: artificial sequence
<220> FEATURE:
<223> OTHER INFORMATION: Primer

<400> SEQUENCE: 160
gctagagatg atagc 15

<210> SEQ ID NO 161
<211> LENGTH: 18
<212> TYPE: DNA
<213> ORGANISM: artificial sequence
<220> FEATURE:
<223> OTHER INFORMATION: Primer

<400> SEQUENCE: 161
ggaagagact atccagcg 18

<210> SEQ ID NO 162
<211> LENGTH: 50
<212> TYPE: DNA
<213> ORGANISM: artificial sequence
<220> FEATURE:
<223> OTHER INFORMATION: Primer

<400> SEQUENCE: 162
gcgcgcccgg gaagaaggag ctcttcacca tgaacaaacc acagtcttgg 50

<210> SEQ ID NO 163
<211> LENGTH: 28
<212> TYPE: DNA
<213> ORGANISM: artificial sequence
<220> FEATURE:
<223> OTHER INFORMATION: Primer

<400> SEQUENCE: 163
gcgcgcccgg gttcatgcca cctctgcg 28

<210> SEQ ID NO 164
<211> LENGTH: 2432
<212> TYPE: DNA
<213> ORGANISM: Erwinia caratovora subsp. atroseptica

<400> SEQUENCE: 164
atgtctgacg gacgactcac cgcacttttt cctgcattcc cacacccggc gtccaatcag 60
cccgtatttg ccgaggcttc accgcacgac gacgagttaa tgacgcaggc cgtaccgcag 120
gtttcctgtc agcaggcgtt ggcgattgcg cagcaagaat atggcttgtc tgggcagatg 180
tcgctgcttc agggcgagcg tgatgtgaat ttctgtctga cggtgacgcc agatgaacgc 240
tacatgctga aagtcatcaa tgcggcagaa cctgccgacg tcagcaattt ccaaaccgcg 300
ctgctgctgc atcttgcccg tcaggcacct gaactgcccg taccgcgtat caggtcgaca 360
aaagcgggtc agtcggaaac aggcgttgag atcgatggtg tactgctgcg tgtgcggctt 420
gtgagctatc tggcaggaat gccgcagtat ctggcctcac cgtcaacggc gctgatgccg 480
cagttggggg gaacgctggc gcagttggat aacgcgcttc acagctttac gcatccggcg 540
gcaaaccgtg cgctgctgtg ggatatcagc cgggcagagc aggtgcgtcc ttacctcgat 600
ttcgtttctg aaccgcagca gtatcagcat cttcagcgta tttttgaccg ttatgacagt 660
aacgttgctc ctctgttgac gacgctacgt cgtcaggtca ttcataacga tctgaatccg 720

-continued

```
cataacgtgc tggtggatgg atcgtcgccg acgcgggtta ctggcattat cgattttggc    780

gatgccgtat ttgccccgtt aatttgcgaa gtcgcgacgg cactggcgta tcagatcggc    840

gatggaaccg atttgttgga gcatgttgtg ccgtttgttg cggcctatca ccaacgcatt    900

ccgttagcac cggaggagat tgcgctgtta cccgatctga tagcgacccg tatggcgctg    960

accctgacca ttgcgcagtg gcgagcatcg cgttatcccg acaatcggga gtatctgctg   1020

cgtaacgtgc cgcgctgttg gcacagtttg cagcgcattg cgacctattc ccatgcgcaa   1080

tttttgactc gcctacagca ggtttgcccg gagaatgcgc gatgaaccag aaaggaatga   1140

cgtctatgac gtctgaaatg acagcgacag aagctttgct ggcgcgccgt cagcgagtgt   1200

tgggcggcgg ttatcgcctg ttttatgaag agccgctgca tgtcgcgcgc ggcgagggcg   1260

tgtggctgtt cgatcaccaa gggaaacgtt atctggatgt ctacaataat gtggcttcgg   1320

tcggacattg ccaccccgcg gtggttgaag ccgtggcgcg acagagcgca caactcaata   1380

cccacacgcg ctatttgcac cacgcgattg tcgattttgc ggaagatttg ctgagcgaat   1440

ttcccgccga attgaacaat gtaatgctga cctgtaccgg cagtgaggct aacgatctgg   1500

cgctgcgtat cgcccgacat gtcacgggcg ggacggggat gttggtgacg cgctgggcgt   1560

atcacggcgt gaccagcgcg ctggcggaac tgtctccgtc gctgggggat ggcgttgtgc   1620

gcggtagcca tgtgaagctg atcgacgcgc cagacactta tcgtcagccc ggtgcatttc   1680

ttaccagcat tcgtgaagcg ctggcgcaga tgcaacggga aggtattcgt cctgcggcgc   1740

tgctggtaga taccattttt tccagcgatg gcgtgttctg tgcgccggaa ggcgaaatgg   1800

cacaggcggc ggcgttgatc cgtcaggcgg gcgggctgtt tattgcggat gaagtgcagc   1860

cgggcttcgg gcgcaccggg gaatcactgt ggggctttgc gcgccacaat gtcgtccctg   1920

atttggtgag tctagggaaa ccgatgggca acggacatcc catcgctgga ttggtggggc   1980

gttccgctct gttcgacgca tttgggcgcg atgtgcgcta tttcaatacc tttggcggca   2040

atccggtttc ctgtcaggcg gcgcacgcgg tgctgcgggt gattcgggaa gagcagttgc   2100

agcagaatgc ccagcgggtc ggtgattatc tgcggcaagg gttgcagcaa ctggcgcagc   2160

atttcccgct gattggtgat attcgggctt acggcctgtt tattggtgcg gagctggtca   2220

gcgatcgcga aagtaaaacg ccggcaagtg aatccgcgtt gcaggtggtg aatgcgatgc   2280

gccaacgtgg tgtgctcatc agcgcgacgg ggccagcggc gaacatactg aaaattcgcc   2340

cgccgctggt gtttctggaa gaacacgccg atgtgttctt aaccacgctg agtgacgttt   2400

tagcgctcat cggcactcgt gcacagagat aa                                2432
```